United States Patent
Brodney et al.

(10) Patent No.: US 10,093,655 B2
(45) Date of Patent: Oct. 9, 2018

(54) HETEROAROMATIC COMPOUNDS AND THEIR USE AS DOPAMINE D1 LIGANDS

(71) Applicant: PFIZER INC., New York, NY (US)

(72) Inventors: Michael Aaron Brodney, Newton, MA (US); Jennifer Elizabeth Davoren, Cambridge, MA (US); Amy Beth Dounay, Colorado Springs, CO (US); Ivan Viktorovich Efremov, Brookline, MA (US); David Lawrence Firman Gray, Groton, MA (US); Michael Eric Green, Boston, MA (US); Jaclyn Louise Henderson, Cambridge, MA (US); Chewah Lee, Wallingford, CT (US); Scot Richard Mente, Arlington, MA (US); Steven Victor O'Neil, East Lyme, CT (US); Bruce Nelsen Rogers, Belmont, MA (US); Lei Zhang, Auburndale, MA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 15/729,111

(22) Filed: Oct. 10, 2017

(65) Prior Publication Data
US 2018/0037571 A1     Feb. 8, 2018

Related U.S. Application Data

(60) Division of application No. 15/349,075, filed on Nov. 11, 2016, now Pat. No. 9,822,097, which is a continuation of application No. 14/311,963, filed on Jun. 23, 2014, now Pat. No. 9,527,831.

(60) Provisional application No. 61/840,144, filed on Jun. 27, 2013.

(51) Int. Cl.
| C07D 401/12 | (2006.01) |
| C07D 401/14 | (2006.01) |
| C07D 403/12 | (2006.01) |
| C07D 405/14 | (2006.01) |
| A61K 31/444 | (2006.01) |
| A61K 31/506 | (2006.01) |
| A61K 31/513 | (2006.01) |
| A61P 25/18  | (2006.01) |
| A61P 25/28  | (2006.01) |
| A61K 31/501 | (2006.01) |

(52) U.S. Cl.
CPC .......... *C07D 401/14* (2013.01); *A61K 31/444* (2013.01); *A61K 31/501* (2013.01); *A61K 31/506* (2013.01); *A61K 31/513* (2013.01); *C07D 401/12* (2013.01); *C07D 403/12* (2013.01); *C07D 405/14* (2013.01)

(58) Field of Classification Search
CPC .. C07D 401/12; C07D 403/12; A61K 31/506; A61K 31/497

USPC .............. 544/310, 406, 239; 514/269, 274, 514/255.06, 252.03
See application file for complete search history.

(56) References Cited

U.S. PATENT DOCUMENTS

| 4,085,111 A | 4/1978 | Oe et al. |
| 4,515,798 A | 5/1985 | Boger et al. |
| 4,550,108 A | 10/1985 | Boger et al. |
| 4,812,468 A | 3/1989 | Boger et al. |
| 4,855,309 A | 8/1989 | Koch et al. |
| 5,066,667 A | 11/1991 | Ehrenfreund et al. |
| 5,116,404 A | 5/1992 | Ishii et al. |
| 5,141,938 A | 8/1992 | Lindner et al. |
| 5,482,951 A | 1/1996 | Ozaki et al. |
| 5,616,594 A | 4/1997 | Ikeda et al. |
| 5,630,962 A | 5/1997 | Schlosser et al. |
| 5,760,033 A | 6/1998 | Yamada |
| 5,892,030 A | 4/1999 | Alig |

(Continued)

FOREIGN PATENT DOCUMENTS

| CA | 1100972 | 5/1981 |
| DE | 2521980 | 12/1975 |

(Continued)

OTHER PUBLICATIONS

Almarsson and M. J. Zaworotko, Chem. Commun. 2004, 17, 1889-1896.

(Continued)

*Primary Examiner* — Venkataraman Balasubramanian
(74) *Attorney, Agent, or Firm* — Feng Shao

(57) ABSTRACT

The present invention provides, in part, compounds of Formula I:

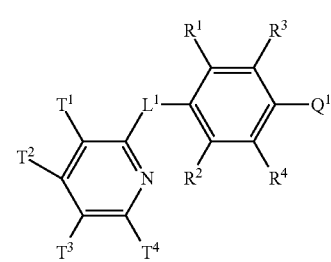

and pharmaceutically acceptable salts thereof; processes for the preparation of; intermediates used in the preparation of; and compositions containing such compounds or salts, and their uses for treating D1-mediated (or D1-associated) disorders including, e.g., schizophrenia (e.g., its cognitive and negative symptoms), cognitive impairment (e.g., cognitive impairment associated with schizophrenia, AD, PD, or pharmacotherapy therapy), and Parkinson's disease.

20 Claims, No Drawings

(56) References Cited

U.S. PATENT DOCUMENTS

| | | | |
|---|---|---|---|
| 6,106,864 A | 8/2000 | Dolan et al. | |
| 6,413,992 B1 | 7/2002 | Tisdell et al. | |
| 6,476,055 B1 | 11/2002 | Iwataki et al. | |
| 6,521,641 B1 | 2/2003 | Klein et al. | |
| 6,833,378 B2 | 12/2004 | Chen | |
| 7,101,883 B2 | 9/2006 | Maduskuie | |
| 7,501,429 B2 | 3/2009 | Weaver et al. | |
| 7,560,551 B2 | 7/2009 | Cee et al. | |
| 8,071,595 B2 | 12/2011 | Ripka et al. | |
| 8,202,877 B2 | 6/2012 | Maechling et al. | |
| 9,107,923 B2* | 8/2015 | Brodney | C07D 405/14 |
| 9,133,190 B2 | 9/2015 | Davoren et al. | |
| 9,139,561 B2* | 9/2015 | Brodney | C07D 405/14 |
| 9,527,831 B2* | 12/2016 | Brodney | C07D 405/14 |
| 9,822,097 B2* | 11/2017 | Brodney | C07D 405/14 |
| 2002/0016328 A1 | 2/2002 | Chen | |
| 2002/0103202 A1 | 8/2002 | Pinto | |
| 2002/0193403 A1 | 12/2002 | Yuan | |
| 2003/0149061 A1 | 8/2003 | Nishihara | |
| 2003/0181420 A1 | 9/2003 | Bayne | |
| 2003/0229081 A1 | 12/2003 | Maduskuie | |
| 2004/0171075 A1 | 9/2004 | Flynn et al. | |
| 2004/0260033 A1 | 12/2004 | Stokes | |
| 2005/0009834 A1 | 1/2005 | Itoh | |
| 2005/0065188 A1 | 3/2005 | Nakao | |
| 2005/0070538 A1 | 3/2005 | Cheng | |
| 2005/0250822 A1 | 11/2005 | Mita | |
| 2006/0009453 A1 | 1/2006 | Geuns-Meyer | |
| 2006/0089371 A1 | 4/2006 | Murata | |
| 2007/0135465 A1 | 1/2007 | Kim | |
| 2007/0219251 A1 | 9/2007 | Gu | |
| 2008/0119488 A1 | 5/2008 | Bayne | |
| 2008/0293720 A1 | 11/2008 | Cleary | |
| 2009/0036495 A1 | 2/2009 | Audoly | |
| 2009/0131403 A1 | 5/2009 | Kusuda | |
| 2009/0163545 A1 | 6/2009 | Goldfarb | |
| 2009/0247574 A1 | 10/2009 | Deka | |
| 2009/0318465 A1 | 12/2009 | Marita | |
| 2010/0009973 A1 | 1/2010 | Rhodes | |
| 2010/0022554 A1 | 1/2010 | Deka | |
| 2010/0063092 A1 | 3/2010 | Cid-Nunez | |
| 2010/0087487 A1 | 4/2010 | Cid-Nunez | |
| 2010/0099715 A1 | 4/2010 | Cid-Nunez | |
| 2010/0137317 A1 | 6/2010 | Ripka | |
| 2010/0144672 A1 | 6/2010 | Frackenpohl | |
| 2010/0144674 A1 | 6/2010 | Trah | |
| 2010/0166655 A1 | 7/2010 | Imogai | |
| 2010/0197655 A1 | 8/2010 | Beaudoin | |
| 2010/0298267 A1 | 11/2010 | Maechling | |
| 2011/0046088 A1 | 2/2011 | Worthington | |
| 2011/0071197 A1 | 3/2011 | Nilsson | |
| 2011/0098269 A1 | 4/2011 | Becknell et al. | |
| 2011/0112193 A1 | 5/2011 | Nilsson | |
| 2012/0071496 A1 | 3/2012 | Maechling | |
| 2012/0077799 A1 | 3/2012 | Kori | |
| 2013/0045229 A1 | 2/2013 | Iadonato | |
| 2013/0303526 A1 | 11/2013 | Ni | |
| 2014/0128374 A1 | 5/2014 | Davoren et al. | |
| 2015/0005313 A1 | 1/2015 | Brodney et al. | |

FOREIGN PATENT DOCUMENTS

| | | |
|---|---|---|
| DE | 3631511 | 3/1988 |
| EP | 145095 | 5/1984 |
| EP | 227055 | 12/1986 |
| EP | 296518 | 12/1988 |
| EP | 1916240 | 4/2008 |
| JP | 51113899 A | 10/1976 |
| JP | 61275271 A | 12/1986 |
| JP | 2059573 A2 | 2/1990 |
| JP | 2059574 A2 | 2/1990 |
| JP | 3261783 A | 11/1991 |
| JP | 5025142 | 2/1993 |
| JP | 5025142 A | 2/1993 |
| JP | 5039272 | 2/1993 |
| JP | 5039272 A | 2/1993 |
| JP | 5202031 | 8/1993 |
| JP | 5202031 A | 8/1993 |
| JP | 8027120 A | 1/1996 |
| JP | 8073446 A | 3/1996 |
| JP | 8217777 A | 8/1996 |
| JP | 9291282 A | 11/1997 |
| JP | 2009062290 A | 12/2003 |
| JP | 2005272452 A | 10/2005 |
| KR | 20120018236 A | 3/2012 |
| WO | 91/11172 | 8/1991 |
| WO | 9318016 | 9/1993 |
| WO | 94/02518 | 2/1994 |
| WO | 199405652 | 3/1994 |
| WO | 199504724 | 2/1995 |
| WO | 98/55148 | 12/1998 |
| WO | 00/35298 | 6/2000 |
| WO | 2005051932 | 6/2005 |
| WO | 2006022396 | 3/2006 |
| WO | 2008094909 | 8/2008 |
| WO | 10068788 | 6/2010 |
| WO | 2010064688 | 6/2010 |
| WO | 2010068788 | 6/2010 |
| WO | 12035421 | 3/2012 |
| WO | 2013/030665 | 3/2013 |
| WO | 2014072881 | 5/2014 |
| WO | 2014/119770 | 8/2014 |

OTHER PUBLICATIONS

Bringmann, G. et al., Atroposelective Synthesis of Axially Chiral Biaryl Compounds. Angew. Chem., Int. Ed. 2005, 44, 5384-5427.
Crystals and the Polarizing Microscope by N. H. Hartshorne and A. Stuart, 4th Edition (Edward Arnold, 1970).
Design of Prodrugs by H. Bundgaard (Elsevier, 1985).
Duncton et al., Org. Lett 2008, 10, 3259-3262.
Erdik, Tetrahedron 1992, 48, 9577-9648.
Farina et al., Organic Reactions 1997, 50, 1-652A.
Finnin and Morgan, J. Pharm. Sci. 1999, 88, 955-958.
Freedman, T. B. et al., Absolute Configuration Determination of Chiral Molecules in the Solution State Using Vibrational Circular Dichroism. Chirality 2003, 15, 743-758.
Frey et al., Tetrahedron 2003, 59, 6363-6373.
Goldman-Rakic PS et al., "Targeting the dopamine D1 receptor in schizophrenia: insights for cognitive dysfunction", Psychopharmacology 174(1):3-16 (2004).
Goulet M, Madras BK "D(1) dopamine receptor agonists are more effective in alleviating advanced than mild parkinsonism in 1-methyl-4-phenyl-1,2,3,6-tetrahydropyridine-treated monkeys", Journal of Pharmacology and Experimental Therapy 292(2):714-24 (2000).
Greene and P. G. M. Wuts, Protective Groups in Organic Synthesis, 3rd Ed., Wiley & Sons, Inc., New York (1999).
Haleblian, J. Pharm. Sci. 1975, 64, 1269-1288.
Horne et al., Tetrahedron Lett. 2009, 50, 5452-5455.
Kalaitzakis et al., Tetrahedron: Asymmetry 2007, 18, 2418-2426.
Liang and Chen, Expert Opinion in Therapeutic Patents 2001, 11, 981-986.
Littke et al., J. Am. Chem. Soc. 2000, 122, 4020-4028.
Missale C, Nash SR, Robinson SW, Jaber M, Caron MG "Dopamine receptors: from structure to function", Physiological Reviews 78:189-225 (1998).
Novel Delivery Systems, vol. 14, ACS Symposium Series (T. Higuchi and W. Stella).
Bioreversible Carriers in Drug Design, Pergamon Press, 1987 (Ed. E. B. Roche, American Pharmaceutical Association).
Pharmaceutical Dosage Forms: Tablets, vol. 1, by H. Lieberman and L. Lachman (Marcel Dekker, New York, 1980).
Prodrugs: Challenges and Reward, 2007 edition, edited by Valentino Stella, Ronald Borchardt, Michael Hageman, Reza Oliyai, Hans Maag, Jefferson Tilley, pp. 134-175 (Springer, 2007).
Ryman-Rasmussen et al., "Differential activation of adenylate cyclase and receptor internalization by novel dopamine D1 receptor agonists", Molecular Pharmacology 68(4):1039-1048 (2005).

(56) References Cited

OTHER PUBLICATIONS

Stereochemistry of Organic Compounds by E. L. Eliel and S. H. Wilen (Wiley, New York, 1994).
Surmeier DJ et al., "The role of dopamine in modulating the structure and function of striatal circuits", Prog. Brain Res. 183:149-67 (2010).
Suzuki, J. Organomet. Chem. 1999, 576, 147-168; N. Miyaura and A. Suzuki, Chem. Rev. 1995, 95, 2457-2483.
Verma et al., Pharmaceutical Technology On-line, 25(2), 1-14 (2001).
Pfizer Inc./Geng Shao, Notice of Co-Pending Applications, Apr. 3, 2015.
Compound 1; Chemical Abstracts Services (CAS): American Chemical Society, Columbus, Ohio, May 26, 2008; Registry No. 1022600-40-3; Chemical name: 3 [4 [[3 chloro 5 (trifluoromethyl)-2-pyridinyl]oxy]phenyl]-1,2,4-oxadiazol-5(2H)-one.
Compound 2; Chemical Abstracts Services (CAS): American Chemical Society, Columbus, Ohio, Jun. 1, 2008; Registry No. 1024231-01-3; Chemical name: 3-chloro-5-(trifluoromethyl)-2-[4-[5-(trifluoromethyl)-1,2,4-oxadiazol-3- yl]phenoxy]-pyridine.
Compound 3; Chemical Abstracts Services (CAS): American Chemical Society, Columbus, Ohio, Jun. 1, 2008; Registry No. 1024375-85-6; Chemical name: 4-[4-[[3-chloro-5-(trifluoromethyl)-2-pyridinyl]oxy]phenyl] N (4-methoxyphenyl)-2-thiazolamine.
Compound 4; Chemical Abstracts Services (CAS): American Chemical Society, Columbus, Ohio, Sep. 17, 2008; Registry No. 1049852-47-2; Chemical name: 2-[4-(4-methyl-2-thiazolyl)phenoxy]-3-pyridinecarboxylic acid.
Compound 5; Chemical Abstracts Services (CAS): American Chemical Society, Columbus, Ohio, Sep. 17, 2008; Registry No. 1049865-39-5; Chemical name: 2-[4-[4-(6-amino-1-ethyl-1,2,3,4-tetrahydro-2,4-dioxo-5-pyrimidinyl)-2-thiazolyl]phenoxy]-3-pyridinecarboxylic acid.
Compound 6; Chemical Abstracts Services (CAS): American Chemical Society, Columbus, Ohio, Sep. 21, 2008; Registry No. 1050928-87-4; Chemical name: 2-[4-[4-(6-amino-1,2,3,4-tetrahydro-1,3-dimethyl-2,4-dioxo-5-pyrimidinyl)-2-thiazolyl]phenoxy]-3-pyridinecarboxylic acid.
Compound 7; Chemical Abstracts Services (CAS): American Chemical Society, Columbus, Ohio, Sep. 21, 2008; Registry No. 1050929-67-3; Chemical name: 2-[4-(5-acetyl-4-methyl-2-thiazolyl)phenoxy]-3-pyridinecarboxylic acid.
Compound 8; Chemical Abstracts Services (CAS): American Chemical Society, Columbus, Ohio, Sep. 28, 2008; Registry No. 1053941-60-8; Chemical name: 2-[4-(1,3-dithiolan-2-yl)phenoxy]-3-pyridinecarboxylic acid.
Compound 9; Chemical Abstracts Services (CAS): American Chemical Society, Columbus, Ohio, Sep. 28, 2008; Registry No. 1053942-83-8; Chemical name: 2-[4-(4-acetyl-1-piperazinyl)phenoxy]-3-pyridinecarboxylic acid.
Compound 10; Chemical Abstracts Services (CAS): American Chemical Society, Columbus, Ohio, Sep. 28, 2008; Registry No. 1054112-67-2; Chemical name: 2-[4-(1,3-dithiolan-2-yl)-2-methoxyphenoxy]-3-pyridinecarboxylic acid.
Compound 11; Chemical Abstracts Services (CAS): American Chemical Society, Columbus, Ohio, Sep. 28, 2008; Registry No. 1054113-23-3; Chemical name: 3-Pyridinecarboxylic acid, 2-[4-(1H-imidazol-1-yl)phenoxy]-.
Compound 12; Chemical Abstracts Services (CAS): American Chemical Society, Columbus, Ohio, Sep. 28, 2008; Registry No. 1054153-57-9; Chemical name: 2-[4-(5-methyl-1,2,4-oxadiazol-3-yl)phenoxy]-3-pyridinecarboxylic acid.
Compound 13; Chemical Abstracts Services (CAS): American Chemical Society, Columbus, Ohio, Sep. 29, 2008; Registry No. 1054349-31-3; Chemical name: 2-[4-(1,3,4-oxadiazol-2-yl)phenoxy]-3-pyridinecarboxylic acid.
Compound 14; Chemical Abstracts Services (CAS): American Chemical Society, Columbus, Ohio, Oct. 17, 2008; Registry No. 1062377-39-2; Chemical name: 2-[4-(5-methyl-1,2,4-oxadiazol-3-yl)phenoxy]-3-nitro-pyridine.
Compound 15; Chemical Abstracts Services (CAS): American Chemical Society, Columbus, Ohio, Oct. 17, 2008; Registry No. 1062377-94-9; Chemical name: 2-[4-(5-methyl-1,2,4-oxadiazol-3-yl)phenoxy]-3-pyridinecarbonitrile.
Compound 16; Chemical Abstracts Services (CAS): American Chemical Society, Columbus, Ohio, Dec. 22, 2008; Registry No. 1088190-75-3; Chemical name: 1-[4-[4-[[3-chloro-5-(trifluoromethyl)-2-pyridinyl]oxy]phenyl]-1-piperazinyl]-ethanone.
Compound 17; Chemical Abstracts Services (CAS): American Chemical Society, Columbus, Ohio, Dec. 28, 2008; Registry No. 1090669-63-8; Chemical name: 2- [4-(1,3,4-oxadiazol-2-yl)phenoxy]-3-pyridinecarbonitrile.
Compound 18; Chemical Abstracts Services (CAS): American Chemical Society, Columbus, Ohio, Dec. 31, 2008; Registry No. 1092345-96-4; Chemical name: 1-[3,5-dichloro-4-[[3-chloro-5-(trifluoromethyl)-2-pyridinyl]oxy]phenyl]-2-imidazolidinone.
Compound 19; Chemical Abstracts Services (CAS): American Chemical Society, Columbus, Ohio, Dec. 31, 2008; Registry No. 1092345-97-5; Chemical name: 1-[3,5-dichloro-4-[[3-chloro-5-(trifluoromethyl)-2-pyridinyl]oxy]phenyl]-3-(phenylmethyl)-2-imidazolidinone.
Compound 20; Chemical Abstracts Services (CAS): American Chemical Society, Columbus, Ohio, Dec. 31, 2008; Registry No. 1092345-98-6; Chemical name: 1-[3,5-dichloro-4-[[3-chloro-5-(trifluoromethyl)-2-pyridinyl]oxy]phenyl]-3-methyl-2-imidazolidinone.
Compound 21; Chemical Abstracts Services (CAS): American Chemical Society, Columbus, Ohio, Dec. 31, 2008; Registry No. 1092346-45-6; Chemical name: 1-[3,5-dichloro-4-[[3-chloro-5-(trifluoromethyl)-2-pyridinyl]oxy]phenyl]-3-(2-pyridinylmethyl)-2-imidazolidinone.
Compound 22; Chemical Abstracts Services (CAS): American Chemical Society, Columbus, Ohio, May 14, 2010; Registry No. 1223232-12-9; Chemical name: 2-[4-(1,3,4-oxadiazol-2-yl)phenoxy]-3-pyridinecarboxylic acid ethyl ester.
Compound 23; Chemical Abstracts Services (CAS): American Chemical Society, Columbus, Ohio, May 14, 2010; Registry No. 1223444-48-1; Chemical name: 2-[4-(1H-imidazol-1-yl)phenoxy]-3-pyridinecarboxylic acid ethyl ester.
Compound 24; Chemical Abstracts Services (CAS): American Chemical Society, Columbus, Ohio, May 14, 2010; Registry No. 1223649-00-0; Chemical name: 2-[4-(5-methyl-1,2,4-oxadiazol-3-yl)phenoxy]-3-pyridinecarboxylic acid ethyl ester.
Compound 25; Chemical Abstracts Services (CAS): American Chemical Society, Columbus, Ohio, Sep. 15, 2010; Registry No. 1241522-13-3; Chemical name: 2-[4-(4-acetyl-1-piperazinyl)phenoxy]-3-pyridinecarboxylic acid ethyl ester.
Compound 26; Chemical Abstracts Services (CAS): American Chemical Society, Columbus, Ohio, Aug. 14, 2011; Registry No. 1317588-81-0; Chemical name: [5-chloro-6-[4-(1,3-dithiolan-2-yl)phenoxy]-3-pyridinyl]-1-piperidinyl-methanone.
Compound 27; Chemical Abstracts Services (CAS): American Chemical Society, Columbus, Ohio, Oct. 11, 2011; Registry No. 1335052-08-8; Chemical name: 3-amino-2-[4-(1-methyl-1H-pyrazol-5-yl)phenoxy]-4-pyridinol.
Compound 28; Chemical Abstracts Services (CAS): American Chemical Society, Columbus, Ohio, May 25, 2012; Registry No. 1374523-36-0; Chemical name: N-[2-[4-(4-acetyl-1-piperazinyl)phenoxy]-3-pyridinyl]-3-methyl-butanamide.
Compound 29; Chemical Abstracts Services (CAS): American Chemical Society, Columbus, Ohio, May 25, 2012; Registry No. 1374527-00-0; Chemical name: N-[2-[4-(4-acetyl-1-piperazinyl)phenoxy]-3-pyridinyl]-acetamide.
Compound 30; Chemical Abstracts Services (CAS): American Chemical Society, Columbus, Ohio, May 25, 2012; Registry No. 1374534-23-2; Chemical name: N-[2-[4-(4-acetyl-1-piperazinyl)phenoxy]-3-pyridinyl]-2-methyl-2-propenamide.
Compound 31; Chemical Abstracts Services (CAS): American Chemical Society, Columbus, Ohio, May 25, 2012; Registry No. 1374537-76-4; Chemical name: N-[2-[4-(4-acetyl-1-piperazinyl)phenoxy]-3- pyridinyl]-cyclobutanecarboxamide.
Compound 32; Chemical Abstracts Services (CAS): American Chemical Society, Columbus, Ohio, May 25, 2012; Registry No.

(56) References Cited

OTHER PUBLICATIONS 1374546-84-5; Chemical name: N-[2-[4-(4-acetyl-1-piperazinyl)phenoxy]-3-pyridinyl]-2-methyl-propanamide.
Compound 33; Chemical Abstracts Services (CAS): American Chemical Society, Columbus, Ohio, Feb. 17, 1999; Registry No. 219766-21-9; Chemical name: 2-[2-bromo-4-(1,3-dithiolan-2-yl)-6-methoxyphenoxy]-3-nitro-pyridine.
Compound 34; Chemical Abstracts Services (CAS): American Chemical Society, Columbus, Ohio, Mar. 8, 2000; Registry No. 258521-13-0; Chemical name: 3-nitro-2-[4-(1,3,4-oxadiazol-2-yl)phenoxy]-pyridine.
Compound 35; Chemical Abstracts Services (CAS): American Chemical Society, Columbus, Ohio, Apr. 14, 2000; Registry No. 261929-12-8; Chemical name: 2-[4-(1,3-dithiolan-2-yl)phenoxy]-3-nitro-pyridine.
Compound 36; Chemical Abstracts Services (CAS): American Chemical Society, Columbus, Ohio, Apr. 28, 2000; Registry No. 263336-09-0; Chemical name: 2-[4-(4,5-dihydro-2-thiazolyl)phenoxy]-3-(trifluoromethyl)-pyridine.
Compound 37; Chemical Abstracts Services (CAS): American Chemical Society, Columbus, Ohio, May 1, 2000; Registry No. 263387-07-1; Chemical name: 3-chloro-2-[4-(5-methyl-1,2,4-oxadiazol-3-yl)phenoxy]-5-(trifluoromethyl)-pyridine.
Compound 38; Chemical Abstracts Services (CAS): American Chemical Society, Columbus, Ohio, May 1, 2000; Registry No. 263387-08-2; Chemical name: 3-chloro-2-[4-[5-(4-chlorophenyl)-1,2,4-oxadiazol-3-yl]phenoxy]-5-(trifluoromethyl)-pyridine.
Compound 39; Chemical Abstracts Services (CAS): American Chemical Society, Columbus, Ohio, Feb. 12, 2001; Registry No. 321432-45-5; Chemical name: 1-[4-[[3-chloro-5-(trifluoromethyl)-2-pyridinyl]oxy]phenyl]-N,N-dimethyl-1H-tetrazol-5-amine.
Compound 40; Chemical Abstracts Services (CAS): American Chemical Society, Columbus, Ohio, May 24, 2001; Registry No. 337924-93-3; Chemical name: 3-chloro-2-[4-(1,2,3-thiadiazol-4-yl)phenoxy]-5-(trifluoromethyl)- pyridine.
Compound 41; Chemical Abstracts Services (CAS): American Chemical Society, Columbus, Ohio, Jul. 11, 2001; Registry No. 345293-43-8; Chemical name: 2-[2-chloro-4-(2H-tetrazol-5-yl)phenoxy]-3-pyridinecarboxylic acid.
Compound 42; Chemical Abstracts Services (CAS): American Chemical Society, Columbus, Ohio, Aug. 28, 2001; Registry No. 353258-79-4; Chemical name: 4-[4-[[3-chloro-5-(trifluoromethyl)-2-pyridinyl]oxy]phenyl]-morpholine.
Compound 43; Chemical Abstracts Services (CAS): American Chemical Society, Columbus, Ohio, Mar. 11, 2002; Registry No. 400085-70-3; Chemical name: 4-[4-[[3-chloro-5-(trifluoromethyl)-2-pyridinyl]oxy]phenyl]-2,4-dihydro-3H-1,2,4-triazol-3-one.
Compound 44; Chemical Abstracts Services (CAS): American Chemical Society, Columbus, Ohio, Mar. 11, 2002; Registry No. 400087-42-5; Chemical name: 3-chloro-2-[4-(1H-pyrazol-3-yl)phenoxy]-5-(trifluoromethyl)-pyridine.
Compound 45; Chemical Abstracts Services (CAS): American Chemical Society, Columbus, Ohio, Dec. 31, 2002; Registry No. 477856-46-5; Chemical name: 2-[4-[[3-chloro-5-(trifluoromethyl)-2-pyridinyl]oxy]phenyl]-4-(2,4-dichlorophenyl)-pyrimidine.
Compound 46; Chemical Abstracts Services (CAS): American Chemical Society, Columbus, Ohio, Dec. 31, 2002; Registry No. 477862-43-4; Chemical name: 2-[4-[[3 chloro-5-(trifluoromethyl)-2-pyridinyl]oxy]phenyl]-4-(2-thienyl)-pyrimidine.
Compound 47; Chemical Abstracts Services (CAS): American Chemical Society, Columbus, Ohio, Jan. 12, 2006; Registry No. 871803-13-3; Chemical name: 2-[4-(1H-imidazol-1-yl)phenoxy]-3-nitro-pyridine.
Compound 48; Chemical Abstracts Services (CAS): American Chemical Society, Columbus, Ohio, Mar. 1, 2007; Registry No. 924083-17-0; Chemical name: 2-[4-(1,3-dithiolan-2-yl)-2-methoxyphenoxy]-3-nitro-pyridine.
Shailaja, M., et al.; Synthesis of novel 3,5-disubstituted 4,5-dihydroisoxazole and 3,4,5-trisubstituted isoxazole derivatives and their biological activity, Indian Journal of Chemistry, Section B: Organic Chemistry Including Medicinal Chemistry (2011), 50B(2), 214-222.
Shailaja, M., et al.; Synthesis and biological activity of novel 2,5-disubstituted-1,3,4-oxadiazoles, Indian Journal of Chemistry, Section B: Organic Chemistry Including Medicinal Chemistry (2010), 49B(8), 1088-1097.
Hagiwara, Kenji, et al., Synthesis and biological activity of 1,2,4-thiadiazolines. 3. Synthesis and insecticidal activity of 4-1,2,4-thiadiazolin-3-ones, Nippon Noyaku Gakkaishi (1994), 19(4), 267-75.
Blanchet, P.J. "Effects of the Full Dopamine D1 Receptor Agonist Dihydrexidine in Parkinson's Disease," Clinical Neuropharmacology, 1998, vol. 21, 339-343.
Cai, J. X. and Arnsten, "Dose-Dependent Effects of the Dopamine D1 Receptor Agonists A77636 or SKF81297 on Spatial Working Memory in Aged Monkeys," J. Pharmacol. Exp. Ther. 283: 183-189, 1997.
Castner, S. A., et al, "Reversal of antipsychotic-induced working memory deficits by short-term dopamine D1 receptor stimulation," Science, vol. 287, No. 5460, pp. 2020-2022, 2000.
Martin, Y. C.,"The Discovery of Novel Selective D1 Dopaminergic Agonists: A-68930, A-77636, A-86929, and ABT-413," International Journal of Medicinal Chemistry, vol. 2011, Article ID 424535, 8 pages, 2011. doi:10.1155/2011/424535.
Mu, Q, et al, "A single 20 mg dose of the full D1 dopamine agonist dihydrexidine (DAR-0100) increases prefrontal perfusion in schizophrenia," Schizophrenia Research 94 (2007), 332-341.
Rascol, O. et, al, ABT-431, a D1 Receptor Agonist Prodrug, I-las Efficacy in Parkinson's Disease, Ann Neurol, 1999, 45, 736-741.

* cited by examiner

HETEROAROMATIC COMPOUNDS AND THEIR USE AS DOPAMINE D1 LIGANDS

This application is a division of U.S. patent application Ser. No. 15/349,075, filed Nov. 11, 2016, now pending, which is in turn a continuation of U.S. patent application Ser. No. 14/311,963, filed Jun. 23, 2014, issued as U.S. Pat. No. 9,527,831 Dec. 27, 2016, which in turn claims the benefit of priority to U.S. Provisional Patent Application Ser. No. 61/840,144 filed Jun. 27, 2013, the disclosure of each of which is hereby incorporated by reference in its entirety.

FIELD OF THE INVENTION

The present invention generally relates to heteroaromatic compounds, which are dopamine D1 ligands, for example dopamine D1 agonists or partial agonists.

BACKGROUND OF THE INVENTION

Dopamine acts upon neurons through two families of dopamine receptors, D1-like receptors (D1Rs) and D2-like receptors (D2Rs). The D1-like receptor family consists of D1 and D5 receptors which are expressed in many regions of the brain. D1 mRNA has been found, for example, in the striatum and nucleus accumbens. See e.g., Missale C, Nash S R, Robinson S W, Jaber M, Caron M G "Dopamine receptors: from structure to function", *Physiological Reviews* 78:189-225 (1998). Pharmacological studies have reported that D1 and D5 receptors (D1/D5), namely D1-like receptors, are linked to stimulation of adenylyl cyclase, whereas D2, D3, and D4 receptors, namely D2-like receptors, are linked to inhibition of cAMP production.

Dopamine D1 receptors are implicated in numerous neuropharmacological and neurobiological functions. For example, D1 receptors are involved in different types of memory function and synaptic plasticity. See e.g., Goldman-Rakic P S et al., "Targeting the dopamine D1 receptor in schizophrenia: insights for cognitive dysfunction", *Psychopharmacology* 174(1):3-16 (2004). Moreover, D1 receptors have been implicated in a variety of psychiatric, neurological, neurodevelopmental, neurodegenerative, mood, motivational, metabolic, cardiovascular, renal, ophthalmic, endocrine, and/or other disorders described herein including schizophrenia (e.g., cognitive and negative symptoms in schizophrenia), cognitive impairment associated with D2 antagonist therapy, ADHD, impulsivity, autism spectrum disorder, mild cognitive impairment (MCI), age-related cognitive decline, Alzheimer's dementia, Parkinson's disease (PD), Huntington's chorea, depression, anxiety, treatment-resistant depression (TRD), bipolar disorder, chronic apathy, anhedonia, chronic fatigue, post-traumatic stress disorder, seasonal affective disorder, social anxiety disorder, postpartum depression, serotonin syndrome, substance abuse and drug dependence, Tourette's syndrome, tardive dyskinesia, drowsiness, sexual dysfunction, migraine, systemic lupus erythematosus (SLE), hyperglycemia, dislipidemia, obesity, diabetes, sepsis, post-ischemic tubular necrosis, renal failure, resistant edema, narcolepsy, hypertension, congestive heart failure, postoperative ocular hypotonia, sleep disorders, pain, and other disorders in a mammal. See e.g., Goulet M, Madras B K "D(1) dopamine receptor agonists are more effective in alleviating advanced than mild parkinsonism in 1-methyl-4-phenyl-1,2,3,6-tetrahydropyridine-treated monkeys", *Journal of Pharmacology and Experimental Therapy* 292(2):714-24 (2000); Surmeier D J et al., "The role of dopamine in modulating the structure and function of striatal circuits", *Prog. Brain Res.* 183:149-67 (2010).

New or improved agents that modulate (such as agonize or partially agonize) D1 are needed for developing new and more effective pharmaceuticals to treat diseases or conditions associated with dysregulated activation of D1, such as those described herein.

SUMMARY OF THE INVENTION

The present invention provides, in part, a compound of Formula I:

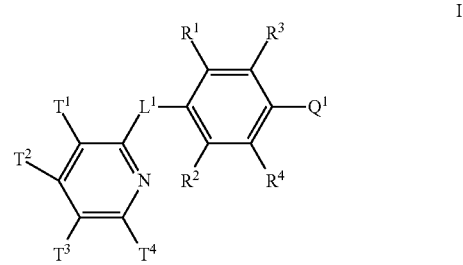

or a pharmaceutically acceptable salt thereof, wherein:
each of $T^1$, $T^2$, $T^3$, and $T^4$ is independently selected from the group consisting of H, halogen, —CN, —SF$_5$, —OH, —N(R$^a$)(R$^b$), —C(=O)—N(R$^a$)(R$^b$), —C(=O)—OR$^c$, —C(=O)—R$^d$, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, —S—($C_{1-6}$ alkyl), $C_{3-7}$ cycloalkyl, 4- to 7-membered heterocycloalkyl, $C_{3-7}$ cycloalkoxy, 5- or 6-membered heteroaryl, cyclopropylmethyl, and cyclobutylmethyl, wherein each of the $C_{1-6}$ alkyl, $C_{2-6}$ alkenyl, $C_{2-6}$ alkynyl, —S—($C_{1-6}$ alkyl), and $C_{1-6}$ alkoxy is optionally substituted with one or more substituents each independently selected from the group consisting of halogen, —OH, —CN, —N(R$^a$)(R$^b$), $C_{1-4}$ alkoxy, $C_{1-4}$ haloalkoxy, and —S—($C_{1-4}$ alkyl); and wherein each of the $C_{3-7}$ cycloalkyl, 4- to 7-membered heterocycloalkyl, $C_{3-7}$ cycloalkoxy, 5- or 6-membered heteroaryl, cyclopropylmethyl, and cyclobutylmethyl of $T^1$, $T^2$, and $T^3$ is optionally substituted with one or more substituents each independently selected from the group consisting of halogen, —OH, —CN, oxo, —N(R$^a$)(R$^b$), —C(=O)OH, —C(=O)—C$_{1-4}$ alkyl, —C(=O)—O—C$_{1-4}$ alkyl, —C(=O)—N(R$^a$)(R$^b$), $C_{1-4}$ alkyl, $C_{1-4}$ haloalkyl, $C_{1-4}$ hydroxylalkyl, $C_{1-4}$ cyanoalkyl, $C_{1-4}$ alkoxy, $C_{1-4}$ haloalkoxy, and —S—($C_{1-4}$ alkyl);

L$^1$ is selected from the group consisting of O, S, NH, N($C_{1-4}$ alkyl), N(—$C_{1-2}$ alkyl-$C_{3-4}$ cycloalkyl), and N($C_{3-6}$ cycloalkyl);

each of R$^a$ and R$^b$ is independently selected from the group consisting of H, $C_{1-4}$ alkyl, $C_{3-7}$ cycloalkyl (e.g., cyclopropyl, cyclobutyl, bicyclo[1.1.1]pentan-1-yl, or bicyclo[1.1.1]pentan-2-yl), and cyclopropylmethyl;

or R$^a$ and R$^b$ together with the N atom to which they are attached form 4- to 7-membered heterocycloalkyl (e.g., azetidinyl, pyrrolidinyl, or 7-azabicyclo[2.2.1]heptan-7-yl) optionally substituted with one or more substituents each independently selected from the group consisting of halogen, —OH, —CN, oxo, —NH$_2$, —NH($C_{1-4}$ alkyl), —N($C_{1-4}$ alkyl)$_2$, —C(=O)OH, —C(=O)—C$_{1-4}$ alkyl, —C(=O)—O—C$_{1-4}$ alkyl, —C(=O)—NH$_2$, —C(=O)—NH($C_{1-4}$ alkyl), —C(=O)—N($C_{1-4}$ alkyl)$_2$, $C_{1-4}$ alkyl, $C_{1-4}$ haloalkyl, C$_{1-4}$ hydroxylalkyl, C$_{1-4}$ cyanoalkyl, C$_{1-4}$ alkoxy, —S—(C$_{1-4}$ alkyl), and C$_{1-4}$ haloalkoxy;

each of R$^c$ and R$^d$ is independently C$_{1-4}$ alkyl, C$_{3-4}$ cycloalkyl-C$_{1-2}$ alkyl-, or C$_{3-4}$ cycloalkyl;

Q$^1$ is selected from the group consisting of Q$^{1a}$, Q$^{1b}$, Q$^{1c}$, Q$^{1d}$, and Q$^{1e}$:

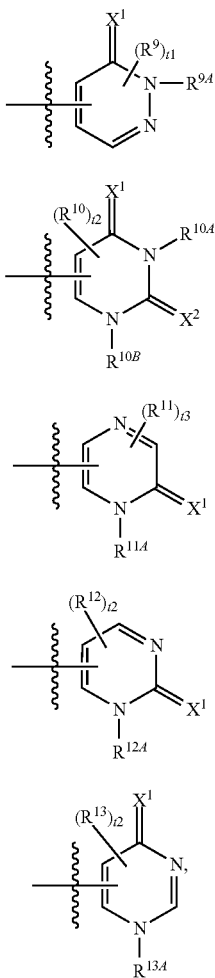

provided (a) that a ring carbon atom of the Q$^1$ ring is attached to the benzene ring of Formula I and (b) that when L$^1$ is NH, then the Q$^1$ ring is substituted with at least one non-H R$^9$, R$^{10}$, R$^{11}$, R$^{12}$, R$^{13}$, R$^{9A}$, R$^{10A}$, R$^{10B}$, R$^{11A}$, R$^{12A}$, or R$^{13A}$;

each of X$^1$ and X$^2$ is independently O or S;

each of R$^1$, R$^2$, R$^3$, and R$^4$ is independently selected from the group consisting of H, halogen, —OH, —NO$_2$, —CN, —SF$_5$, C$_{1-6}$ alkyl, C$_{1-6}$ haloalkyl, C$_{1-6}$ haloalkoxy, C$_{2-6}$ alkenyl, C$_{2-6}$ alkynyl, C$_{3-7}$ cycloalkyl, a 4- to 10-membered heterocycloalkyl, —N(R$^5$)(R$^6$), —N(R$^7$)(C(=O)R$^8$), —C(=O)—N(R$^5$)(R$^6$), —C(=O)—R$^8$, —C(=O)—OR$^8$, —N(R$^7$)(S(=O)$_2$R$^8$), —S(=O)$_2$—N(R$^5$)(R$^6$), —SR$^8$, and —OR$^8$, wherein each of the C$_{1-6}$ alkyl, C$_{3-7}$ cycloalkyl, and heterocycloalkyl is optionally substituted with 1, 2, or 3 substituents each independently selected from the group consisting of halogen, —CN, oxo, —OH, C$_{1-4}$ alkyl, C$_{1-4}$ alkoxy, C$_{1-4}$ haloalkyl, C$_{1-4}$ haloalkoxy, C$_{3-6}$ cycloalkyl, —N(R$^5$)(R$^6$), —N(R$^7$)(C(=O)R$^8$), —C(=O)—OR$^8$, —C(=O)H, —C(=O)R$^8$, —C(=O)N(R$^5$)(R$^6$), —N(R$^7$)(S(=O)$_2$R$^8$), —S(=O)$_2$—N(R$^5$)(R$^6$), —SR$^8$, and —OR$^8$;

or R$^2$ and R$^4$ together with the two carbon atoms to which they are attached form a fused 5- or 6-membered heteroaryl, a fused 5- or 6-membered heterocycloalkyl ring, a fused 5- or 6-membered cycloalkyl ring, or a fused benzene ring, wherein each of the fused rings is optionally substituted with 1, 2, or 3 substituents each independently selected from the group consisting of halo, —CN, —OH, C$_{1-4}$ alkyl, C$_{1-4}$ alkoxy, C$_{1-4}$ haloalkyl, and C$_{1-4}$ haloalkoxy, and wherein the fused heterocycloalkyl ring or fused cycloalkyl ring is further optionally substituted with 1, 2, or 3 oxo;

R$^5$ is H, C$_{1-4}$ alkyl, C$_{1-4}$ haloalkyl, or C$_{3-7}$ cycloalkyl;

R$^6$ is H or selected from the group consisting of C$_{1-4}$ alkyl, C$_{1-4}$ haloalkyl, C$_{3-7}$ cycloalkyl, a 4- to 10-membered heterocycloalkyl, C$_{6-10}$ aryl, a 5- to 10-membered heteroaryl, (C$_{3-7}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, and (5- to 10-membered heteroaryl)-C$_{1-4}$ alkyl-, wherein each of the selections from the group is optionally substituted with 1, 2, 3, or 4 substituents each independently selected from the group consisting of —OH, —CN, C$_{1-4}$ alkyl, C$_{3-7}$ cycloalkyl, C$_{1-4}$ hydroxylalkyl, —S—C$_{1-4}$ alkyl, —C(=O)H, —C(=O)—C$_{1-4}$ alkyl, —C(=O)—O—C$_{1-4}$ alkyl, —C(=O)—NH$_2$, —C(=O)—N(C$_{1-4}$ alkyl)$_2$, C$_{1-4}$ haloalkyl, C$_{1-4}$ alkoxy, and C$_{1-4}$ haloalkoxy;

or R$^5$ and R$^6$ together with the N atom to which they are attached form a 4- to 10-membered heterocycloalkyl or a 5- to 10-membered heteroaryl, each optionally substituted with 1, 2, 3, 4, or 5 substituents each independently selected from the group consisting of halogen, —OH, oxo, —C(=O)H, —C(=O)—C$_{1-4}$ alkyl, —C(=O)OH, —C(=O)—O—C$_{1-4}$ alkyl, —C(=O)—NH$_2$, —C(=O)—N(C$_{1-4}$ alkyl)$_2$, —CN, C$_{1-4}$ alkyl, C$_{1-4}$ alkoxy, C$_{1-4}$ hydroxylalkyl, C$_{1-4}$ haloalkyl, and C$_{1-4}$ haloalkoxy;

R$^7$ is selected from the group consisting of H, C$_{1-4}$ alkyl, and C$_{3-7}$ cycloalkyl;

R$^8$ is selected from the group consisting of C$_{1-6}$ alkyl, C$_{3-7}$ cycloalkyl, a 4- to 10-membered heterocycloalkyl, C$_{6-10}$ aryl, a 5- to 10-membered heteroaryl, (C$_{3-7}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, and (5- to 10-membered heteroaryl)-C$_{1-4}$ alkyl-, wherein each of the selections from the group is optionally substituted with 1, 2, or 3 substituents each independently selected from the group consisting of halogen, —CF$_3$, —CN, —OH, oxo, —S—C$_{1-4}$ alkyl, C$_{1-4}$ alkyl, C$_{1-4}$ haloalkyl, C$_{2-6}$ alkenyl, C$_{2-6}$ alkynyl, C$_{3-7}$ cycloalkyl, C$_{1-4}$ alkoxy, and C$_{1-4}$ haloalkoxy;

each R$^9$ and R$^{12}$ is independently selected from the group consisting of halogen, —OH, —CN, —SF$_5$, —NO$_2$, C$_{1-6}$ alkyl, C$_{1-6}$ haloalkyl, C$_{1-6}$ hydroxylalkyl, C$_{1-6}$ alkoxy, C$_{1-6}$ haloalkoxy, C$_{3-7}$ cycloalkyl, C$_{2-6}$ alkenyl, C$_{2-6}$ alkynyl, a 4- to 10-membered heterocycloalkyl, a 5- to 10-membered heteroaryl, (C$_{3-7}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, (5- to 10-membered heteroaryl)-C$_{1-4}$ alkyl-, —N(R$^5$)(R$^6$), —N(R$^7$)(C(=O)R$^8$), —S(=O)$_2$N(R$^5$)(R$^6$), —C(=O)—N(R$^5$)(R$^6$), —C(=O)—R$^8$, —C(=O)—OR$^8$, —SR$^8$, and —OR$^8$, wherein each of the C$_{1-6}$ alkyl, C$_{3-7}$ cycloalkyl, 4- to 10-membered heterocycloalkyl, 5- to 10-membered heteroaryl, (C$_{3-7}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, and (5- to 10-membered heteroaryl)-C$_{1-4}$ alkyl- is optionally substituted with 1, 2, 3, or 4 substituents each independently selected from the group consisting of halogen, —OH, —CN, —NO$_2$, C$_{1-4}$ alkyl, C$_{1-4}$ hydroxylalkyl, C$_{1-4}$ alkoxy, —N(R$^5$)(R$^6$), —S—(C$_{1-4}$ alkyl), —S(=O)$_2$—(C$_{1-4}$ alkyl), C$_{6-10}$ aryloxy, [($C_{6-10}$ aryl)-$C_{1-4}$ alkyloxy- optionally substituted with 1 or 2 $C_{1-4}$ alkyl], oxo, —C(=O)H, —C(=O)—$C_{1-4}$ alkyl, —C(=O)O—$C_{1-4}$ alkyl, —C(=O)NH$_2$, —NHC(=O)H, —NHC(=O)—($C_{1-4}$ alkyl), $C_{3-7}$ cycloalkyl, a 5- or 6-membered heteroaryl, $C_{1-4}$ haloalkyl, and $C_{1-4}$ haloalkoxy;

each of $R^{10}$, $R^{11}$ and $R^{13}$ is independently selected from the group consisting of halogen, —OH, —CN, —SF$_5$, —NO$_2$, $C_{1-6}$ alkyl, $C_{1-6}$ haloalkyl, $C_{1-6}$ hydroxylalkyl, $C_{1-6}$ alkoxy, $C_{1-6}$ haloalkoxy, $C_{3-7}$ cycloalkyl, $C_{2-6}$ alkenyl, $C_{2-6}$ alkynyl, $C_{6-10}$ aryl, a 4- to 10-membered heterocycloalkyl, a 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, (5- to 10-membered heteroaryl)-$C_{1-4}$ alkyl-, —N($R^5$)($R^6$), —N($R^7$)(C(=O)$R^8$), —S(=O)$_2$N($R^5$)($R^6$), —C(=O)—N($R^5$)($R^6$), —C(=O)—$R^8$, —C(=O)—OR$^8$, —SR$^8$, and —OR$^8$, wherein each of the $C_{1-6}$ alkyl, $C_{3-7}$ cycloalkyl, $C_{6-10}$ aryl, 4- to 10-membered heterocycloalkyl, 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl- is optionally substituted with 1, 2, 3, or 4 substituents each independently selected from the group consisting of halogen, —OH, —CN, —NO$_2$, $C_{1-4}$ alkyl, $C_{1-4}$ hydroxylalkyl, $C_{1-4}$ alkoxy, —N($R^5$)($R^6$), —S—($C_{1-4}$ alkyl), —S(=O)$_2$—($C_{1-4}$ alkyl), $C_{6-10}$ aryloxy, [($C_{6-10}$ aryl)-$C_{1-4}$ alkyloxy- optionally substituted with 1 or 2 $C_{1-4}$ alkyl], oxo, —C(=O)H, —C(=O)—$C_{1-4}$ alkyl, —C(=O)O—$C_{1-4}$ alkyl, —C(=O)NH$_2$, —NHC(=O)H, —NHC(=O)—($C_{1-4}$ alkyl), $C_{3-7}$ cycloalkyl, a 5- or 6-membered heteroaryl, $C_{1-4}$ haloalkyl, and $C_{1-4}$ haloalkoxy;

each of $R^{9A}$ and $R^{10A}$ is independently selected from the group consisting of H, $C_{1-6}$ alkyl, $C_{1-6}$ hydroxylalkyl, $C_{2-6}$ alkenyl, —S(=O)$_2$N($R^5$)($R^6$), —C(=O)—N($R^5$)($R^6$), —C(=O)—$R^8$, —C(=O)—OR$^8$, —SR$^{15}$, —C($R^{14}$)$_2$—OH, —C($R^{14}$)$_2$—OS(=O)$_2$H, —C($R^{14}$)$_2$—OP(=O)(OH)$_2$, —C($R^{14}$)$_2$—OR$^{15}$, —C($R^{14}$)$_2$—OC(=O)—$R^{15}$, —C($R^{14}$)$_2$—N($R^5$)($R^6$), each of $R^{10B}$, $R^{11A}$, $R^{12A}$, and $R^{13A}$ is independently selected from the group consisting of H, $C_{1-6}$ alkyl, $C_{1-6}$ haloalkyl, $C_{1-6}$ hydroxylalkyl, $C_{3-7}$ cycloalkyl, $C_{3-6}$ alkenyl, $C_{3-6}$ alkynyl, $C_{6-10}$ aryl, a 4- to 10-membered heterocycloalkyl, a 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, (5- to 10-membered heteroaryl)-$C_{1-4}$ alkyl-, —S(=O)$_2$N($R^5$)($R^6$), —C(=O)—N($R^5$)($R^6$), —C(=O)—$R^8$, and —C(=O)—OR$^8$, wherein each of the $C_{1-6}$ alkyl, $C_{3-7}$ cycloalkyl, $C_{6-10}$ aryl, 4- to 10-membered heterocycloalkyl, 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl-, is optionally substituted with 1, 2, 3, or 4 substituents each independently selected from the group consisting of halogen, —OH, —CN, —NO$_2$, $C_{1-4}$ alkyl, $C_{1-4}$ hydroxylalkyl, $C_{1-4}$ alkoxy, —N($R^5$)($R^6$), —S—($C_{1-4}$ alkyl), —S(=O)$_2$—($C_{1-4}$ alkyl), $C_{6-10}$ aryloxy, [($C_{6-10}$ aryl)-$C_{1-4}$ alkyloxy- optionally substituted with 1 or 2 $C_{1-4}$ alkyl], oxo, —C(=O)H, —C(=O)—$C_{1-4}$ alkyl, —C(=O)O—$C_{1-4}$ alkyl, —C(=O)NH$_2$, —NHC(=O)H, —NHC(=O)—($C_{1-4}$ alkyl), —OC(=O)—$C_{1-4}$ alkyl, $C_{3-7}$ cycloalkyl, a 5- or 6-membered heteroaryl, $C_{1-4}$ haloalkyl, and $C_{1-4}$ haloalkoxy;

each $R^{14}$ is independently H or selected from the group consisting of $C_{1-10}$ alkyl, $C_{3-14}$ cycloalkyl, $C_{2-10}$ alkenyl, $C_{2-10}$ alkynyl, $C_{6-10}$ aryl, 4- to 10-membered heterocycloalkyl, 5- to 10-membered heteroaryl, ($C_{3-14}$ cycloalkyl)-$C_{1-10}$ alkyl-, (4- to 14-membered heterocycloalkyl)-$C_{1-10}$ alkyl-, ($C_{6-10}$ aryl)-$C_{1-10}$ alkyl-, (5- to 10-membered heteroaryl)-$C_{1-10}$ alkyl-, wherein each of the selections of the group is optionally substituted with 1, 2, 3, or 4 substituents each independently selected from the group consisting of halogen, —OH, —CN, —NO$_2$, $C_{1-4}$ alkyl, $C_{1-4}$ hydroxylalkyl, $C_{1-4}$ alkoxy, —N($R^5$)($R^6$), —N($R^7$)C(=O)$R^8$, —N($R^7$)C(=O)OR$^8$, —N($R^7$)S(=O)$_2$$R^8$, —S(=O)$_2$N($R^5$)($R^6$), —C(=O)—N($R^5$)($R^6$), —C(=O)—$R^8$, —C(=O)—OR$^8$, —SR$^8$, —OR$^8$, —S(=O)$_2$—$R^8$, $C_{6-10}$ aryloxy, [($C_{6-10}$ aryl)-$C_{1-4}$ alkyloxy- optionally substituted with 1 or 2 $C_{1-4}$ alkyl], oxo, —C(=O)H, —NHC(=O)H, $C_{3-7}$ cycloalkyl, a 5- or 6-membered heteroaryl, $C_{1-4}$ haloalkyl, and $C_{1-4}$ haloalkoxy;

$R^{15}$ is selected from the group consisting of $C_{1-20}$ alkyl, $C_{3-14}$ cycloalkyl, $C_{2-20}$ alkenyl, $C_{2-20}$ alkynyl, $C_{6-10}$ aryl, 4- to 14-membered heterocycloalkyl, 5- to 10-membered heteroaryl, ($C_{3-14}$ cycloalkyl)-$C_{1-20}$ alkyl-, (4- to 14-membered heterocycloalkyl)-$C_{1-20}$ alkyl-, ($C_{6-10}$ aryl)-$C_{1-20}$ alkyl-, (5- to 10-membered heteroaryl)-$C_{1-20}$ alkyl-, wherein each of the selections of the group is optionally substituted with 1, 2, 3, or 4 substituents each independently selected from the group consisting of halogen, —OH, —CN, —NO$_2$, $C_{1-4}$ alkyl, $C_{1-4}$ hydroxylalkyl, $C_{1-4}$ alkoxy, —N($R^5$)($R^6$), —N($R^7$)C(=O)$R^8$, —N($R^7$)C(=O)OR$^8$, —N($R^7$)S(=O)$_2$$R^8$, —S(=O)$_2$N($R^5$)($R^6$), —C(=O)—N($R^5$)($R^6$), —C(=O)—$R^8$, —C(=O)—OR$^8$, —SR$^8$, —OR$^8$, —S(=O)$_2$—$R^8$, $C_{6-10}$ aryloxy, [($C_{6-10}$ aryl)-$C_{1-4}$ alkyloxy- optionally substituted with 1 or 2 $C_{1-4}$ alkyl], oxo, —C(=O) H, —NHC(=O)H, $C_{3-7}$ cycloalkyl, a 5- or 6-membered heteroaryl, $C_{1-4}$ haloalkyl, and $C_{1-4}$ haloalkoxy;

t1 is 0, 1, or 2;

t2 is 0 or 1; and t3 is 0, 1, or 2.

The present invention also provides a composition (e.g., a pharmaceutical composition) comprising a compound of Formula I or a pharmaceutically acceptable salt thereof.

Compounds of Formula I and pharmaceutically acceptable salts thereof are D1 modulators (e.g., D1 agonists or partial agonists). According, the present invention further provides a method for treating a D1-mediated (or D1-associated) disorder (e.g., cognitive impairment such as cognitive impairment associated with schizophrenia or cognitive impairment associated with Alzheimer's disease; schizophrenia; Alzheimer's disease; or Parkinson's disease), comprising administering to a mammal (e.g., a human) in need thereof an amount of a compound of Formula I or a pharmaceutically acceptable salt thereof effective in modulating (e.g., agonizing or partially agonizing) D1.

As used herein, the term "n-membered" where n is an integer typically describes the number of ring-forming atoms in a moiety where the number of ring-forming atoms is n. For example, pyridine is an example of a 6-membered heteroaryl ring and thiophene is an example of a 5-membered heteroaryl group.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to include $C_1$ alkyl (methyl), $C_2$ alkyl (ethyl), $C_3$ alkyl, $C_4$ alkyl, $C_5$ alkyl, and $C_6$ alkyl. For another example, the term "a 5- to 10-membered heteroaryl group" is specifically intended to include any 5-, 6-, 7-, 8-, 9- or 10-membered heteroaryl group.

As used herein, the term "alkyl" is defined to include saturated aliphatic hydrocarbons including straight chains and branched chains. In some embodiments, the alkyl group has 1 to 20 carbon atoms, 1 to 10 carbon atoms, 1 to 6 carbon atoms, or 1 to 4 carbon atoms. For example, the term "$C_{1-20}$ alkyl" refers to linear or branched aliphatic hydrocarbon chains of 1 to 20 carbon atoms; the term "$C_{1-10}$ alkyl" refers to linear or branched aliphatic hydrocarbon chains of 1 to 10 carbon atoms. For another example, as used herein, the term "$C_{1-6}$ alkyl," as well as the alkyl moieties of other groups referred to herein (e.g., $C_{1-6}$ alkoxy) refers to linear or branched radicals of 1 to 6 carbon atoms (e.g., methyl, ethyl, n-propyl, isopropyl, n-butyl, isobutyl, sec-butyl, tert-butyl, n-pentyl, or n-hexyl). For yet another example, the term "$C_{1-4}$ alkyl" refers to linear or branched aliphatic hydrocarbon chains of 1 to 4 carbon atoms; the term "$C_{1-3}$ alkyl" refers to linear or branched aliphatic hydrocarbon chains of 1 to 3 carbon atoms; the term "$C_{1-2}$ alkyl" refers to linear or branched aliphatic hydrocarbon chains of 1 to 2 carbon atoms; and the term "$C_1$ alkyl" refers to methyl. An alkyl group optionally can be substituted by one or more (e.g. 1 to 5) suitable substituents.

As used herein, the term "alkenyl" refers to aliphatic hydrocarbons having at least one carbon-carbon double bond, including straight chains and branched chains having at least one carbon-carbon double bond. In some embodiments, the alkenyl group has 2 to 20 carbon atoms, 2 to 10 carbon atoms, 2 to 6 carbon atoms, 3 to 6 carbon atoms, or 2 to 4 carbon atoms. For example, as used herein, the term "$C_{2-20}$ alkenyl" refers to straight or branched chain unsaturated radicals (having at least one carbon-carbon double bond) of 2 to 20 carbon atoms; the term "$C_{2-10}$ alkenyl" refers to straight or branched chain unsaturated radicals (having at least one carbon-carbon double bond) of 2 to 10 carbon atoms; the term "$C_{3-6}$ alkenyl" refers to straight or branched chain unsaturated radicals (having at least one carbon-carbon double bond) of 3 to 4 carbon atoms; and the term "$C_{2-4}$ alkenyl" refers to straight or branched chain unsaturated radicals (having at least one carbon-carbon double bond) of 2 to 4 carbon atoms. For another example, the term "$C_{2-6}$ alkenyl" means straight or branched chain unsaturated radicals (having at least one carbon-carbon double bond) of 2 to 6 carbon atoms, including, but not limited to, ethenyl, 1-propenyl, 2-propenyl (allyl), isopropenyl, 2-methyl-1-propenyl, 1-butenyl, 2-butenyl, and the like. An alkenyl group optionally can be substituted by one or more (e.g. 1 to 5) suitable substituents. When the compounds of Formula I contain an alkenyl group, the alkenyl group may exist as the pure E form, the pure Z form, or any mixture thereof.

As used herein, the term "alkynyl" refers to aliphatic hydrocarbons having at least one carbon-carbon triple bond, including straight chains and branched chains having at least one carbon-carbon triple bond. In some embodiments, the alkynyl group has 2 to 20, 2 to 10, 2 to 6, or 3 to 6 carbon atoms. For example, as used herein, the term "$C_{2-6}$ alkynyl" refers to straight or branched hydrocarbon chain alkynyl radicals as defined above, having 2 to 6 carbon atoms. For another example, the term "$C_{2-20}$ alkynyl" is used herein to mean straight or branched hydrocarbon chain alkynyl radicals as defined above, having 2 to 20 carbon atoms; the term "$C_{2-10}$ alkynyl" refers to straight or branched hydrocarbon chain alkynyl radicals as defined above, having 2 to 10 carbon atoms; and the term "$C_{3-6}$ alkynyl" refers to straight or branched hydrocarbon chain alkynyl radicals as defined above, having 3 to 6 carbon atoms. An alkynyl group optionally can be substituted by one or more (e.g. 1 to 5) suitable substituents.

As used herein, the term "cycloalkyl" refers to saturated or unsaturated, non-aromatic, monocyclic or polycyclic (such as bicyclic) hydrocarbon rings (e.g., monocyclics such as cyclopropyl, cyclobutyl, cyclopentyl, cyclohexyl, cycloheptyl, cyclooctyl, cyclononyl, or bicyclics including spiro, fused, or bridged systems (such as bicyclo[1.1.1]pentanyl, bicyclo[2.2.1]heptanyl, bicyclo[3.2.1]octanyl or bicyclo [5.2.0]nonanyl, decahydronaphthalenyl, etc.). The cycloalkyl group has 3 to 15 carbon atoms. In some embodiments the cycloalkyl may optionally contain one, two or more non-cumulative non-aromatic double or triple bonds and/or one to three oxo groups. In some embodiments, the bicycloalkyl group has 6 to 14 carbon atoms. For example, the term "$C_{3-14}$ cycloalkyl" refers to saturated or unsaturated, non-aromatic, monocyclic or polycyclic (such as bicyclic) hydrocarbon rings of 3 to 14 ring-forming carbon atoms (e.g., cyclopropyl, cyclobutyl, cyclopentyl, cyclohexyl, bicyclo[1.1.1]pentanyl, or cyclodecanyl); and the term "$C_{3-7}$ cycloalkyl" refers to saturated or unsaturated, non-aromatic, monocyclic or polycyclic (such as bicyclic) hydrocarbon rings of 3 to 7 ring-forming carbon atoms (e.g., cyclopropyl, cyclobutyl, cyclopentyl, cyclohexyl, bicyclo [1.1.1]pentan-1-yl, or bicyclo[1.1.1]pentan-2-yl). For another example, the term "$C_{3-6}$ cycloalkyl" refers to saturated or unsaturated, non-aromatic, monocyclic or polycyclic (such as bicyclic) hydrocarbon rings of 3 to 6 ring-forming carbon atoms. For yet another example, the term "$C_{3-4}$ cycloalkyl" refers to cyclopropyl or cyclobutyl. Also included in the definition of cycloalkyl are moieties that have one or more aromatic rings (including aryl and heteroaryl) fused to the cycloalkyl ring, for example, benzo or thienyl derivatives of cyclopentane, cyclopentene, cyclohexane, and the like (e.g., 2,3-dihydro-1H-indene-1-yl, or 1H-inden-2(3H)-one-1-yl). The cycloalkyl group optionally can be substituted by 1 or more (e.g., 1 to 5) suitable substituents.

As used herein, the term "aryl" refers to all-carbon monocyclic or fused-ring polycyclic aromatic groups having a conjugated pi-electron system. The aryl group has 6 or 10 carbon atoms in the ring(s). Most commonly, the aryl group has 6 carbon atoms in the ring. For example, as used herein, the term "$C_{6-10}$ aryl" means aromatic radicals containing from 6 to 10 carbon atoms such as phenyl or naphthyl. The aryl group optionally can be substituted by 1 or more (e.g., 1 to 5) suitable substituents.

As used herein, the term "heteroaryl" refers to monocyclic or fused-ring polycyclic aromatic heterocyclic groups with one or more heteroatom ring members (ring-forming atoms) each independently selected from O, S and N in at least one ring. The heteroaryl group has 5 to 14 ring-forming atoms, including 1 to 13 carbon atoms, and 1 to 8 heteroatoms selected from O, S, and N. In some embodiments, the heteroaryl group has 5 to 10 ring-forming atoms including one to four heteroatoms. The heteroaryl group can also contain one to three oxo or thiono (i.e. =S) groups. In some embodiments, the heteroaryl group has 5 to 8 ring-forming atoms including one, two or three heteroatoms. For example, the term "5-membered heteroaryl" refers to a monocyclic heteroaryl group as defined above with 5 ring-forming atoms in the monocyclic heteroaryl ring; the term "6-membered heteroaryl" refers to a monocyclic heteroaryl group as defined above with 6 ring-forming atoms in the monocyclic heteroaryl ring; and the term "5- or 6-membered heteroaryl" refers to a monocyclic heteroaryl group as defined above with 5 or 6 ring-forming atoms in the monocyclic heteroaryl ring. For another example, term "5- or 10-membered heteroaryl" refers to a monocyclic or bicyclic heteroaryl group as defined above with 5, 6, 7, 8, 9 or 10 ring-forming atoms in the monocyclic or bicyclic heteroaryl ring. A heteroaryl group optionally can be substituted by 1 or more (e.g., 1 to 5) suitable substituents. Examples of monocyclic heteroaryls include those with 5 ring-forming atoms including one to three heteroatoms or those with 6 ring-forming atoms including one, two or three nitrogen heteroatoms. Examples of fused bicyclic heteroaryls include two fused 5- and/or 6-membered monocyclic rings including one to four heteroatoms.

Examples of heteroaryl groups include pyridinyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, 1H-imidazo[4,5-c]pyridinyl, imidazo[1,2-a]pyridinyl, 1H-pyrrolo[3,2-c]pyridinyl, imidazo[1,2-a]pyrazinyl, imidazo[2,1-c][1,2,4]triazinyl, imidazo[1,5-a]pyrazinyl, imidazo[1,2-a]pyrimidinyl, 1H-indazolyl, 9H-purinyl, imidazo[1,2-a]pyrimidinyl, [1,2,4]triazolo[1,5-a]pyrimidinyl, [1,2,4]triazolo[4,3-b]pyridazinyl, isoxazolo[5,4-c]pyridazinyl, isoxazolo[3,4-c]pyridazinyl, pyridone, pyrimidone, pyrazinone, pyrimidinone, 1H-imidazol-2(3H)-one, 1H-pyrrole-2,5-dione, 3-oxo-2H-pyridazinyl, 1H-2-oxo-pyrimidinyl, 1H-2-oxo-pyridinyl, 2,4(1H,3H)-dioxo-pyrimidinyl, 1H-2-oxo-pyrazinyl, and the like. The heteroaryl group optionally can be substituted by 1 or more (e.g., 1 to 5) suitable substituents.

As used herein, the term "heterocycloalkyl" refers to a monocyclic or polycyclic [including 2 or more rings that are fused together, including spiro, fused, or bridged systems, for example, a bicyclic ring system], saturated or unsaturated, non-aromatic 4- to 15-membered ring system (such as a 4- to 14-membered ring system, 4- to 10-membered ring system, 5- to 10-membered ring system, 4- to 7-membered ring system, 4- to 6-membered ring system, or 5- to 6-membered ring system), including 1 to 14 ring-forming carbon atoms and 1 to 10 ring-forming heteroatoms each independently selected from O, S and N. For example, the term "4- to 14-membered heterocycloalkyl" refers to a monocyclic or polycyclic, saturated or unsaturated, non-aromatic 4- to 14-membered ring system that comprises one or more ring-forming heteroatoms each independently selected from O, S and N; and the term "4- to 10-membered heterocycloalkyl" refers to a monocyclic or polycyclic, saturated or unsaturated, non-aromatic 4- to 10-membered ring system that comprises one or more ring-forming heteroatoms each independently selected from O, S and N. For another example, the term "4- to 6-membered heterocycloalkyl" refers to a monocyclic or polycyclic, saturated or unsaturated, non-aromatic 4- to 6-membered ring system that comprises one or more ring-forming heteroatoms each independently selected from O, S and N; and the term "5- to 6-membered heterocycloalkyl" refers to a monocyclic or polycyclic, saturated or unsaturated, non-aromatic 5- to 6-membered ring system that comprises one or more ring-forming heteroatoms each independently selected from O, S and N. The heterocycloalkyl group optionally can be substituted by 1 or more (e.g., 1 to 5) suitable substituents. The heterocycloalkyl group can also optionally include one to three oxo or thiono groups.

Examples of such heterocycloalkyl rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydrothiadiazinyl, morpholinyl, oxetanyl, tetrahydrodiazinyl, oxazinyl, oxathiazinyl, quinuclidinyl, chromanyl, isochromanyl, benzoxazinyl, 7-azabicyclo[2.2.1]heptan-1-yl, 7-azabicyclo[2.2.1]heptan-2-yl, 7-azabicyclo[2.2.1]heptan-7-yl, 2-azabicyclo[2.2.1]heptan-3-yl, 3-azabicyclo[3.1.0]hexanyl, 3-azabicyclo[4.1.0]heptanyl and the like. Further examples of heterocycloalkyl rings include tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperidin-4-yl, piperazin-1-yl, piperazin-2-yl, 1,3-oxazolidin-3-yl, 1,4-oxazepan-1-yl, isothiazolidinyl, 1,3-thiazolidin-3-yl, 1,2-pyrazolidin-2-yl, 1,2-tetrahydrothiazin-2-yl, 1,3-thiazinan-3-yl, 1,2-tetrahydrodiazin-2-yl, 1,3-tetrahydrodiazin-1-yl, 1,4-oxazin-4-yl, oxazolidinonyl, 2-oxo-piperidinyl (e.g., 2-oxo-piperidin-1-yl), and the like. Also included in the definition of heterocycloalkyl are moieties that have one or more aromatic rings (including aryl and heteroaryl) fused to the nonaromatic heterocycloalkyl ring, for example pyridinyl, pyrimidinyl, thiophenyl, pyrazolyl, phthalimidyl, naphthalimidyl, and benzo derivatives of the nonaromatic heterocycloalkyl rings. Examples of such aromatic-fused heterocycloalkyl groups include indolinyl, isoindolinyl, isoindolin-1-one-3-yl, 5,7-dihydro-6H-pyrrolo[3,4-b]pyridin-6-yl, 6,7-dihydro-5H-pyrrolo[3,4-d]pyrimidin-6-yl, 4,5,6,7-tetrahydrothieno[2,3-c]pyridine-5-yl, 5,6-dihydrothieno[2,3-c]pyridin-7(4H)-one-5-yl, 1,4,5,6-tetrahydropyrrolo[3,4-c]pyrazol-5-yl, and 3,4-dihydroisoquinolin-1(2H)-one-3-yl groups. The heterocycloalkyl group is optionally substituted by 1 or more (e.g., 1 to 5) suitable substituents. Examples of heterocycloalkyl groups include 5- or 6-membered monocyclic rings and 9- or 10-membered fused bicyclic rings.

As used herein, the term "halo" or "halogen" group is defined to include fluorine, chlorine, bromine or iodine.

As used herein, the term "haloalkyl" refers to an alkyl group having one or more halogen substituents (up to perhaloalkyl, i.e., every hydrogen atom of the alkyl group has been replaced by a halogen atom). For example, the term "$C_{1-6}$ haloalkyl" refers to a $C_{1-6}$ alkyl group having one or more halogen substituents (up to perhaloalkyl, i.e., every hydrogen atom of the alkyl group has been replaced by a halogen atom). For another example, the term "$C_{1-4}$ haloalkyl" refers to a $C_{1-4}$ alkyl group having one or more halogen substituents (up to perhaloalkyl, i.e., every hydrogen atom of the alkyl group has been replaced by a halogen atom); the term "$C_{1-3}$ haloalkyl" refers to a $C_{1-3}$ alkyl group having one or more halogen substituents (up to perhaloalkyl, i.e., every hydrogen atom of the alkyl group has been replaced by a halogen atom); and the term "$C_{1-2}$ haloalkyl" refers to a $C_{1-2}$ alkyl group (i.e. methyl or ethyl) having one or more halogen substituents (up to perhaloalkyl, i.e., every hydrogen atom of the alkyl group has been replaced by a halogen atom). For yet another example, the term "$C_1$ haloalkyl" refers to a methyl group having one, two, or three halogen substituents. Examples of haloalkyl groups include $CF_3$, $C_2F_5$, $CHF_2$, $CH_2F$, $CH_2CF_3$, $CH_2Cl$ and the like.

As used herein, the term "halocycloalkyl" refers to a cycloalkyl group having one or more halogen substituents (up to perhalocycloalkyl, i.e., every hydrogen atom of the cycloalkyl group has been replaced by a halogen atom). For example, the term "$C_{3-4}$ halocycloalkyl" refers to a cyclopropyl or cyclobutyl group having one or more halogen substituents. An example of halocycloalkyl is 2-fluorocyclopropan-1-yl.

As used herein, the term "alkoxy" or "alkyloxy" refers to an —O-alkyl group. For example, the term "$C_{1-6}$ alkoxy" or "$C_{1-6}$ alkyloxy" refers to an —O—($C_{1-6}$ alkyl) group; and the term "$C_{1-4}$ alkoxy" or "$C_{1-4}$ alkyloxy" refers to an —O—($C_{1-4}$ alkyl) group; For another example, the term "$C_{1-2}$ alkoxy" or "$C_{1-2}$ alkyloxy" refers to an —O—($C_{1-2}$ alkyl) group. Examples of alkoxy include methoxy, ethoxy, propoxy (e.g., n-propoxy and isopropoxy), tert-butoxy, and the like. The alkoxy or alkyloxy group optionally can be substituted by 1 or more (e.g., 1 to 5) suitable substituents.

As used here, the term "haloalkoxy" refers to an —O-haloalkyl group. For example, the term "$C_{1-6}$ haloalkoxy" refers to an —O—($C_{1-6}$ haloalkyl) group. For another example, the term "$C_{1-4}$ haloalkoxy" refers to an —O—($C_{1-4}$ haloalkyl) group; and the term "$C_{1-2}$ haloalkoxy" refers to an —O—($C_{1-2}$ haloalkyl) group. For yet another example, the term "$C_1$ haloalkoxy" refers to a methoxy group having one, two, or three halogen substituents. An example of haloalkoxy is —$OCF_3$ or —$OCHF_2$.

As used herein, the term "cycloalkoxy" or "cycloalkyloxy" refers to an —O-cycloalkyl group. For example, the term "$C_{3-7}$ cycloalkoxy" or "$C_{3-7}$ cycloalkyloxy" refers to an —O—($C_{3-7}$ cycloalkyl) group. For another example, the term "$C_{3-6}$ cycloalkoxy" or "$C_{3-6}$ cycloalkyloxy" refers to an —O—($C_{3-6}$ cycloalkyl) group. Examples of cycloalkoxy include $C_{3-6}$ cycloalkoxy (e.g., cyclopropoxy, cyclobutoxy, cyclopentoxy, cyclohexanoxy, and the like). The cycloalkoxy or cycloalkyloxy group optionally can be substituted by 1 or more (e.g., 1 to 5) suitable substituents.

As used here, the term "$C_{6-10}$ aryloxy" refers to an —O—($C_{6-10}$ aryl) group. An example of a $C_{6-10}$ aryloxy group is —O-phenyl [i.e., phenoxy]. The $C_{6-10}$ aryloxy y group optionally can be substituted by 1 or more (e.g., 1 to 5) suitable substituents.

As used herein, the term "fluoroalkyl" refers to an alkyl group having one or more fluorine substituents (up to perfluoroalkyl, i.e., every hydrogen atom of the alkyl group has been replaced by fluorine). For example, the term "$C_{1-2}$ fluoroalkyl" refers to a $C_{1-2}$ alkyl group having one or more fluorine substituents (up to perfluoroalkyl, i.e., every hydrogen atom of the $C_{1-2}$ alkyl group has been replaced by fluorine). For another example, the term "$C_1$ fluoroalkyl" refers to a $C_1$ alkyl group (i.e., methyl) having 1, 2, or 3 fluorine substituents). Examples of fluoroalkyl groups include $CF_3$, $C_2F_5$, $CH_2CF_3$, $CHF_2$, $CH_2F$, and the like.

As used here, the term "fluoroalkoxy" refers to an —O-fluoroalkyl group. For example, the term "$C_{1-2}$ fluoroalkoxy" refers to an —O—$C_{1-2}$ fluoroalkyl group. For another example, the term "$C_1$ fluoroalkoxy" refers to a methoxy group having one, two, or three fluorine substituents. An example of C, fluoroalkoxy is —$OCF_3$ or —$OCHF_2$.

As used herein, the term "hydroxylalkyl" or "hydroxyalkyl" refers to an alkyl group having one or more (e.g., 1, 2, or 3) OH substituents. The term "$C_{1-6}$ hydroxylalkyl" or "$C_{1-6}$ hydroxyalkyl" refers to a $C_{1-6}$ alkyl group having one or more (e.g., 1, 2, or 3) OH substituents. The term "$C_{1-4}$ hydroxylalkyl" or "$C_{1-4}$ hydroxyalkyl" refers to a $C_{1-4}$ alkyl group having one or more (e.g., 1, 2, or 3) OH substituents; the term "$C_{1-3}$ hydroxylalkyl" or "$C_{1-3}$ hydroxyalkyl" refers to a $C_{1-3}$ alkyl group having one or more (e.g., 1, 2, or 3) OH substituents; and the term "$C_{1-2}$ hydroxylalkyl" or "$C_{1-2}$ hydroxyalkyl" refers to a $C_{1-2}$ alkyl group having one or more (e.g., 1, 2, or 3) OH substituents. An example of hydroxylalkyl is —$CH_2OH$ or —$CH_2CH_2OH$.

As used herein, the term "cyanoalkyl" refers to an alkyl group having one or more (e.g., 1, 2, or 3) —CN (i.e. —C≡N or cyano) substituents. For example, The term "$C_{1-4}$ cyanoalkyl" refers to a $C_{1-4}$ alkyl group having one or more (e.g., 1, 2, or 3) —CN substituents. An Example of cyanoalkyl is —$CH_2$—CN or —$CH_2CH_2$—CN.

As used herein, the term "oxo" refers to =O. When an oxo is substituted on a carbon atom, they together form a carbonyl moiety [—C(=O)—]. When an oxo is substituted on a sulfur atom, they together form a sulfinyl moiety [—S(=O)—]; when two oxo groups are substituted on a sulfur atom, they together form a sulfonyl moiety [—S(=O)$_2$—].

As used herein, the term "optionally substituted" means that substitution is optional and therefore includes both unsubstituted and substituted atoms and moieties. A "substituted" atom or moiety indicates that any hydrogen on the designated atom or moiety can be replaced with a selection from the indicated substituent group (up to that every hydrogen atom on the designated atom or moiety is replaced with a selection from the indicated substituent group), provided that the normal valency of the designated atom or moiety is not exceeded, and that the substitution results in a stable compound. For example, if a methyl group (i.e., $CH_3$) is optionally substituted, then up to 3 hydrogen atoms on the carbon atom can be replaced with substituent groups.

As used herein, unless specified, the point of attachment of a substituent can be from any suitable position of the substituent. For example, piperidinyl can be piperidin-1-yl (attached through the N atom of the piperidinyl), piperidin-2-yl (attached through the C atom at the 2-position of the piperidinyl), piperidin-3-yl (attached through the C atom at the 3-position of the piperidinyl), or piperidin-4-yl (attached through the C atom at the 4-position of the piperidinyl). For another example, pyridinyl (or pyridyl) can be 2-pyridinyl (or pyridin-2-yl), 3-pyridinyl (or pyridin-3-yl), or 4-pyridinyl (or pyridin-4-yl).

When a bond to a substituent is shown to cross a bond connecting two atoms in a ring, then such substituent may be bonded to any of the ring-forming atoms in that ring that are substitutable (i.e., bonded to one or more hydrogen atoms), unless otherwise specified or otherwise implicit from the context. For example, as shown in Formula a-101 below, $R^9$ may be bonded to either of the two ring carbon atoms each of which bears a hydrogen atom (but not shown), but not to the N to which $R^{9A}$ is bonded (even wherein $R^{9A}$ is H). For another example, as shown in Formula a-102 below, $R^9$ may be bonded to either of the two ring carbon atoms each of which bears a hydrogen atom (but not shown), but not to the N that is shown to be bonded to a H atom. For yet another example, as shown in Formula a-103 below, $R^{12}$ may be bonded to either of the two ring carbon atoms each of which bears a hydrogen atom (but not shown), but not the the ring carbon atom that is shown to be bonded to a H atom.

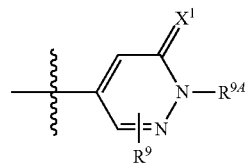

a-101

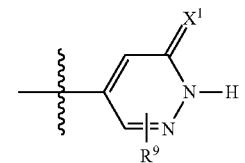

a-102

-continued a-103

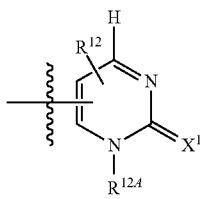

When a substituted or optionally substituted moiety is described without indicating the atom via which such moiety is bonded to a substituent, then the substituent may be bonded via any appropriate atom in such moiety. For example in a substituted arylalkyl, a substituent on the arylalkyl [e.g., $(C_{6-10}$ aryl)-$C_{1-4}$ alkyl-] can be bonded to any carbon atom on the alkyl part or on the aryl part of the arylalkyl. Combinations of substituents and/or variables are permissible only if such combinations result in stable compounds.

As noted above, the compounds of Formula I may exist in the form of pharmaceutically acceptable salts such as acid addition salts and/or base addition salts of the compounds of Formula I. The phrase "pharmaceutically acceptable salt(s)", as used herein, unless otherwise indicated, includes acid addition or base salts which may be present in the compounds of Formula I.

Pharmaceutically acceptable salts of the compounds of Formula I include the acid addition and base salts thereof.

Suitable acid addition salts are formed from acids which form non-toxic salts. Examples include the acetate, adipate, aspartate, benzoate, besylate, bicarbonate/carbonate, bisulfate/sulfate, borate, camphorsulfonate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulfate and hemicalcium salts.

For a review on suitable salts, see "Handbook of Pharmaceutical Salts: Properties, Selection, and Use" by Stahl and Wermuth (Wiley-VCH, 2002). Methods for making pharmaceutically acceptable salts of compounds of Formula I are known to one of skill in the art.

As used herein the terms "Formula I", "Formula I or pharmaceutically acceptable salts thereof", "pharmaceutically acceptable salts of the compound or the salt [of Formula I]" are defined to include all forms of the compound of Formula I, including hydrates, solvates, isomers (including for example rotational stereoisomers), crystalline and non-crystalline forms, isomorphs, polymorphs, metabolites, and prodrugs thereof.

As it is known to the person skilled in the art, amine compounds (i.e., those comprising one or more nitrogen atoms), for example tertiary amines, can form N-oxides (also known as amine oxides or amine N-oxides). An N-oxide has the formula of $(R^{100}R^{200}R^{300})N^+$—$O^-$ wherein the parent amine $(R^{100}R^{200}R^{300})N$ can be for example, a tertiary amine (for example, each of $R^{100}$, $R^{200}$, $R^{300}$ is independently alkyl, arylalkyl, aryl, heteroaryl, or the like), a heterocyclic or heteroaromatic amine [for example, $(R^{100}R^{200}R^{300})N$ together forms 1-alkylpiperidine, 1-alkylpyrrolidine, 1-benzylpyrrolidine, or pyridine]. For instance, an imine nitrogen, especially heterocyclic or heteroaromatic imine nitrogen, or pyridine-type nitrogen

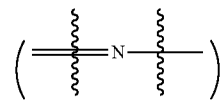

atom [such as a nitrogen atom in pyridine, pyridazine, or pyrazine], can be N-oxidized to form the N-oxide comprising the group

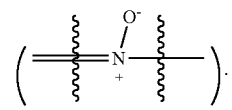

Thus, a compound according to the present invention comprising one or more nitrogen atoms (e.g., an imine nitrogen atom) may be capable of forming an N-oxide thereof (e.g., mono-N-oxides, bis-N-oxides or multi-N-oxides, or mixtures thereof depending on the number of nitrogen atoms suitable to form stable N-oxides).

As used herein, the term "N-oxide(s)" refer to all possible, and in particular all stable, N-oxide forms of the amine compounds (e.g., compounds comprising one or more imine nitrogen atoms) described herein, such as mono-N-oxides (including different isomers when more than one nitrogen atom of an amine compound can form a mono-N-oxide) or multi-N-oxides (e.g., bis-N-oxides), or mixtures thereof in any ratio.

Compounds of Formula I and their salts described herein further include N-oxides thereof.

Compounds of Formula I (including salts thereof) may exist in a continuum of solid states ranging from fully amorphous to fully crystalline. The term 'amorphous' refers to a state in which the material lacks long-range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from apparent solid to a material with liquid properties occurs, which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ('melting point').

Compounds of Formula I (including salts thereof) may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of Formula I (including salts thereof) may exist as clathrates or other complexes (e.g., co-crystals). Included within the scope of the invention are complexes such as clathrates, drug-host inclusion complexes wherein the drug and host are present in stoichiometric or non-stoichiometric amounts. Also included are complexes of the compounds of Formula I containing two or more organic and/or inorganic components, which may be in stoichiometric or non-stoichiometric amounts. The resulting complexes may be ionized, partially ionized, or non-ionized. Co-crystals are typically defined as crystalline complexes of neutral molecular constituents that are bound together through non-covalent interactions, but could also be a complex of a neutral molecule with a salt. Co-crystals may be prepared by melt crystallization, by recrystallization from solvents, or by physically grinding the components together; see O. Almarsson and M. J. Zaworotko, *Chem. Commun.* 2004, 17, 1889-1896. For a general review of multi-component complexes, see J. K. Haleblian, *J. Pharm. Sci.* 1975, 64, 1269-1288.

The compounds of the invention (including salts thereof) may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$N$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970).

The invention also relates to prodrugs of the compounds of Formula I. Thus certain derivatives of compounds of Formula I which may have little or no pharmacological activity themselves can, when administered into or onto the body, be converted into compounds of Formula I having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

Prodrugs in accordance with the invention can, for example, be produced by replacing appropriate functionalities present in the compounds of Formula I with certain moieties known to those skilled in the art as 'pro-moieties' as described, for example, in Design of Prodrugs by H. Bundgaard (Elsevier, 1985), or in Prodrugs: Challenges and Reward, 2007 edition, edited by Valentino Stella, Ronald Borchardt, Michael Hageman, Reza Oliyai, Hans Maag, Jefferson Tilley, pages 134-175 (Springer, 2007).

Moreover, certain compounds of Formula I may themselves act as prodrugs of other compounds of Formula I.

Also included within the scope of the invention are metabolites of compounds of Formula I, that is, compounds formed in vivo upon administration of the drug.

The compounds of Formula I (including salts thereof) include all stereoisomers and tautomers. Stereoisomers of Formula I include cis and trans isomers, optical isomers such as R and S enantiomers, diastereomers, geometric isomers, rotational isomers, atropisomers, and conformational isomers of the compounds of Formula I, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

In some embodiments, the compounds of Formula I (including salts thereof) may have asymmetric carbon atoms. The carbon-carbon bonds of the compounds of Formula I may be depicted herein using a solid line (-), a solid wedge (━━), or a dotted wedge (▪▪▪▪▪). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

In some embodiments, the compounds of Formula I (including salts thereof) may exist in and/or be isolated as atropisomers (e.g., one or more atropenantiomers). Those skilled in the art would recognize that atropisomerism may exist in a compound that has two or more aromatic rings (for example, two aromatic rings linked through a single bond). See e.g., Freedman, T. B. et al., Absolute Configuration Determination of Chiral Molecules in the Solution State Using Vibrational Circular Dichroism. *Chirality* 2003, 15, 743-758; and Bringmann, G. et al., Atroposelective Synthesis of Axially Chiral Biaryl Compounds. *Angew. Chem., Int. Ed.* 2005, 44, 5384-5427.

When any racemate crystallizes, crystals of different types are possible. One type is the racemic compound (true racemate) wherein one homogeneous form of crystal is produced containing both enantiomers in equimolar amounts. Another type is a racemic mixture or conglomerate wherein two forms of crystal are produced in equal or different molar amounts each comprising a single enantiomer.

The compounds of Formula I (including salts thereof) may exhibit the phenomena of tautomerism and structural isomerism. For example, the compounds of Formula I may exist in several tautomeric forms, including the enol and imine form, the amide and imidic acid form, and the keto and enamine form and geometric isomers and mixtures thereof. All such tautomeric forms are included within the scope of the compounds of Formula I. Tautomers may exist as mixtures of a tautomeric set in solution. In solid form, usually one tautomer predominates.

Even though one tautomer may be described, the present invention includes all tautomers of the compounds of Formula I. For example, when one of the following two tautomers of the invention is disclosed in the experimental section herein, those skilled in the art would readily recognize that the invention also includes the other.

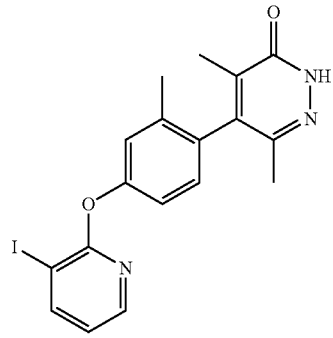

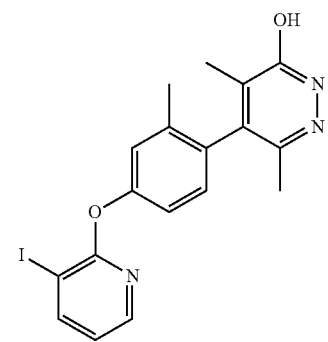

For another example, when one of the following three tautomers of the invention is disclosed in the experimental section herein, those skilled in the art would readily recognize that the invention also includes each of the others.

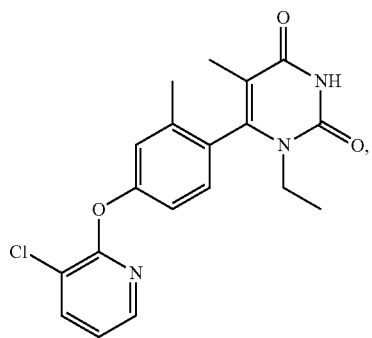

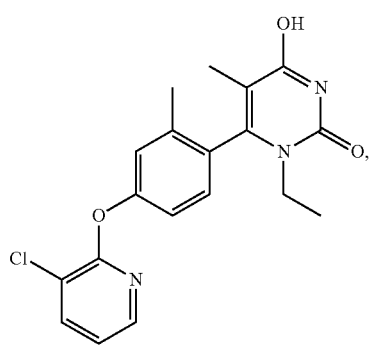

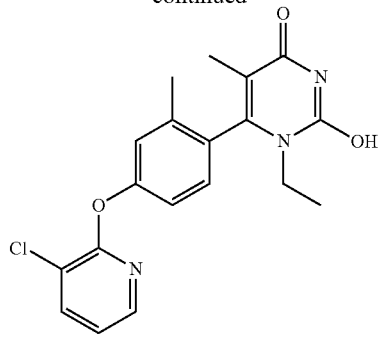

The present invention includes all pharmaceutically acceptable isotopically-labelled compounds of Formula I (including salts thereof) wherein one or more atoms are replaced by atoms having the same atomic number, but an atomic mass or mass number different from the atomic mass or mass number which predominates in nature.

Examples of isotopes suitable for inclusion in the compounds of the invention (including salts thereof) include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of Formula I, for example, those incorporating a radioactive isotope, are useful in drug and/or substrate tissue distribution studies. The radioactive isotopes tritium, i.e., $^3$H, and carbon-14, i.e., $^{14}$C, are particularly useful for this purpose in view of their ease of incorporation and ready means of detection.

Substitution with heavier isotopes such as deuterium, i.e., $^2$H, may afford certain therapeutic advantages resulting from greater metabolic stability, for example, increased in vivo half-life or reduced dosage requirements, and hence may be preferred in some circumstances.

Substitution with positron-emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of Formula I (including salts thereof) can generally be prepared by conventional techniques known to those skilled in the art or by processes analogous to those described in the accompanying Examples and Preparations using an appropriate isotopically-labeled reagent in place of the non-labeled reagent previously employed.

An embodiment of the present invention is a compound of Formula I or a pharmaceutically acceptable salt thereof, wherein $L^1$ is O.

An embodiment of the present invention is a compound of Formula I or a pharmaceutically acceptable salt thereof, wherein $L^1$ is S.

An embodiment of the present invention is a compound of Formula I or a pharmaceutically acceptable salt thereof, wherein $L^1$ is NH, N($C_{1-4}$ alkyl), N(—$C_{1-2}$ alkyl-$C_{3-4}$ cycloalkyl), or N($C_{3-6}$ cycloalkyl). In a further embodiment, $L^1$ is NH.

An embodiment of the present invention is a compound of Formula I or a pharmaceutically acceptable salt thereof, wherein $Q^1$ is $Q^{1a}$. In a further embodiment, $X^1$ is O.

An embodiment of the present invention is a compound of Formula I or a pharmaceutically acceptable salt thereof, wherein the compound of Formula I is a compound of Formula IA-1, IA-2, IA-3, IA-4, IA-5, IA-6, IA-7, IA-8, IA-9, or IA-10:

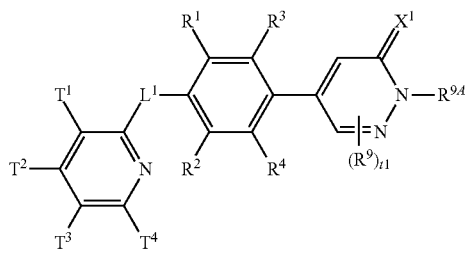
IA-1

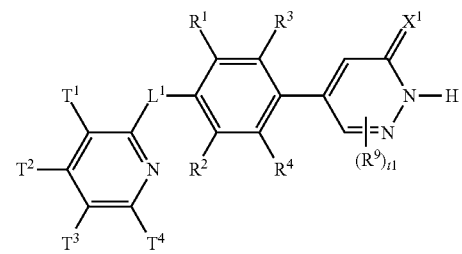
IA-2

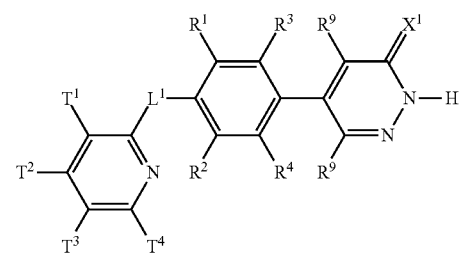
IA-3

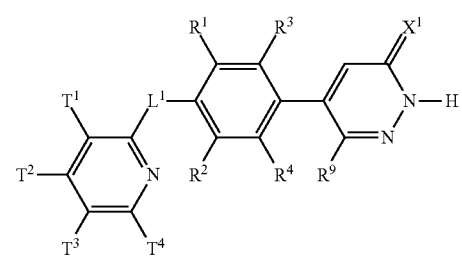
IA-4

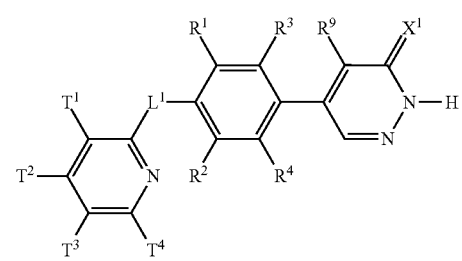
IA-5

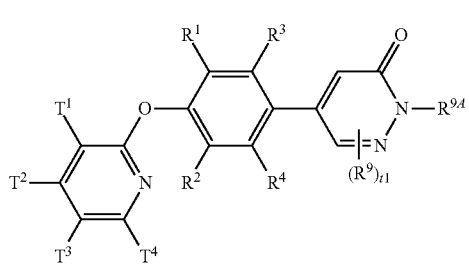
IA-6

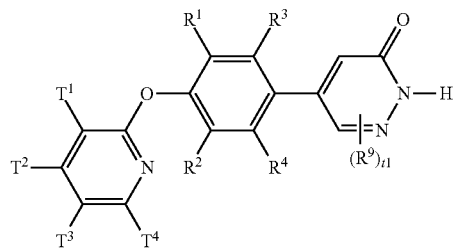
IA-7

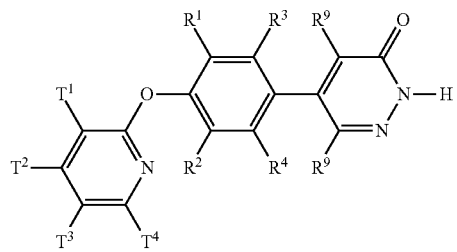
IA-8

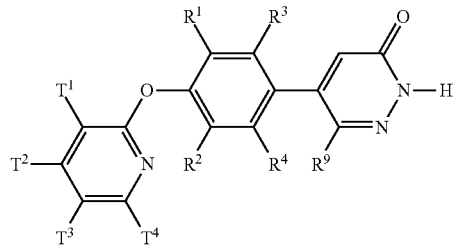
IA-9

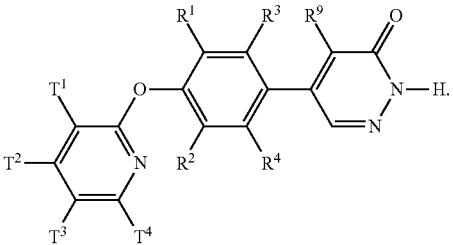
IA-10

In one embodiment of a compound of Formula I or a pharmaceutically acceptable salt thereof wherein $Q^1$ is $Q^{1a}$, or in one embodiment of a compound of Formula IA-1, IA-2, IA-3, IA-4, IA-5, IA-6, IA-7, IA-8, IA-9, or IA-10, or a pharmaceutically acceptable salt thereof, each $R^9$ is independently selected from the group consisting of —CN, $C_{1-4}$ alkyl, $C_{1-4}$ haloalkyl, $C_{3-4}$ cycloalkyl, cyclopropylmethyl, and cyclobutylmethyl, wherein the $C_{1-4}$ alkyl of $R^9$ is optionally substituted with one or more substituents each independently selected from the group consisting of halogen, —OH, —CN, $C_{1-4}$ alkoxy, and $C_{1-4}$ haloalkoxy; and wherein each of the $C_{3-4}$ cycloalkyl, cyclopropylmethyl, and cyclobutylmethyl of $R^9$ is optionally substituted with one or more substituents each independently selected from the group consisting of halogen, —OH, —CN, $C_{1-4}$ alkyl, $C_{1-4}$ haloalkyl, $C_{1-4}$ hydroxylalkyl, $C_{1-4}$ cyanoalkyl, $C_{1-4}$ alkoxy, and $C_{1-4}$ haloalkoxy; and $R^{9A}$ is selected from the group consisting of H, $C_{1-3}$ alkyl, $C_{1-3}$ hydroxylalkyl, allyl, —S(=O)$_2$N(R$^5$)(R$^6$), —C(=O)—N(R$^5$)(R$^6$), —C(=O)—R$^8$, —C(=O)—OR$^8$, —C(R$^{14}$)$_2$—OH, —C(R$^{14}$)$_2$—OS(=O)$_2$H, —C(R$^{14}$)$_2$—OP(=O)(OH)$_2$, —C(R$^{14}$)$_2$—OR$^{15}$, and —C(R$^{14}$)$_2$—OC(=O)—R$^{15}$. In a further embodiment, each $R^9$ is independently selected from the group consisting of $C_{1-3}$ alkyl, $C_{1-3}$ haloalkyl, and cyclopropyl. In a yet further embodiment, each $R^9$ is independently selected from the group consisting of $C_{1-3}$ alkyl and cyclopropyl. In a still further embodiment, each $R^9$ is independently methyl or ethyl. In a yet still further embodiment, each $R^9$ is methyl.

In one embodiment of a compound of Formula IA-1 or IA-6, or a pharmaceutically acceptable salt thereof, $R^{9A}$ is selected from the group consisting of H, $C_{1-3}$ alkyl, $C_{1-3}$ hydroxylalkyl, and allyl. In a further embodiment, $R^{9A}$ is not H.

In one embodiment of a compound of Formula IA-1 or IA-6, or a pharmaceutically acceptable salt thereof, $R^{9A}$ is selected from the group consisting of H, $-S(=O)_2N(R^5)(R^6)$, $-C(=O)-N(R^5)(R^6)$, $-C(=O)-R^8$, $-C(=O)-OR^8$, $-C(R^{14})_2-OH$, $-C(R^{14})_2-OS(=O)_2H$, $-C(R^{14})_2-OP(=O)(OH)_2$, $-C(R^{14})_2-OR^{15}$, and $-C(R^{14})_2-OC(=O)-R^{15}$. In a further embodiment, $R^{9A}$ is selected from the group consisting of H, $-S(=O)_2N(R^5)(R^6)$, $-C(=O)-N(R^5)(R^6)$, $-C(=O)-R^8$, $-C(=O)-OR^8$, $-CH_2-OH$, $-CH_2-OS(=O)_2H$, $-CH_2-OP(=O)(OH)_2$, $-CH_2-OR^{15}$, and $-CH_2-OC(=O)-R^{15}$. In a yet further embodiment, $R^{9A}$ is not H.

An embodiment of the present invention is a compound of Formula I or a pharmaceutically acceptable salt thereof, wherein $Q^1$ is $Q^{1b}$. In a further embodiment, $X^1$ is O. In another further embodiment, $X^2$ is O. In a yet further embodiment, each of $X^1$ and $X^2$ is O.

An embodiment of the present invention is a compound of Formula I or a pharmaceutically acceptable salt thereof, wherein the compound of Formula I is a compound of Formula IB-1, IB-2, IB-3, IB-4, or IB-5, IB-6, IB-7, IB-8, IB-9, or IB-10:

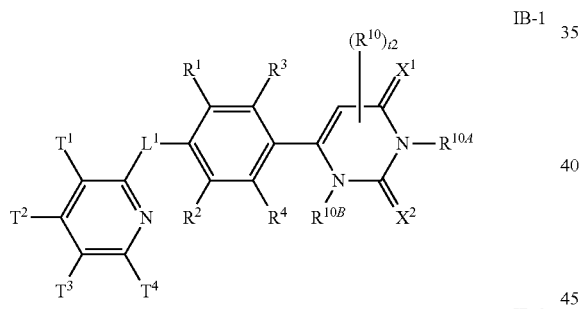

IB-1

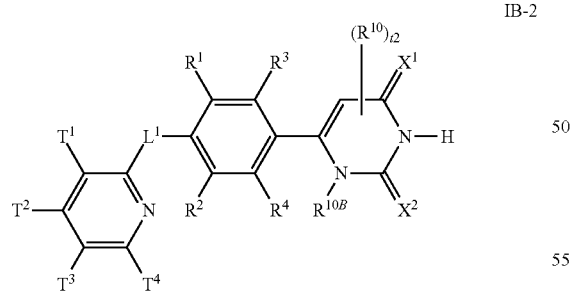

IB-2

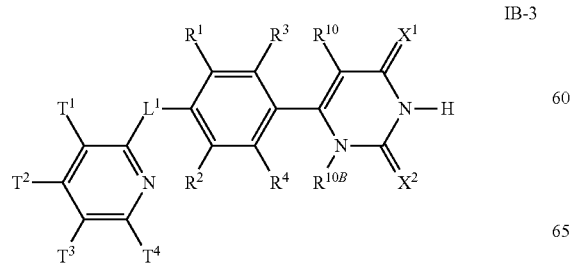

IB-3

-continued

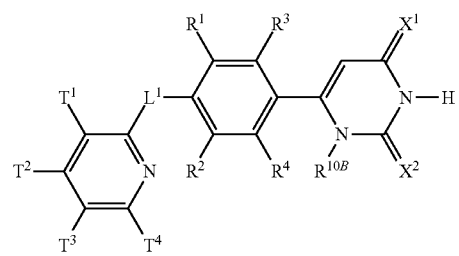

IB-4

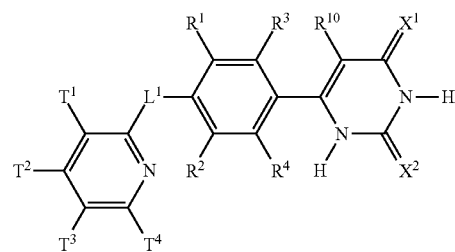

IB-5

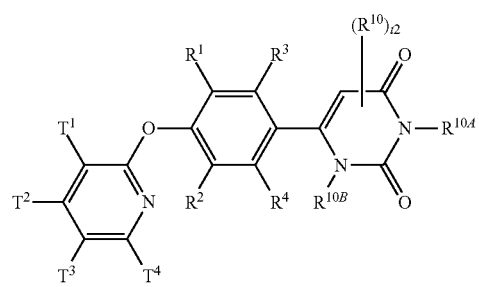

IB-6

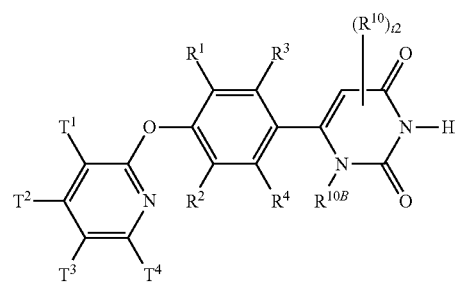

IB-7

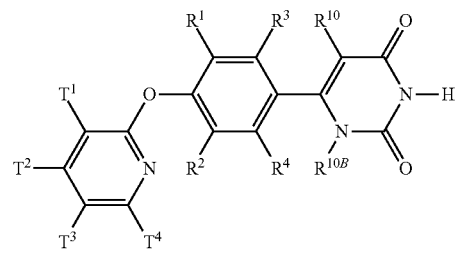

IB-8

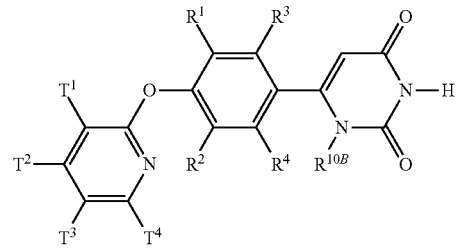

IB-9

-continued

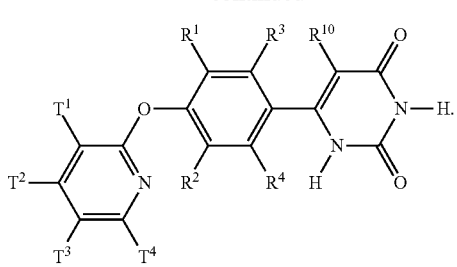

IB-10

In one embodiment of a compound of Formula I or a pharmaceutically acceptable salt thereof of the present invention wherein $Q^1$ is $Q1^b$, or in one embodiment of a compound of Formula IB-1, IB-2, IB-3, IB-4, IB-5, IB-6, IB-7, IB-8, IB-9, or IB-10, or a pharmaceutically acceptable salt thereof, of the present invention:

$R^{10}$ is selected from the group consisting of —CN, $C_{1-4}$ alkyl, $C_{3-4}$ cycloalkyl, cyclopropylmethyl, and cyclobutylmethyl, wherein the $C_{1-4}$ alkyl of $R^{10}$ is optionally substituted with one or more substituents each independently selected from the group consisting of halogen, —OH, —CN, $C_{1-4}$ alkoxy, and $C_{1-4}$ haloalkoxy; and wherein each of the $C_{3-4}$ cycloalkyl, cyclopropylmethyl, and cyclobutylmethyl of $R^{10}$ is optionally substituted with one or more substituents each independently selected from the group consisting of halogen, —OH, —CN, $C_{1-4}$ alkyl, $C_{1-4}$ haloalkyl, $C_{1-4}$ hydroxylalkyl, $C_{1-4}$ cyanoalkyl, $C_{1-4}$ alkoxy, and $C_{1-4}$ haloalkoxy;

$R^{10A}$ is selected from the group consisting of H, $C_{1-3}$ alkyl, $C_{1-3}$ hydroxylalkyl, $C_{2-4}$ alkenyl, —S(=O)$_2$N(R$^5$)(R$^6$), —C(=O)—N(R$^5$)(R$^6$), —C(=O)—R$^8$, —C(=O)—OR$^8$, —C(R$^{14}$)$_2$—OH, —C(R$^{14}$)$_2$—OS(=O)$_2$H, —C(R$^{14}$)$_2$—OP(=O)(OH)$_2$, —C(R$^{14}$)$_2$—OR$^{15}$, and —C(R$^{14}$)$_2$—OC(=O)—R$^{15}$; and $R^{10B}$ is selected from the group consisting of $C_{1-4}$ alkyl, $C_{3-4}$ cycloalkyl, cyclopropylmethyl, and cyclobutylmethyl, wherein the $C_{1-4}$ alkyl of $R^{10B}$ is optionally substituted with one or more substituents each independently selected from the group consisting of halogen, —OH, —CN, $C_{1-4}$ alkoxy, and $C_{1-4}$ haloalkoxy; and wherein each of the $C_{3-4}$ cycloalkyl, cyclopropylmethyl, and cyclobutylmethyl of $R^{10B}$ is optionally substituted with one or more substituents each independently selected from the group consisting of halogen, —OH, —CN, $C_{1-4}$ alkyl, $C_{1-4}$ haloalkyl, $C_{1-4}$ hydroxylalkyl, $C_{1-4}$ cyanoalkyl, $C_{1-4}$ alkoxy, and $C_{1-4}$ haloalkoxy.

In a further embodiment of the above compound of Formula I or a pharmaceutically acceptable salt thereof wherein $Q^1$ is $Q1^b$, or in a further embodiment of the above compound of Formula IB-1, IB-2, IB-3, IB-4, IB-5, IB-6, IB-7, IB-8, IB-9, or IB-10, or a pharmaceutically acceptable salt thereof, each of $R^{10}$ and $R^{10B}$ is independently selected from the group consisting of $C_{1-3}$ alkyl, $C_{1-3}$ haloalkyl, and cyclopropyl. In a yet further embodiment, each of $R^{10}$ and $R^{10B}$ is independently selected from the group consisting of $C_{1-3}$ alkyl and cyclopropyl. In a still further embodiment, each of $R^{10}$ and $R^{10B}$ is independently methyl or ethyl. In a yet still further embodiment, each of $R^{10}$ and $R^{10B}$ is methyl.

In one embodiment of a compound of Formula IB-1 or IB-6, or a pharmaceutically acceptable salt thereof, $R^{10A}$ is selected from the group consisting of H, $C_{1-3}$ alkyl, $C_{1-3}$ hydroxylalkyl, and $C_{2-4}$ alkenyl (e.g., allyl). In a further embodiment, $R^{10A}$ is not H.

In one embodiment of a compound of Formula IB-1 or IB-6, or a pharmaceutically acceptable salt thereof, $R^{10A}$ is selected from the group consisting of H, —S(=O)$_2$N(R$^5$)(R$^6$), —C(=O)—N(R$^5$)(R$^6$), —C(=O)—R$^8$, —C(=O)—OR$^8$, —C(R$^{14}$)$_2$—OH, —C(R$^{14}$)$_2$—OS(=O)$_2$H, —C(R$^{14}$)$_2$—OP(=O)(OH)$_2$, —C(R$^{14}$)$_2$—OR$^{15}$, and —C(R$^{14}$)$_2$—OC(=O)—R$^{15}$. In a further embodiment, $R^{10A}$ is selected from the group consisting of H, —S(=O)$_2$N(R$^5$)(R$^6$), —C(=O)—N(R$^5$)(R$^6$), —C(=O)—R$^8$, —C(=O)—OR$^8$, —CH$_2$—OH, —CH$_2$—OS(=O)$_2$H, —CH$_2$—OP(=O)(OH)$_2$, —CH$_2$—OR$^{15}$, and —CH$_2$—OC(=O)—R$^{15}$. In a yet further embodiment, $R^{10A}$ is not H.

An embodiment of the present invention is a compound of Formula I or a pharmaceutically acceptable salt thereof, wherein $Q^1$ is $Q1^c$. In a further embodiment, $X^1$ is O.

An embodiment of the present invention is a compound of Formula I or a pharmaceutically acceptable salt thereof, wherein the compound of Formula I is a compound of Formula IC-1, IC-2, IC-3, IC-4, IC-5, or IC-6:

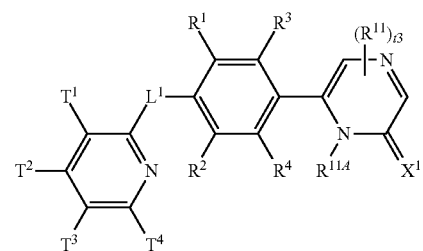

IC-1

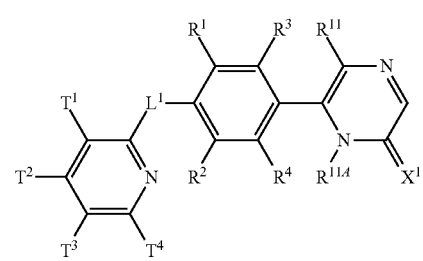

IC-2

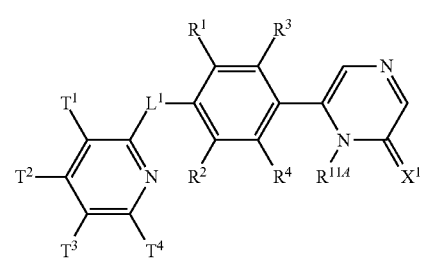

IC-3

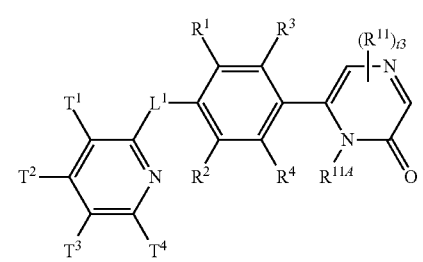

IC-4

-continued

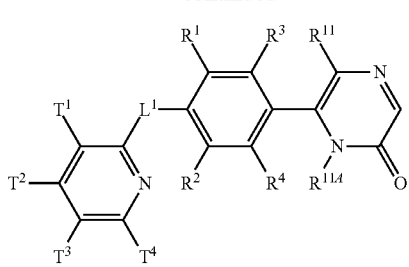

IC-5

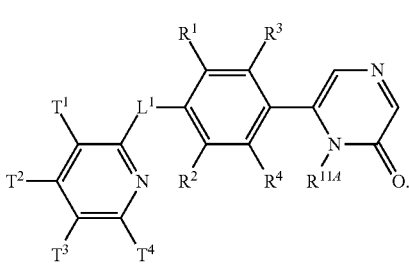

IC-6

In one embodiment of a compound of Formula I or a pharmaceutically acceptable salt thereof of the present invention wherein $Q^1$ is $Q1^c$, or in one embodiment of a compound of Formula IC-1, IC-2, IC-3, IC-4, IC-5, or IC-6, or a pharmaceutically acceptable salt thereof, of the present invention:

each $R^{11}$ is independently selected from the group consisting of —CN, $C_{1-4}$ alkyl, $C_{3-4}$ cycloalkyl, cyclopropylmethyl, and cyclobutylmethyl, wherein the $C_{1-4}$ alkyl of $R^{11}$ is optionally substituted with one or more substituents each independently selected from the group consisting of halogen, —OH, —CN, $C_{1-4}$ alkoxy, and $C_{1-4}$ haloalkoxy; and wherein each of the $C_{3-4}$ cycloalkyl, cyclopropylmethyl, and cyclobutylmethyl of $R^{11}$ is optionally substituted with one or more substituents each independently selected from the group consisting of halogen, —OH, —CN, $C_{1-4}$ alkyl, $C_{1-4}$ haloalkyl, $C_{1-4}$ hydroxylalkyl, $C_{1-4}$ cyanoalkyl, $C_{1-4}$ alkoxy, and $C_{1-4}$ haloalkoxy; and $R^{11A}$ is selected from the group consisting of $C_{1-4}$ alkyl, $C_{3-4}$ cycloalkyl, cyclopropylmethyl, and cyclobutylmethyl, wherein the $C_{1-4}$ alkyl of $R^{11A}$ is optionally substituted with one or more substituents each independently selected from the group consisting of halogen, —OH, —CN, $C_{1-4}$ alkoxy, and $C_{1-4}$ haloalkoxy; and wherein each of the $C_{3-4}$ cycloalkyl, cyclopropylmethyl, and cyclobutylmethyl of $R^{11A}$ is optionally substituted with one or more substituents each independently selected from the group consisting of halogen, —OH, —CN, $C_{1-4}$ alkyl, $C_{1-4}$ haloalkyl, $C_{1-4}$ hydroxylalkyl, $C_{1-4}$ cyanoalkyl, $C_{1-4}$ alkoxy, and $C_{1-4}$ haloalkoxy.

In a further embodiment of the above compound of Formula I or a pharmaceutically acceptable salt thereof wherein $Q^1$ is $Q1^c$, or in a further embodiment of the above compound of Formula IC-1, IC-2, IC-3, IC-4, IC-5, or IC-6, or a pharmaceutically acceptable salt thereof, each of $R^{11}$ and $R^{11A}$ is independently selected from the group consisting of $C_{1-3}$ alkyl, $C_{1-3}$ haloalkyl, and cyclopropyl. In a yet further embodiment, each of $R^{11}$ and $R^{11A}$ is independently selected from the group consisting of $C_{1-3}$ alkyl and cyclopropyl. In a still further embodiment, each of $R^{11}$ and $R^{11A}$ is independently methyl or ethyl. In a yet still further embodiment, each of $R^{11}$ and $R^{11A}$ is methyl.

An embodiment of the present invention is a compound of Formula I or a pharmaceutically acceptable salt thereof, wherein $Q^1$ is $Q1^d$. In a further embodiment, $X^1$ is O.

An embodiment of the present invention is a compound of Formula I or a pharmaceutically acceptable salt thereof, wherein the compound of Formula I is a compound of Formula ID-1, ID-2, ID-3, ID-4, ID-5, ID-6, ID-7, ID-8, ID-9, or ID-10:

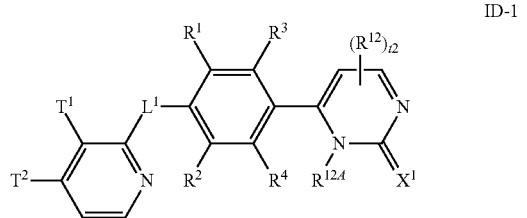

ID-1

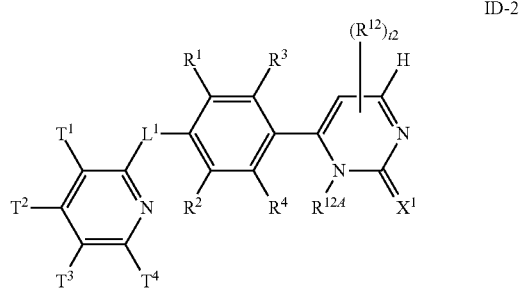

ID-2

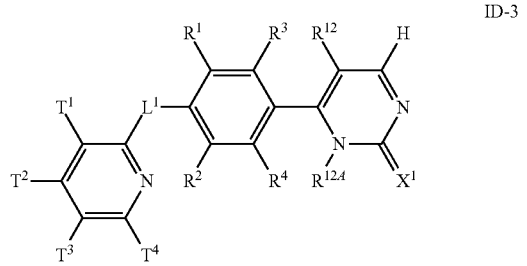

ID-3

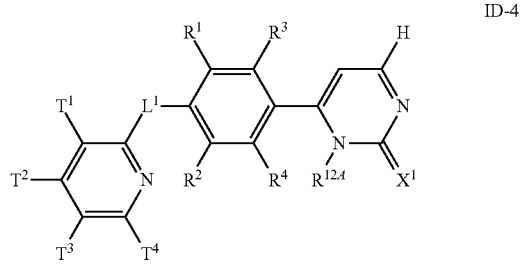

ID-4

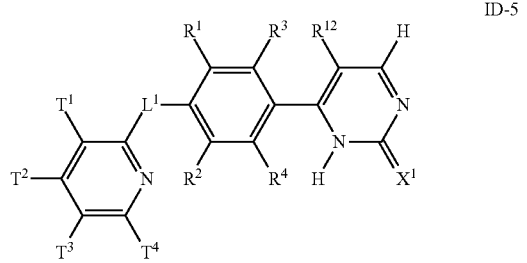

ID-5

-continued

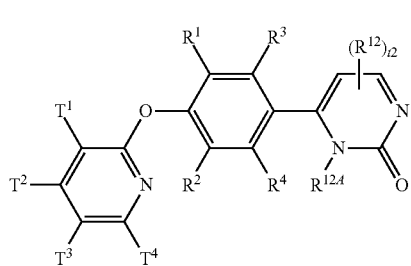

ID-6

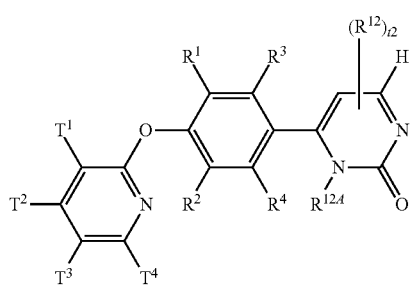

ID-7

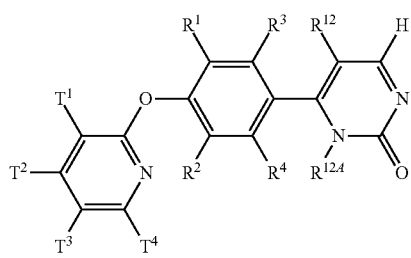

ID-8

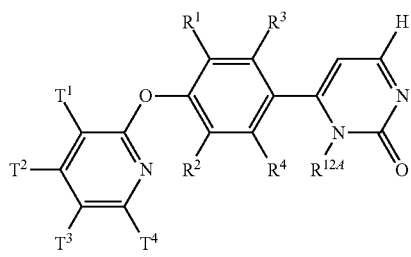

ID-9

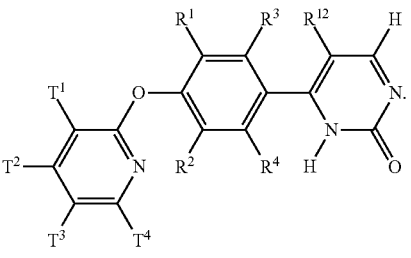

ID-10

In one embodiment of a compound of Formula I or a pharmaceutically acceptable salt thereof wherein $Q^1$ is $Q1^d$, or in one embodiment of a compound of Formula ID-1, ID-2, ID-3, ID-4, ID-5, ID-6, ID-7, ID-8, ID-9, or ID-10, or a pharmaceutically acceptable salt thereof, each $R^{12}$ is independently selected from the group consisting of —CN, $C_{1-4}$ alkyl, $C_{3-4}$ cycloalkyl, cyclopropylmethyl, and cyclobutylmethyl, wherein the $C_{1-4}$ alkyl of $R^{12}$ is optionally substituted with one or more substituents each independently selected from the group consisting of halogen, —OH, —CN, $C_{1-4}$ alkoxy, and $C_{1-4}$ haloalkoxy; and wherein each of the $C_{3-4}$ cycloalkyl, cyclopropylmethyl, and cyclobutylmethyl of $R^{12}$ is optionally substituted with one or more substituents each independently selected from the group consisting of halogen, —OH, —CN, $C_{1-4}$ alkyl, $C_{1-4}$ haloalkyl, $C_{1-4}$ hydroxylalkyl, $C_{1-4}$ cyanoalkyl, $C_{1-4}$ alkoxy, and $C_{1-4}$ haloalkoxy; and $R^{12A}$ is selected from the group consisting of $C_{1-4}$ alkyl, $C_{3-4}$ cycloalkyl, cyclopropylmethyl, and cyclobutylmethyl, wherein the $C_{1-4}$ alkyl of $R^{12A}$ is optionally substituted with one or more substituents each independently selected from the group consisting of halogen, —OH, —CN, $C_{1-4}$ alkoxy, and $C_{1-4}$ haloalkoxy; and wherein each of the $C_{3-4}$ cycloalkyl, cyclopropylmethyl, and cyclobutylmethyl of $R^{12A}$ is optionally substituted with one or more substituents each independently selected from the group consisting of halogen, —OH, —CN, $C_{1-4}$ alkyl, $C_{1-4}$ haloalkyl, $C_{1-4}$ hydroxylalkyl, $C_{1-4}$ cyanoalkyl, $C_{1-4}$ alkoxy, and $C_{1-4}$ haloalkoxy. In a further embodiment, each of $R^{12}$ and $R^{12A}$ is independently selected from the group consisting of $C_{1-3}$ alkyl, $C_{1-3}$ haloalkyl, and cyclopropyl. In a yet further embodiment, each of $R^{12}$ and $R^{12A}$ is independently selected from the group consisting of $C_{1-3}$ alkyl and cyclopropyl. In a sill further embodiment, each of $R^{12}$ and $R^{12A}$ is independently methyl or ethyl. In a yet still further embodiment, each of $R^{12}$ and $R^{12A}$ is methyl.

An embodiment of the present invention is a compound of Formula I or a pharmaceutically acceptable salt thereof, wherein $Q^1$ is $Q^{1e}$. In a further embodiment, $X^1$ is O.

An embodiment of the present invention is a compound of Formula I or a pharmaceutically acceptable salt thereof, wherein the compound of Formula I is a compound of Formula IE-1, IE-2, IE-3, IE-4, or IE-5, IE-6, IE-7, IE-8, IE-9, or IE-10:

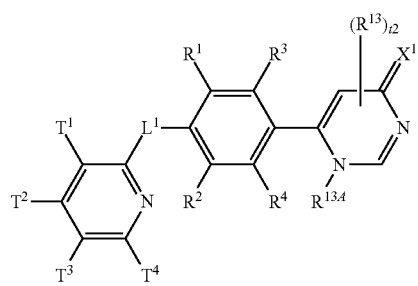

IE-1

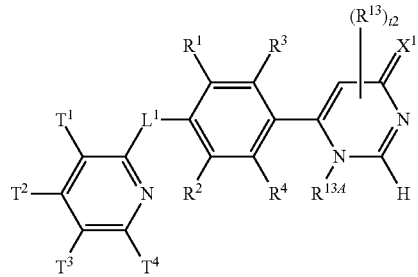

IE-2

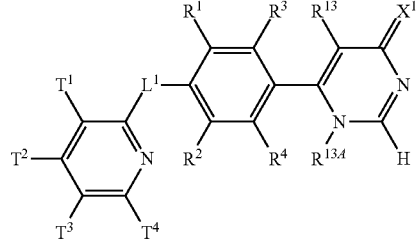

IE-3

IE-4
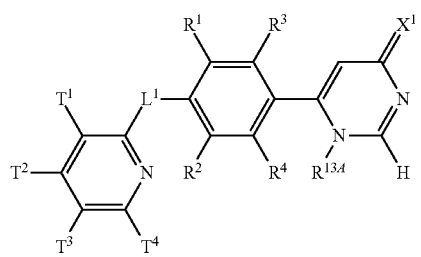

IE-5
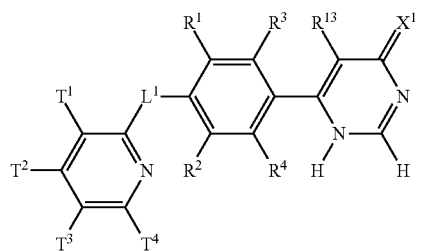

IE-6
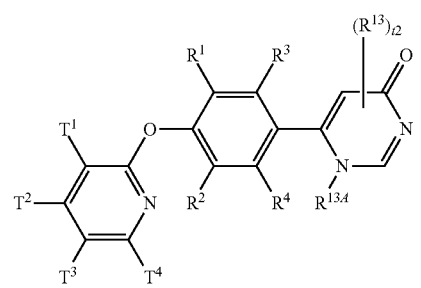

IE-7
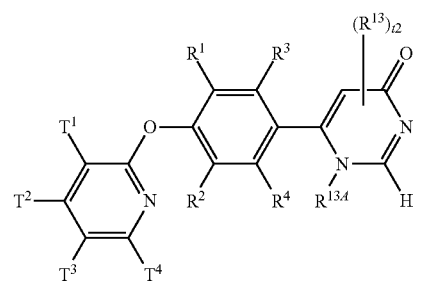

IE-8
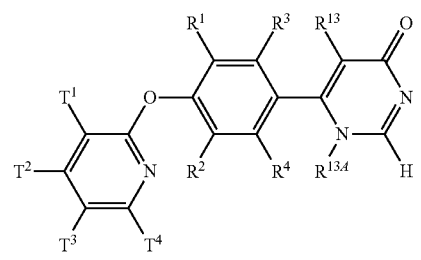

IE-9
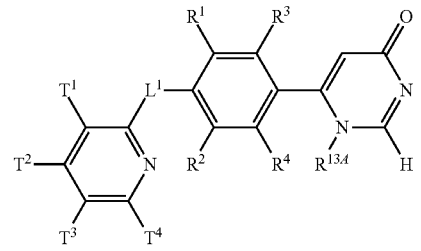

IE-10
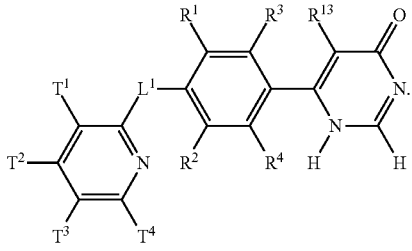

In one embodiment of a compound of Formula I or a pharmaceutically acceptable salt thereof wherein $Q^1$ is $Q1^e$, or in one embodiment of a compound of Formula IE-1, IE-2, IE-3, IE-4, IE-5, IE-6, IE-7, IE-8, IE-9, or IE-10, or a pharmaceutically acceptable salt thereof, each $R^{13}$ is independently selected from the group consisting of —CN, $C_{1-4}$ alkyl, $C_{3-4}$ cycloalkyl, cyclopropylmethyl, and cyclobutylmethyl, wherein the $C_{1-4}$ alkyl of $R^{13}$ is optionally substituted with one or more substituents each independently selected from the group consisting of halogen, —OH, —CN, $C_{1-4}$ alkoxy, and $C_{1-4}$ haloalkoxy; and wherein each of the $C_{3-4}$ cycloalkyl, cyclopropylmethyl, and cyclobutylmethyl of $R^{13}$ is optionally substituted with one or more substituents each independently selected from the group consisting of halogen, —OH, —CN, $C_{1-4}$ alkyl, $C_{1-4}$ haloalkyl, $C_{1-4}$ hydroxylalkyl, $C_{1-4}$ cyanoalkyl, $C_{1-4}$ alkoxy, and $C_{1-4}$ haloalkoxy; and $R^{13A}$ is selected from the group consisting of $C_{1-4}$ alkyl, $C_{3-4}$ cycloalkyl, cyclopropylmethyl, and cyclobutylmethyl, wherein the $C_{1-4}$ alkyl of $R^{13A}$ is optionally substituted with one or more substituents each independently selected from the group consisting of halogen, —OH, —CN, $C_{1-4}$ alkoxy, and $C_{1-4}$ haloalkoxy; and wherein each of the $C_{3-4}$ cycloalkyl, cyclopropylmethyl, and cyclobutylmethyl of $R^{13A}$ is optionally substituted with one or more substituents each independently selected from the group consisting of halogen, —OH, —CN, $C_{1-4}$ alkyl, $C_{1-4}$ haloalkyl, $C_{1-4}$ hydroxylalkyl, $C_{1-4}$ cyanoalkyl, $C_{1-4}$ alkoxy, and $C_{1-4}$ haloalkoxy. In a further embodiment, each of $R^{13}$ and $R^{13A}$ is independently selected from the group consisting of $C_{1-3}$ alkyl, $C_{1-3}$ haloalkyl, and cyclopropyl. In a yet further embodiment, each of $R^{13}$ and $R^{13A}$ is independently selected from the group consisting of $C_{1-3}$ alkyl and cyclopropyl. In a still further embodiment, each of $R^{13}$ and $R^{13A}$ is independently methyl or ethyl. In a yet still further embodiment, each of $R^{13}$ and $R^{13A}$ is methyl.

In one embodiment of a compound of Formula I (e.g., a compound of one of Formulas IA-1 to IA-10, IB-1 to IB-10, IC-1 to IC-6, ID-1 to ID-10, and IE-1 to IE-10, i.e., a compound of Formula IA-1, IA-2, IA-3, IA-4, IA-5, IA-6, IA-7, IA-8, IA-9, IA-10, IB-1, IB-2, IB-3, IB-4, IB-5, IB-6, IB-7, IB-8, IB-9, IB-10, IC-1, IC-2, IC-3, IC-4, IC-5, IC-6, ID-1, ID-2, ID-3, ID-4, ID-5, ID-6, ID-7, ID-8, ID-9, ID-10, IE-1, IE-2, IE-3, IE-4, IE-5, IE-6, IE-7, IE-8, IE-9, or IE-10), or a pharmaceutically acceptable salt thereof, each of $R^1$ and $R^2$ is independently selected from the group consisting of H, halogen, —CN, $C_{1-6}$ alkyl, $C_{1-6}$ haloalkyl, $C_{1-6}$ alkoxy, $C_{1-6}$ haloalkoxy, $C_{3-6}$ cycloalkyl, —C(=O)—($C_{1-4}$ alkyl), —C(=O)OH, and C(=O)—O—($C_{1-4}$ alkyl), wherein each of the $C_{1-6}$ alkyl and $C_{3-6}$ cycloalkyl is optionally substituted with 1, 2, 3, 4, or 5 substituents each independently selected from halogen, —OH, —CN, $C_{1-4}$ alkyl, $C_{1-4}$ haloalkyl, $C_{1-4}$ alkoxy, and $C_{1-4}$ haloalkoxy. In a further embodiment, each of $R^1$ and $R^2$ is independently selected from the group consisting of H, halogen, —$C_{1-4}$ alkyl, $C_{1-4}$ alkoxy, and $C_{3-4}$ cycloalkyl, wherein each of the $C_{1-4}$ alkyl and $C_{1-4}$ alkoxy of $R^1$ and $R^2$ is optionally substituted with 1, 2, 3, 4, or 5 substituents each independently selected from halogen, —OH, $C_{1-4}$ alkoxy, and $C_{1-4}$ haloalkoxy; and wherein the $C_{3-4}$ cycloalkyl of $R^1$ and $R^2$ is optionally substituted with 1, 2, 3, 4, or 5 substituents each independently selected from halogen, —OH, $C_{1-4}$ alkyl, $C_{1-4}$ haloalkyl, $C_{1-4}$ alkoxy, and $C_{1-4}$ haloalkoxy. In a yet further embodiment, each of $R^1$ and $R^2$ is independently H, methyl, or halogen (e.g., F). In a still further embodiment, each of $R^1$ and $R^2$ is independently H or halogen (e.g., F). In a yet further embodiment, each of $R^1$ and $R^2$ is H.

In one embodiment of a compound of Formula I (e.g., a compound of one of Formulas IA-1 to IA-10, IB-1 to IB-10, IC-1 to IC-6, ID-1 to ID-10, and IE-1 to IE-10), or a pharmaceutically acceptable salt thereof, each of $R^3$ and $R^4$ is independently selected from the group consisting of H, halogen, —CN, —$C_{1-4}$ alkyl, $C_{1-4}$ alkoxy, and $C_{3-4}$ cycloalkyl, wherein each of the $C_{1-4}$ alkyl and $C_{1-4}$ alkoxy of $R^3$ and $R^4$ is optionally substituted with 1, 2, 3, 4, or 5 substituents each independently selected from halogen, —OH, $C_{1-4}$ alkoxy, and $C_{1-4}$ haloalkoxy; and wherein the $C_{3-4}$ cycloalkyl of $R^3$ and $R^4$ is optionally substituted with 1, 2, 3, 4, or 5 substituents each independently selected from halogen, —OH, $C_{1-4}$ alkyl, $C_{1-4}$ haloalkyl, $C_{1-4}$ alkoxy, and $C_{1-4}$ haloalkoxy. In a further embodiment, each of $R^3$ and $R^4$ is independently H, F, Cl, CN, or methyl wherein the methyl is optionally substituted with 1, 2, or 3 substituents each independently selected from the group consisting of halogen, —OH, and $C_{1-4}$ alkoxy. In a yet further embodiment, $R^3$ is H; and $R^4$ is H, halogen, or methyl, wherein the methyl is optionally substituted with 1, 2, or 3 substituents each independently selected from the group consisting of halogen, —OH, and $C_{1-4}$ alkoxy. In a still further embodiment, $R^3$ is H and $R^4$ is methyl.

In one embodiment of a compound of Formula I (e.g., a compound of one of Formulas IA-1 to IA-10, IB-1 to IB-10, IC-1 to IC-6, ID-1 to ID-10, and IE-1 to IE-10), or a pharmaceutically acceptable salt thereof, each of $R^1$ and $R^2$ is independently H, methyl, or halogen (e.g., F or Cl); and each of $R^3$ and $R^4$ is independently H, halogen (e.g., F or Cl), CN, or methyl wherein the methyl is optionally substituted with 1, 2, or 3 substituents each independently selected from the group consisting of halogen, —OH, and $C_{1-4}$ alkoxy. In a further embodiment, each of $R^1$, $R^2$, and $R^3$ is H, and $R^4$ is H, halogen, or methyl. In a yet further embodiment, $R^4$ is H or methyl. In a still further embodiment, $R^4$ is methyl.

In one embodiment of a compound of Formula I (e.g., a compound of one of Formulas IA-1 to IA-10, IB-1 to IB-10, IC-1 to IC-6, ID-1 to ID-10, and IE-1 to IE-10), or a pharmaceutically acceptable salt thereof, each of $R^1$ and $R^3$ is independently H, halogen, —CN, methyl, or methoxy, wherein each of the methyl and methoxy is optionally substituted with 1, 2, or 3 substituents each independently selected from the group consisting of halogen, —OH, and $C_{1-4}$ alkoxy; and $R^2$ and $R^4$ together with the two carbon atoms to which they are attached form a fused 5- or 6-membered heteroaryl, a fused 5- or 6-membered heterocycloalkyl ring, a fused 5- or 6-membered cycloalkyl ring, or a fused benzene ring, wherein each of the fused rings is optionally substituted with 1, 2, or 3 substituents each independently selected from the group consisting of halo, —CN, —OH, $C_{1-4}$ alkyl, $C_{1-4}$ alkoxy, $C_{1-4}$ haloalkyl, and $C_{1-4}$ haloalkoxy, and wherein the fused heterocycloalkyl ring or fused cycloalkyl ring is further optionally substituted with 1, 2, or 2 oxo. In a further embodiment, each of $R^1$ and $R^3$ is independently H, halogen, —CN, methyl, $C_{1-4}$ fluoroalkyl, methoxy, or $C_1$ fluoroalkoxy. In a yet further embodiment, $R^2$ and $R^4$ together with the two carbon atoms to which they are attached form an optionally substituted fused 5- or 6-membered heteroaryl. In a still further embodiment, each of $R^1$ and $R^3$ is H.

In one embodiment of a compound of Formula I (e.g., a compound of one of Formulas IA-1 to IA-10, IB-1 to IB-10, IC-1 to IC-6, ID-1 to ID-10, and IE-1 to IE-10), or a pharmaceutically acceptable salt thereof, each of $T^1$, $T^2$, $T^3$, and $T^4$ is independently selected from the group consisting of H, halogen, —CN, $C_{1-4}$ alkyl, $C_{1-4}$ haloalkyl, $C_{2-4}$ alkenyl, $C_{1-4}$ alkoxy, $C_{1-4}$ haloalkoxy, and $C_{3-4}$ cycloalkyl, wherein each of the $C_{1-4}$ alkyl, $C_{2-4}$ alkenyl, and $C_{1-4}$ alkoxy of $T^1$, $T^2$, $T^3$, and $T^4$ is optionally substituted with one or more substituents each independently selected from the group consisting of halogen, —OH, —CN, $C_{1-4}$ alkoxy, and $C_{1-4}$ haloalkoxy; and wherein the $C_{3-4}$ cycloalkyl of $T^1$, $T^2$, $T^3$, and $T^4$ is optionally substituted with one or more substituents each independently selected from the group consisting of halogen, —OH, —CN, $C_{1-4}$ alkyl, $C_{1-4}$ haloalkyl, $C_{1-4}$ hydroxylalkyl, $C_{1-4}$ cyanoalkyl, $C_{1-4}$ alkoxy, and $C_{1-4}$ haloalkoxy. In a further embodiment, each of $T^1$, $T^2$, $T^3$, and $T^4$ is independently selected from the group consisting of H, halogen, $C_{1-4}$ alkyl, $C_{1-4}$ hydroxylalkyl, $C_{1-4}$ haloalkyl, $C_{1-4}$ alkoxy, $C_{1-4}$ haloalkoxy, $C_{3-4}$ cycloalkyl, and $C_{3-4}$ halocycloalkyl. In a further embodiment, at least one of $T^1$, $T^2$, $T^3$, and $T^4$ is other than H.

In one embodiment of a compound of Formula I (e.g., a compound of one of Formulas IA-1 to IA-10, IB-1 to IB-10, IC-1 to IC-6, ID-1 to ID-10, and IE-1 to IE-10), or a pharmaceutically acceptable salt thereof, $T^1$ is other than H. In a further embodiment, $T^1$ is selected from the group consisting of halogen, $C_{3-4}$ cycloalkyl, $C_{1-4}$ alkyl, $C_{1-4}$ haloalkyl, $C_{1-4}$ alkoxy, and $C_{1-4}$ haloalkoxy, wherein each of the $C_{3-4}$ cycloalkyl and $C_{1-4}$ alkyl is optionally substituted with one or more substituents each independently selected from the group consisting of halogen and —OH. In a yet further embodiment, $T^1$ is selected from the group consisting of halogen, $C_{3-4}$ cycloalkyl, $C_{3-4}$ halocycloalkyl, $C_{1-4}$ alkyl, $C_{1-4}$ haloalkyl, $C_{1-4}$ hydroxylalkyl, $C_{1-4}$ alkoxy, and $C_{1-4}$ haloalkoxy. In a still further embodiment, $T^1$ is selected from the group consisting of halogen, cyclopropyl, halocyclopropyl, methyl, ethyl, $C_{1-2}$ haloalkyl, $C_{1-2}$ hydroxylalkyl, methoxy, ethoxy, and $C_{1-2}$ haloalkoxy. In a further embodiment, $T^1$ is selected from the group consisting of halogen, cyclopropyl, halocyclopropyl, methyl, $C_1$ haloalkyl, methoxy, and $C_1$ haloalkoxy. In a further embodiment, $T^1$ is selected from the group consisting of $C_{3-4}$ cycloalkyl, $C_{3-4}$ halocycloalkyl, $C_{1-4}$ alkyl, and $C_{1-4}$ haloalkyl.

In one embodiment of a compound of Formula I (e.g., a compound of one of Formulas IA-1 to IA-10, IB-1 to IB-10, IC-1 to IC-6, ID-1 to ID-10, and IE-1 to IE-10), or a pharmaceutically acceptable salt thereof, $T^1$ is selected from the group consisting of $C_{1-4}$ alkyl and $C_{1-4}$ haloalkyl. In a further embodiment, $T^1$ is selected from the group consisting of methyl, ethyl, and $C_{1-2}$ haloalkyl. In a further embodiment, $T^1$ is $C_{1-2}$ haloalkyl (e.g., $C_{1-2}$ fluoroalkyl).

In one embodiment of a compound of Formula I (e.g., a compound of one of Formulas IA-1 to IA-10, IB-1 to IB-10, IC-1 to IC-6, ID-1 to ID-10, and IE-1 to IE-10), or a pharmaceutically acceptable salt thereof, $T^1$ is selected from the group consisting of $C_{1-4}$ alkoxy, and $C_{1-4}$ haloalkoxy. In a further embodiment, $T^1$ is selected from the group consisting of methoxy, ethoxy, and $C_{1-2}$ haloalkoxy. In a further embodiment, $T^1$ is $C_{1-2}$ haloalkoxy (e.g., $C_{1-2}$ fluoroalkoxy).

In one embodiment of a compound of Formula I (e.g., a compound of one of Formulas IA-1 to IA-10, IB-1 to IB-10, IC-1 to IC-6, ID-1 to ID-10, and IE-1 to IE-10), or a pharmaceutically acceptable salt thereof, $T^1$ is halogen.

In one embodiment of a compound of Formula I (e.g., a compound of one of Formulas IA-1 to IA-10, IB-1 to IB-10, IC-1 to IC-6, ID-1 to ID-10, and IE-1 to IE-10), or a pharmaceutically acceptable salt thereof, $T^1$ is selected from the group consisting of $C_{3-4}$ cycloalkyl and $C_{3-4}$ halocycloalkyl. In a further embodiment, $T^1$ is $C_{3-4}$ cycloalkyl.

In one embodiment of a compound of Formula I (e.g., a compound of one of Formulas IA-1 to IA-10, IB-1 to IB-10, IC-1 to IC-6, ID-1 to ID-10, and IE-1 to IE-10), or a pharmaceutically acceptable salt thereof, $T^2$ is selected from the group consisting of H, halogen, —CN, $C_{3-4}$ cycloalkyl, $C_{3-4}$ halocycloalkyl, $C_{1-4}$ alkyl, $C_{1-4}$ haloalkyl, $C_{1-4}$ alkoxy, and $C_{1-4}$ haloalkoxy, wherein each of the $C_{3-4}$ cycloalkyl and $C_{1-4}$ alkyl is optionally substituted with one or more substituents each independently selected from the group consisting of halogen and —OH. In a further embodiment, $T^2$ is selected from the group consisting of H, halogen, —CN, $C_{3-4}$ cycloalkyl, $C_{3-4}$ halocycloalkyl, $C_{1-4}$ alkyl, $C_{1-4}$ haloalkyl, $C_{1-4}$ hydroxylalkyl, $C_{1-4}$ alkoxy, and $C_{1-4}$ haloalkoxy. In a yet further embodiment, $T^2$ is selected from the group consisting of H, halogen, methyl, ethyl, $C_{1-2}$ haloalkyl, $C_{1-2}$ hydroxylalkyl, $C_{1-2}$ alkoxy, and $C_{1-2}$ haloalkoxy. In a still further embodiment, $T^2$ is selected from the group consisting of H, halogen, methyl, —CH$_2$OH, and $C_1$ haloalkyl. In a yet still further embodiment, $T^2$ is H.

In one embodiment of a compound of Formula I (e.g., a compound of one of Formulas IA-1 to IA-10, IB-1 to IB-10, IC-1 to IC-6, ID-1 to ID-10, and IE-1 to IE-10), or a pharmaceutically acceptable salt thereof, $T^3$ is selected from the group consisting of H, halogen, —CN, $C_{3-4}$ cycloalkyl, $C_{3-4}$ halocycloalkyl, $C_{1-4}$ alkyl, $C_{1-4}$ haloalkyl, $C_{1-4}$ hydroxylalkyl, $C_{1-4}$ alkoxy, and $C_{1-4}$ haloalkoxy. In a further embodiment, $T^3$ is selected from the group consisting of H, halogen, methyl, —CH$_2$OH, and $C_1$ haloalkyl (e.g., $C_1$ fluoroalkyl). In a yet further embodiment, $T^3$ is H.

In one embodiment of a compound of Formula I (e.g., a compound of one of Formulas IA-1 to IA-10, IB-1 to IB-10, IC-1 to IC-6, ID-1 to ID-10, and IE-1 to IE-10), or a pharmaceutically acceptable salt thereof, $T^4$ is H, halogen, methyl, —CH$_2$OH, or $C_1$ haloalkyl. In a further embodiment, $T^4$ is H or F. In a yet further embodiment, $T^4$ is H.

In one embodiment of a compound of Formula I (e.g., a compound of one of Formulas IA-1 to IA-10, IB-1 to IB-10, IC-1 to IC-6, ID-1 to ID-10, and IE-1 to IE-10), or a pharmaceutically acceptable salt thereof, each of $T^1$, $T^2$, and $T^3$ is independently selected from the group consisting of H, halogen, $C_{1-2}$ alkyl, $C_{1-2}$ haloalkyl, $C_{1-2}$ hydroxylalkyl, $C_{1-2}$ alkoxy, $C_{1-2}$ haloalkoxy, cyclopropyl, and halocyclopropyl; and $T^4$ is H. In a further embodiment, each of $T^1$, $T^2$, and $T^3$ is independently selected from the group consisting of H, halogen, methyl, $C_1$ haloalkyl, —CH$_2$OH, cyclopropyl, methoxy, and $C_1$ haloalkoxy; and $T^4$ is H. In a yet further embodiment, each of $T^1$, $T^2$, and $T^3$ is independently selected from the group consisting of H, halogen (F, Cl, Br, or I), methyl, $C_1$ fluoroalkyl (e.g., CF$_3$ or CHF$_2$), —CH$_2$OH, cyclopropyl, methoxy, and $C_1$ fluoroalkoxy (e.g., —OCF$_3$ or —OCHF$_2$); and $T^4$ is H. In a still further embodiment, $T^1$ is other than H and at least one of $T^2$ and $T^3$ is H. In a further embodiment, each of $T^2$ and $T^3$ is H.

In one embodiment of a compound of Formula I (e.g., a compound of one of Formulas IA-1 to IA-10, IB-1 to IB-10, IC-1 to IC-6, ID-1 to ID-10, and IE-1 to IE-10), or a pharmaceutically acceptable salt thereof, $T^1$ is selected from the group consisting of halogen (F, Cl, Br, or I), methyl, —CH$_2$OH, $C_1$ fluoroalkyl (e.g., CF$_3$ or CHF$_2$), methoxy, $C_1$ fluoroalkoxy (e.g., —OCF$_3$ or —OCHF$_2$), cyclopropyl, and fluorocyclopropyl; and each of $T^2$, $T^3$, and $T^4$ is H.

In one embodiment of a compound of Formula I (e.g., a compound of one of Formulas IA-1 to IA-10, IB-1 to IB-10, IC-1 to IC-6, ID-1 to ID-10, and IE-1 to IE-10), or a pharmaceutically acceptable salt thereof, $T^1$ is selected from the group consisting of halogen, $C_{1-2}$ alkyl, $C_{1-2}$ haloalkyl, $C_{1-2}$ hydroxylalkyl, $C_{1-2}$ alkoxy, $C_{1-2}$ haloalkoxy, cyclopropyl, and halocyclopropyl; each of $T^2$ and $T^3$ is independently selected from the group consisting of H, halogen, $C_{1-2}$ alkyl, $C_{1-2}$ haloalkyl, $C_{1-2}$ hydroxylalkyl, $C_{1-2}$ alkoxy, $C_{1-2}$ haloalkoxy, cyclopropyl, and halocyclopropyl; and $T^4$ is H. In one further embodiment, one of $T^2$ and $T^3$ is H and the other is not H. In another further embodiment, $T^2$ is H and $T^3$ is not H. In yet another further embodiment, $T^2$ is not H and $T^3$ is H.

In one embodiment, the compound of Formula I or a salt thereof is a compound of Formula IA-1 or a salt thereof. In one embodiment, the compound of Formula I or a salt thereof is a compound of Formula IA-2 or a salt thereof. In one embodiment, the compound of Formula I or a salt thereof is a compound of Formula IA-3 or a salt thereof. In one embodiment, the compound of Formula I or a salt thereof is a compound of Formula IA-4 or a salt thereof. In one embodiment, the compound of Formula I or a salt thereof is a compound of Formula IA-5 or a salt thereof. In one embodiment, the compound of Formula I or a salt thereof is a compound of Formula IA-6 or a salt thereof. In one embodiment, the compound of Formula I or a salt thereof is a compound of Formula IA-7 or a salt thereof. In one embodiment, the compound of Formula I or a salt thereof is a compound of Formula IA-8 or a salt thereof. In one embodiment, the compound of Formula I or a salt thereof is a compound of Formula IA-9 or a salt thereof. In one embodiment, the compound of Formula I or a salt thereof is a compound of Formula IA-10 or a salt thereof.

In one embodiment, the compound of Formula I or a salt thereof is a compound of Formula IB-1 or a salt thereof. In one embodiment, the compound of Formula I or a salt thereof is a compound of Formula IB-2 or a salt thereof. In one embodiment, the compound of Formula I or a salt thereof is a compound of Formula IB-3 or a salt thereof. In one embodiment, the compound of Formula I or a salt thereof is a compound of Formula IB-4 or a salt thereof. In one embodiment, the compound of Formula I or a salt thereof is a compound of Formula IB-5 or a salt thereof. In one embodiment, the compound of Formula I or a salt thereof is a compound of Formula IB-6 or a salt thereof. In one embodiment, the compound of Formula I or a salt thereof is a compound of Formula IB-7 or a salt thereof. In one embodiment, the compound of Formula I or a salt thereof is a compound of Formula IB-8 or a salt thereof. In one embodiment, the compound of Formula I or a salt thereof is a compound of Formula IB-9 or a salt thereof. In one embodiment, the compound of Formula I or a salt thereof is a compound of Formula IB-10 or a salt thereof .
. . .

In one embodiment, the compound of Formula I or a salt thereof is a compound of Formula IC-1 or a salt thereof. In one embodiment, the compound of Formula I or a salt thereof is a compound of Formula IC-2 or a salt thereof. In one embodiment, the compound of Formula I or a salt thereof is a compound of Formula IC-3 or a salt thereof. In one embodiment, the compound of Formula I or a salt thereof is a compound of Formula IC-4 or a salt thereof. In one embodiment, the compound of Formula I or a salt thereof is a compound of Formula IC-5 or a salt thereof. In In one embodiment, the compound of Formula I or a salt thereof is a compound of Formula IC-6 or a salt thereof.

In one embodiment, the compound of Formula I or a salt thereof is a compound of Formula ID-1 or a salt thereof. In one embodiment, the compound of Formula I or a salt thereof is a compound of Formula ID-2 or a salt thereof. In one embodiment, the compound of Formula I or a salt thereof is a compound of Formula ID-3 or a salt thereof. In one embodiment, the compound of Formula I or a salt thereof is a compound of Formula ID-4 or a salt thereof. In one embodiment, the compound of Formula I or a salt thereof is a compound of Formula ID-5 or a salt thereof. In one embodiment, the compound of Formula I or a salt thereof is a compound of Formula ID-6 or a salt thereof. In one embodiment, the compound of Formula I or a salt thereof is a compound of Formula ID-7 or a salt thereof. In one embodiment, the compound of Formula I or a salt thereof is a compound of Formula ID-8 or a salt thereof. In one embodiment, the compound of Formula I or a salt thereof is a compound of Formula ID-9 or a salt thereof. In one embodiment, the compound of Formula I or a salt thereof is a compound of Formula ID-10 or a salt thereof.

In one embodiment, the compound of Formula I or a salt thereof is a compound of Formula IE-1 or a salt thereof. In one embodiment, the compound of Formula I or a salt thereof is a compound of Formula IE-2 or a salt thereof. In one embodiment, the compound of Formula I or a salt thereof is a compound of Formula IE-3 or a salt thereof. In one embodiment, the compound of Formula I or a salt thereof is a compound of Formula IE-4 or a salt thereof. In one embodiment, the compound of Formula I or a salt thereof is a compound of Formula IE-5 or a salt thereof. In one embodiment, the compound of Formula I or a salt thereof is a compound of Formula IE-6 or a salt thereof. In one embodiment, the compound of Formula I or a salt thereof is a compound of Formula IE-7 or a salt thereof. In one embodiment, the compound of Formula I or a salt thereof is a compound of Formula IE-8 or a salt thereof. In one embodiment, the compound of Formula I or a salt thereof is a compound of Formula IE-9 or a salt thereof. In one embodiment, the compound of Formula I or a salt thereof is a compound of Formula IE-10 or a salt thereof.

In one embodiment of a compound of Formula IA-1, IA-2, IA-3, IA-4, IA-5, IA-6, IA-7, IA-8, IA-9, or IA-10, or a pharmaceutically acceptable salt thereof, each $R^9$ is independently selected from the group consisting of $C_{1-3}$ alkyl, $C_{1-3}$ haloalkyl, and cyclopropyl; each of $R^1$ and $R^2$ is independently H, methyl, or halogen (e.g., F); each of $R^3$ and $R^4$ is independently H, F, Cl, CN, or methyl wherein the methyl is optionally substituted with 1, 2, or 3 substituents each independently selected from the group consisting of halogen, —OH, and $C_{1-4}$ alkoxy; $T^1$ is selected from the group consisting of halogen, $C_{1-2}$ alkyl, $C_{1-2}$ haloalkyl, $C_{1-2}$ hydroxylalkyl, $C_{1-2}$ alkoxy, $C_{1-2}$ haloalkoxy, cyclopropyl, and halocyclopropyl; each of $T^2$ and $T^3$ is independently selected from the group consisting of H, halogen, $C_{1-2}$ alkyl, $C_{1-2}$ haloalkyl, $C_{1-2}$ hydroxylalkyl, $C_{1-2}$ alkoxy, $C_{1-2}$ haloalkoxy, cyclopropyl, and halocyclopropyl; and $T^4$ is H. In one further embodiment, each $R^9$ is independently selected from the group consisting of $C_{1-3}$ alkyl and cyclopropyl; each of $R^1$ and $R^2$ is H; $R^3$ is H; and $R^4$ is methyl. In one yet further embodiment, the compound or a salt thereof is a compound of Formula IA-1 or a salt thereof. In another yet further embodiment, the compound or a salt thereof is a compound of Formula IA-2 or a salt thereof. In another yet further embodiment, the compound or a salt thereof is a compound of Formula IA-3 or a salt thereof. In another yet further embodiment, the compound or a salt thereof is a compound of Formula IA-4 or a salt thereof. In another yet further embodiment, the compound or a salt thereof is a compound of Formula IA-5 or a salt thereof. In another yet further embodiment, the compound or a salt thereof is a compound of Formula IA-6 or a salt thereof. In another yet further embodiment, the compound or a salt thereof is a compound of Formula IA-7 or a salt thereof. In another yet further embodiment, the compound or a salt thereof is a compound of Formula IA-8 or a salt thereof. In another yet further embodiment, the compound or a salt thereof is a compound of Formula IA-9 or a salt thereof. In another yet further embodiment, the compound or a salt thereof is a compound of Formula IA-10 or a salt thereof.

In one embodiment of a compound of Formula IB-1, IB-2, IB-3, IB-4, IB-5, IB-6, IB-7, IB-8, IB-9, or IB-10, or a pharmaceutically acceptable salt thereof, each of $R^{10}$ and $R^{10B}$ is independently selected from the group consisting of $C_{1-3}$ alkyl, $C_{1-3}$ haloalkyl, and cyclopropyl; each of $R^1$ and $R^2$ is independently H, methyl, or halogen (e.g., F); each of $R^3$ and $R^4$ is independently H, F, Cl, CN, or methyl wherein the methyl is optionally substituted with 1, 2, or 3 substituents each independently selected from the group consisting of halogen, —OH, and $C_{1-4}$ alkoxy; $T^1$ is selected from the group consisting of halogen, $C_{1-2}$ alkyl, $C_{1-2}$ haloalkyl, $C_{1-2}$ hydroxylalkyl, $C_{1-2}$ alkoxy, $C_{1-2}$ haloalkoxy, cyclopropyl, and halocyclopropyl; each of $T^2$ and $T^3$ is independently selected from the group consisting of H, halogen, $C_{1-2}$ alkyl, $C_{1-2}$ haloalkyl, $C_{1-2}$ hydroxylalkyl, $C_{1-2}$ alkoxy, $C_{1-2}$ haloalkoxy, cyclopropyl, and halocyclopropyl; and $T^4$ is H. In one further embodiment, each of $R^{10}$ and $R^{10B}$ is independently selected from the group consisting of $C_{1-3}$ alkyl and cyclopropyl; each of $R^1$ and $R^2$ is H; $R^3$ is H; and $R^4$ is methyl. In one yet further embodiment, the compound or a salt thereof is a compound of Formula IB-1 or a salt thereof. In another yet further embodiment, the compound or a salt thereof is a compound of Formula IB-2 or a salt thereof. In another yet further embodiment, the compound or a salt thereof is a compound of Formula IB-3 or a salt thereof. In another yet further embodiment, the compound or a salt thereof is a compound of Formula IB-4 or a salt thereof. In another yet further embodiment, the compound or a salt thereof is a compound of Formula IB-5 or a salt thereof. In another yet further embodiment, the compound or a salt thereof is a compound of Formula IB-6 or a salt thereof. In another yet further embodiment, the compound or a salt thereof is a compound of Formula IB-7 or a salt thereof. In another yet further embodiment, the compound or a salt thereof is a compound of Formula IB-8 or a salt thereof. In another yet further embodiment, the compound or a salt thereof is a compound of Formula IB-9 or a salt thereof. In another yet further embodiment, the compound or a salt thereof is a compound of Formula IB-10 or a salt thereof.

In one embodiment of a compound of Formula IC-1, IC-2, IC-3, IC-4, IC-5 or IC-6, or a pharmaceutically acceptable salt thereof, each of $R^{11}$ and $R^{11A}$ is independently selected from the group consisting of $C_{1-3}$ alkyl, $C_{1-3}$ haloalkyl, and cyclopropyl; each of $R^1$ and $R^2$ is independently H, methyl, or halogen (e.g., F); each of $R^3$ and $R^4$ is independently H, F, Cl, CN, or methyl wherein the methyl is optionally substituted with 1, 2, or 3 substituents each independently selected from the group consisting of halogen, —OH, and $C_{1-4}$ alkoxy; $T^1$ is selected from the group consisting of halogen, $C_{1-2}$ alkyl, $C_{1-2}$ haloalkyl, $C_{1-2}$ hydroxylalkyl, $C_{1-2}$ alkoxy, $C_{1-2}$ haloalkoxy, cyclopropyl, and halocyclopropyl; each of $T^2$ and $T^3$ is independently selected from the group consisting of H, halogen, $C_{1-2}$ alkyl, $C_{1-2}$ haloalkyl, $C_{1-2}$ hydroxylalkyl, $C_{1-2}$ alkoxy, $C_{1-2}$ haloalkoxy, cyclopropyl, and halocyclopropyl; and $T^4$ is H. In one further embodiment, each of $R^{11}$ and $R^{11A}$ is independently selected from the group consisting of $C_{1-3}$ alkyl and cyclopropyl; each of $R^1$ and $R^2$ is H; $R^3$ is H; and $R^4$ is methyl. In one yet further embodiment, the compound or a salt thereof is a compound of Formula IC-1 or a salt thereof. In another yet further embodiment, the compound or a salt thereof is a compound of Formula IC-2 or a salt thereof. In another yet further embodiment, the compound or a salt thereof is a compound of Formula IC-3 or a salt thereof. In another yet further embodiment, the compound or a salt thereof is a compound of Formula IC-4 or a salt thereof. In another yet further embodiment, the compound or a salt thereof is a compound of Formula IC-5 or a salt thereof.

In one embodiment of a compound of Formula ID-1, ID-2, ID-3, ID-4, ID-5, ID-6, ID-7, ID-8, ID-9, or ID-10, or a pharmaceutically acceptable salt thereof, each of $R^{12}$ and $R^{12A}$ is independently selected from the group consisting of $C_{1-3}$ alkyl, $C_{1-3}$ haloalkyl, and cyclopropyl; each of $R^1$ and $R^2$ is independently H, methyl, or halogen (e.g., F); each of $R^3$ and $R^4$ is independently H, F, Cl, CN, or methyl wherein the methyl is optionally substituted with 1, 2, or 3 substituents each independently selected from the group consisting of halogen, —OH, and $C_{1-4}$ alkoxy; $T^1$ is selected from the group consisting of halogen, $C_{1-2}$ alkyl, $C_{1-2}$ haloalkyl, $C_{1-2}$ hydroxylalkyl, $C_{1-2}$ alkoxy, $C_{1-2}$ haloalkoxy, cyclopropyl, and halocyclopropyl; each of $T^2$ and $T^3$ is independently selected from the group consisting of H, halogen, $C_{1-2}$ alkyl, $C_{1-2}$ haloalkyl, $C_{1-2}$ hydroxylalkyl, $C_{1-2}$ alkoxy, $C_{1-2}$ haloalkoxy, cyclopropyl, and halocyclopropyl; and $T^4$ is H. In one further embodiment, each of $R^{12}$ and $R^{12A}$ is independently selected from the group consisting of $C_{1-3}$ alkyl and cyclopropyl; each of $R^1$ and $R^2$ is H; $R^3$ is H; and $R^4$ is methyl. In one yet further embodiment, the compound or a salt thereof is a compound of Formula ID-1 or a salt thereof. In another yet further embodiment, the compound or a salt thereof is a compound of Formula ID-2 or a salt thereof. In another yet further embodiment, the compound or a salt thereof is a compound of Formula ID-3 or a salt thereof. In another yet further embodiment, the compound or a salt thereof is a compound of Formula ID-4 or a salt thereof. In another yet further embodiment, the compound or a salt thereof is a compound of Formula ID-5 or a salt thereof. In another yet further embodiment, the compound or a salt thereof is a compound of Formula ID-6 or a salt thereof. In another yet further embodiment, the compound or a salt thereof is a compound of Formula ID-7 or a salt thereof. In another yet further embodiment, the compound or a salt thereof is a compound of Formula ID-8 or a salt thereof. In another yet further embodiment, the compound or a salt thereof is a compound of Formula ID-9 or a salt thereof. In another yet further embodiment, the compound or a salt thereof is a compound of Formula ID-10 or a salt thereof.

In one embodiment of a compound of Formula IE-1, IE-2, IE-3, IE-4, IE-5, IE-6, IE-7, IE-8, IE-9, or IE-10, or a pharmaceutically acceptable salt thereof, each of $R^{13}$ and $R^{13A}$ is independently selected from the group consisting of $C_{1-3}$ alkyl, $C_{1-3}$ haloalkyl, and cyclopropyl; each of $R^1$ and $R^2$ is independently H, methyl, or halogen (e.g., F); each of $R^3$ and $R^4$ is independently H, F, Cl, CN, or methyl wherein the methyl is optionally substituted with 1, 2, or 3 substituents each independently selected from the group consisting of halogen, —OH, and $C_{1-4}$ alkoxy; $T^1$ is selected from the group consisting of halogen, $C_{1-2}$ alkyl, $C_{1-2}$ haloalkyl, $C_{1-2}$ hydroxylalkyl, $C_{1-2}$ alkoxy, $C_{1-2}$ haloalkoxy, cyclopropyl, and halocyclopropyl; each of $T^2$ and $T^3$ is independently selected from the group consisting of H, halogen, $C_{1-2}$ alkyl, $C_{1-2}$ haloalkyl, $C_{1-2}$ hydroxylalkyl, $C_{1-2}$ alkoxy, $C_{1-2}$ haloalkoxy, cyclopropyl, and halocyclopropyl; and $T^4$ is H. In one further embodiment, each of $R^{13}$ and $R^{13A}$ is independently selected from the group consisting of $C_{1-3}$ alkyl and cyclopropyl; each of $R^1$ and $R^2$ is H; $R^3$ is H; and $R^4$ is methyl. In one yet further embodiment, the compound or a salt thereof is a compound of Formula IE-1 or a salt thereof. In another yet further embodiment, the compound or a salt thereof is a compound of Formula IE-2 or a salt thereof. In another yet further embodiment, the compound or a salt thereof is a compound of Formula IE-3 or a salt thereof. In another yet further embodiment, the compound or a salt thereof is a compound of Formula IE-4 or a salt thereof. In another yet further embodiment, the compound or a salt thereof is a compound of Formula IE-5 or a salt thereof. In another yet further embodiment, the compound or a salt thereof is a compound of Formula IE-6 or a salt thereof. In another yet further embodiment, the compound or a salt thereof is a compound of Formula IE-7 or a salt thereof. In another yet further embodiment, the compound or a salt thereof is a compound of Formula IE-8 or a salt thereof. In another yet further embodiment, the compound or a salt thereof is a compound of Formula IE-9 or a salt thereof. In another yet further embodiment, the compound or a salt thereof is a compound of Formula IE-10 or a salt thereof.

In one embodiment, the invention also provides one or more of the compounds described in Examples 1-81 in the Examples section of the subject application, and pharmaceutically acceptable salts of the compounds or the N-oxides.

One embodiment of the prevent invention provides a compound selected from:
(−)-6-{4-[(3-cyclopropylpyridin-2-yl)oxy]-2-methylphenyl}-1,5-dimethylpyrimidine-2,4(1H,3H)-dione;
(−)-6-{4-[(3-chloro-5-fluoropyridin-2-yl)oxy]-2-methylphenyl}-1,5-dimethylpyrimidine-2,4(1H,3H)-dione;
6-{4-[(3-chloropyridin-2-yl)oxy]-2-methyl phenyl}-5-ethyl-1-methylpyrimidine-2,4(1H,3H)-dione;
(−)-1,5-dimethyl-6-(2-methyl-4-{[3-(trifluoromethyl)pyridin-2-yl]oxy}phenyl)pyrimidine-2,4(1H,3H)-dione;
(−)-6-{4-[(3-chloro-5-methylpyridin-2-yl)oxy]-2-methylphenyl}-1,5-dimethylpyrimidine-2,4(1H,3H)-dione;
6-{4-[(3-chloro-4-methylpyridin-2-yl)oxy]phenyl}-1,5-dimethylpyrimidine-2,4(1H,3H)-dione;
(−)-6-(4-{[3-(difluoromethoxy)pyridin-2-yl]oxy}-2-methylphenyl)-1,5-dimethylpyrimidine-2,4(1H,3H)-dione;
(+)-5-(4-{[3-(difluoromethyl)pyridin-2-yl]oxy}-2-methylphenyl)-4,6-dimethylpyridazin-3(2H)-one;
6-{4-[(3-chloropyridin-2-yl)sulfanyl]-2-methylphenyl}-1,5-dimethylpyrimidine-2,4(1H,3H)-dione;
5-{4-[(3-chloro-4-methylpyridin-2-yl)oxy]-2-methyl phenyl}-4,6-dimethylpyridazin-3(2H)-one;
5-{4-[(3-cyclopropyl pyridin-2-yl)oxy]-2-methylphenyl}-4,6-dimethyl pyridazin-3(2H)-one;
5-{4-[(3-iodopyridin-2-yl)oxy]-2-methylphenyl}-4,6-dimethyl pyridazin-3(2H)-one;
(−)-6-{4-[(3-chloropyridin-2-yl)oxy]-2-methyl phenyl}-1,5-dimethylpyrimidine-2,4(1H,3H)-dione;
5-{4-[(3-chloropyridin-2-yl)oxy]-2-methylphenyl}-4,6-dimethylpyridazin-3(2H)-one;
5-(4-{[3-(difluoromethoxy)pyridin-2-yl]oxy}-2-methyl phenyl)-4,6-dimethylpyridazin-3(2H)-one;
5-(4-{[4-methoxy-3-(trifluoromethyl)pyridin-2-yl]oxy}-2-methylphenyl)-4,6-dimethylpyridazin-3(2H)-one;
(+)-4,6-dimethyl-5-(2-methyl-4-{[3-(trifluoromethyl)pyridin-2-yl]oxy}phenyl)pyridazin-3(2H)-one;

6-{4-[(3-cyclopropylpyridin-2-yl)oxy]phenyl}-1,5-dimethylpyrimidine-2,4(1H,3H)-dione;

6-{4-[(3-chloro-4-methylpyridin-2-yl)oxy]-2-methyl phenyl}-1,5-dimethylpyrazin-2(1H)-one;

6-{4-[(3-chloro-4-methylpyridin-2-yl)oxy]-2-methyl phenyl}-1,5-dimethylpyrimidin-2(1H)-one; and 1-cyclopropyl-6-(4-((3-(difluoromethyl)pyridin-2-yl)oxy)-2-methylphenyl)-5-methylpyrimidine-2,4(1H,3H)-dione, or a pharmaceutically acceptable salt thereof.

The present invention also provides compositions (e.g., pharmaceutical compositions) comprising a compound of Formula I (including a pharmaceutically acceptable salt thereof).

Accordingly, in one embodiment, the invention provides a pharmaceutical composition comprising (a therapeutically effective amount of) a compound of Formula I (or a pharmaceutically acceptable salt thereof) and optionally comprising a pharmaceutically acceptable carrier. In one further embodiment, the invention provides a pharmaceutical composition comprising (a therapeutically effective amount of) a compound of Formula I (or a pharmaceutically acceptable salt thereof), optionally comprising a pharmaceutically acceptable carrier and, optionally, at least one additional medicinal or pharmaceutical agent (such as an antipsychotic agent or anti-schizophrenia agent described below). In one embodiment, the additional medicinal or pharmaceutical agent is an anti-schizophrenia agent as described below.

The pharmaceutically acceptable carrier may comprise any conventional pharmaceutical carrier or excipient. Suitable pharmaceutical carriers include inert diluents or fillers, water and various organic solvents (such as hydrates and solvates). The pharmaceutical compositions may, if desired, contain additional ingredients such as flavorings, binders, excipients and the like. Thus for oral administration, tablets containing various excipients, such as citric acid, may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Non-limiting examples of materials, therefore, include lactose or milk sugar and high molecular weight polyethylene glycols. When aqueous suspensions or elixirs are desired for oral administration, the active compound therein may be combined with various sweetening or flavoring agents, coloring matters or dyes and, if desired, emulsifying agents or suspending agents, together with diluents such as water, ethanol, propylene glycol, glycerin, or combinations thereof.

The pharmaceutical composition may, for example, be in a form suitable for oral administration as a tablet, capsule, pill, powder, sustained release formulation, solution or suspension, for parenteral injection as a sterile solution, suspension or emulsion, for topical administration as an ointment or cream or for rectal administration as a suppository.

Exemplary parenteral administration forms include solutions or suspensions of active compounds in sterile aqueous solutions, for example, aqueous propylene glycol or dextrose solutions. Such dosage forms may be suitably buffered, if desired.

The pharmaceutical composition may be in unit dosage forms suitable for single administration of precise dosages. One of ordinary skill in the art would appreciate that the composition may be formulated in sub-therapeutic dosage such that multiple doses are envisioned.

In one embodiment the composition comprises a therapeutically effective amount of a compound of Formula I (or a pharmaceutically acceptable salt thereof) and a pharmaceutically acceptable carrier.

Compounds of Formula I (including pharmaceutically acceptable salts thereof) are D1 modulators. In some embodiments, a compound of Formula I is a D1 agonist [i.e., binding (having affinity for) and activating D1 receptors]. In some embodiments, using dopamine as a reference full D1 agonist, a compound of Formula I is a superagonist (i.e., a compound that is capable of producing a greater maximal response than the endogenous D1 agonist, dopamine, for a D1 receptor, and thus exhibiting an efficacy of more than about 100%, for example 120%).

In some embodiments, using dopamine as a reference full agonist, a compound of Formula I is a full D1 agonist (i.e., having an efficacy of about 100%, for example, 90%-100%, compared to that of dopamine). In some embodiments, using dopamine as a reference full D1 agonist, a compound of Formula I is a partial agonist [i.e., a compound having only partial efficacy (i.e., less than 100%, for example 10%-80% or 50%-70%) at a D1 receptor relative to the full agonist, dopamine, although it binds and activates a D1 receptor]. A D1 agonist (including superagonist, full agonist, and partial agonist) can agonize or partially agonize an activity of D1. In some embodiments, the $EC_{50}$ of a compound of Formula I with respect to D1 is less than about 10 µM, 5 µM, 2 µM, 1 µM, 500 nM, 200 nM, 100 nM, 50, 40, 30, 20, 10, 5, 2, or 1 nM.

The present invention further provides a method for modulating (such as agonizing or partially agonizing) an activity of D1 receptor (either in vitro or in vivo), comprising contacting (including incubating) the D1 receptor with a compound of Formula I (such as one selected from Examples 1-81), or a pharmaceutically acceptable salt thereof.

Another embodiment of the invention includes a method for treating a D1-mediated (or D1-associated) disorder, comprising administering to a mammal (e.g., a human) in need thereof an amount of a compound of Formula I (including a pharmaceutically acceptable salt thereof) effective in modulating (e.g., agonizing or partially agonizing) D1.

The compounds of Formula I used for treatment of a D1-mediated disorder also include pharmaceutically acceptable salts of the compounds.

D1-mediated (or D1-associated) disorders include neurological disorders [such as Tourette's syndrome; tardive dyskinesia; Parkinson's disease (including e.g., cognitive impairment associated with PD); cognitive disorders {including amnesia, age-related cognitive decline, dementia [e.g., senile dementia, Alzheimer's-associated dementia, HIV-associated dementia, Huntington's-associated dementia, Lewy body dementia, vascular dementia, frontotemporal dementia, drug-related dementia (for example, dementia associated with pharmacotherapy therapy such as D2 antagonist therapy)], delirium, and cognitive impairment (e.g., cognitive impairment associated with AD or cognitive impairment associated with PD), and mild cognitive impairment}; Huntington's chorea/disease; and restless leg syndrome (RLS)]; psychiatric disorders [such as cognitive impairment (e.g., cognitive impairment associated with schizophrenia or cognitive impairment associated with pharmacotherapy therapy (e.g., D2 antagonist therapy)); anxiety (including acute stress disorder, generalized anxiety disorder, social anxiety disorder, panic disorder, post-traumatic stress disorder, and obsessive-compulsive disorder); factitious disorder (including acute hallucinatory mania); impulse control disorders/impulsivity (including compulsive gambling and intermittent explosive disorder); mood disorders (including bipolar I disorder, bipolar II disorder, mania, mixed affective state, depression {e.g., age-related depression, major depression, chronic depression, seasonal depression, psychotic depression, postpartum depression, and treatment resistant depression (TRD)}; psychomotor disorders; psychotic disorders [including schizophrenia (including, for example, cognitive and negative symptoms in schizophrenia), schizoaffective disorder, schizophreniform, and delusional disorder]; substance abuse and drug dependence (including narcotic dependence, alcoholism, amphetamine dependence, cocaine addiction, nicotine dependence, and drug withdrawal syndrome); drug abuse relapse, eating disorders (including anorexia, bulimia, binge eating disorder, overeating, hyperphagia, and pagophagia); autism spectrum disorder (e.g., autism); chronic apathy, anhedonia, chronic fatigue, seasonal affective disorder, and pediatric psychiatric disorders (including attention deficit disorder, attention deficit hyperactive disorder (ADHD), conduct disorder, and autism)], endocrine disorders (such as hyperprolactinemia), or other disorders including drowsiness, excessive daytime sleepiness, cachexia, inattention, sexual dysfunction (e.g., erectile dysfunction, post-SSRI sexual dysfunction), pain, migraine, systemic lupus erythematosus (SLE), hyperglycemia, atherosclerosis, dislipidemia, obesity, diabetes, sepsis, post-ischemic tubular necrosis, renal failure, hyponatremia, resistant edema, narcolepsy, cardiovascular disease (e.g., hypertension), congestive heart failure, postoperative ocula hypotonia, sleep disorders, and serotonin syndrome.

Another embodiment of the invention provides a method for treating neurological disorders [such as Tourette's syndrome; tardive dyskinesia; Parkinson's disease; cognitive disorders {including amnesia, senile dementia, HIV-associated dementia, Alzheimer's-associated dementia, Huntington's-associated dementia, Lewy body dementia, vascular dementia, drug-related dementia (for example, cognitive impairment associated with D2 antagonist therapy), delirium, and mild cognitive impairment)}; RLS; and Huntington's chorea/disease], psychiatric disorders [such as anxiety (including acute stress disorder, generalized anxiety disorder, social anxiety disorder, panic disorder, post-traumatic stress disorder and obsessive-compulsive disorder); factitious disorder (including acute hallucinatory mania); impulse control disorders/impulsivity (including compulsive gambling and intermittent explosive disorder); mood disorders (including bipolar I disorder, bipolar II disorder, mania, mixed affective state, major depression, chronic depression, seasonal depression, psychotic depression, and postpartum depression); psychomotor disorders; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, and pagophagia); and pediatric psychiatric disorders (including attention deficit disorder, attention deficit/hyperactive disorder, conduct disorder, and autism)], or endocrine disorders (such as hyperprolactinemia) in a mammal, for example a human, comprising administering to said mammal a therapeutically effective amount of a compound of Formula I or a pharmaceutically acceptable salt thereof.

Another embodiment of the invention includes a method for treating a disorder in a mammal (e.g., a human), which method comprises administering to said mammal a therapeutically effective amount of a compound of Formula I or a pharmaceutically acceptable salt thereof, wherein the disorder is selected from schizophrenia (e.g., cognitive and negative symptoms in schizophrenia), cognitive impairment [e.g., cognitive impairment associated with schizophrenia, cognitive impairment associated with AD, cognitive impairment associated with PD, cognitive impairment associated with pharmacotherapy therapy (e.g., D2 antagonist therapy), and mild cognitive impairment], attention deficit hyperactivity disorder (ADHD), impulsivity, compulsive gambling, an eating disorder (e.g., anorexia, bulimia, binge eating disorder, overeating, hyperphagia, and pagophagia), autism spectrum disorder, mild cognitive impairment (MCI), age-related cognitive decline, dementia (e.g., senile dementia, HIV-associated dementia, Alzheimer's dementia, Lewy body dementia, vascular dementia, or frontotemporal dementia), restless leg syndrome (RLS), Parkinson's disease, Huntington's chorea, anxiety, depression (e.g., age-related depression), major depressive disorder (MDD), treatment resistant depression (TRD), bipolar disorder, chronic apathy, anhedonia, chronic fatigue, post-traumatic stress disorder, seasonal affective disorder, social anxiety disorder, post-partum depression, serotonin syndrome, substance abuse and drug dependence, drug abuse relapse, Tourette's syndrome, tardive dyskinesia, drowsiness, excessive daytime sleepiness, cachexia, inattention, sexual dysfunction (e.g., erectile dysfunction or post-SSRI sexual dysfunction), migraine, systemic lupus erythematosus (SLE), hyperglycemia, atherosclerosis, dislipidemia, obesity, diabetes, sepsis, post-ischemic tubular necrosis, renal failure, hyponatremia, resistant edema, narcolepsy, hypertension, congestive heart failure, postoperative ocular hypotonia, sleep disorders, and pain.

Another embodiment of the invention includes a method for treating schizophrenia (e.g., cognitive and negative symptoms in schizophrenia or cognitive impairment associated with schizophrenia) or psychosis in a mammal, for example a human, comprising administering to said mammal (e.g., a human) a therapeutically effective amount of a compound of Formula I or a pharmaceutically acceptable salt thereof.

Another embodiment of the invention includes a method for treating schizophrenia (e.g., cognitive and negative symptoms in schizophrenia or cognitive impairment associated with schizophrenia) in a mammal, for example a human, comprising administering to said mammal a therapeutically effective amount of a compound of Formula I or a pharmaceutically acceptable salt thereof.

Another embodiment of the invention includes a method for the treatment of cognitive impairment [e.g., cognitive impairment associated with schizophrenia, cognitive impairment associated with AD, or cognitive impairment associated with PD] in a mammal, for example a human, comprising administering to said mammal a therapeutically effective amount of a compound of Formula I or a pharmaceutically acceptable salt thereof.

Another embodiment of the invention includes a method for treating AD (e.g., treating cognitive impairment associated with AD), PD (e.g., treating cognitive impairment associated with PD), RLS, depression, or MDD in a mammal, for example a human, comprising administering to said mammal a therapeutically effective amount of a compound of Formula I or a pharmaceutically acceptable salt thereof.

The term "therapeutically effective amount" as used herein refers to that amount of the compound (including a pharmaceutically acceptable salt thereof) being administered which will relieve to some extent one or more of the symptoms of the disorder being treated. In reference to the treatment of a D1-mediated disorder (e.g., schizophrenia), a therapeutically effective amount refers to that amount which has the effect of relieving to some extent (or, for example, eliminating) one or more symptoms associated with a D1-mediated disorder (e.g., schizophrenia, or cognitive and negative symptoms in schizophrenia, or cognitive impairment associated with schizophrenia).

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined herein. The term "treating" also includes adjuvant and neo-adjuvant treatment of a subject.

Administration of the compounds of Formula I may be effected by any method that enables delivery of the compounds to the site of action. These methods include oral routes, intranasal routes, inhaled routes, intraduodenal routes, parenteral injection (including intravenous, subcutaneous, intramuscular, intravascular or infusion), topical, and rectal administration.

In one embodiment of the present invention, the compounds of Formula I may be administered/effected by oral routes.

Dosage regimens may be adjusted to provide the optimum desired response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. Dosage unit form, as used herein, refers to physically discrete units suited as unitary dosages for the mammalian subjects to be treated; each unit containing a predetermined quantity of active compound calculated to produce the desired therapeutic effect in association with the required pharmaceutical carrier. The specifications for the dosage unit forms of the invention are dictated by a variety of factors such as the unique characteristics of the therapeutic agent and the particular therapeutic or prophylactic effect to be achieved. In one embodiment of the present invention, the compounds of Formula I may be used to treat humans.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. Thus, the present invention encompasses intra-patient dose-escalation as determined by the skilled artisan. Determining appropriate dosages and regimens for administration of the chemotherapeutic agent is well-known in the relevant art and would be understood to be encompassed by the skilled artisan once provided the teachings disclosed herein.

The amount of the compound of Formula I or a pharmaceutically acceptable salt thereof administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases still larger doses may be employed without causing any harmful side effect, provided that such larger doses are first divided into several small doses for administration throughout the day.

As used herein, the term "combination therapy" refers to the administration of a compound of Formula I or a pharmaceutically acceptable salt thereof together with an at least one additional pharmaceutical or medicinal agent (e.g., an anti-schizophrenia agent), either sequentially or simultaneously.

The present invention includes the use of a combination of a compound of Formula I (or a pharmaceutically acceptable salt thereof) and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I (including an N-oxide thereof or a pharmaceutically acceptable salt of the compound or the N-oxide); (b) a second pharmaceutically active agent; and (c) a pharmaceutically acceptable carrier, vehicle or diluent.

Various pharmaceutically active agents may be selected for use in conjunction with the compounds of Formula I (including or pharmaceutically acceptable salts thereof), depending on the disease, disorder, or condition to be treated. Pharmaceutically active agents that may be used in combination with the compositions of the present invention include, without limitation:

(i) acetylcholinesterase inhibitors such as donepezil hydrochloride (ARICEPT, MEMAC); or Adenosine $A_{2A}$ receptor antagonists such as Preladenant (SCH 420814) or SCH 412348;

(ii) amyloid-ß (or fragments thereof), such as $Aß_{1-15}$ conjugated to pan HLA DR-binding epitope (PADRE) and ACC-001 (Elan/Wyeth);

(iii) antibodies to amyloid-ß (or fragments thereof), such as bapineuzumab (also known as AAB-001) and AAB-002 (Wyeth/Elan);

(iv) amyloid-lowering or -inhibiting agents (including those that reduce amyloid production, accumulation and fibrillization) such as colostrinin and bisnorcymserine (also known as BNC);

(v) alpha-adrenergic receptor agonists such as clonidine (CATAPRES);

(vi) beta-adrenergic receptor blocking agents (beta blockers) such as carteolol;

(vii) anticholinergics such as amitriptyline (ELAVIL, ENDEP);

(viii) anticonvulsants such as carbamazepine (TEGRETOL, CARBATROL);

(ix) antipsychotics, such as lurasidone (also known as SM-13496; Dainippon Sumitomo);

(x) calcium channel blockers such as nilvadipine (ESCOR, NIVADIL);

(xi) catechol O-methyltransferase (COMT) inhibitors such as tolcapone (TASMAR);

(xii) central nervous system stimulants such as caffeine;

(xiii) corticosteroids such as prednisone (STERAPRED, DELTASONE);

(xiv) dopamine receptor agonists such as apomorphine (APOKYN);

(xv) dopamine receptor antagonists such as tetrabenazine (NITOMAN, XENAZINE, dopamine D2 antagonist such as Quetiapine);

(xvi) dopamine reuptake inhibitors such as nomifensine maleate (MERITAL);

(xvii) gamma-aminobutyric acid (GABA) receptor agonists such as baclofen (LIORESAL, KEMSTRO);

(xviii) histamine 3 ($H_3$) antagonists such as ciproxifan;

(xix) immunomodulators such as glatiramer acetate (also known as copolymer-1; COPAXONE);

(xx) immunosuppressants such as methotrexate (TREXALL, RHEUMATREX);

(xxi) interferons, including interferon beta-1a (AVONEX, REBIF) and interferon beta-1b (BETASERON, BETAFERON);

(xxii) levodopa (or its methyl or ethyl ester), alone or in combination with a DOPA decarboxylase inhibitor (e.g., carbidopa (SINEMET, CARBILEV, PARCOPA));

(xxiii) N-methyl-D-aspartate (NMDA) receptor antagonists such as memantine (NAMENDA, AXURA, EBIXA);

(xxiv) monoamine oxidase (MAO) inhibitors such as selegiline (EMSAM);

(xxv) muscarinic receptor (particularly M1 subtype) agonists such as bethanechol chloride (DUVOID, URECHOLINE);

(xxvi) neuroprotective drugs such as 2,3,4,9-tetrahydro-1H-carbazol-3-one oxime; (xxvii) nicotinic receptor agonists such as epibatidine;

(xxviii) norepinephrine (noradrenaline) reuptake inhibitors such as atomoxetine (STRATTERA);

(xxix) phosphodiesterase (PDE) inhibitors, for example, PDE9 inhibitors such as BAY 73-6691 (Bayer AG) and PDE 10 (e.g. PDE10A) inhibitors such as papaverine;

(xxx) other PDE inhibitors including (a) PDE1 inhibitors (e.g., vinpocetine), (b) PDE2 inhibitors (e.g., erythro-9-(2-hydroxy-3-nonyl)adenine (EHNA)), (c) PDE4 inhibitors (e.g., rolipram), and (d) PDE5 inhibitors (e.g., sildenafil (VIAGRA, REVATIO));

(xxxi) quinolines such as quinine (including its hydrochloride, dihydrochloride, sulfate, bisulfate and gluconate salts);

(xxxii) β-secretase inhibitors such as WY-25105;

(xxxiii) γ-secretase inhibitors such as LY-411575 (Lilly);

(xxxiv) serotonin (5-hydroxytryptamine) 1A ($5\text{-HT}_{1A}$) receptor antagonists such as spiperone;

(xxxv) serotonin (5-hydroxytryptamine) 4 ($5\text{-HT}_4$) receptor agonists such as PRX-03140 (Epix);

(xxxvi) serotonin (5-hydroxytryptamine) 6 ($5\text{-HT}_6$) receptor antagonists such as mianserin (TORVOL, BOLVIDON, NORVAL);

(xxxvii) serotonin (5-HT) reuptake inhibitors such as alaproclate, citalopram (CELEXA, CIPRAMIL);

(xxxviii) trophic factors, such as nerve growth factor (NGF), basic fibroblast growth factor (bFGF; ERSOFERMIN), neurotrophin-3 (NT-3), cardiotrophin-1, brain-derived neurotrophic factor (BDNF), neublastin, meteorin, and glial-derived neurotrophic factor (GDNF), and agents that stimulate production of trophic factors, such as propentofylline;

and the like.

The compound of Formula I (including a pharmaceutically acceptable salt thereof) is optionally used in combination with another active agent. Such an active agent may be, for example, an atypical antipsychotic or an anti-Parkinson's disease agent or an anti-Alzheimer's agent. Accordingly, another embodiment of the invention provides methods of treating a D1-mediated disorder (e.g., a neurological and psychiatric disorder associated with D1), comprising administering to a mammal an effective amount of a compound of Formula I (including an N-oxide thereof or a pharmaceutically acceptable salt of the compound or the N-oxide) and further comprising administering another active agent.

As used herein, the term "another active agent" refers to any therapeutic agent, other than the compound of Formula I (including or a pharmaceutically acceptable salt thereof) that is useful for the treatment of a subject disorder. Examples of additional therapeutic agents include antidepressants, antipsychotics (such as anti-schizophrenia), anti-pain, anti-Parkinson's disease agents, anti-LID (levodopa-induced dyskinesia), anti-Alzheimer's and anti-anxiety agents. Examples of particular classes of antidepressants that can be used in combination with the compounds of the invention include norepinephrine reuptake inhibitors, selective serotonin reuptake inhibitors (SSRIs), NK-1 receptor antagonists, monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, and atypical antidepressants. Suitable norepinephrine reuptake inhibitors include tertiary amine tricyclics and secondary amine tricyclics. Examples of suitable tertiary amine tricyclics and secondary amine tricyclics include amitriptyline, clomipramine, doxepin, imipramine, trimipramine, dothiepin, butriptyline, iprindole, lofepramine, nortriptyline, protriptyline, amoxapine, desipramine and maprotiline. Examples of suitable selective serotonin reuptake inhibitors include fluoxetine, fluvoxamine, paroxetine, and sertraline. Examples of monoamine oxidase inhibitors include isocarboxazid, phenelzine, and tranylcyclopramine. Examples of suitable reversible inhibitors of monoamine oxidase include moclobemide. Examples of suitable serotonin and noradrenaline reuptake inhibitors of use in the present invention include venlafaxine. Examples of suitable atypical anti-depressants include bupropion, lithium, nefazodone, trazodone and viloxazine. Examples of anti-Alzheimer's agents include Dimebon, NMDA receptor antagonists such as memantine; and cholinesterase inhibitors such as donepezil and galantamine. Examples of suitable classes of anti-anxiety agents that can be used in combination with the compounds of the invention include benzodiazepines and serotonin 1A (5-HT1A) agonists or antagonists, especially 5-HT1A partial agonists, and corticotropin releasing factor (CRF) antagonists. Suitable benzodiazepines include alprazolam, chlordiazepoxide, clonazepam, chlorazepate, diazepam, halazepam, lorazepam, oxazepam, and prazepam. Suitable 5-HT1A receptor agonists or antagonists include buspirone, flesinoxan, gepirone, and ipsapirone. Suitable atypical antipsychotics include paliperidone, bifeprunox, ziprasidone, risperidone, aripiprazole, olanzapine, and quetiapine. Suitable nicotine acetylcholine agonists include ispronicline, varenicline and MEM 3454. Anti-pain agents include pregabalin, gabapentin, clonidine, neostigmine, baclofen, midazolam, ketamine and ziconotide. Examples of suitable anti-Parkinson's disease agents include L-DOPA (or its methyl or ethyl ester), a DOPA decarboxylase inhibitor (e.g., carbidopa (SINEMET, CARBILEV, PARCOPA), an Adenosine $A_{2A}$ receptor antagonist [e.g., Preladenant (SCH 420814) or SCH 412348], benserazide (MADOPAR), α-methyldopa, monofluoromethyldopa, difluoromethyldopa, brocresine, or m-hydroxybenzylhydrazine), a dopamine agonist [such as apomorphine (APOKYN), bromocriptine (PARLODEL), cabergoline (DOSTINEX), dihydrexidine, dihydroergocryptine, fenoldopam (CORLOPAM), lisuride (DOPERGIN), pergolide (PERMAX), piribedil (TRIVASTAL, TRASTAL), pramipexole (MIRAPEX), quinpirole, ropinirole (REQUIP), rotigotine (NEUPRO), SKF-82958 (GlaxoSmithKline), and sarizotan], a monoamine oxidase (MAO) inhibitor [such as selegiline (EMSAM), selegiline hydrochloride (L-deprenyl, ELDEPRYL, ZELAPAR), dimethylselegilene, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), CHF-3381 (Chiesi Farmaceutici), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL)], a catechol O-methyltransferase (COMT) inhibitor [such as tolcapone (TASMAR), entacapone (COMTAN), and tropolone], an N-methyl-D-aspartate (NMDA) receptor antagonist [such as amantadine (SYMMETREL)], anticholinergics [such as amitriptyline (ELAVIL, ENDEP), butriptyline, benztropine mesylate (COGENTIN), trihexyphenidyl (ARTANE), diphenhydramine (BENADRYL), orphenadrine (NORFLEX), hyoscyamine, atropine (ATROPEN), scopolamine (TRANSDERM-SCOP), scopolamine methylbromide (PARMINE), dicycloverine (BENTYL, BYCLOMINE, DIBENT, DILOMINE, tolterodine (DETROL), oxybutynin (DITROPAN, LYRINEL XL, OXYTROL), penthienate bromide, propantheline (PRO-BANTHINE), cyclizine, imipramine hydrochloride (TOFRANIL), imipramine maleate (SURMONTIL), lofepramine, desipramine (NORPRAMIN), doxepin (SINEQUAN, ZONALON), trimipramine (SURMONTIL), and glycopyrrolate (ROBINUL)], or a combination thereof. Examples of anti-schizophrenia agents include ziprasidone, risperidone, olanzapine, quetiapine, aripiprazole, asenapine, blonanserin, or iloperidone.

As noted above, the compounds of Formula I (including pharmaceutically acceptable salts thereof) may be used in combination with one or more additional anti-schizophrenia agents which are described herein. When a combination therapy is used, the one or more additional anti-schizophrenia agents may be administered sequentially or simultaneously with the compound of the invention. In one embodiment, the additional anti-schizophrenia agent is administered to a mammal (e.g., a human) prior to administration of the compound of the invention. In another embodiment, the additional anti-schizophrenia agent is administered to the mammal after administration of the compound of the invention. In another embodiment, the additional anti-schizophrenia agent is administered to the mammal (e.g., a human) simultaneously with the administration of the compound of the invention (or an N-oxide thereof or a pharmaceutically acceptable salt of the foregoing).

The invention also provides a pharmaceutical composition for the treatment of schizophrenia in a mammal, including a human, which comprises an amount of a compound of Formula I (or a pharmaceutically acceptable salt thereof), as defined above (including hydrates, solvates and polymorphs of said compound or pharmaceutically acceptable salts thereof), in combination with one or more (for example one to three) anti-schizophrenia agents such as ziprasidone, risperidone, olanzapine, quetiapine, aripiprazole, asenapine, blonanserin, or iloperidone, wherein the amounts of the active agent and the combination when taken as a whole are therapeutically effective for treating schizophrenia.

The invention also provides a pharmaceutical composition for the treatment of Parkinson's disease in a mammal (including cognition impairment associated with PD), including a human, which comprises an amount of a compound of Formula I (or a pharmaceutically acceptable salt thereof), as defined above (including hydrates, solvates and polymorphs of said compound or pharmaceutically acceptable salts thereof), in combination with one or more (for example one to three) anti-Parkinson's disease agents such as L-DOPA, wherein the amounts of the active agent and the combination when taken as a whole are therapeutically effective for treating Parkinson's disease.

It will be understood that the compounds of Formula I depicted above are not limited to a particular stereoisomer (e.g. enantiomer or atropisomer) shown, but also include all stereoisomers and mixtures thereof.

DETAILED DESCRIPTION OF THE INVENTION

Compounds of the invention, including salts thereof, can be prepared using known organic synthesis techniques and can be synthesized according to any of numerous possible synthetic routes.

The reactions for preparing compounds of the invention can be carried out in suitable solvents, which can be readily selected by one of skill in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, $3^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high-performance liquid chromatography (HPLC) or thin layer chromatography (TLC).

Compounds of Formula I and intermediates thereof may be prepared according to the following reaction schemes and accompanying discussion. Unless otherwise indicated, $R^1$, $R^2$, $R^3$, $R^4$, $R^5$, $R^6$, $R^7$, $R^8$, $R^9$, $R^{10}$, $R^{10B}$, $R^{11}$, $R^{11A}$, $T^1$, $T^2$, $T^3$, $T^4$, $Q^1$, and $X^1$, and structural Formula I in the reaction schemes and discussion that follow are as defined above. In general, the compounds of this invention may be made by processes which include processes analogous to those known in the chemical arts, particularly in light of the description provided herein. Certain processes for the manufacture of the compounds of this invention and intermediates thereof are provided as further features of the invention and are illustrated by the following reaction schemes. Other processes are described in the experimental section. The schemes and examples provided herein (including the corresponding description) are for illustration only, and not intended to limit the scope of the present invention.

a base (such as $Cs_2CO_3$), a metal catalyst [such as a palladium catalyst, e.g., $Pd(OAc)_2$], and a ligand [such as 1,1'-binaphthalene-2,2'-diylbis(diphenylphosphane) (BINAP)] in an appropriate solvent, such as 1,4-dioxane. A compound of Formula 1-3 can subsequently be reacted with a compound of Formula $Q^1$-$Z^2$ [wherein $Z^2$ can be Br; $B(OH)_2$; $B(OR)_2$ wherein each R is independently H or $C_{1-6}$ alkyl, or wherein the two (OR) groups, together with the B atom to which they are attached, form a 5- to 10-membered heterocycloalkyl optionally substituted with one or more

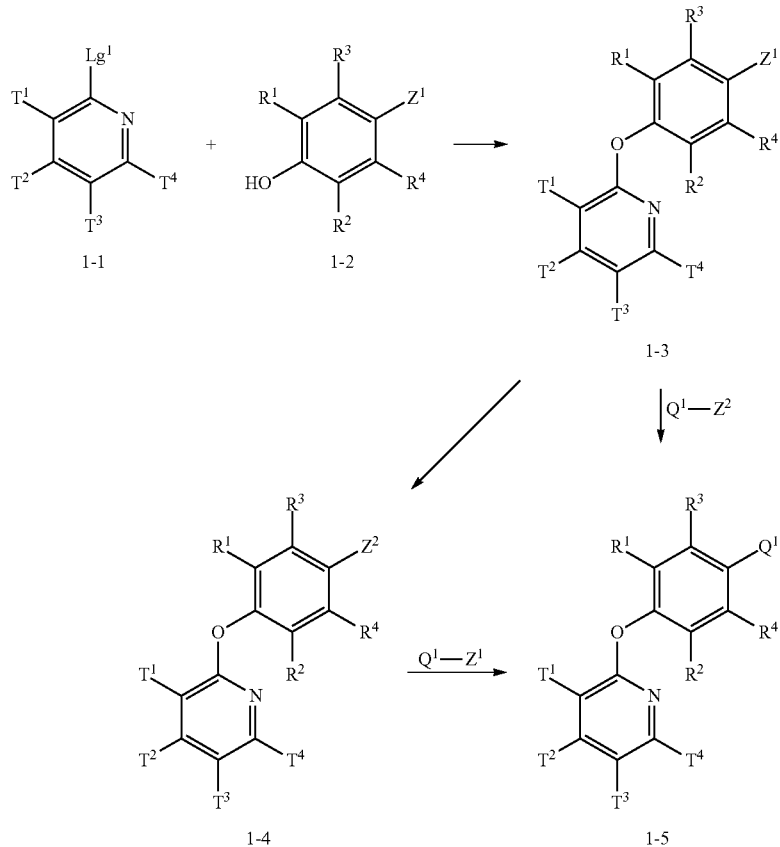

Scheme 1

Scheme 1 refers to preparation of compounds of Formula 1-5 (i.e., compounds of Formula I wherein $L^1$ is O). Referring to Scheme 1, compounds of Formula 1-1 [where $Lg^1$ is a suitable leaving group such as halo (e.g., F, Cl or Br)] and 1-2 [wherein $Z^1$ can be, e.g., halogen (e.g., Br or I) or trifluoromethanesulfonate (triflate)] are commercially available or can be made by methods described herein or other methods well known to those skilled in the art. A compound of Formula 1-3 can be prepared by coupling a compound of Formula 1-1 with a compound of Formula 1-2 under suitable conditions. The coupling can be accomplished, for example, by heating a mixture of a compound of Formula 1-1 with a compound of Formula 1-2 in the presence of a base, such as $Cs_2CO_3$, in an appropriate solvent, such as dimethyl sulfoxide (DMSO). Alternatively, a metal-catalyzed (such as using a palladium or copper catalyst) coupling may be employed to accomplish the aforesaid coupling. In this variant of the coupling, a mixture of a compound of Formula 1-1 and a compound of Formula 1-2 can be heated in the presence of $C_{1-6}$ alkyl; a trialkyltin moiety; or the like] by a metal-catalyzed (such as using a palladium catalyst) coupling reaction to obtain a compound of Formula I. Compounds of Formula $Q^1$-$Z^2$ are commercially available or can be made by methods described herein or by methods analogous to those described in the chemical art. Alternatively, a compound of Formula 1-3 can be converted to a compound of Formula 1-4 (wherein $Z^2$ is defined as above). For example, a compound of Formula 1-3 (wherein $Z^1$ is halogen such as Br or I) can be converted to a compound of Formula 1-4 [wherein $Z^2$ is $B(OH)_2$; $B(OR)_2$ wherein each R is independently H or $C_{1-6}$ alkyl, or wherein the two (OR) groups, together with the B atom to which they are attached, form a 5- to 10-membered heterocycloalkyl or heteroaryl optionally substituted with one or more $C_{1-6}$ alkyl] by methods described herein or other methods well known to those skilled in the art. In this example, this reaction can be accomplished, for example, by reacting a compound of Formula 1-3 (wherein $Z^1$ is halogen such as Br) with 4,4,4',4',5,5,5',5'-octamethyl-2,2'-bi-1,3,2-dioxaborolane, a suitable base (such as potassium acetate), and a palladium catalyst {such as [1,1'-bis(diphenylphosphino)ferrocene]dichloropalladium(II)} in a suitable solvent such as 1,4-dioxane. In another example, a compound of Formula 1-3 (wherein $Z^1$ is halogen such as Br) can be converted to a compound of Formula 1-4 (wherein $Z^2$ is a trialkyltin moiety) by alternate methods described herein or other methods well known to those skilled in the art. In this example, this reaction can be accomplished, for example, by reacting a compound of Formula 1-3 (wherein $Z^1$ is halogen such as Br) with a hexaalkyldistannane (such as hexamethyldistannane) in the presence of a palladium catalyst [such as tetrakis(triphenylphosphine)palladium(0)] in a suitable solvent such as 1,4-dioxane. A compound of Formula 1-4 can then be reacted with a compound of Formula $Q^1$-$Z^1$ (wherein $Z^1$ is defined as above) by a metal-catalyzed (such as using a palladium catalyst) coupling reaction to obtain a compound of Formula I. Compounds of Formula $Q^1$-$Z^1$ are commercially available or can be made by methods described herein or by methods analogous to those described in the chemical art. The type of reaction employed depends on the selection of $Z^1$ and $Z^2$. For example, when $Z^1$ is halogen or triflate and the $Q^1$-$Z^2$ reagent is a boronic acid or boronic ester, a Suzuki reaction may be used [A. Suzuki, *J. Organomet. Chem.* 1999, 576, 147-168; N. Miyaura and A. Suzuki, *Chem. Rev.* 1995, 95, 2457-2483; A. F. Littke et al., *J. Am. Chem. Soc.* 2000, 122, 4020-4028]. In some specific embodiments, an aromatic iodide, bromide, or triflate of Formula 1-3 is combined with an aryl or heteroaryl boronic acid or boronic ester of Formula $Q^1$-$Z^2$ and a suitable base, such as potassium phosphate, in a suitable organic solvent such as tetrahydrofuran (THF). A palladium catalyst is added, such as S-Phos precatalyst {also known as chloro(2-dicyclohexylphosphino-2',6'-dimethoxy-1,1'-biphenyl)[2-(2-aminoethylphenyl)]palladium(II)-tert-butyl methyl ether adduct}, and the reaction mixture is heated. Alternatively, when $Z^1$ is halogen or triflate and $Z^2$ is trialkyltin, a Stille coupling may be employed [V. Farina et al., *Organic Reactions* 1997, 50, 1-652]. More specifically, a compound of Formula 1-3 (wherein $Z^1$ is Br, I, or triflate) may be combined with a compound of Formula $Q^1$-$Z^2$ (wherein the $Q^1$-$Z^2$ compound is a $Q^1$-stannane compound) in the presence of a palladium catalyst, such as dichlorobis(triphenylphosphine)palladium(II), in a suitable organic solvent such as toluene, and the reaction may be heated. Where $Z^1$ is Br, I, or triflate and $Z^2$ is Br or I, a Negishi coupling may be used [E. Erdik, *Tetrahedron* 1992, 48, 9577-9648]. More specifically, a compound of Formula 1-3 (wherein $Z^1$ is Br, I, or triflate) may be transmetallated by treatment with 1 to 1.1 equivalents of an alkyllithium reagent followed by a solution of 1.2 to 1.4 equivalents of zinc chloride in an appropriate solvent such as THF at a temperature ranging from −80° C. to −65° C. After warming to a temperature between 10° C. and 30° C., the reaction mixture may be treated with a compound of Formula $Q^1$-$Z^2$ (wherein $Z^2$ is Br or I), and heated at 50° C. to 70° C. with addition of a catalyst such as tetrakis(triphenylphosphine)palladium(0). The reaction may be carried out for times ranging from 1 to 24 hours to yield the compound of Formula 1-5.

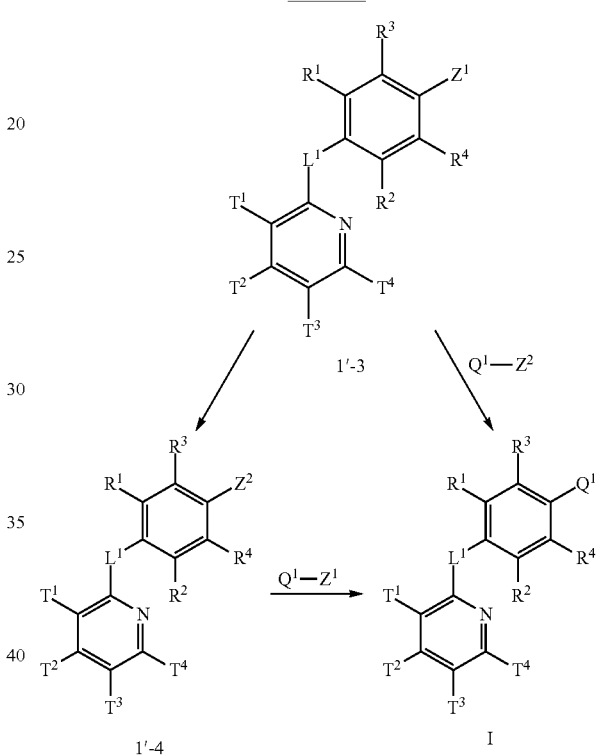

Scheme 1'

Similar to the chemical transformations described in Scheme 1, compounds of Formula I can be prepared starting from compounds of Formula 1'-3 according to Scheme 1'

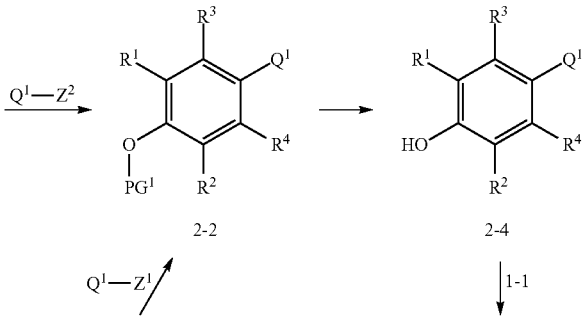

Scheme 2

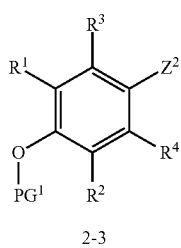

2-3

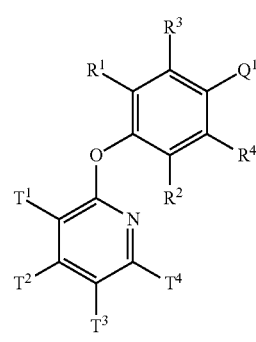

1-5

Scheme 2 also refers to preparation of compounds of Formula 1-5. Referring to Scheme 2, compounds of Formula 1-5 may be prepared utilizing analogous chemical transformations to those described in Scheme 1, but with a different ordering of steps. Compounds of Formula 2-1 [wherein $Pg^1$ is a suitable protecting group such as methyl, benzyl, tetrahydropyranyl (THP), or tert-butyldimethyl (TBS)] are commercially available or can be made by methods described herein or other methods well known to those skilled in the art. A compound of Formula 2-1 can be converted to a compound of Formula 2-2 either directly or after conversion to a compound of Formula 2-3 using methods analogous to those described in Scheme 1. A compound of Formula 2-2 may then be deprotected, using appropriate conditions depending on the selection of the $Pg^1$ group, to obtain a compound of Formula 2-4, which in turn can be coupled with a compound of Formula 1-1 in Scheme 1 to afford a compound of Formula 1-5. The coupling conditions employed may be analogous to those described for the preparation of a compound of Formula 1-3 in Scheme 1.

Scheme 3

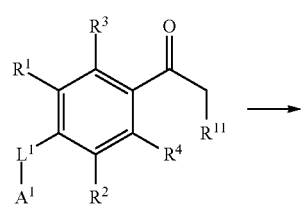

3-1

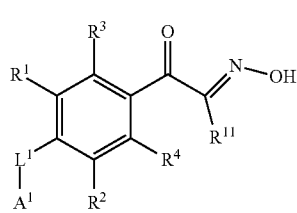

3-2

3-3

3-4

3-5

$A^1$ is $Pg^2$ or a moiety of $A^{1a}$.

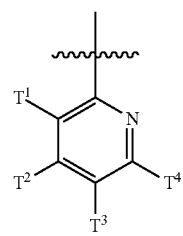

$A^{1a}$

Scheme 3 refers to a preparation of a compound of Formula 3-5 wherein $A^1$ is a moiety of Formula $A^{1a}$ or a suitable protecting group $Pg^2$. (e.g., methyl, benzyl, THP, or TBS). Referring to Scheme 3, compounds of Formula 3-1 are commercially available or can be made by methods described herein or other methods well known to those skilled in the art. A compound of Formula 3-2 can be prepared by reacting an arylketone of Formula 3-1 with an alkyl nitrite (e.g., isoamyl nitrite) in the presence of an acid (such as hydrochloric acid). The resulting oxime of Formula 3-2 can be converted to the diketone of Formula 3-3 upon treatment with formaldehyde (or its equivalent such as metaformaldehyde or polyformaldehyde) in the presence of an acid (such as an aqueous hydrochloric acid solution). Diketones of Formula 3-3 can be reacted with glycinamide or a salt thereof (such as an acetic acid salt) in the presence of a base such as sodium hydroxide to obtain pyrazinones of Formula 3-4. Alkylation of the pyrazinone nitrogen to obtain a compound of Formula 3-5 can be achieved by treatment of a compound of Formula 3-4 with a base [such as lithium diisopropylamide (LDA), lithium bis(trimethylsilyl)amide (LHMDS), and the like] and a compound of the formula $R^{11A}$—$Z^3$ [wherein $Z^3$ is an acceptable leaving group such as Cl, Br, I, methanesulfonate (mesylate), and the like and wherein $R^{11A}$ is for example $C_{1-3}$ alkyl (e.g., methyl)]. Suitable reaction solvents typically can be selected from polar aprotic solvents such as N,N-dimethylformamide (DMF), 1,4-dioxane, or THF.

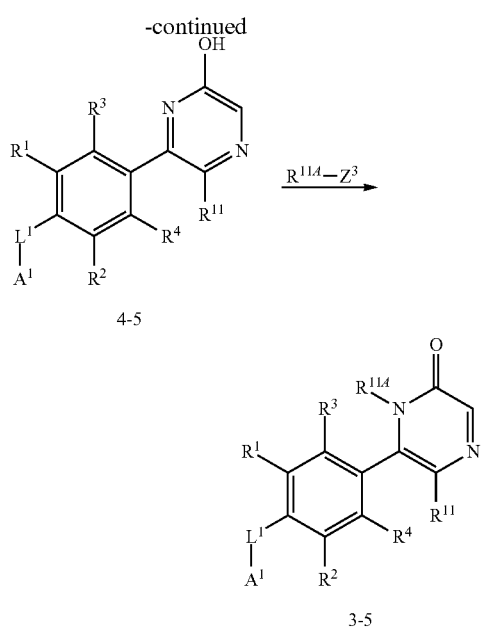

$A^1$ is $Pg^2$ or a moiety of $A^{1a}$:

$A^{1a}$

Alternatively, a compound of Formula 3-5 may be prepared as in Scheme 4 wherein $L^1$ is O, NH, N($C_{1-4}$ alkyl) and N($C_{3-6}$ cycloalkyl). Referring to Scheme 4, compounds of Formula 4-1 and 4-2 are commercially available or can be made by methods described herein or other methods well known to those skilled in the art. A compound of Formula 4-3 can be prepared by coupling a compound of Formula 4-1 with a compound of Formula 4-2. The aforesaid coupling may be accomplished by reacting a compound of Formula 4-1 with a compound of Formula 4-2 in the presence of a suitable base (such as potassium carbonate), a suitable catalyst [such as tetrakis(triphenylphosphine)palladium(0)], and a suitable solvent (such as ethanol). A compound of Formula 4-3 can be reacted with maleic anhydride and hydrogen peroxide in a solvent (such as dichloromethane) to provide a compound of Formula 4-4, which may contain a mixture of N-oxide regioisomers. A compound of Formula 4-5 can be prepared from a compound of Formula 4-4 by heating with acetic anydride; the initial product can be saponified using a base (such as NaOH) in a suitable polar solvent (such as water or methanol). A compound of Formula 3-5 can be prepared from a compound of Formula 4-5 by reaction with a suitable base (such as LDA, LHMDS and the like), lithium bromide, and a compound of the formula $R^{11A}$—$Z^3$ (wherein $Z^3$ is an acceptable leaving group such as Cl, Br, I, mesylate, and the like). Suitable reaction solvents typically can be selected from polar aprotic solvents (such as DMF, 1,4-dioxane, or THF).

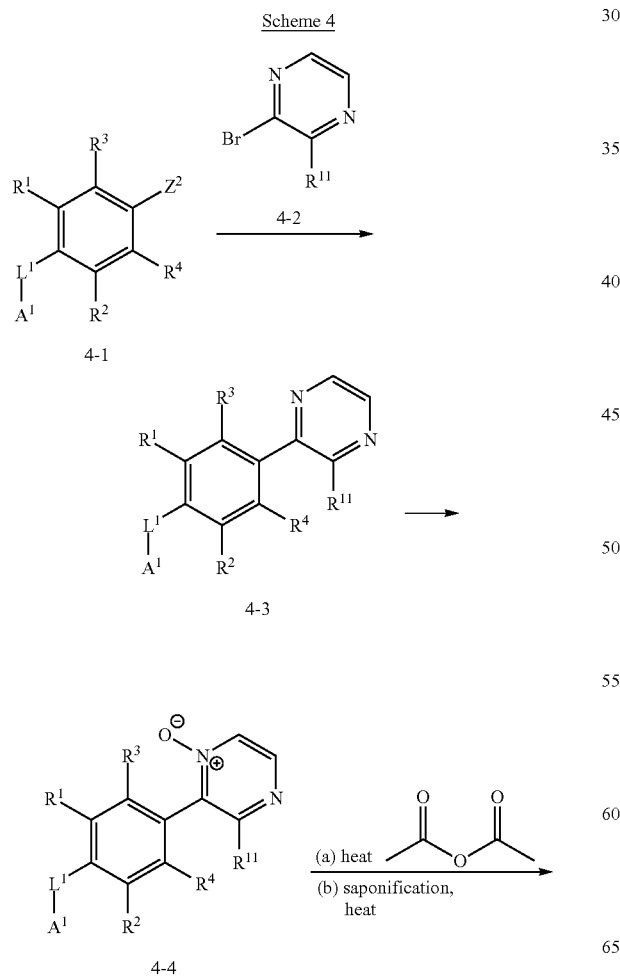

Scheme 5

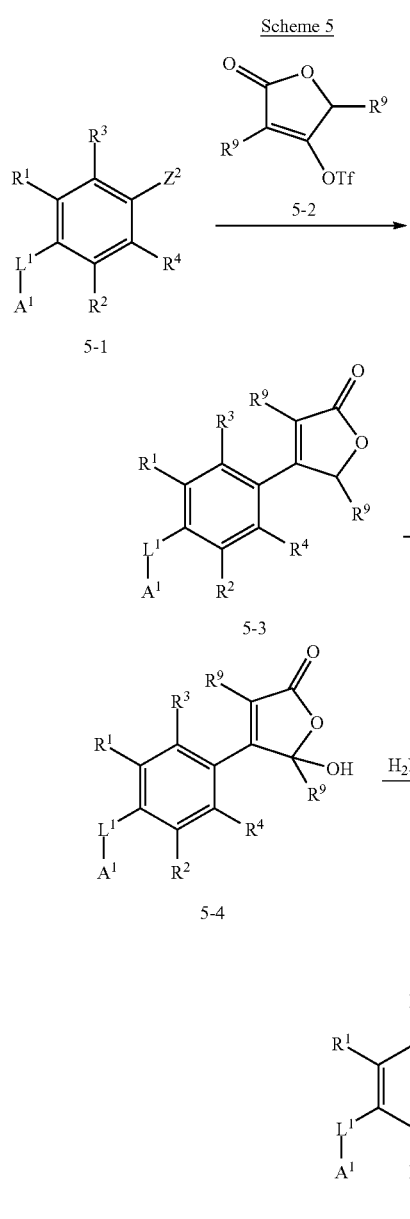

$A^1$ is $Pg^2$ or a moiety of $A^{1a}$:

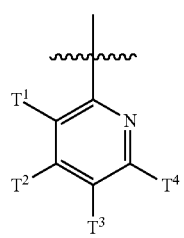

Scheme 5 refers to a preparation of a compound of Formula 5-5 wherein $L^1$ is O, NH, N($C_{1-4}$ alkyl) and N($C_{3-6}$ cycloalkyl) and $A^1$ is a moiety of Formula $A^{1a}$ or a $Pg^2$ (such as a benzyl group). Referring to Scheme 5, compounds of Formula 5-1 and 5-2 are commercially available or can be made by methods described herein or other methods well known to those skilled in the art. A compound of Formula 5-3 can be prepared by coupling a compound of Formula 5-1 with an enol trifluoromethanesulfonate of Formula 5-2. The aforesaid coupling may be accomplished by reacting a compound of Formula 5-1 with a trifluoromethanesulfonate of Formula 5-2 in the presence of a suitable base (such as potassium carbonate or sodium carbonate), a suitable catalyst [such as palladium(II) acetate], optionally a suitable ligand (such as tricyclohexylphosphine), and optionally a suitable phase-transfer catalyst such as tetrabutylammonium chloride. Suitable reaction solvents typically can be selected from polar aprotic solvents such as 1,4-dioxane or THF. A compound of Formula 5-3 can be reacted with 1 to 5 equivalents of a suitable base [such as 1,8-diazabicyclo [5.4.0]undec-7-ene (DBU)] under an oxygen atmosphere to obtain a compound of Formula 5-4. Suitable reaction solvents typically can be selected from polar aprotic solvents such as DMF, 1,4-dioxane, or THF. A compound of Formula 5-5 can be obtained by reacting a compound of Formula 5-4 with hydrazine in a suitable solvent such as 1-butanol.

Scheme 6

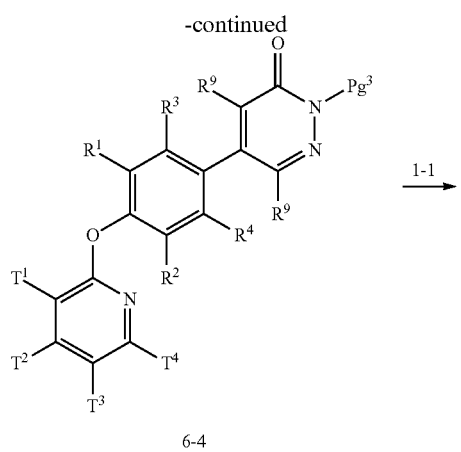

6-4

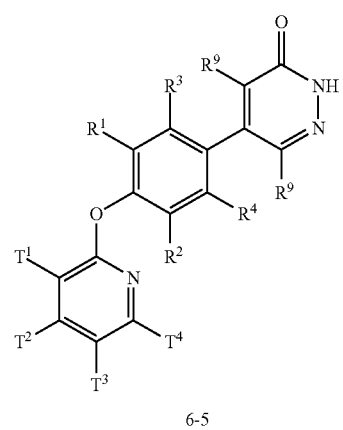

6-5

Scheme 6 refers to a preparation of a compound of Formula 6-5. Referring to Scheme 6, a compound of Formula 6-1 can be prepared as described in Scheme 5, wherein $Pg^2$ is a suitable protecting group (such as benzyl). A compound of Formula 6-1 can be converted to a suitably protected compound of Formula 6-2 using methods described herein or other methods well known to those skilled in the art, wherein $Pg^3$ is a suitable protecting group (such as THP) that can be removed under orthogonal reaction conditions to $Pg^2$. A compound of Formula 6-3 can be prepared by selective removal of $Pg^2$ under suitable deprotection conditions depending on the selection of $Pg^2$. For example, when $Pg^2$ is a benzyl group, it can be removed by treatment with palladium (10% on carbon) under hydrogenation condition in a suitable solvent, such as methanol and ethyl acetate. Using the aforementioned reaction conditions described in Scheme 1, a compound of Formula 6-3 can be coupled with a reagent of Formula 1-1 to yield a compound of Formula 6-4. A compound of Formula 6-5 can be obtained by removing $Pg^3$ under suitable deprotection conditions depending on the selection of $Pg^3$. For example, when $Pg^3$ is THP, it can be removed under acidic conditions, such as hydrogen chloride in a suitable solvent, such as dichloromethane.

Scheme 7

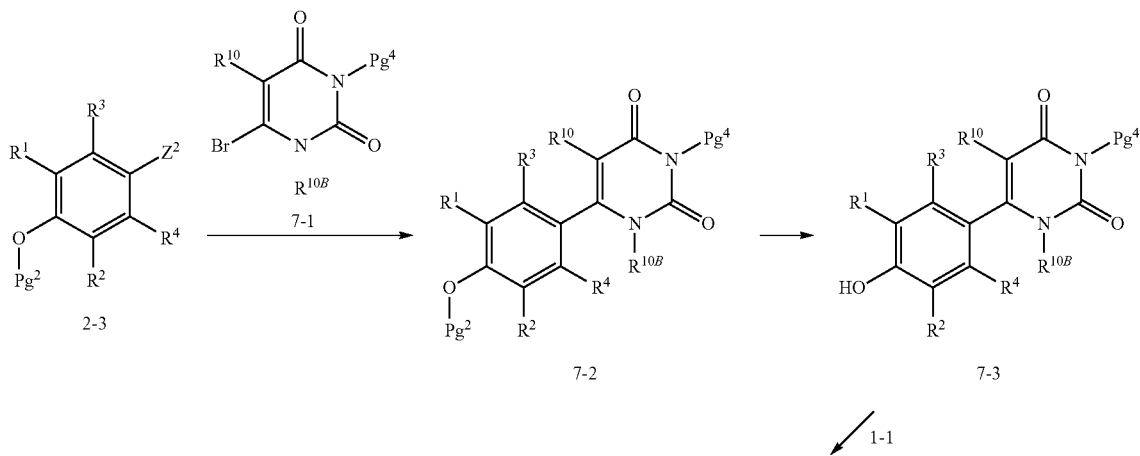

61

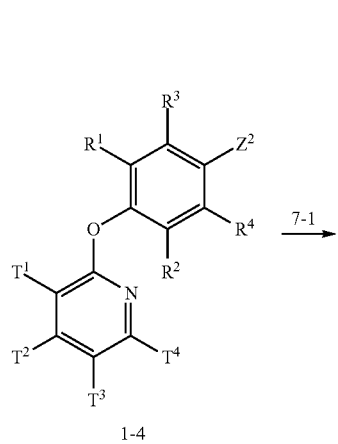

1-4

-continued

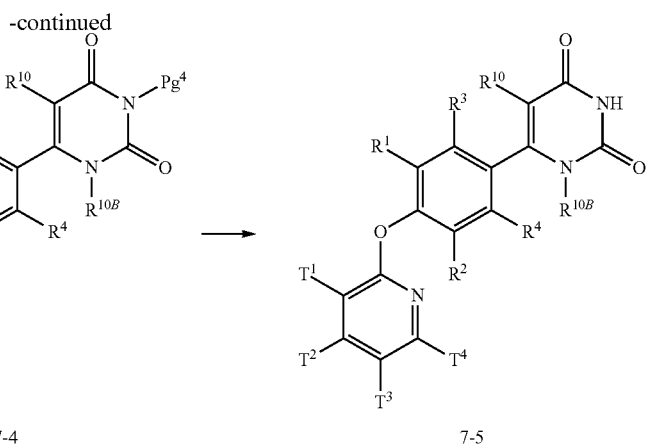

7-4      7-5

Scheme 7 refers to a preparation of a compound of Formula 7-5 [wherein $R^{10}$ is, for example, $C_{1-3}$ alkyl (e.g., methyl); $R^{10B}$ is, for example, H or $C_{1-3}$ alkyl (e.g., methyl); and $Pg^4$ is a suitable protecting group [e.g., 2-(trimethylsilyl) ethoxymethyl (SEM), tert-butoxycarbonyl (Boc), or benzyloxymethyl acetal (BOM)]. Referring to Scheme 7, compounds of Formula 2-3 and 7-1 are commercially available or can be prepared by methods described herein or other methods well known to those skilled in the art. A compound of Formula 7-2 can be prepared by coupling a compound of Formula 2-3 with a compound of Formula 7-1, in the presence of a suitable base (such as potassium carbonate) and a suitable catalyst {such as [1,1'-bis(diphenylphosphino) ferrocene]dichloropalladium(II)}. A compound of Formula 7-3 can be prepared by selective removal of $Pg^2$ under suitable de-protection conditions depending on the selection of $Pg^2$. For example, when $Pg^2$ is a benzyl group, it can be removed by treatment with palladium (10% on carbon) under hydrogenation condition in a suitable solvent, such as methanol and ethyl acetate. Using the aforementioned reaction conditions described in Scheme 1, a compound of Formula 7-3 can be coupled with a reagent of Formula 1-1 to yield a compound of Formula 7-4. Alternatively, a compound of Formula 7-4 can be prepared from intermediate 1-4, following the coupling conditions described in Scheme 1. A compound of Formula 7-5 can then be obtained from a compound of Formula 7-4 by removing $Pg^4$ under suitable deprotection conditions that are known to those skilled in the art.

62

Scheme 8

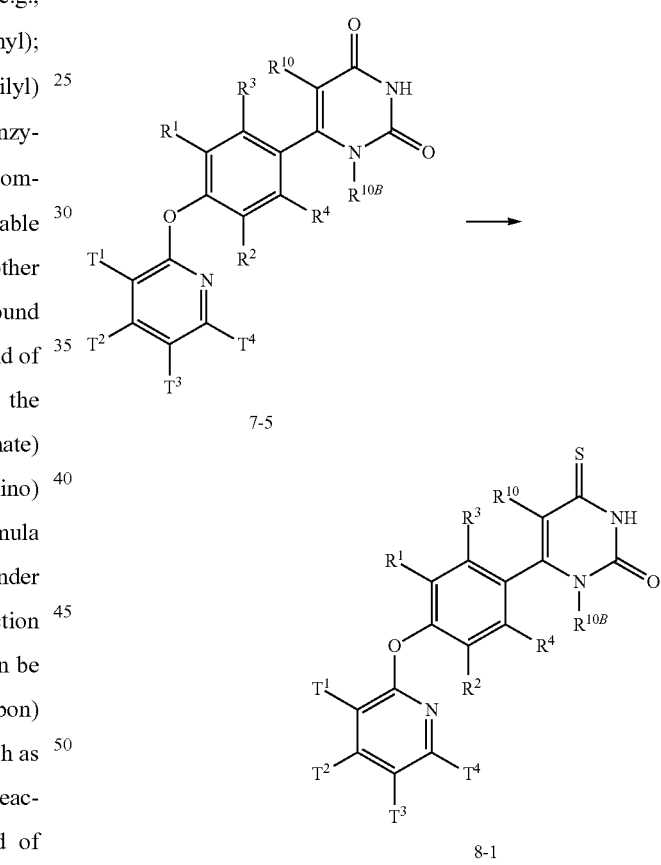

Scheme 8 refers to a preparation of a compound of Formula 8-1 [wherein $R^{10}$ is, for example, $C_{1-3}$alkyl (e.g., methyl); $R^{10B}$ is, for example, H or $C_{1-3}$alkyl (e.g., methyl)]. Referring to Scheme 8, compounds of Formula 8-1 can be prepared by treating a compound of Formula 7-5 with a suitable thianation reagent, such as Lawesson's reagent [2,4-bis(4-methoxyphenyl)-1,3,2,4-dithiadiphosphetane-2,4-dithione] or phosphorus pentasulfide, in a suitable solvent such as toluene.

Scheme 9

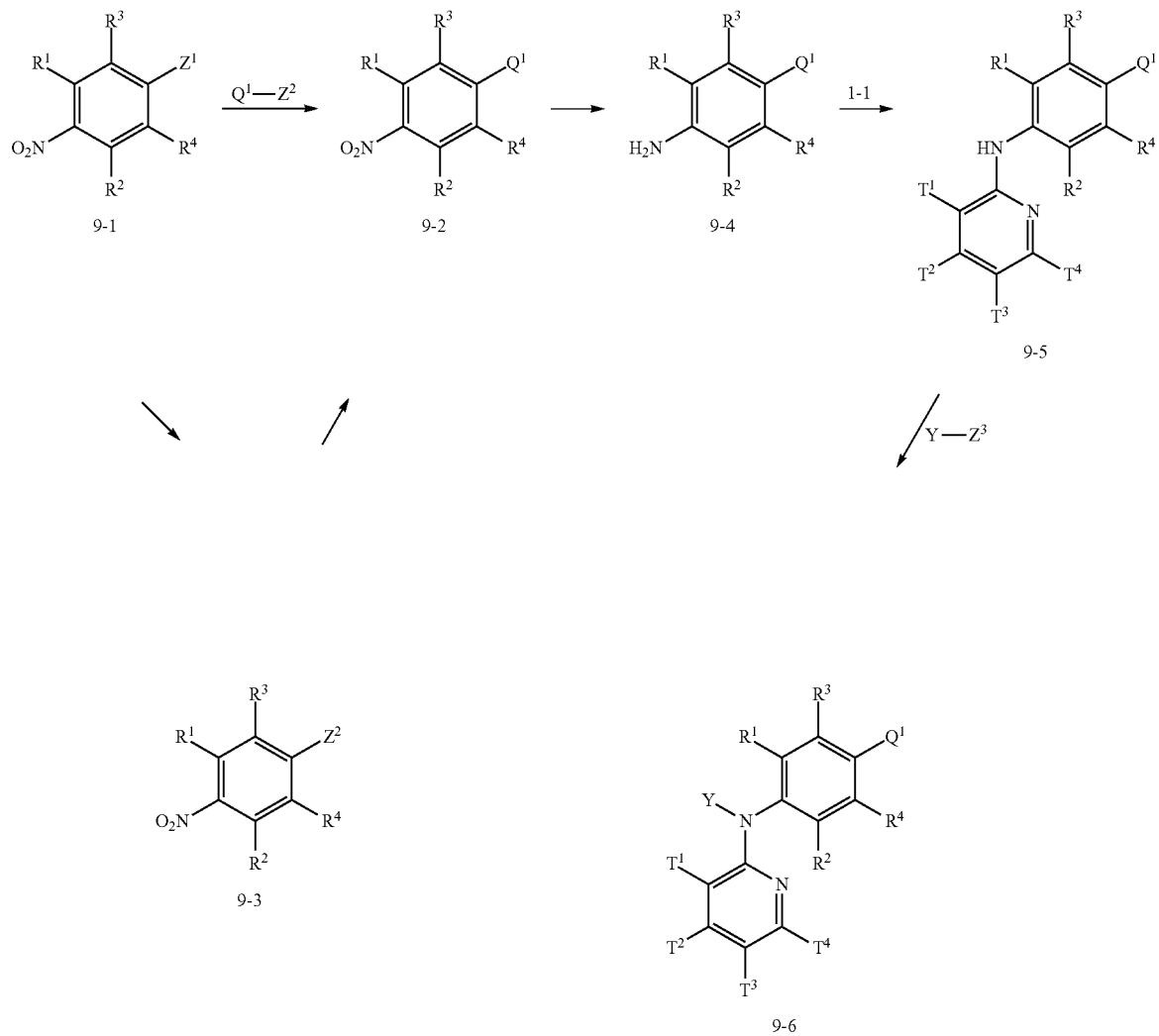

Scheme 9 refers to preparation of compounds of Formula 9-5 and 9-6. Referring to Scheme 9, compounds of Formula 9-1 are commercially available or can be made by methods described herein or other methods well known to those skilled in the art. A compound of Formula 9-1 can be converted to a compound of Formula 9-2 either directly or after conversion to a compound of Formula 9-3 using methods analogous to those described in Scheme 1. The nitro group of a compound of Formula 9-2 can then be converted to an amine via hydrogenation in the presence of a suitable catalyst, such as palladium (10% on carbon), to yield a compound of Formula 9-4. A compound of Formula 9-4 can then be coupled with a compound of Formula 1-1 in Scheme 1 to afford a compound of Formula 9-5. The coupling conditions employed may be analogous to those described for the preparation of a compound of Formula 1-3 in Scheme 1. A compound of Formula 9-6 can be prepared via N-alkylation of a compound of formula 9-5 using a reagent of Y—$Z^3$, wherein Y is $C_{1-4}$ alkyl, or $C_{3-6}$ cycloalkyl, and $Z^3$ is an acceptable leaving group such as Cl, Br, I, mesylate, and the like.

Scheme 10

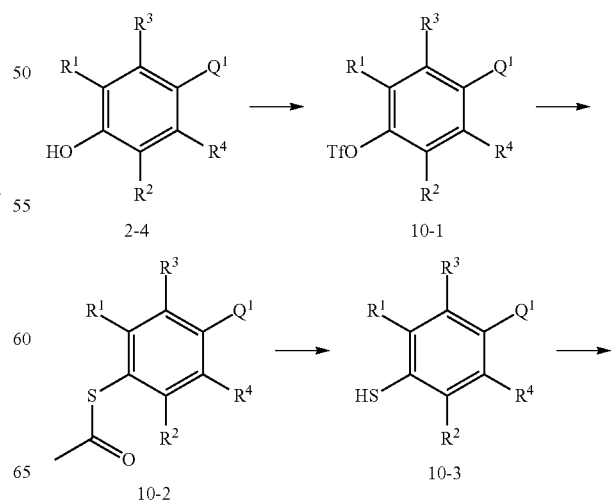

-continued

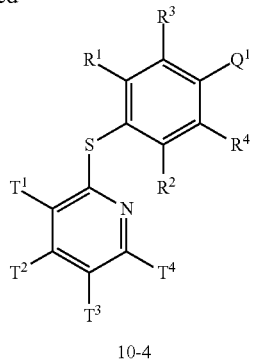

10-4

Scheme 10 refers to preparation of compounds of Formula 10-4. Referring to Scheme 10, a compound of Formula 10-1 can be prepared via triflation of a compound of Formula 2-4 (Scheme 2) using a suitable reagent such as trifluoromethanesulfonic anhydride in the presence of a suitable base such as triethylamine. A compound of Formula 10-1 can be converted to a compound of Formula 10-2 by coupling with potassium thioacetate, in the presence of a suitable metal catalyst, such as tris(dibenzylideneacetone)dipalladium(0), and a suitable ligand, such as (R)-(−)-1-[($S_P$)-2-(dicyclohexylphosphino)ferrocenyl]ethyldi-tert-butylphosphine, in a suitable solvent, such as toluene. A compound of Formula 10-2 can then be hydrolyzed to obtain a compound of Formula 10-3, which in turn can be coupled with a compound of Formula 1-1 in Scheme 1 to afford a compound of Formula 10-4. The coupling conditions employed may be analogous to those described for the preparation of a compound of Formula 1-3 in Scheme 1. A compound of Formula 10-4 may then be deprotected, using appropriate conditions depending on the selection of the $Pg^1$ group, to obtain a compound of Formula I.

Additional starting materials and intermediates useful for making the compounds of the present invention can be obtained from chemical vendors such as Sigma-Aldrich or can be made according to methods described in the chemical art.

Those skilled in the art can recognize that in all of the Schemes described herein, if there are functional (reactive) groups present on a part of the compound structure such as a substituent group, for example $R^1$, $R^2$, $R^3$, $R^4$, $R^5$, $R^6$, $R^7$, $R^8$, $R^9$, $R^{10}$, $R^{10B}$, $R^{11}$, $R^{11A}$, $T^1$, $T^2$, $T^3$, $T^4$, $Q^1$, and $X^1$ etc., further modification can be made if appropriate and/or desired, using methods well known to those skilled in the art. For example, a —CN group can be hydrolyzed to afford an amide group; a carboxylic acid can be converted to an amide; a carboxylic acid can be converted to an ester, which in turn can be reduced to an alcohol, which in turn can be further modified. For another example, an OH group can be converted into a better leaving group such as a methanesulfonate, which in turn is suitable for nucleophilic substitution, such as by a cyanide ion ($CN^-$). For another example, an —S— can be oxidized to —S(=O)— and/or —S(=O)$_2$—. For yet another example, an unsaturated bond such as C=C or C≡C can be reduced to a saturated bond by hydrogenation. In some embodiments, a primary amine or a secondary amine moiety (present on a substituent group such as $R^3$, $R^4$, $R^9$, $R^{10}$, etc.) can be converted to an amide, sulfonamide, urea, or thiourea moiety by reacting it with an appropriate reagent such as an acid chloride, a sulfonyl chloride, an isocyanate, or a thioisocyanate compound. One skilled in the art will recognize further such modifications. Thus, a compound of Formula I having a substituent that contains a functional group can be converted to another compound of Formula I having a different substituent group.

Similarly, those skilled in the art can also recognize that in all of the schemes described herein, if there are functional (reactive) groups present on a substituent group such as $R^3$, $R^4$, $R^9$, $R^{10}$, etc., these functional groups can be protected/deprotected in the course of the synthetic scheme described here, if appropriate and/or desired. For example, an OH group can be protected by a benzyl, methyl, or acetyl group, which can be deprotected and converted back to the OH group in a later stage of the synthetic process. For another example, an $NH_2$ group can be protected by a benzyloxycarbonyl (Cbz) or Boc group; conversion back to the $NH_2$ group can be carried out at a later stage of the synthetic process via deprotection.

As used herein, the term "reacting" (or "reaction" or "reacted") refers to the bringing together of designated chemical reactants such that a chemical transformation takes place generating a compound different from any initially introduced into the system. Reactions can take place in the presence or absence of solvent.

Compounds of Formula I may exist as stereoisomers, such as atropisomers, racemates, enantiomers, or diastereomers. Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of Formula I (and chiral precursors thereof) may be obtained in enantiomerically enriched form using chromatography, typically HPLC, on an asymmetric resin with a mobile phase consisting of a hydrocarbon, typically heptane or hexane, containing from 0% to 50% 2-propanol, typically from 2% to 20%, and from 0% to 5% of an alkylamine, typically 0.1% diethylamine. Concentration of the eluate affords the enriched mixture. Stereoisomeric conglomerates may be separated by conventional techniques known to those skilled in the art. See, e.g., *Stereochemistry of Organic Compounds* by E. L. Eliel and S. H. Wilen (Wiley, New York, 1994), the disclosure of which is incorporated herein by reference in its entirety. Suitable stereoselective techniques are well-known to those of ordinary skill in the art.

Where a compound of Formula I contains an alkenyl or alkenylene (alkylidene) group, geometric cis/trans (or Z/E) isomers are possible. Cis/trans isomers may be separated by conventional techniques well known to those skilled in the art, for example, chromatography and fractional crystallization. Salts of the present invention can be prepared according to methods known to those of skill in the art.

The compounds of Formula I that are basic in nature are capable of forming a wide variety of salts with various inorganic and organic acids. Although such salts must be pharmaceutically acceptable for administration to animals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the basic compounds of this invention can be prepared by treating the basic compound with a substantially equivalent amount of the selected mineral or organic acid in an aqueous solvent medium or in a suitable organic solvent, such as methanol or ethanol. Upon evaporation of the solvent, the desired solid salt is obtained. The desired acid salt can also be precipitated from a solution of the free base in an organic solvent by adding an appropriate mineral or organic acid to the solution.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, isonicotinic acid, lactic acid, pantothenic acid, bitartric acid, ascorbic acid, 2,5-dihydroxybenzoic acid, gluconic acid, saccharic acid, formic acid, methanesulfonic acid, ethanesulfonic acid, benzenesulfonic acid, p-toluenesulfonic acid, and pamoic [i.e., 4,4'-methanediylbis(3-hydroxynaphthalene-2-carboxylic acid)] acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as ethanesulfonic acid, or the like.

Those compounds of Formula I that are acidic in nature are capable of forming base salts with various pharmacologically acceptable cations. Examples of such salts include the alkali metal or alkaline earth metal salts, and particularly the sodium and potassium salts. These salts are all prepared by conventional techniques. The chemical bases which are used as reagents to prepare the pharmaceutically acceptable base salts of this invention are those which form non-toxic base salts with the acidic compounds of Formula I. These salts may be prepared by any suitable method, for example, treatment of the free acid with an inorganic or organic base, such as an amine (primary, secondary or tertiary), an alkali metal hydroxide or alkaline earth metal hydroxide, or the like. These salts can also be prepared by treating the corresponding acidic compounds with an aqueous solution containing the desired pharmacologically acceptable cations, and then evaporating the resulting solution to dryness, for example under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are, for example, employed in order to ensure completeness of reaction and maximum yields of the desired final product.

Pharmaceutically acceptable salts of compounds of Formula I (including compounds of Formula Ia or Ib) may be prepared by one or more of three methods:

(i) by reacting the compound of Formula I with the desired acid or base;

(ii) by removing an acid- or base-labile protecting group from a suitable precursor of the compound of Formula I or by ring-opening a suitable cyclic precursor, for example, a lactone or lactam, using the desired acid or base; or (iii) by converting one salt of the compound of Formula I to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionization in the resulting salt may vary from completely ionized to almost non-ionized.

Polymorphs can be prepared according to techniques well-known to those skilled in the art, for example, by crystallization.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture may have almost identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, New York, 1994).

The invention also includes isotopically labeled compounds of Formula I wherein one or more atoms is replaced by an atom having the same atomic number, but an atomic mass or mass number different from the atomic mass or mass number usually found in nature. Isotopically labeled compounds of Formula I (or pharmaceutically acceptable salts thereof or N-oxides thereof) can generally be prepared by conventional techniques known to those skilled in the art or by processes analogous to those described herein, using an appropriate isotopically labeled reagent in place of the non-labeled reagent otherwise employed.

Prodrugs in accordance with the invention can, for example, be produced by replacing appropriate functionalities present in the compounds of Formula I with certain moieties known to those skilled in the art as 'pro-moieties' as described, for example, in *Design of Prodrugs* by H. Bundgaard (Elsevier, 1985).

The compounds of Formula I should be assessed for their biopharmaceutical properties, such as solubility and solution stability (across pH), permeability, etc., in order to select the most appropriate dosage form and route of administration for treatment of the proposed indication.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention (or pharmaceutically acceptable salts thereof) and methods for their preparation will be readily apparent to those skilled in the art. Such compositions and methods for their preparation may be found, for example, in *Remington's Pharmaceutical Sciences,* 19th Edition (Mack Publishing Company, 1995).

The compounds of the invention (including pharmaceutically acceptable salts thereof and N-oxides thereof) may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropyl methyl cellulose) and typically comprise a carrier, for example, water, ethanol, polyethylene glycol, propylene glycol, methyl cellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described by Liang and Chen, *Expert Opinion in Therapeutic Patents* 2001, 11, 981-986.

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinized starch and sodium alginate. Generally, the disintegrant will comprise from 1 weight % to 25 weight %, for example, from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulfate. Lubricants generally comprise from 0.25 weight % to 10 weight %, for example, from 0.5 weight % to 3 weight % of the tablet.

Other possible ingredients include anti-oxidants, colorants, flavoring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt-congealed, or extruded before tabletting. The final formulation may comprise one or more layers and may be coated or uncoated; it may even be encapsulated.

The formulation of tablets is discussed in *Pharmaceutical Dosage Forms: Tablets,* Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of Formula I, a film-forming polymer, a binder, a solvent, a humectant, a plasticizer, a stabilizer or emulsifier, a viscosity-modifying agent and a solvent. Some components of the formulation may perform more than one function.

The compound of Formula I (or pharmaceutically acceptable salts thereof or N-oxides thereof) may be water-soluble or insoluble. A water-soluble compound typically comprises from 1 weight % to 80 weight %, more typically from 20 weight % to 50 weight %, of the solutes. Less soluble compounds may comprise a smaller proportion of the composition, typically up to 30 weight % of the solutes. Alternatively, the compound of Formula I may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavorings and flavor enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al., *Pharmaceutical Technology On-line,* 25(2), 1-14 (2001). The use of chewing gum to achieve controlled release is described in WO 00/35298.

The compounds of the invention (including pharmaceutically acceptable salts thereof) may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (for example to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art.

The solubility of compounds of Formula I (including pharmaceutically acceptable salts thereof) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(DL-lactic-coglycolic acid) (PLGA) microspheres.

The compounds of the invention (including pharmaceutically acceptable salts thereof) may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated. See e.g., Finnin and Morgan, *J. Pharm. Sci.* 1999, 88, 955-958.

Other means of topical administration include delivery by electroporation, iontophoresis, phonophoresis, sonophoresis and microneedle or needle-free (e.g., Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention (including pharmaceutically acceptable salts thereof) can also be administered intranasally or by inhalation, typically in the form of a dry powder (either alone; as a mixture, for example, in a dry blend with lactose; or as a mixed component particle, for example, mixed with phospholipids, such as phosphatidylcholine) from a dry powder inhaler, as an aerosol spray from a pressurized container, pump, spray, atomizer (for example an atomizer using electrohydrodynamics to produce a fine mist), or nebulizer, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurized container, pump, spray, atomizer, or nebulizer contains a solution or suspension of the compound(s) of the invention comprising, for example, ethanol, aqueous ethanol, or a suitable alternative agent for dispersing, solubilizing, or extending release of the active, a propellant(s) as solvent and an optional surfactant, such as sorbitan trioleate, oleic acid, or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

Capsules (made, for example, from gelatin or hydroxypropyl methyl cellulose), blisters and cartridges for use in an inhaler or insufflator may be formulated to contain a powder mix of the compound of the invention, a suitable powder base such as lactose or starch and a performance modifier such as L-leucine, mannitol, or magnesium stearate. The lactose may be anhydrous or in the form of the monohydrate. Other suitable excipients include dextran, glucose, maltose, sorbitol, xylitol, fructose, sucrose and trehalose.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation may comprise a compound of Formula I or a pharmaceutically acceptable salt thereof, propylene glycol, sterile water, ethanol and sodium chloride. Alternative solvents which may be used instead of propylene glycol include glycerol and polyethylene glycol.

Suitable flavors, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.01 to 100 mg of the compound of Formula I. The overall daily dose will typically be in the range 1 µg to 200 mg, which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention (including pharmaceutically acceptable salts thereof) may also be administered directly to the eye or ear, typically in the form of drops of a micronized suspension or solution in isotonic, pH-adjusted, sterile saline. Other formulations suitable for ocular and aural administration include ointments, gels, biodegradable (e.g., absorbable gel sponges, collagen) and non-biodegradable (e.g., silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropyl methyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention (including pharmaceutically acceptable salts thereof) may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e., as a carrier, diluent, or solubilizer. Most commonly used for these purposes are alpha-, beta- and gamma-cyclodextrins, examples of which may be found in International Patent Applications Nos. WO 91/11172, WO 94/02518 and WO 98/55148.

Since the present invention has an aspect that relates to the treatment of the disease/conditions described herein with a combination of active ingredients which may be administered separately, the invention also relates to combining separate pharmaceutical compositions in kit form. The kit comprises two separate pharmaceutical compositions: a compound of Formula I a prodrug thereof or a salt of such compound or prodrug and a second compound as described above. The kit comprises means for containing the separate compositions such as a container, a divided bottle or a divided foil packet. Typically the kit comprises directions for the administration of the separate components. The kit form is particularly advantageous when the separate components are for example administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. In some embodiments, the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, etc. . . . Second Week, Monday, Tuesday, . . . " etc. Other variations of memory aids will be readily apparent. A "daily dose" can be a single tablet or capsule or several pills or capsules to be taken on a given day. Also, a daily dose of Formula I compound can consist of one tablet or capsule while a daily dose of the second compound can consist of several tablets or capsules and vice versa. The memory aid should reflect this.

In another specific embodiment of the invention, a dispenser designed to dispense the daily doses one at a time in the order of their intended use is provided. For example, the dispenser is equipped with a memory aid, so as to further facilitate compliance with the regimen. An example of such a memory aid is a mechanical counter which indicates the number of daily doses that has been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

The invention will be described in greater detail by way of specific examples. The following examples are offered for illustrative purposes, and are not intended to limit the invention in any manner. Those of skill in the art will readily recognize a variety of non-critical parameters that can be changed or modified to yield essentially the same results. Additional compounds within the scope of this invention may be prepared using the methods illustrated in these Examples, either alone or in combination with techniques generally known in the art. In the following Examples and Preparations, "DMSO" means dimethyl sulfoxide, "N" where referring to concentration means Normal, "M" means molar, "mL" means milliliter, "mmol" means millimoles, "μmol" means micromoles, "eq." means equivalent, "° C." means degrees Celsius, "MHz" means megahertz, "HPLC" means high-performance liquid chromatography.

EXAMPLES

Experiments were generally carried out under inert atmosphere (nitrogen or argon), particularly in cases where oxygen- or moisture-sensitive reagents or intermediates were employed. Commercial solvents and reagents were generally used without further purification.

Anhydrous solvents were employed where appropriate, generally AcroSeal® products from Acros Organics or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide and tetrahydrofuran; b) <180 ppm for methanol, ethanol, 1,4-dioxane and diisopropylamine. For very sensitive reactions, solvents were further treated with metallic sodium, calcium hydride or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate atropisomers (or atropenantiomers) of certain compounds of the invention. In some examples, the optical rotation of an atropisomer was measured using a polarimeter. According to its observed rotation data (or its specific rotation data), an atropisomer (or atropenantiomer) with a clockwise rotation was designated as the (+)-atropisomer [or the (+) atropenantiomer] and an atropisomer (or atropenantiomer) with a counter-clockwise rotation was designated as the (−)-atropisomer [or the (−) atropenantiomer].

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate $R_f$s or retention times.

Examples 1 and 2

(+)-6-{4-[(3-Cyclopropylpyridin-2-yl)oxy]-2-methylphenyl}-1,5-dimethylpyrimidine-2,4(1H,3H)-dione (1) and (−)-6-{4-[(3-Cyclopropylpyridin-2-yl)oxy]-2-methylphenyl}-1,5-dimethylpyrimidine-2,4(1H,3H)-dione (2)

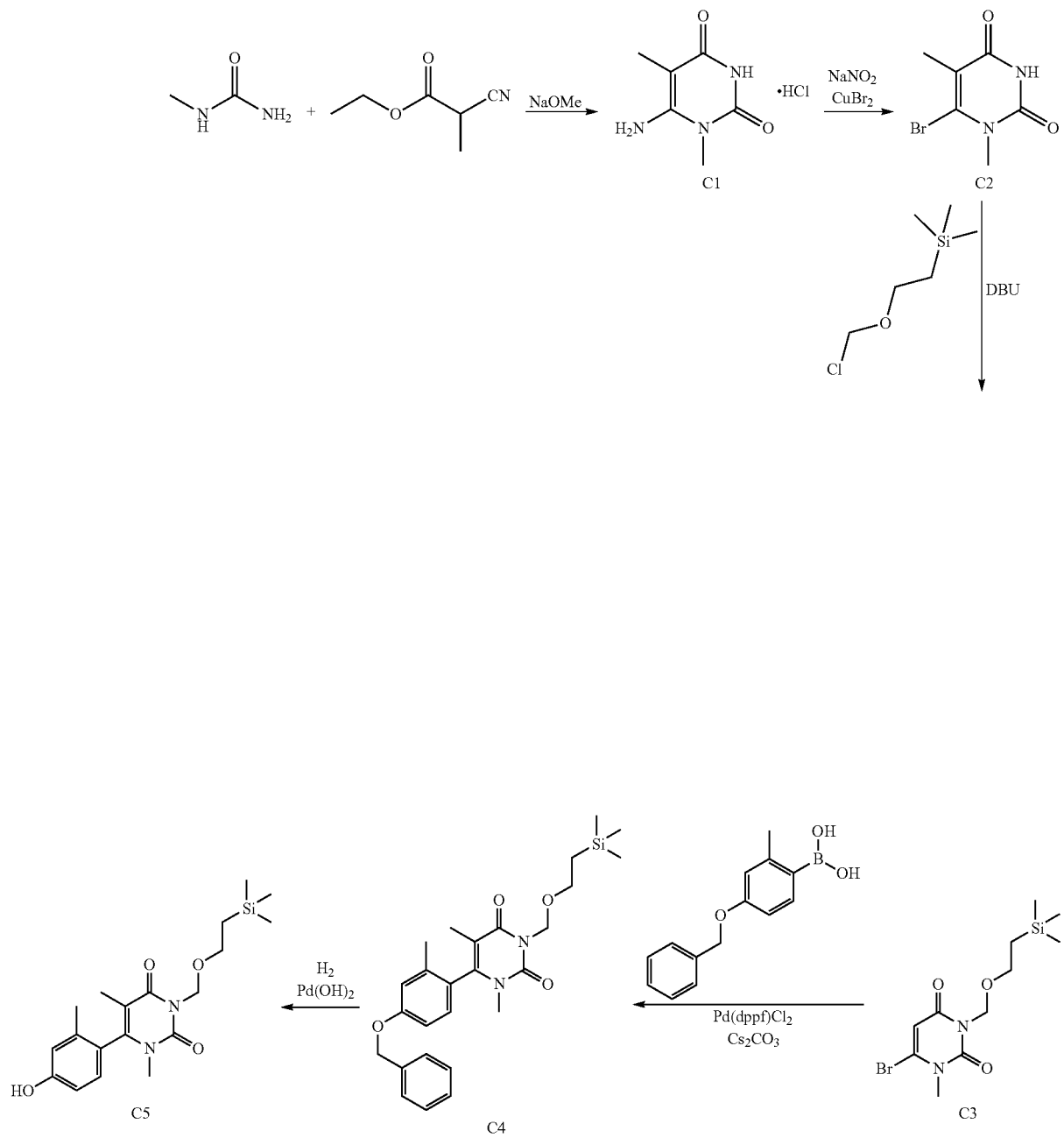

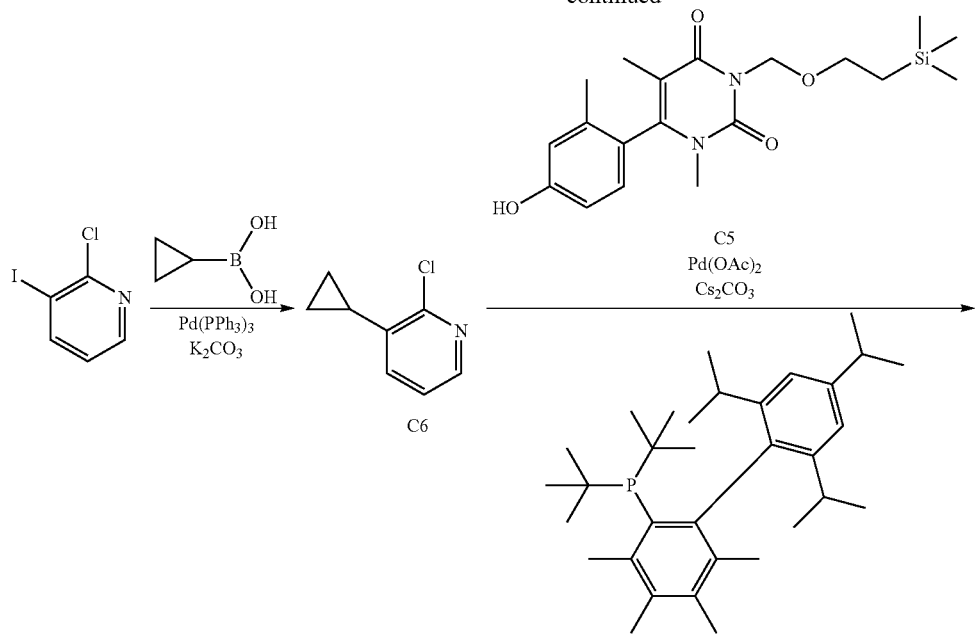
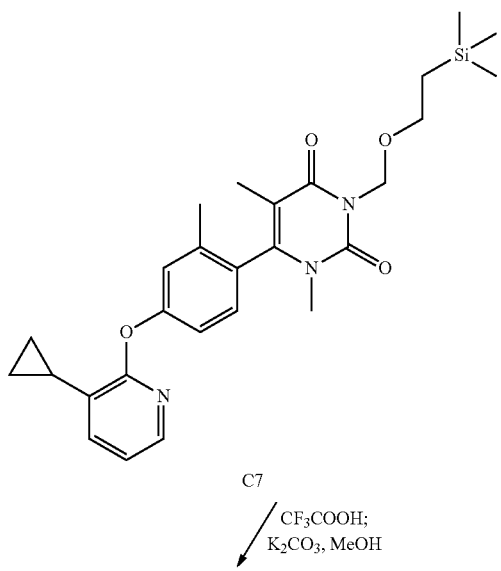
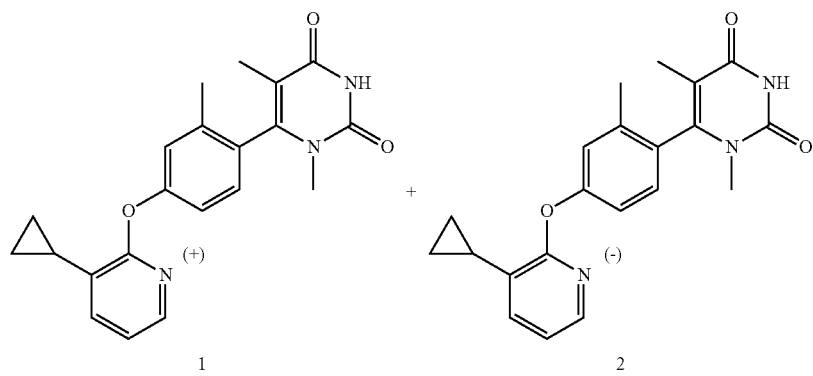

Step 1. Synthesis of 6-amino-1,5-dimethylpyrimidine-2,4(1H,3H)-dione, hydrochloride salt (C1)

A solution of sodium methoxide in methanol (4.4 M, 27 mL, 119 mmol) was added to a solution of ethyl 2-cyanopropanoate (95%, 13.2 mL, 99.6 mmol) and 1-methylurea (98%, 8.26 g, 109 mmol) in methanol (75 mL), and the reaction mixture was heated at reflux for 18 hours, then cooled to room temperature. After removal of solvent in vacuo, the residue was repeatedly evaporated under reduced pressure with acetonitrile (3×50 mL), then partitioned between acetonitrile (100 mL) and water (100 mL). Aqueous 6 M hydrochloric acid was slowly added until the pH had reached approximately 2; the resulting mixture was stirred for 1 hour. The precipitate was collected via filtration and washed with tert-butyl methyl ether, affording the product as a white solid. Yield: 15.2 g, 79.3 mmol, 80%. LCMS m/z 156.1 [M+H]$^+$. $^1$H NMR (400 MHz, DMSO-d$_6$) δ 10.38 (br s, 1H), 6.39 (s, 2H), 3.22 (s, 3H), 1.67 (s, 3H).

Step 2. Synthesis of 6-bromo-1,5-dimethylpyrimidine-2,4(1H,3H)-dione (C2)

A 1:1 mixture of acetonitrile and water (120 mL) was added to a mixture of C1 (9.50 g, 49.6 mmol), sodium nitrite (5.24 g, 76 mmol), and copper(II) bromide (22.4 g, 100 mmol) {Caution: bubbling and slight exotherm!}, and the reaction mixture was allowed to stir at room temperature for 66 hours. Addition of aqueous sulfuric acid (1 N, 200 mL) and ethyl acetate (100 mL) provided a precipitate, which was collected via filtration and washed with water and ethyl acetate to afford the product as a light yellow solid (7.70 g). The organic layer of the filtrate was concentrated to a smaller volume, during which additional precipitate formed; this was isolated via filtration and washed with 1:1 ethyl acetate/heptane to provide additional product (0.4 g). Total yield: 8.1 g, 37 mmol, 75%. GCMS m/z 218, 220 [M+]. $^1$H NMR (400 MHz, DMSO-d$_6$) δ 11.58 (br s, 1H), 3.45 (s, 3H), 1.93 (s, 3H).

Step 3. Synthesis of 6-bromo-1,5-dimethyl-3-{[2-(trimethylsilyl)ethoxy]methyl}pyrimidine-2,4(1H,3H)-dione (C3)

To a mixture of C2 (21.9 g, 99.8 mmol) and 2-(trimethylsilyl)ethoxymethyl chloride (20 g, 120 mmol) in acetonitrile (400 mL) was added 1,8-diazabicyclo[5.4.0]undec-7-ene (DBU, 18.3 g, 120 mmol), and the reaction mixture was stirred at 60° C. for 18 hours. Additional 2-(trimethylsilyl)ethoxymethyl chloride (5 g, 30 mmol) and 1,8-diazabicyclo[5.4.0]undec-7-ene (4.6 g, 30 mmol) were added, and stirring was continued at 60° C. for 18 hours. After the mixture had been concentrated in vacuo, the residue was diluted with water (500 mL) and extracted with ethyl acetate (3×300 mL). The combined organic layers were concentrated; purification using chromatography on silica gel (Gradient: 20% to 50% ethyl acetate in petroleum ether) afforded the product as a colorless oil. Yield: 22.5 g, 64.4 mmol, 64%. $^1$H NMR (400 MHz, CDCl$_3$) δ 5.41 (s, 2H), 3.61-3.72 (m, 5H), 2.13 (s, 3H), 0.93-1.02 (m, 2H), 0.00 (s, 9H).

Step 4. Synthesis of 6-[4-(benzyloxy)-2-methylphenyl]-1,5-dimethyl-3-{[2-(trimethylsilyl)ethoxy]methyl}pyrimidine-2,4(1H,3H)-dione (C4)

To a mixture of C3 (10 g, 29 mmol), [4-(benzyloxy)-2-methylphenyl]boronic acid (10.4 g, 43.0 mmol) and cesium carbonate (28 g, 86 mmol) in 1,4-dioxane (400 mL) was added [1,1'-bis(diphenylphosphino)ferrocene]dichloropalladium(II) (2.2 g, 3.0 mmol). The reaction mixture was heated at reflux for 4 hours, then filtered. The filtrate was concentrated, and the residue was purified by silica gel chromatography (Gradient: 10% to 20% ethyl acetate in petroleum ether) to provide the product as a light yellow solid. Yield: 10 g, 21 mmol, 72%. $^1$H NMR (400 MHz, CDCl$_3$) δ 7.34-7.49 (m, 5H), 7.00 (d, half of AB quartet, J=8.3 Hz, 1H), 6.91-6.97 (m, 2H), 5.50 (AB quartet, J$_{AB}$=9.2 Hz, Δν$_{AB}$=4.1 Hz, 2H), 5.10 (s, 2H), 3.73-3.79 (m, 2H), 3.03 (s, 3H), 2.15 (s, 3H), 1.65 (s, 3H), 1.00-1.06 (m, 2H), 0.03 (s, 9H).

Step 5. Synthesis of 6-(4-hydroxy-2-methylphenyl)-1,5-dimethy-3-{[2-(trimethylsilyl)ethoxy]methyl}pyrimidine-2,4(1H,3H)-dione (C5)

A mixture of C4 (10 g, 21 mmol) and palladium hydroxide (2 g, dry) in methanol (300 mL) was stirred at room temperature for 24 hours under 40 psi of hydrogen. After filtration of the reaction mixture, the filtrate was concentrated to provide the product as a light yellow solid. Yield: 8.0 g, 21 mmol, 100%. $^1$H NMR (400 MHz, CDCl$_3$) δ 6.92 (d, half of AB quartet, J=8.2 Hz, 1H), 6.81-6.87 (m, 2H), 5.52 (AB quartet, J$_{AB}$=9.5 Hz, Δν$_{AB}$=2.7 Hz, 2H), 3.73-3.80 (m, 2H), 3.03 (s, 3H), 2.11 (s, 3H), 1.65 (s, 3H), 0.99-1.05 (m, 2H), 0.01 (s, 9H).

Step 6. Synthesis of 2-chloro-3-cyclopropylpyridine (C6)

To a mixture of 2-chloro-3-iodopyridine (2.39 g, 9.98 mmol), cyclopropylboronic acid (860 mg, 10 mmol) and potassium carbonate (4.14 g, 30.0 mmol) in 1,4-dioxane (50 mL) was added tetrakis(triphenylphosphine)palladium(0) (1.16 g, 1.00 mmol). The reaction mixture was stirred at 120° C. for 4 hours, then diluted with ethyl acetate (50 mL) and filtered. The filtrate was concentrated and the residue was purified by silica gel chromatography (Gradient: 10% to 30% ethyl acetate in petroleum ether) to afford the product as a colorless oil. Yield: 1 g, 6 mmol, 60%. $^1$H NMR (400 MHz, CDCl$_3$) δ 8.20 (dd, J=4.7, 1.8 Hz, 1H), 7.24-7.28 (m, 1H), 7.14 (br dd, J=7.6, 4.8 Hz, 1H), 2.12-2.21 (m, 1H), 1.04-1.11 (m, 2H), 0.67-0.72 (m, 2H).

Step 7. Synthesis of 6-{4-[(3-cyclopropylpyridin-2-yl)oxy]-2-methylphenyl}-1,5-dimethyl-3-{[2-(trimethylsilyl)ethoxy]methyl}pyrimidine-2,4(1H,3H)-dione (C7)

Palladium(II) acetate (61 mg, 0.27 mmol) and di-tert-butyl[3,4,5,6-tetramethyl-2',4',6'-tri(propan-2-yl)biphenyl-2-yl]phosphane (130 mg, 0.27 mmol) were added to a mixture of C6 (615 mg, 4.00 mmol), C5 (1.0 g, 2.6 mmol) and cesium carbonate (2.6 g, 8.0 mmol) in 1,4-dioxane (25 mL). The reaction mixture was stirred at 120° C. under microwave irradiation for 5 hours, then diluted with ethyl acetate (50 mL) and filtered. After removal of solvents in vacuo, the residue was purified via silica gel chromatography (Gradient: 0% to 25% ethyl acetate in petroleum ether) to provide the product as a yellow gum. Yield: 900 mg, 1.8 mmol, 69%. LCMS m/z 494.1 [M+H]$^+$. $^1$H NMR (400 MHz, CDCl$_3$) δ 8.02 (dd, J=4.8, 1.8 Hz, 1H), 7.30 (dd, J=7.4, 1.8 Hz, 1H), 7.11-7.14 (m, 1H), 7.08-7.10 (m, 2H), 7.01 (dd, J=7.5, 4.8 Hz, 1H), 5.51 (AB quartet, J$_{AB}$=9.3 Hz, Δv$_{AB}$=3.8 Hz, 2H), 3.74-3.80 (m, 2H), 3.08 (s, 3H), 2.18 (s, 3H), 2.16-2.24 (m, 1H), 1.70 (s, 3H), 1.00-1.06 (m, 4H), 0.74-0.79 (m, 2H), 0.03 (s, 9H).

Step 8. Synthesis of (+)-6-{4-[(3-cyclopropylpyridin-2-yl)oxy]-2-methylphenyl}-1,5-dimethylpyrimidine-2,4(1H,3H)-dione (1) and (−)-6-{4-[(3-cyclopropylpyridin-2-yl)oxy]-2-methylphenyl}-1,5-dimethylpyrimidine-2,4(1H, 3H)-dione (2)

Trifluoroacetic acid (1.5 mL) was added to a solution of C7 (875 mg, 1.77 mmol) in dichloromethane (8 mL). The reaction mixture was stirred at room temperature for 2 hours and concentrated in vacuo; the residue was dissolved in methanol (10 mL), treated with potassium carbonate (1.22 g, 8.83 mmol) and stirred at room temperature for 18 hours. After removal of solids via filtration, the filtrate was concentrated under reduced pressure and partitioned between ethyl acetate and water. The aqueous layer was extracted three times with ethyl acetate, and the combined organic layers were washed sequentially with water and with saturated aqueous sodium chloride solution, dried over sodium sulfate, filtered, and concentrated in vacuo. Purification via silica gel chromatography (Gradient: 0% to 100% ethyl acetate in heptane) afforded a mixture of 1 and 2, which was separated via reversed phase chiral chromatography (Column: Chiral Technologies, Chiralpak IA; Gradient: heptane in ethanol). The first-eluting atropenantiomer, obtained as a solid that exhibited a positive (+) rotation, was designated as Example 1. Yield: 210 mg, 0.578 mmol, 33%. The second-eluting atropenantiomer, also obtained as a solid but with a negative (−) rotation, was designated as Example 2. Yield: 190 mg, 0.523 mmol, 30%. 1: LCMS m/z 364.2 [M+H]$^+$. $^1$H NMR (400 MHz, CD$_3$OD) δ 7.94 (br d, J=5 Hz, 1H), 7.48 (br d, J=7.6 Hz, 1H), 7.22 (d, J=8.2 Hz, 1H), 7.03-7.14 (m, 3H), 3.04 (s, 3H), 2.20 (s, 3H), 2.15-2.23 (m, 1H), 1.63 (s, 3H), 0.99-1.06 (m, 2H), 0.75-0.82 (m, 2H). 2: LCMS m/z 364.2 [M+H]$^+$. $^1$H NMR (400 MHz, CD$_3$OD) δ 7.94 (dd, J=4.8, 1.7 Hz, 1H), 7.48 (dd, J=7.5, 1.8 Hz, 1H), 7.22 (d, J=8.3 Hz, 1H), 7.09-7.14 (m, 2H), 7.06 (dd, J=8.4, 2.3 Hz, 1H), 3.04 (s, 3H), 2.20 (s, 3H), 2.15-2.23 (m, 1H), 1.63 (s, 3H), 0.99-1.06 (m, 2H), 0.75-0.82 (m, 2H).

Examples 3 and 4

(−)-6-{4-[(3-Chloro-5-fluoropyridin-2-yl)oxy]-2-methylphenyl}-1,5-dimethylpyrimidine-2,4(1H,3H)-dione (3) and (+)-6-{4-[(3-Chloro-5-fluoropyridin-2-yl)oxy]-2-methylphenyl}-1,5-dimethylpyrimidine-2,4(1H,3H)-dione (4)

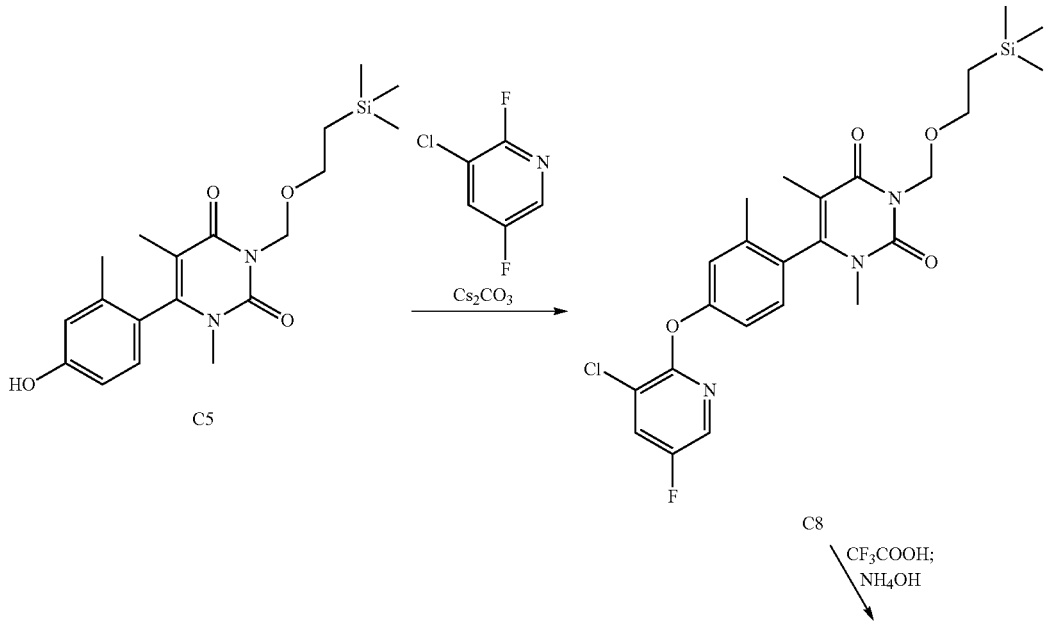

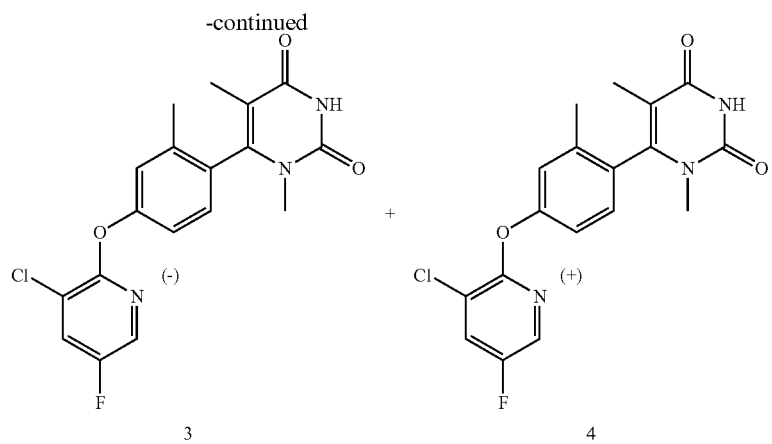

Step 1. Synthesis of 6-{4-[(3-chloro-5-fluoropyridin-2-yl)oxy]-2-methylphenyl}-1,5-dimethyl-3-{[2-(trimethylsilyl) ethoxy]methyl}pyrimidine-2,4(1H, 3H)-dione (C8)

Cesium carbonate (476 mg, 1.46 mmol) was added to a mixture of 3-chloro-2,5-difluoropyridine (97%, 150 mg, 0.97 mmol) and C5 (366 mg, 0.972 mmol) in dimethyl sulfoxide (5 mL), and the reaction mixture was stirred at 80° C. for 6 hours. Water was added, and the mixture was extracted three times with ethyl acetate; the combined organic layers were washed with saturated aqueous sodium chloride solution, dried over sodium sulfate, filtered, and concentrated in vacuo. Silica gel chromatography (Gradient: 10% to 40% ethyl acetate in heptane) provided the product as a sticky solid. Yield: 414 mg, 0.818 mmol, 84%. $^1$H NMR (400 MHz, CDCl$_3$) δ 7.96 (d, J=2.7 Hz, 1H), 7.64 (dd, J=7.1, 2.7 Hz, 1H), 7.09-7.15 (m, 3H), 5.51 (AB quartet, $J_{AB}$=9.3 Hz, $\Delta v_{AB}$=3.4 Hz, 2H), 3.74-3.80 (m, 2H), 3.07 (s, 3H), 2.19 (s, 3H), 1.69 (s, 3H), 1.00-1.06 (m, 2H), 0.03 (s, 9H).

Step 2. Synthesis of (−)-6-{4-[(3-chloro-5-fluoropyridin-2-yl)oxy]-2-methylphenyl}-1,5-dimethylpyrimidine-2,4(1H,3H)-dione (3) and (+)-6-{4-[(3-chloro-5-fluoropyridin-2-yl)oxy]-2-methylphenyl}-1,5-dimethylpyrimidine-2,4(1H, 3H)-dione (4)

Trifluoroacetic acid (812 μL, 10.9 mmol) was added to a solution of C8 (187 mg, 0.370 mmol) in dichloromethane (3.0 mL), and the reaction mixture was stirred at room temperature for 1 hour. Solvents were removed in vacuo, and the residue was taken up in tetrahydrofuran (4.5 mL) and treated with concentrated aqueous ammonium hydroxide (9 mL). After 4 hours, the reaction mixture was concentrated under reduced pressure, combined with the crude product from an identical reaction carried out on C8 (200 mg, 0.395 mmol), and purified via chromatography on silica gel (Gradient: 20% to 40% ethyl acetate in heptane), to provide the racemic product as a white solid. Yield: 219 mg, 0.583 mmol, 76%. This was separated into its atropenantiomers via chiral chromatography (Column: Phenomenex Lux Cellulose-1; Gradient: 50% to 100% ethanol in heptane). The first-eluting atropenantiomer, which was obtained as a white solid, exhibited a negative (−) rotation and was designated as Example 3. Yield: 25 mg, 66 μmol, 9%. The second-eluting atropenantiomer was also a white solid, but exhibited a positive (+) rotation; this was designated as Example 4. Yield: 62 mg, 160 μmol, 21%. 3: LCMS m/z 376.1, 378.0 [M+H]$^+$. $^1$H NMR (400 MHz, CDCl$_3$) δ 8.35 (br s, 1H), 7.97 (d, J=2.7 Hz, 1H), 7.64 (dd, J=7.1, 2.8 Hz, 1H), 7.11-7.16 (m, 3H), 3.04 (s, 3H), 2.20 (s, 3H), 1.67 (s, 3H). 4: LCMS m/z 376.2, 378.2 [M+H]$^+$. $^1$H NMR (400 MHz, CDCl$_3$) δ 8.46 (br s, 1H), 7.97 (d, J=2.7 Hz, 1H), 7.64 (dd, J=7.1, 2.7 Hz, 1H), 7.12-7.16 (m, 3H), 3.04 (s, 3H), 2.20 (br s, 3H), 1.67 (s, 3H).

Example 5

6-{4-[(3-Chloropyridin-2-yl)oxy]-2-methylphenyl}-1-ethyl-5-methylpyrimidine-2,4(1H,3H)-dione (5)

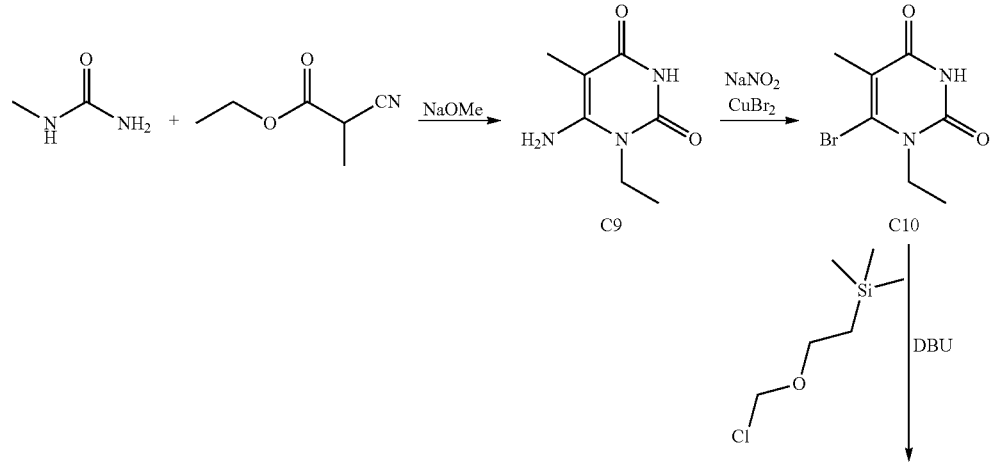

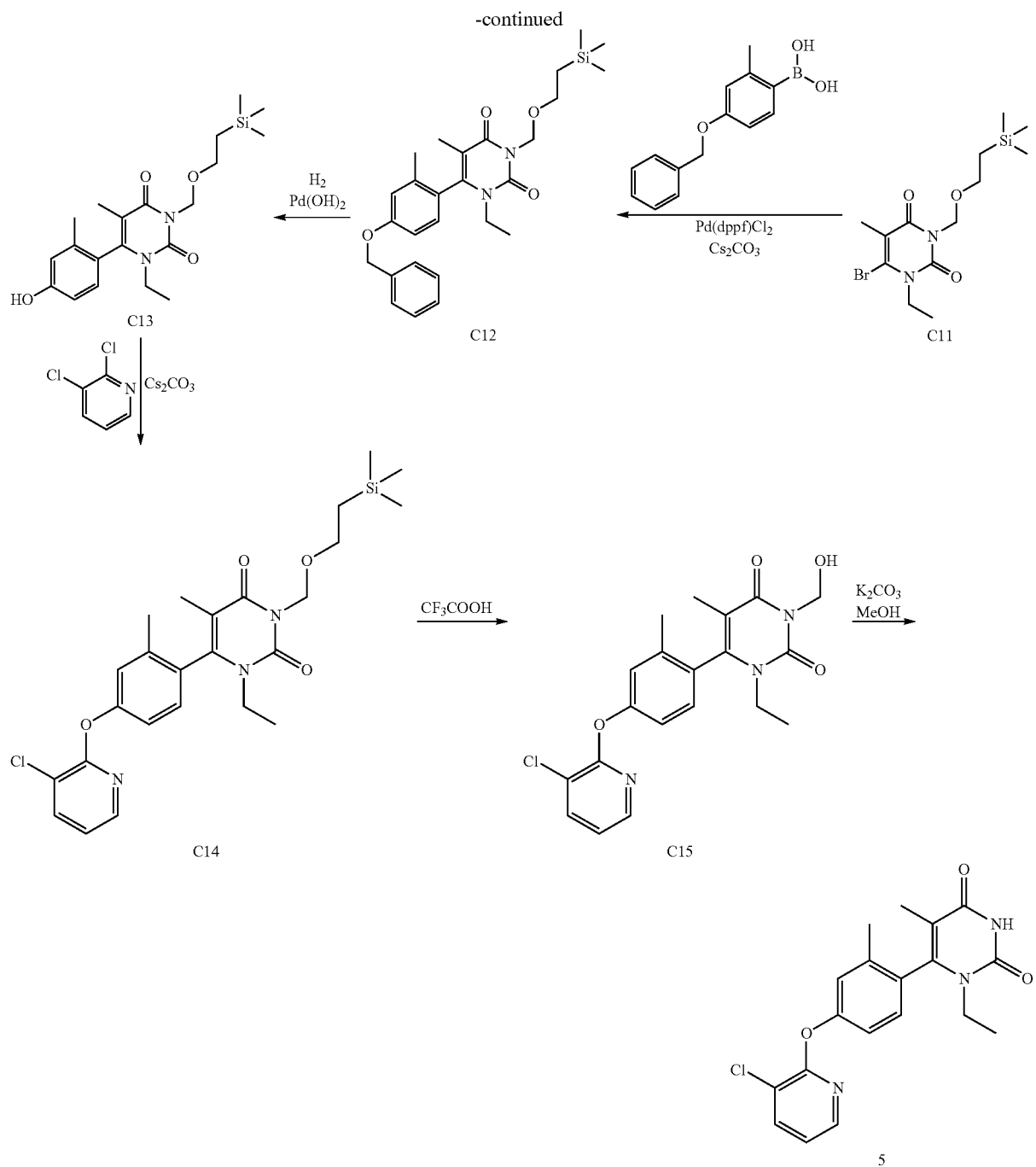

Step 1. Synthesis of 6-amino-1-ethyl-5-methylpyrimidine-2,4(1H,3H)-dione (C9)

Sodium hydride (1.84 g, 76.7 mmol) was added in portions to a solution of 1-ethylurea (5.7 g, 65 mmol) and ethyl 2-cyanopropanoate (7.5 g, 59 mmol) in methanol (60 mL) that had been cooled to 0 to 5° C. The reaction mixture was stirred for 18 hours and then was concentrated in vacuo. Acetonitrile (200 mL) was added, and the mixture was again concentrated to dryness. The residue was diluted with a mixture of acetonitrile (100 mL) and water (30 mL); 12 M aqueous hydrochloric acid was added drop-wise until the pH was approximately 1-2. After the mixture had been stirred for 1 hour, the precipitate was collected via filtration and washed with tert-butyl methyl ether, affording the product as a white solid. Yield: 8.15 g, 48.2 mmol, 82%. $^1$H NMR (400 MHz, DMSO-$d_6$) δ 3.84 (q, J=6.9 Hz, 2H), 1.66 (s, 3H), 1.07 (t, J=7.0 Hz, 3H).

Step 2. Synthesis of 6-bromo-1-ethyl-5-methylpyrimidine-2,4(1H,3H)-dione (C10)

To a solution of C9 (6.2 g, 36.6 mmol) in a 1:1 mixture of acetonitrile and water (70 mL) were added sodium nitrite (3.8 g, 55 mmol) and copper(II) bromide (16.4 g, 73.4 mmol), and the reaction mixture was stirred for 18 hours at room temperature. A mixture of 1 N aqueous sulfuric acid (100 mL) and ethyl acetate (50 mL) was added, and stirring was continued for 1 hour, at which time the organic layer was separated, and the aqueous layer was extracted with dichloromethane (2×100 mL). The combined organic layers were concentrated in vacuo; silica gel chromatography (Gradient: 0% to 50% ethyl acetate in petroleum ether) provided the product as a green solid. Yield: 5.0 g, 21 mmol, 57%. $^1$H NMR (400 MHz, CDCl$_3$) δ 8.87 (br s, 1H), 4.21 (q, J=7.0 Hz, 2H), 2.11 (s, 3H), 1.32 (t, J=7.0 Hz, 3H).

Step 3. Synthesis of 6-bromo-1-ethyl-5-methyl-3-{[2-(trimethylsilyl)ethoxy]methyl}pyrimidine-2,4(1H,3H)-dione (C11)

Compound C10 was converted to the product using the method described for synthesis of C3 in Examples 1 and 2. The product was obtained as a yellow gum. Yield: 1.28 g, 3.52 mmol, 17%. $^1$H NMR (400 MHz, CDCl$_3$) δ 5.41 (s, 2H), 4.24 (q, J=7.1 Hz, 2H), 3.65-3.72 (m, 2H), 2.13 (s, 3H), 1.31 (t, J=7.1 Hz, 3H), 0.94-1.01 (m, 2H), 0.00 (s, 9H).

Step 4. Synthesis of 6-[4-(benzyloxy)-2-methylphenyl]-1-ethyl-5-methyl-3-{[2-(trimethylsilyl)ethoxy]methyl}pyrimidine-2,4(1H,3H)-dione (C12)

Compound C11 was converted to the product using the method described for synthesis of C4 in Examples 1 and 2. The product was obtained as a yellow gum. Yield: 1.09 g, 2.27 mmol, 78%. $^1$H NMR (400 MHz, CDCl$_3$) δ 7.34-7.49 (m, 5H), 7.05 (d, J=8.2 Hz, 1H), 6.91-6.97 (m, 2H), 5.50 (s, 2H), 5.10 (s, 2H), 3.79-3.89 (m, 1H), 3.74-3.80 (m, 2H), 3.23-3.34 (m, 1H), 2.15 (s, 3H), 1.62 (s, 3H), 1.00-1.07 (m, 5H), 0.03 (s, 9H).

Step 5. Synthesis of 1-ethyl-6-(4-hydroxy-2-methylphenyl)-5-methyl-3-{[2-(trimethylsilyl)ethoxy]methyl}pyrimidine-2,4(1H,3H)-dione (C13)

The product, obtained as a gray solid, was synthesized from C12 using the method described for synthesis of C5 in Examples 1 and 2. Yield: 800 mg, 2.05 mmol, 90%. $^1$H NMR (400 MHz, CDCl$_3$) δ 6.99 (d, J=8.2 Hz, 1H), 6.79-6.85 (m, 2H), 5.51 (s, 2H), 3.79-3.89 (m, 1H), 3.73-3.80 (m, 2H), 3.24-3.34 (m, 1H), 2.12 (s, 3H), 1.62 (s, 3H), 0.99-1.06 (m, 5H), 0.02 (s, 9H).

Step 6. Synthesis of 6-{4-[(3-chloropyridin-2-yl)oxy]-2-methylphenyl}-1-ethyl-5-methyl-3-{[2-(trimethylsilyl)ethoxy]methyl}pyrimidine-2,4(1H,3H)-dione (C14)

Cesium carbonate (127 mg, 0.390 mmol) and C13 (50 mg, 0.13 mmol) were added to a solution of 2,3-dichloropyridine (38 mg, 0.26 mmol) in dimethyl sulfoxide (3 mL), and the reaction mixture was heated at 80° C. for 18 hours. After removal of solids via filtration, the filtrate was partitioned between ethyl acetate (20 mL) and water (20 mL), and the aqueous layer was extracted with ethyl acetate (2×20 mL). The combined organic layers were concentrated in vacuo and the residue was purified by preparative thin-layer chromatography on silica gel (Eluent: 3:1 petroleum ether/ethyl acetate) to afford the product as a yellow gum. Yield: 31 mg, 62 μmol, 48%. $^1$H NMR (400 MHz, CDCl$_3$) δ 8.08 (dd, J=4.7, 1.4 Hz, 1H), 7.81 (dd, J=7.7, 1.4 Hz, 1H), 7.11-7.19 (m, 3H), 7.05 (dd, J=7.6, 4.9 Hz, 1H), 5.50 (s, 2H), 3.81-3.93 (m, 1H), 3.72-3.80 (m, 2H), 3.25-3.37 (m, 1H), 2.19 (s, 3H), 1.65 (s, 3H), 0.98-1.10 (m, 5H), 0.02 (s, 9H).

Step 7. Synthesis of 6-{4-[(3-chloropyridin-2-yl)oxy]-2-methylphenyl}-1-ethyl-3-(hydroxymethyl)-5-methylpyrimidine-2,4(1H,3H)-dione (C15)

Compound C14 (31 mg, 62 μmol) was treated with trifluoroacetic acid (3 mL), and the reaction mixture was stirred at room temperature for 1 hour. Removal of solvent in vacuo provided the product (24.8 mg), which was used for the next step without further purification.

Step 8. Synthesis of 6-{4-[(3-chloropyridin-2-yl)oxy]-2-methylphenyl}-1-ethyl-5-methylpyrimidine-2,4(1H,3H)-dione (5)

To a solution of C15 (from the previous step, 24.8 mg, <62 μmol) in methanol (5 mL) was added potassium carbonate (83 mg, 0.60 mmol), and the reaction mixture was stirred at room temperature for 1 hour. After removal of solids via filtration, the filtrate was concentrated and the residue was purified by preparative thin-layer chromatography on silica gel (Eluent: 20:1 dichloromethane/methanol) to afford the product as a white solid. Yield: 7.7 mg, 21 μmol, 34% over two steps. LCMS m/z 372.0 [M+H]$^+$. $^1$H NMR (400 MHz, CD$_3$OD) δ 8.07 (dd, J=4.8, 1.5 Hz, 1H), 7.98 (dd, J=7.8, 1.6 Hz, 1H), 7.32 (d, J=8.2 Hz, 1H), 7.12-7.21 (m, 3H), 3.78-3.89 (m, 1H), 3.27-3.38 (m, 1H, assumed; partially obscured by solvent peak), 2.21 (s, 3H), 1.60 (s, 3H), 1.07 (t, J=7.1 Hz, 3H).

Example 6

6-{4-[(3-Chloropyridin-2-yl)oxy]-2-methylphenyl}-5-ethyl-1-methylpyrimidine-2,4(1H,3H)-dione (6)

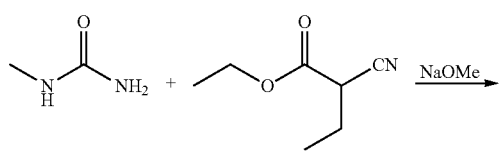

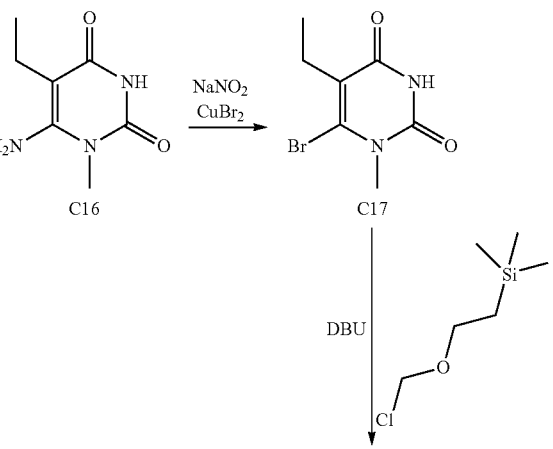

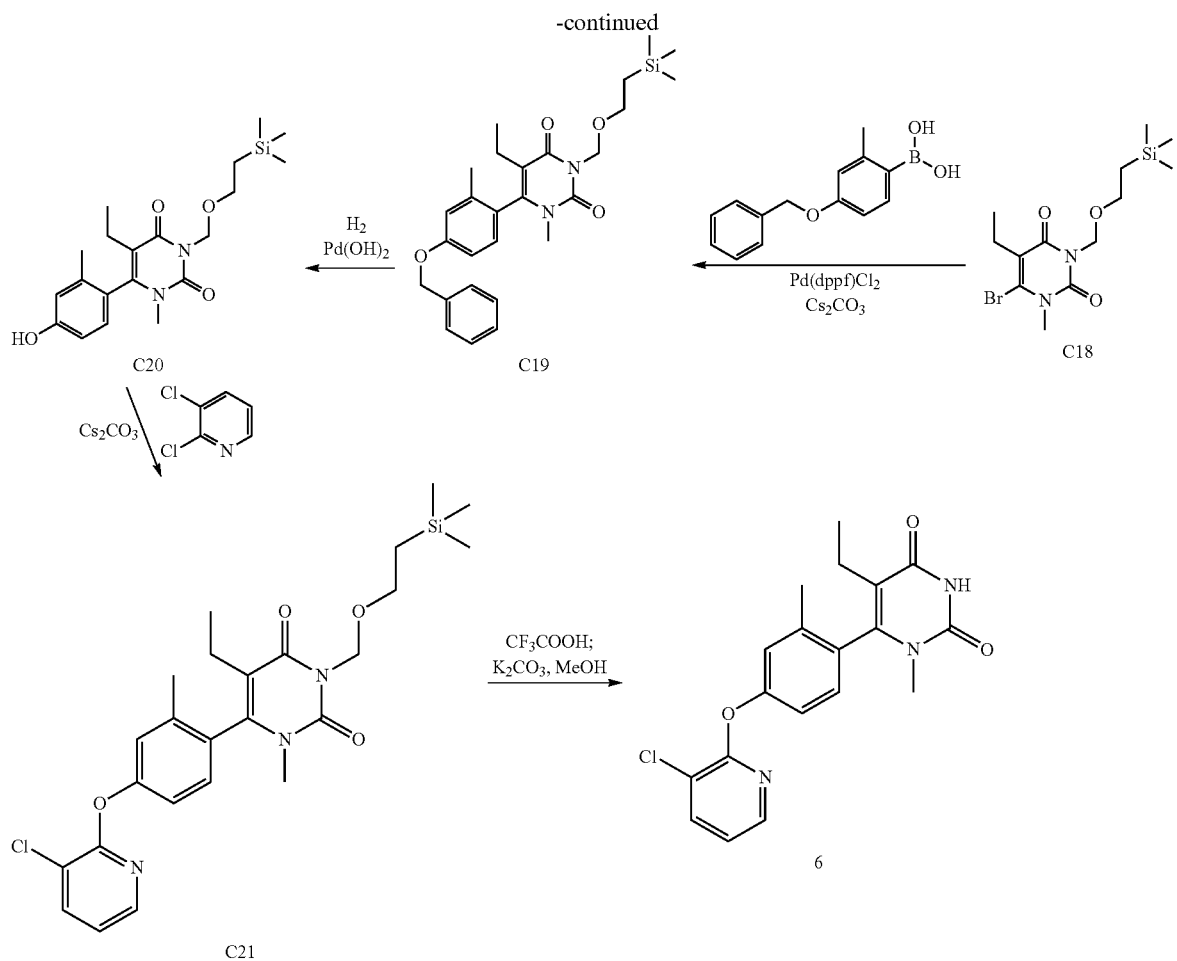

Step 1. Synthesis of 6-amino-5-ethyl-1-methylpyrimidine-2,4(1H,3H)-dione (C16)

Ethyl 2-cyanobutanoate was reacted with 1-methylurea according to the method described for synthesis of C9 in Example 5. The product was obtained as a white solid. Yield: 5.95 g, 35.2 mmol, 66%. $^1$H NMR (400 MHz, DMSO-$d_6$) δ 10.36 (s, 1H), 6.41 (s, 2H), 3.22 (s, 3H), 2.22 (q, J=7.3 Hz, 2H), 0.87 (t, J=7.3 Hz, 3H).

Step 2. Synthesis of 6-bromo-5-ethyl-1-methylpyrimidine-2,4(1H,3H)-dione (C17)

To a solution of C16 (5.95 g, 35.2 mmol) in a 1:1 mixture of acetonitrile and water (80 mL) were added sodium nitrite (3.6 g, 52 mmol) and copper(II) bromide (15.7 g, 70.3 mmol), and the reaction mixture was stirred for 18 hours at room temperature. A mixture of 1 N aqueous sulfuric acid (100 mL) and ethyl acetate (50 mL) was added, and stirring was continued for 1 hour. The resulting solid was collected via filtration and the filter cake was washed with aqueous ethyl acetate, providing the product as a white solid (4 g). The organic layer of the filtrate was separated and the aqueous layer was extracted with dichloromethane (2×100 mL); the combined organic layers were concentrated in vacuo to afford additional product as a green solid (3 g). Yield: 7 g, 30 mmol, 85%. $^1$H NMR (400 MHz, CDCl$_3$) δ 8.92 (br s, 1H), 3.62 (s, 3H), 2.58 (q, J=7.4 Hz, 2H), 1.09 (t, J=7.4 Hz, 3H).

Step 3. Synthesis of 6-bromo-5-ethyl-1-methyl-3-{[2-(trimethylsilyl)ethoxy]methyl}pyrimidine-2,4(1H,3H)-dione (C18)

Compound C17 was converted to the product using the method described for synthesis of C3 in Examples 1 and 2. The product was obtained as a yellow gum. Yield: 3.1 g, 8.5 mmol, 28%. $^1$H NMR (400 MHz, CDCl$_3$) δ 5.41 (s, 2H), 3.66 (s, 3H), 3.64-3.72 (m, 2H), 2.61 (q, J=7.4 Hz, 2H), 1.09 (t, J=7.4 Hz, 3H), 0.95-1.01 (m, 2H), 0.00 (s, 9H).

Step 4. Synthesis of 6-[4-(benzyloxy)-2-methylphenyl]-5-ethyl-1-methyl-3-{[2-(trimethylsilyl)ethoxy]methyl}pyrimidine-2,4(1H,3H)-dione (C19)

Compound C18 was converted to the product using the method employed for synthesis of C4 in Examples 1 and 2. The product was obtained as a yellow gum. Yield: 1.26 g, 2.62 mmol, 59%. $^1$H NMR (400 MHz, CDCl$_3$) δ 7.34-7.49 (m, 5H), 7.03 (d, J=8.0 Hz, 1H), 6.91-6.97 (m, 2H), 5.47-5.54 (m, 2H), 5.10 (s, 2H), 3.73-3.80 (m, 2H), 3.00 (s, 3H), 2.18-2.29 (m, 1H), 2.16 (s, 3H), 1.86-1.97 (m, 1H), 0.99-1.07 (m, 2H), 0.91 (t, J=7.3 Hz, 3H), 0.03 (s, 9H).

Step 5. Synthesis of 5-ethyl-6-(4-hydroxy-2-methylphenyl)-1-methyl-3-{[2-(trimethylsilyl)ethoxy]methyl}pyrimidine-2,4(1H,3H)-dione (C20)

The product, obtained as a gray solid, was synthesized from C19 using the method described for synthesis of C5 in Examples 1 and 2. Yield: 850 mg, 2.18 mmol, 83%. LCMS m/z 413.2 [M+Na$^+$]. $^1$H NMR (400 MHz, CDCl$_3$) δ 6.97 (d, J=7.9 Hz, 1H), 6.79-6.86 (m, 2H), 5.48-5.54 (m, 2H), 3.73-3.80 (m, 2H), 3.01 (s, 3H), 2.18-2.30 (m, 1H), 2.13 (s, 3H), 1.86-1.97 (m, 1H), 0.99-1.06 (m, 2H), 0.90 (t, J=7.3 Hz, 3H), 0.02 (s, 9H).

Step 6. Synthesis of 6-{4-[(3-chloropyridin-2-yl)oxy]-2-methylphenyl}-5-ethyl-1-methyl-3-{[2-(trimethylsilyl)ethoxy]methyl}pyrimidine-2,4(1H,3H)-dione (C21)

A mixture of C20 (80 mg, 0.20 mmol), 2,3-dichloropyridine (45 mg, 0.30 mmol) and cesium carbonate (199 mg, 0.611 mmol) in dimethyl sulfoxide (8 mL) was heated at 120° C. for 18 hours. After addition of water and ethyl acetate, the mixture was extracted with ethyl acetate. The combined organic layers were dried, filtered, and concentrated under reduced pressure. Preparative thin-layer chromatography on silica gel (Eluent: 1:1 petroleum ether/ethyl acetate) afforded the product as a colorless oil. Yield: 82 mg, 0.16 mmol, 80%.

Step 7. Synthesis of 6-{4-[(3-chloropyridin-2-yl)oxy]-2-methylphenyl}-5-ethyl-1-methylpyrimidine-2,4(1H,3H)-dione (6)

A solution of C21 (82 mg, 0.16 mmol) in trifluoroacetic acid (3 mL) was heated at 80° C. for 1 hour. After removal of solvent in vacuo, the residue was dissolved in methanol (5 mL), treated with potassium carbonate (68 mg, 0.49 mmol), and stirred at room temperature for 1 hour. The reaction mixture was filtered, and the filtrate was concentrated; purification via preparative thin-layer chromatography (Eluent: ethyl acetate) provided the product as a white solid. Yield: 28 mg, 75 μmol, 47%. LCMS m/z 372.0 [M+H]$^+$. $^1$H NMR (400 MHz, CD$_3$OD) δ 8.07 (br d, J=4 Hz, 1H), 7.97 (d, J=7.5 Hz, 1H), 7.29 (d, J=8.3 Hz, 1H), 7.11-7.21 (m, 3H), 3.01 (s, 3H), 2.22 (s, 3H), 2.17-2.27 (m, 1H), 1.87-1.98 (m, 1H), 0.93 (t, J=7.3 Hz, 3H).

Examples 7 and 8

(−)-1,5-Dimethyl-6-(2-methyl-4-{[3-(trifluoromethyl)pyridin-2-yl]oxy}phenyl)pyrimidine-2,4(1H,3H)-dione (7) and (+)-1,5-Dimethyl-6-(2-methyl-4-{[3-(trifluoromethyl)pyridin-2-yl]oxy}phenyl)pyrimidine-2,4(1H,3H)-dione (8)

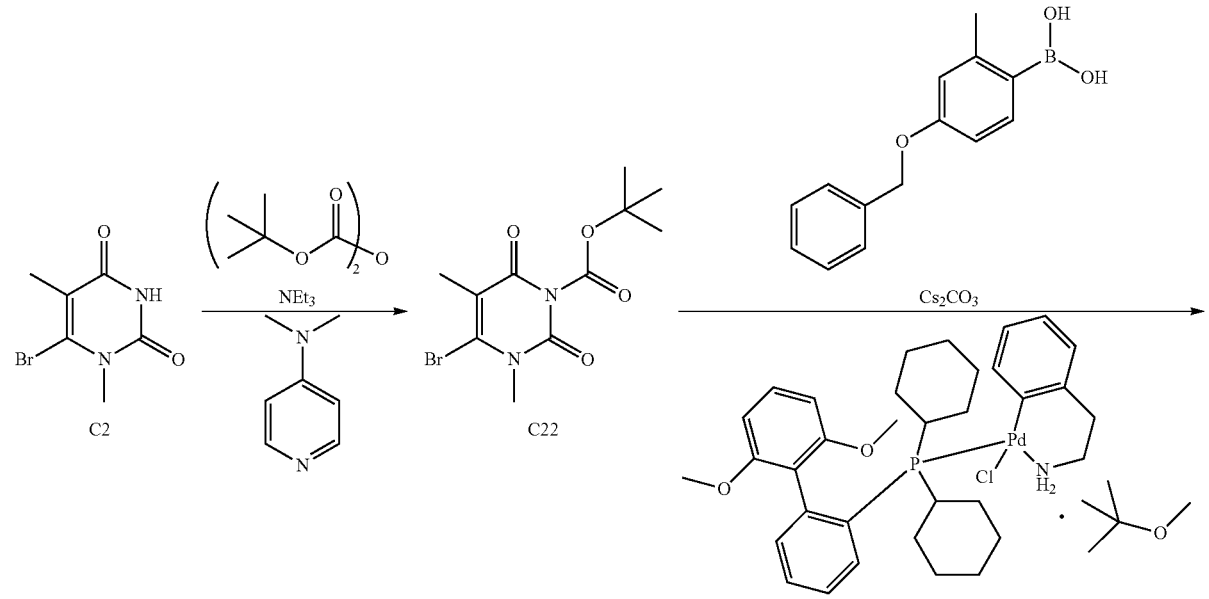

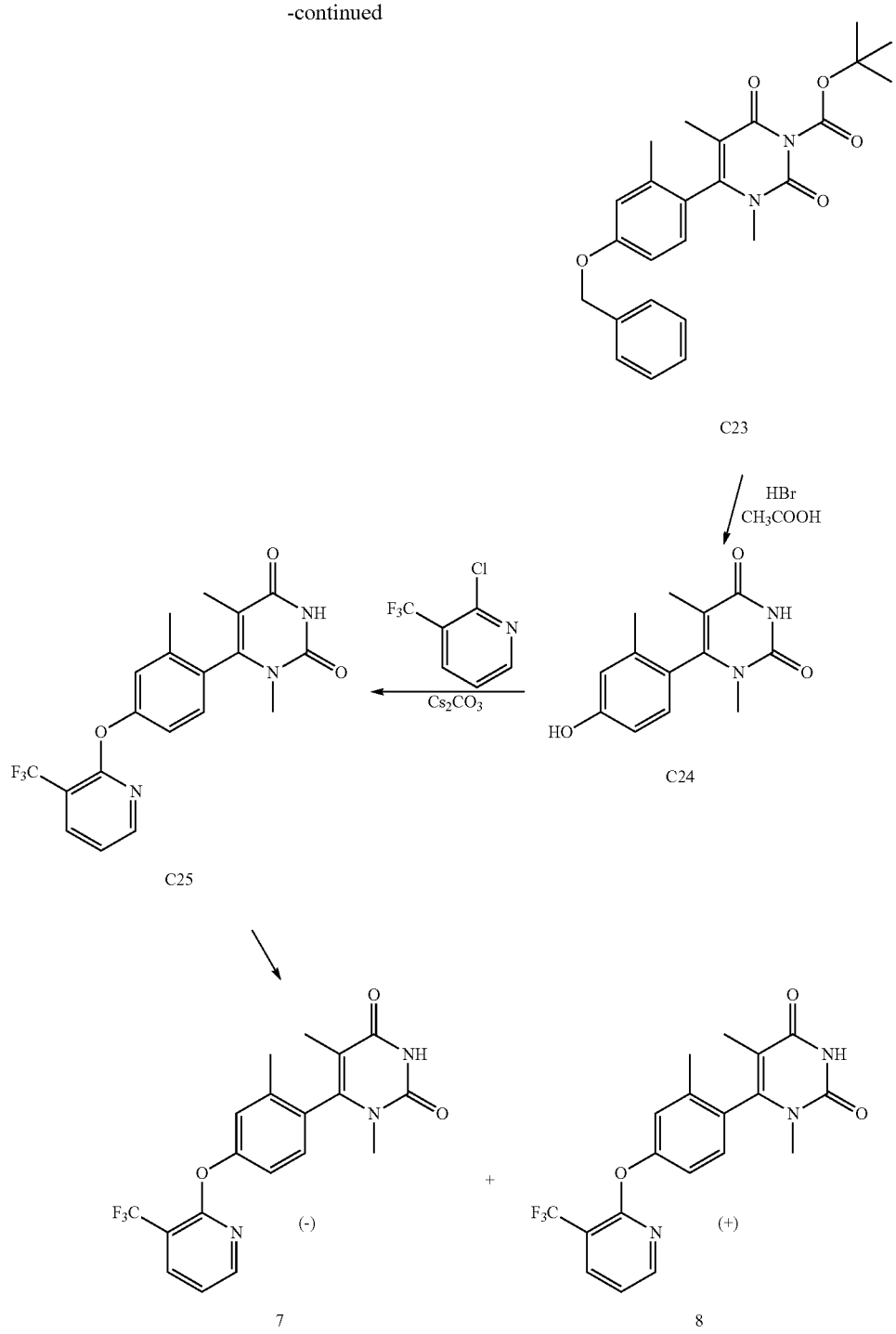

Step 1. Synthesis of tert-butyl 4-bromo-3,5-dimethyl-2,6-dioxo-3,6-dihydropyrimidine-1(2H)-carboxylate (C22)

Compound C2 (800 mg, 3.65 mmol), di-tert-butyl dicarbonate (99%, 966 mg, 4.38 mmol), triethylamine (0.62 mL, 4.4 mmol) and 4-(dimethylamino)pyridine (45 mg, 0.36 mmol) were combined in tetrahydrofuran (15 mL) and heated to 70° C. for 1 hour, then allowed to stir at room temperature for 18 hours. The reaction mixture was concentrated in vacuo, and the residue was purified via chromatography on silica gel (Gradient: 10% to 25% ethyl acetate in heptane) to provide the product as a white solid. Yield: 1.10 g, 3.45 mmol, 94%. $^1$H NMR (400 MHz, CDCl$_3$) δ 3.64 (s, 3H), 2.12 (s, 3H), 1.61 (s, 9H).

Step 2. Synthesis of tert-butyl 4-[4-(benzyloxy)-2-methylphenyl]-3,5-dimethyl-2,6-dioxo-3,6-dihydropyrimidine-1(2H)-carboxylate (C23)

A mixture of C22 (1.00 g, 3.13 mmol), [4-(benzyloxy)-2-methylphenyl]boronic acid (98%, 1.16 g, 4.68 mmol), chloro(2-dicyclohexylphosphino-2',6'-dimethoxy-1,1'-biphenyl)[2-(2-aminoethylphenyl)]palladium(II)-tert-butyl methyl ether adduct (S-Phos precatalyst) (119 mg, 0.156 mmol), and cesium carbonate (3.06 g, 9.39 mmol) in 2-methyltetrahydrofuran (10 mL) and water (3 mL) was heated at 50° C. for 66 hours. The reaction mixture was diluted with water and ethyl acetate, and then filtered to remove suspended solids. The filtrate was extracted several times with ethyl acetate, and the combined organic layers were washed with saturated aqueous sodium chloride solution, dried over magnesium sulfate, filtered, and concentrated in vacuo. The resulting solid was suspended in a 1:3 mixture of ethyl acetate and heptane, stirred for several minutes, and filtered, providing the product as a white solid. Yield: 970 mg, 2.22 mmol, 71%. LCMS m/z 337.2 [(M-Boc)+H]$^+$. $^1$H NMR (400 MHz, CDCl$_3$) δ 7.34-7.48 (m, 5H), 6.91-7.01 (m, 3H), 5.10 (s, 2H), 3.01 (s, 3H), 2.16 (br s, 3H), 1.66 (s, 9H), 1.64 (s, 3H).

Step 3. Synthesis of 6-(4-hydroxy-2-methylphenyl)-1,5-dimethylpyrimidine-2,4(1H,3H)-dione (C24)

Compound C23 (250 mg, 0.573 mmol) was mixed with a 30% solution of hydrogen bromide in acetic acid (1 mL, 5 mmol) and allowed to stir for 18 hours at room temperature. After removal of acetic acid under reduced pressure, the residue was dissolved in a minimal quantity of ethanol and diluted with 4 M aqueous hydrochloric acid to provide a slightly cloudy mixture; this was evaporated to dryness, and the resulting solid was suspended in 4 N aqueous hydrochloric acid, stirred for several minutes, and filtered, affording the product as a yellow solid. Yield: 125 mg, 0.508 mmol, 89%. LCMS m/z 247.2 [M+H]$^+$. $^1$H NMR (400 MHz, DMSO-d$_6$) δ 11.36 (br s, 1H), 9.71 (v br s, 1H), 6.99 (d, J=8.2 Hz, 1H), 6.76 (d, J=2.3 Hz, 1H), 6.72 (d, J=8.1, 2.3 Hz, 1H), 2.82 (s, 3H), 2.03 (s, 3H), 1.44 (s, 3H).

Step 4. Synthesis of 1,5-dimethyl-6-(2-methyl-4-{[3-(trifluoromethyl)pyridin-2-yl]oxy}phenyl)pyrimidine-2,4(1H,3H)-dione (C25)

2-Chloro-3-(trifluoromethyl)pyridine (98%, 269 mg, 1.45 mmol), C24 (325 mg, 1.32 mmol) and cesium carbonate (521 mg, 1.60 mmol) were combined in N,N-dimethylformamide (6 mL) and the resulting suspension was heated at 100° C. for 18 hours. After it had cooled to room temperature, the reaction mixture was diluted with aqueous 1 M hydrochloric acid and extracted several times with ethyl acetate. The combined organic layers were washed twice with water and once with saturated aqueous sodium chloride solution, dried over magnesium sulfate, filtered, and concentrated in vacuo. The resulting solid was suspended in a 1:1 mixture of ethyl acetate and heptane, stirred for several minutes and collected by filtration, providing the product as a white solid. Yield: 440 mg, 1.12 mmol, 85%. LCMS m/z 392.2 [M+H]$^+$. $^1$H NMR (400 MHz, CDCl$_3$) δ 8.31-8.36 (m, 2H), 8.05 (br d, J=7.5 Hz, 1H), 7.13-7.22 (m, 4H), 3.06 (s, 3H), 2.21 (s, 3H), 1.69 (s, 3H).

Step 5. Isolation of (−)-1,5-dimethyl-6-(2-methyl-4-{[3-(trifluoromethyl)pyridin-2-yl]oxy}phenyl)pyrimidine-2,4(1H,3H)-dione (7) and (+)-1,5-dimethyl-6-(2-methyl-4-{[3-(trifluoromethyl)pyridin-2-yl]oxy}phenyl)pyrimidine-2,4(1H,3H)-dione (8)

Racemate C25 (1.30 g, 3.32 mmol) was separated into its atropenantiomers via chiral chromatography (Column: Phenomenex Lux Cellulose-2; Gradient: heptane/ethanol). The first-eluting atropenantiomer, obtained as a tan solid that exhibited a negative (−) rotation, was designated as Example 7. Yield: 536 mg, 1.37 mmol, 41%. The second-eluting atropenantiomer, also obtained as a tan solid but with a positive (+) rotation, was designated as Example 8. Yield: 553 mg, 1.41 mmol, 42%. 7: LCMS m/z 392.2 [M+H]$^+$. $^1$H NMR (400 MHz, CDCl$_3$) δ 8.34 (ddq, J=4.9, 1.9, 0.6 Hz, 1H), 8.30 (br s, 1H), 8.05 (ddq, J=7.6, 1.9, 0.7 Hz, 1H), 7.13-7.21 (m, 4H), 3.06 (s, 3H), 2.21 (br s, 3H), 1.69 (s, 3H). 8: LCMS m/z 392.2 [M+H]$^+$. $^1$H NMR (400 MHz, CDCl$_3$) δ 8.34 (br d, J=4.9 Hz, 1H), 8.30 (br s, 1H), 8.05 (br d, J=7.5 Hz, 1H), 7.13-7.22 (m, 4H), 3.06 (s, 3H), 2.21 (br s, 3H), 1.69 (s, 3H).

Examples 9 and 10

(+)-6-{4-[(3-Chloro-5-methylpyridin-2-yl)oxy]-2-methylphenyl}-1,5-dimethylpyrimidine-2,4(1H,3H)-dione (9) and (−)-6-{4-[(3-Chloro-5-methylpyridin-2-yl)oxy]-2-methylphenyl}-1,5-dimethylpyrimidine-2,4(1H,3H)-dione (10)

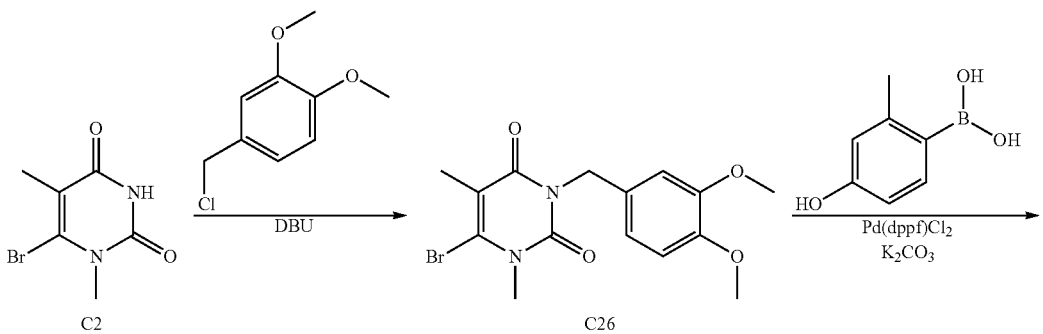

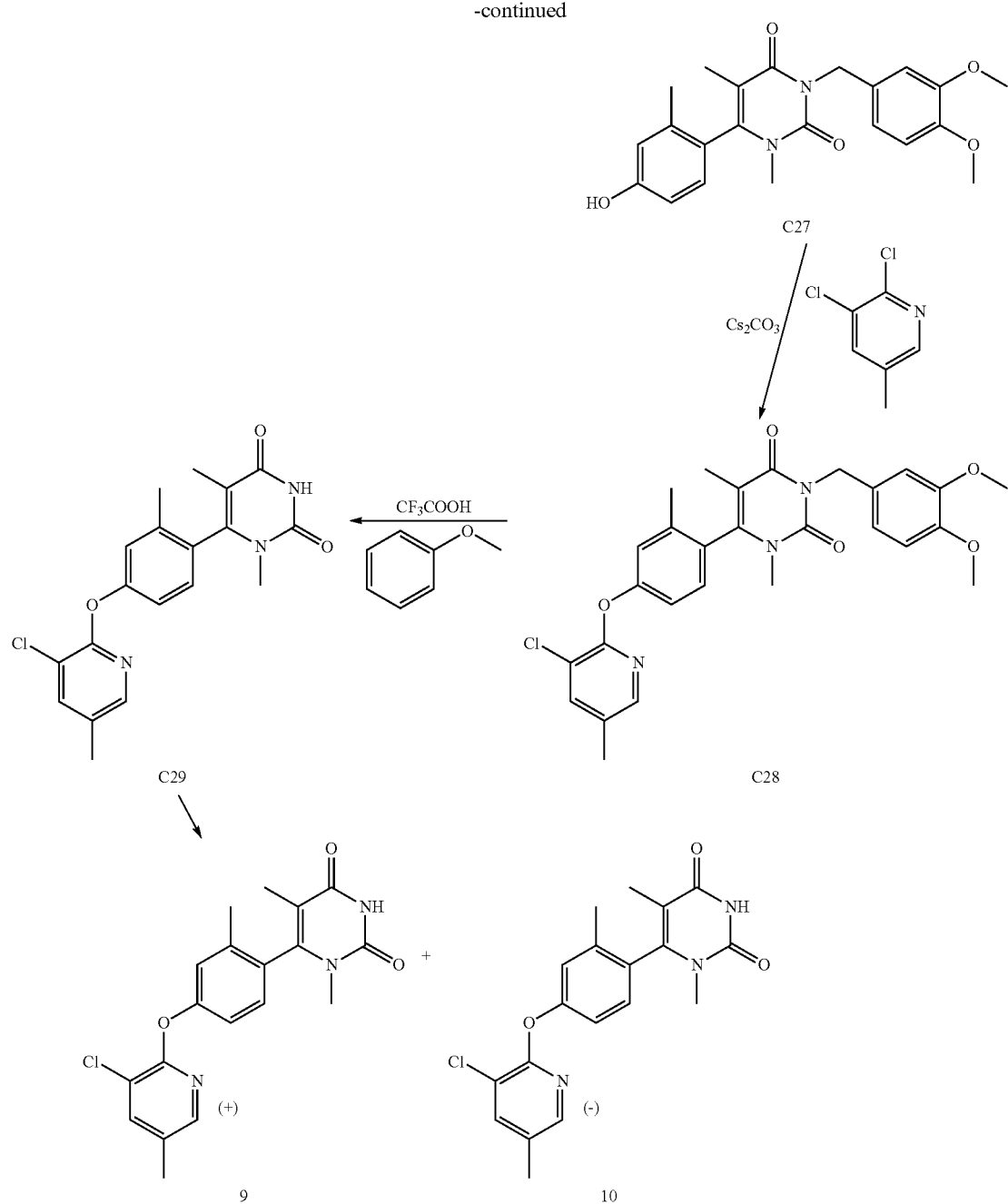

Step 1. Synthesis of 6-bromo-3-(3,4-dimethoxybenzyl)-1,5-dimethylpyrimidine-2,4(1H,3H)-dione (C26)

1,8-Diazabicyclo[5.4.0]undec-7-ene (98%, 5.57 mL, 36.5 mmol) was added to a suspension of C2 (4.00 g, 18.3 mmol) and 4-(chloromethyl)-1,2-dimethoxybenzene (5.16 g, 27.6 mmol) in acetonitrile (80 mL), and the reaction mixture was heated at 60° C. for 18 hours. After removal of solvent in vacuo, the residue was purified via silica gel chromatography (Gradient: 25% to 50% ethyl acetate in heptane) to afford the product as a white solid. Yield: 5.70 g, 15.4 mmol, 84%. $^1$H NMR (400 MHz, CDCl$_3$) δ 7.08-7.12 (m, 2H), 6.80 (d, J=8.0 Hz, 1H), 5.07 (s, 2H), 3.88 (s, 3H), 3.85 (s, 3H), 3.65 (s, 3H), 2.14 (s, 3H).

Step 2. Synthesis of 3-(3,4-dimethoxybenzyl)-6-(4-hydroxy-2-methylphenyl)-1,5-dimethylpyrimidine-2,4(1H,3H)-dione (C27)

An aqueous solution of potassium carbonate (3.0 M, 14 mL, 42 mmol) was added to a mixture of C26 (5.00 g, 13.5 mmol), (4-hydroxy-2-methylphenyl)boronic acid (4.12 g, 27.1 mmol), [1,1'-bis(diphenylphosphino)ferrocene]dichloropalladium(II), dichloromethane complex (98%, 1.13 g, 1.36 mmol) and 1,4-dioxane (120 mL). After the reaction mixture had been heated at 100° C. for 18 hours, it was cooled to room temperature, diluted with ethyl acetate and water, and filtered through diatomaceous earth. The organic layer from the filtrate was washed sequentially with saturated aqueous sodium bicarbonate solution and with saturated aqueous sodium chloride solution, dried over magnesium sulfate, filtered, and concentrated in vacuo. Purification using silica gel chromatography (Gradient: 25% to 75% ethyl acetate in heptane) afforded the product as a white foam. Yield: 2.71 g, 6.84 mmol, 51%. LCMS m/z 397.2 [M+H]$^+$. $^1$H NMR (400 MHz, CDCl$_3$) δ 7.22 (d, J=2.0 Hz, 1H), 7.19 (dd, J=8.1, 2.0 Hz, 1H), 6.93 (d, J=8.2 Hz, 1H), 6.83 (d, J=8.3 Hz, 1H), 6.80-6.82 (m, 1H), 6.76-6.80 (m, 1H), 5.16 (AB quartet, J$_{AB}$=13.3 Hz, Δν$_{AB}$=19.2 Hz, 2H), 3.91 (s, 3H), 3.87 (s, 3H), 3.02 (s, 3H), 2.11 (br s, 3H), 1.66 (s, 3H).

Step 3. Synthesis of 6-{4-[(3-chloro-5-methylpyridin-2-yl)oxy]-2-methylphenyl}-3-(3,4-dimethoxybenzyl)-1,5-dimethylpyrimidine-2,4(1H,3H)-dione (C28)

A mixture of 2,3-dichloro-5-methylpyridine (735 mg, 4.54 mmol), C27 (1.5 g, 3.8 mmol) and cesium carbonate (2.46 g, 7.55 mmol) in dimethyl sulfoxide (36 mL) was stirred at 100° C. for 40 hours, and at 120° C. for a further 48 hours. The reaction mixture was diluted with water (300 mL) and extracted with ethyl acetate (3×200 mL); the combined organic layers were dried, filtered, and concentrated in vacuo. Silica gel chromatography (Gradient: 10% to 60% ethyl acetate in petroleum ether) provided the product as a yellow solid. Yield: 1.7 g, 3.2 mmol, 84%. $^1$H NMR (400 MHz, CDCl$_3$) δ 7.89-7.92 (m, 1H), 7.64-7.66 (m, 1H), 7.23 (br d, J=1.9 Hz, 1H), 7.20 (br dd, J=8.2, 1.9 Hz, 1H), 7.10-7.12 (br s, 1H), 7.06-7.09 (m, 2H), 6.83 (d, J=8.2 Hz, 1H), 5.16 (AB quartet, J$_{AB}$=13.4 Hz, Δν$_{AB}$=20.4 Hz, 2H), 3.91 (s, 3H), 3.87 (s, 3H), 3.06 (s, 3H), 2.32 (s, 3H), 2.16 (s, 3H), 1.68 (s, 3H).

Step 4. Synthesis of 6-{4-[(3-chloro-5-methylpyridin-2-yl)oxy]-2-methylphenyl}-1,5-dimethylpyrimidine-2,4(1H,3H)-dione (C29)

This experiment was carried out in three batches. A mixture of C28 (600 mg, 1.15 mmol) and methoxybenzene (622 mg, 5.75 mmol) in trifluoroacetic acid (20 mL) was stirred at 120° C. for 48 hours, then at 125° C. for another 48 hours. The three batches were combined, concentrated under reduced pressure, and purified via chromatography on silica gel (Gradient: 10% to 70% ethyl acetate in petroleum ether). The product was obtained as a light brown solid. Yield: 690 mg, 1.86 mmol, 54%. LCMS m/z 371.8, 373.9 [M+H]$^+$. $^1$H NMR (400 MHz, CD$_3$OD) δ 7.90-7.92 (m, 1H), 7.82-7.84 (m, 1H), 7.23 (d, J=8.4 Hz, 1H), 7.14 (br d, J=2.2 Hz, 1H), 7.08 (br dd, J=8.2, 2.2 Hz, 1H), 3.03 (s, 3H), 2.33 (br s, 3H), 2.20 (br s, 3H), 1.62 (s, 3H).

Step 5. Isolation of (+)-6-{4-[(3-chloro-5-methylpyridin-2-yl)oxy]-2-methylphenyl}-1,5-dimethylpyrimidine-2,4(1H,3H)-dione (9) and (−)-6-{4-[(3-chloro-5-methylpyridin-2-yl)oxy]-2-methylphenyl}-1,5-dimethylpyrimidine-2,4(1H,3H)-dione (10)

Compound C29 (690 mg, 1.86 mmol) was separated into its atropenantiomers via supercritical fluid chromatography (Column: Chiral Technologies, Chiralcel OJ-H, 5 μm; Eluent: 7:3 carbon dioxide/methanol). The first-eluting atropenantiomer, obtained as a solid that exhibited a positive (+) rotation, was designated as Example 9. Yield: 240 mg, 0.645 mmol, 35%. The second-eluting atropenantiomer, also obtained as a solid but with a negative (−) rotation, was designated as Example 10. Yield: 250 mg, 0.672 mmol, 36%. 9: LCMS m/z 372.1, 374.1 [M+H]$^+$. $^1$H NMR (400 MHz, CDCl$_3$) δ 8.36 (br s, 1H), 7.91-7.93 (m, 1H), 7.65-7.66 (m, 1H), 7.13-7.14 (m, 1H), 7.10-7.11 (m, 2H), 3.04 (s, 3H), 2.32-2.34 (m, 3H), 2.18-2.19 (m, 3H), 1.67 (s, 3H). 10: LCMS m/z 372.1, 374.1 [M+H]$^+$. $^1$H NMR (400 MHz, CDCl$_3$) δ 8.35 (br s, 1H), 7.91-7.93 (m, 1H), 7.65-7.66 (m, 1H), 7.13-7.14 (m, 1H), 7.10-7.11 (m, 2H), 3.04 (s, 3H), 2.33 (dd, J=0.7, 0.7 Hz, 3H), 2.19 (d, J=0.6 Hz, 3H), 1.67 (s, 3H).

Example 11

6-{4-[(3-Chloro-4-methylpyridin-2-yl)oxy]phenyl}-1,5-dimethylpyrimidine-2,4(1H,3H)-dione (11)

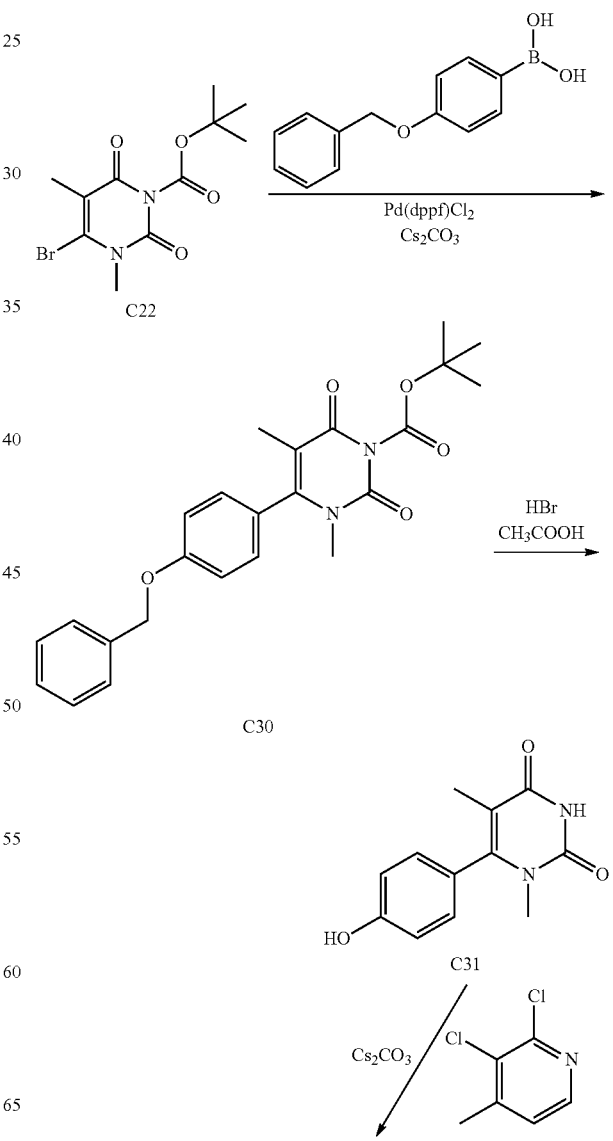

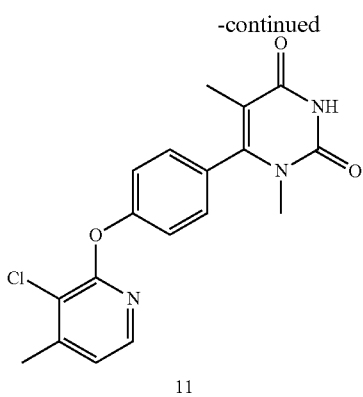

11

Step 1. Synthesis of tert-butyl 4-[4-(benzyloxy)phenyl]-3,5-dimethyl-2,6-dioxo-3,6-dihydropyrimidine-1 (2H)-carboxylate (C30)

A solution of C22 (23.3 g, 73.0 mmol), [4-(benzyloxy)phenyl]boronic acid (25 g, 110 mmol), [1,1'-bis(diphenylphosphino)ferrocene]dichloropalladium(II) (2.68 g, 3.66 mmol), and cesium carbonate (95.2 g, 292 mmol) in 2-methyltetrahydrofuran (360 mL) and water (120 mL) was purged with nitrogen and heated to 50° C. for 5 hours. After cooling to room temperature, the reaction mixture was stirred at room temperature for 18 hours, then diluted with water and ethyl acetate. The mixture was filtered, and the filtrate was extracted several times with ethyl acetate. The combined organic layers were washed with saturated aqueous sodium chloride solution, dried over magnesium sulfate, filtered, and concentrated in vacuo. The resulting solid was combined with the solid collected from the initial filtration, and extracted several times with hot ethyl acetate; the combined ethyl acetate extracts were concentrated under reduced pressure. The residue was suspended in a 1:3 mixture of ethyl acetate and heptane, stirred for several minutes, and filtered, affording the product as a gray solid, which was used without additional purification. Yield: 21.8 g, 51.6 mmol, 71%. LCMS m/z 323.1 [(M-Boc)+H]$^+$. $^1$H NMR (400 MHz, DMSO-$d_6$), characteristic peaks: δ 7.46-7.51 (m, 2H), 7.42 (br dd, J=7.5, 7.4 Hz, 2H), 7.32-7.38 (m, 3H), 7.18 (br d, J=8.8 Hz, 2H), 5.16 (s, 2H), 2.92 (s, 3H), 1.54 (s, 9H).

Step 2. Synthesis of 6-(4-hydroxyphenyl)-1,5-dimethylpyrimidine-2,4(1H,3H)-dione (C31)

Compound C30 (21.8 g, 51.6 mmol) was mixed with a 30% solution of hydrogen bromide in acetic acid (100 mL, 520 mmol) and stirred at room temperature for 4 hours. Acetic acid was removed under reduced pressure, and the resulting oil was dissolved in a minimal quantity of ethanol and diluted with water, providing a slightly cloudy mixture. After this was evaporated to dryness, the resulting solid was suspended in water and stirred for several minutes. Filtration afforded the product as a tan solid, which was used without additional purification. Yield: 11.4 g, 49.1 mmol, 95%. LCMS m/z 233.1 [M+H]$^+$. $^1$H NMR (400 MHz, DMSO-$d_6$) δ 11.34 (br s, 1H), 9.85 (br s, 1H), 7.14 (br d, J=8.6 Hz, 2H), 6.89 (br d, J=8.6 Hz, 2H), 2.88 (s, 3H), 1.50 (s, 3H).

Step 3. Synthesis of 6-{4-[(3-chloro-4-methylpyridin-2-yl)oxy]phenyl}-1,5-dimethylpyrimidine-2,4 (1H, 3H)-dione (11)

Cesium carbonate (32.6 g, 100 mmol) was added to a mixture of C31 (11.4 g, 49.1 mmol) and 2,3-dichloro-4-methylpyridine (11.9 g, 73.4 mmol) in 1-methylpyrrolidin-2-one (100 mL), and the reaction mixture was heated at 140° C. for 24 hours. Additional 2,3-dichloro-4-methylpyridine (4.0 g, 25 mmol) was added, and heating was continued for 24 hours. The reaction mixture was cooled to approximately 50° C. and poured into ice water (500 mL); the resulting suspension was stirred for 5 minutes and then filtered. The collected solid was dissolved in hot ethanol (600 mL), treated with charcoal and magnesium sulfate, and stirred under heating for 10 minutes. The hot mixture was filtered through diatomaceous earth, and the hot filtrate was diluted with heptane (400 mL) while stirring, then cooled to 0° C. After stirring for 45 minutes at 0° C., the mixture was filtered to afford the crude product as an off-white solid (11.75 g). The filtrate was concentrated under reduced pressure, suspended in diethyl ether, and filtered to provide a solid, which was extracted several times with hot ethyl acetate; the combined ethyl acetate extracts were concentrated in vacuo, yielding additional crude product (2 g). The two lots of crude product were combined and recrystallized from ethyl acetate/heptane to afford the final product as a white solid. Yield: 11.1 g, 31.0 mmol, 63%. LCMS m/z 358.2, 360.2 [M+H]$^+$. $^1$H NMR (400 MHz, DMSO-$d_6$) δ 11.42 (br s, 1H), 8.00 (d, J=5.0 Hz, 1H), 7.42 (br d, J=8.8 Hz, 2H), 7.30 (br d, J=8.7 Hz, 2H), 7.21 (br d, J=5.0 Hz, 1H), 2.91 (s, 3H), 2.44 (s, 3H), 1.53 (s, 3H).

Example 12

6-(4-{[3-(Difluoromethyl)pyridin-2-yl]oxy}-2-methylphenyl)-1-ethyl-5-methylpyrimidine-2,4(1H,3H)-dione (12)

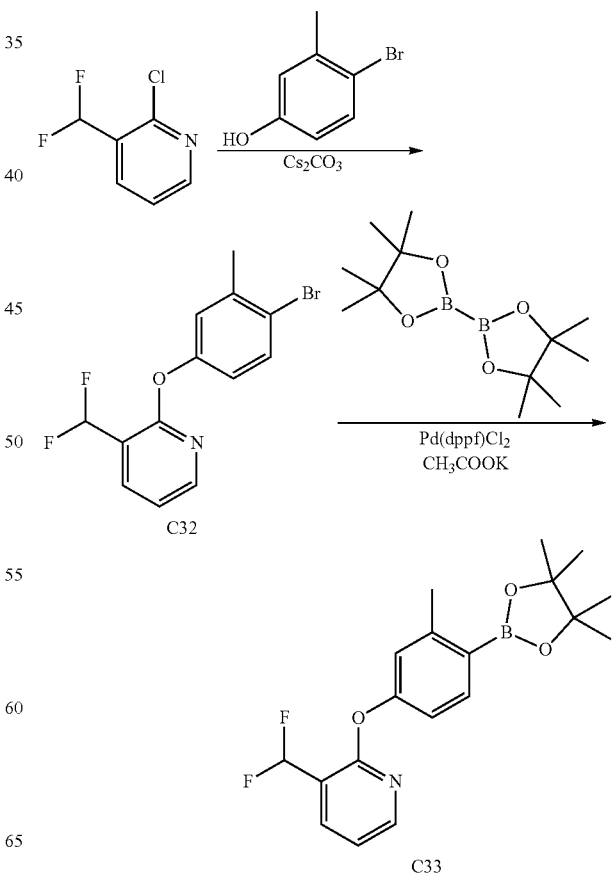

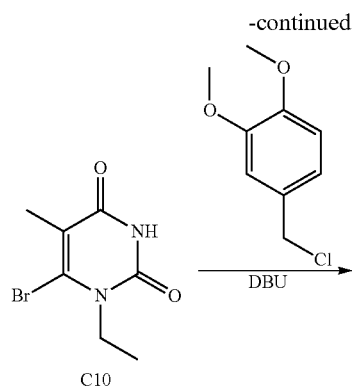

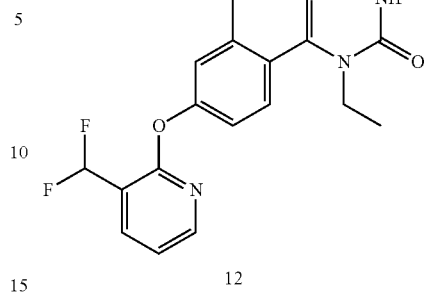

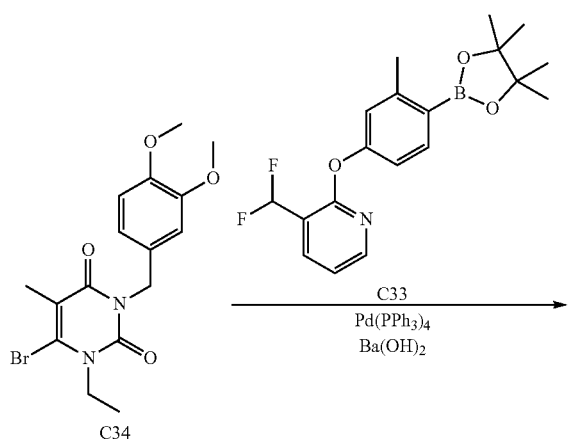

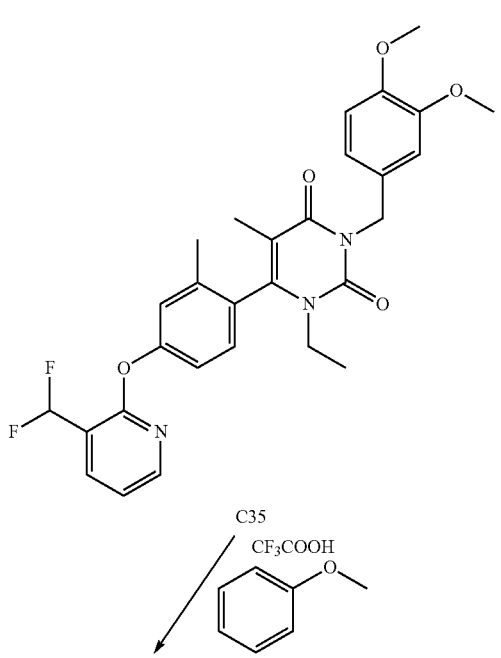

Step 1. Synthesis of 2-(4-bromo-3-methylphenoxy)-3-(difluoromethyl)pyridine (C32)

To a mixture of 2-chloro-3-(difluoromethyl)pyridine (15 g, 92 mmol) and cesium carbonate (90 g, 280 mmol) in dimethyl sulfoxide (300 mL) was added 4-bromo-3-methylphenol (19.8 g, 106 mmol). The reaction mixture was stirred at 100° C. for 18 hours, then diluted with water (1 L) and extracted with ethyl acetate (5×200 mL). The combined organic layers were dried, filtered, and concentrated in vacuo. Silica gel chromatography (Eluent: 40:1 petroleum ether/ethyl acetate) afforded the product as a white solid. Yield: 27 g, 86 mmol, 93%. $^1$H NMR (400 MHz, CD$_3$OD) δ 8.19 (br d, J=4 Hz, 1H), 8.07 (d, J=7.2 Hz, 1H), 7.56 (d, J=8.5 Hz, 1H), 7.19-7.25 (m, 1H), 7.10 (br d, J=2.5 Hz, 1H), 7.08 (t, J$_{HF}$=54.8 Hz, 1H), 6.90 (dd, J=8.6, 2.6 Hz, 1H), 2.39 (s, 3H).

Step 2. Synthesis of 3-(difluoromethyl)-2-[3-methyl-4-(4,4,5,5-tetramethyl-1,3,2-dioxaborolan-2-yl)phenoxy]pyridine (C33)

To a mixture of C32 (27 g, 86 mmol), 4,4,4',4',5,5,5',5'-octamethyl-2,2'-bi-1,3,2-dioxaborolane (32.8 g, 129 mmol) and potassium acetate (25.8 g, 263 mmol) in 1,4-dioxane (500 mL) was added [1,1'-bis(diphenylphosphino)ferrocene]dichloropalladium(II) (6.3 g, 8.6 mmol). The mixture was stirred at 100° C. for 18 hours, then filtered. After concentration of the filtrate under reduced pressure, the residue was purified via silica gel chromatography (Eluent: petroleum ether) to provide the product as a yellow oil. Yield: 16 g, 44 mmol, 51%. LCMS m/z 362.0 [M+H]$^+$. $^1$H NMR (400 MHz, CD$_3$OD) δ 8.18-8.22 (m, 1H), 8.07 (br d, J=7 Hz, 1H), 7.75 (d, J=8.0 Hz, 1H), 7.22 (dd, J=7.6, 5.0 Hz, 1H), 7.07 (t, J$_{HF}$=55.0 Hz, 1H), 6.93 (br d, J=2 Hz, 1H), 6.90 (br dd, J=8, 2 Hz, 1H), 2.52 (s, 3H), 1.35 (s, 12H).

Step 3. Synthesis of 6-bromo-3-(3,4-dimethoxybenzyl)-1-ethyl-5-methylpyrimidine-2,4(1H,3H)-dione (C34)

Compound C10 was converted to the product according to the method used for synthesis of C26 in Examples 9 and 10. The product was obtained as a light yellow oil. Yield: 720 mg, 1.88 mmol, 84%. $^1$H NMR (400 MHz, CDCl$_3$) δ 7.07-7.14 (m, 2H), 6.80 (d, J=8.2 Hz, 1H), 5.06 (s, 2H), 4.23 (q, J=7.0 Hz, 2H), 3.88 (s, 3H), 3.85 (s, 3H), 2.13 (s, 3H), 1.30 (t, J=7.0 Hz, 3H).

Step 4. Synthesis of 6-(4-{[3-(difluoromethyl)pyridin-2-yl]oxy}-2-methylphenyl)-3-(3,4-dimethoxybenzyl)-1-ethyl-5-methylpyrimidine-2,4(1H,3H)-dione (C35)

To a mixture of C34 (57.5 mg, 0.150 mmol), C33 (108 mg, 0.299 mmol), and tetrakis(triphenylphosphine)palladium(0) (17 mg, 15 µmol) in a mixture of 1,4-dioxane (3 mL) and water (20 drops) was added barium hydroxide (77 mg, 0.45 mmol). The reaction mixture was stirred at 60° C. for 20 hours, then diluted with saturated aqueous ammonium chloride solution (20 mL) and extracted with ethyl acetate (3×20 mL). The combined organic layers were dried, filtered, and concentrated in vacuo. Preparative high-performance liquid chromatography afforded the product as a white solid. Yield: 30 mg, 56 µmol, 37%. LCMS m/z 538.0 [M+H]$^+$. $^1$H NMR (400 MHz, CDCl$_3$) δ 8.28 (br d, J=4 Hz, 1H), 8.04 (d, J=7.2 Hz, 1H), 7.10-7.25 (m, 6H), 7.02 (t, J$_{HF}$=55.1 Hz, 1H), 6.83 (d, J=8.2 Hz, 1H), 5.17 (s, 2H), 3.90 (s, 3H), 3.87 (s, 3H), 3.81-3.9 (m, 1H), 3.27-3.38 (m, 1H), 2.18 (s, 3H), 1.66 (s, 3H), 1.07 (t, J=7.0 Hz, 3H).

Step 5. Synthesis of 6-(4-{[3-(difluoromethyl)pyridin-2-yl]oxy}-2-methylphenyl)-1-ethyl-5-methylpyrimidine-2,4(1H,3H)-dione (12)

Compound C35 was deprotected using the method described for synthesis of C29 in Examples 9 and 10. In this case, purification was carried out via reversed phase high-performance liquid chromatography (Column: Waters Sunfire C18, 5 µm; Mobile phase A: 0.05% trifluoroacetic acid in water (v/v); Mobile phase B: 0.05% trifluoroacetic acid in acetonitrile (v/v); Gradient: 30% to 50% B). LCMS m/z 388.1 [M+H]$^+$. $^1$H NMR (600 MHz, DMSO-d$_6$) δ 8.34 (br d, J=4.5 Hz, 1H), 8.13 (br d, J=7.2 Hz, 1H), 7.35 (d, J=8.3 Hz, 1H), 7.32 (dd, J=7.4, 5.0 Hz, 1H), 7.28 (t, J$_{HF}$=54.4 Hz, 1H), 7.24 (br d, J=2.1 Hz, 1H), 7.18 (br dd, J=8.2, 2.3 Hz, 1H), 3.63-3.71 (m, 1H), 3.08-3.15 (m, 1H), 2.15 (s, 3H), 1.45 (s, 3H), 0.95 (t, J=7.0 Hz, 3H).

Example 13

(−)-6-(4-{[3-(Difluoromethoxy)pyridin-2-yl]oxy}-2-methylphenyl)-1,5-dimethylpyrimidine-2,4(1H,3H)-dione (13)

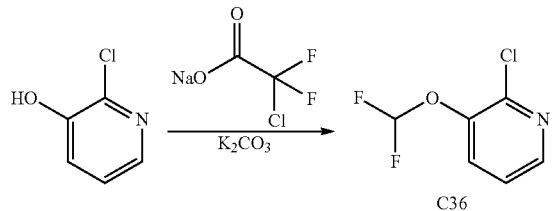

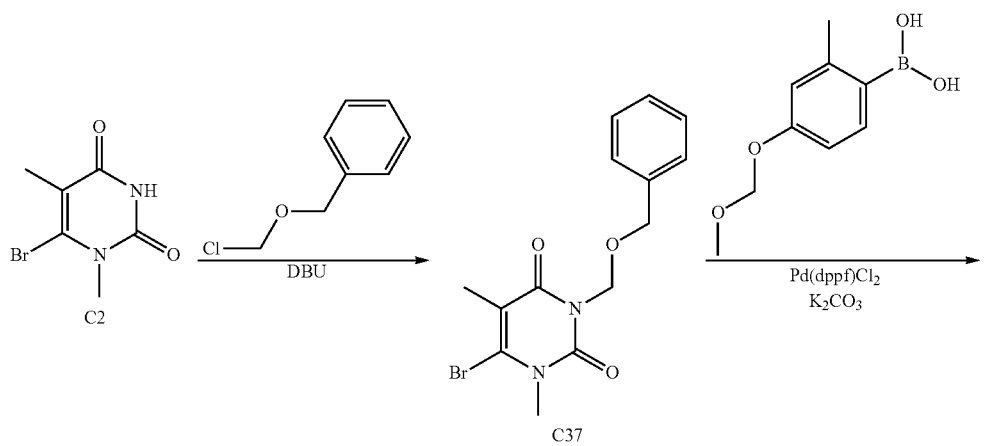

-continued

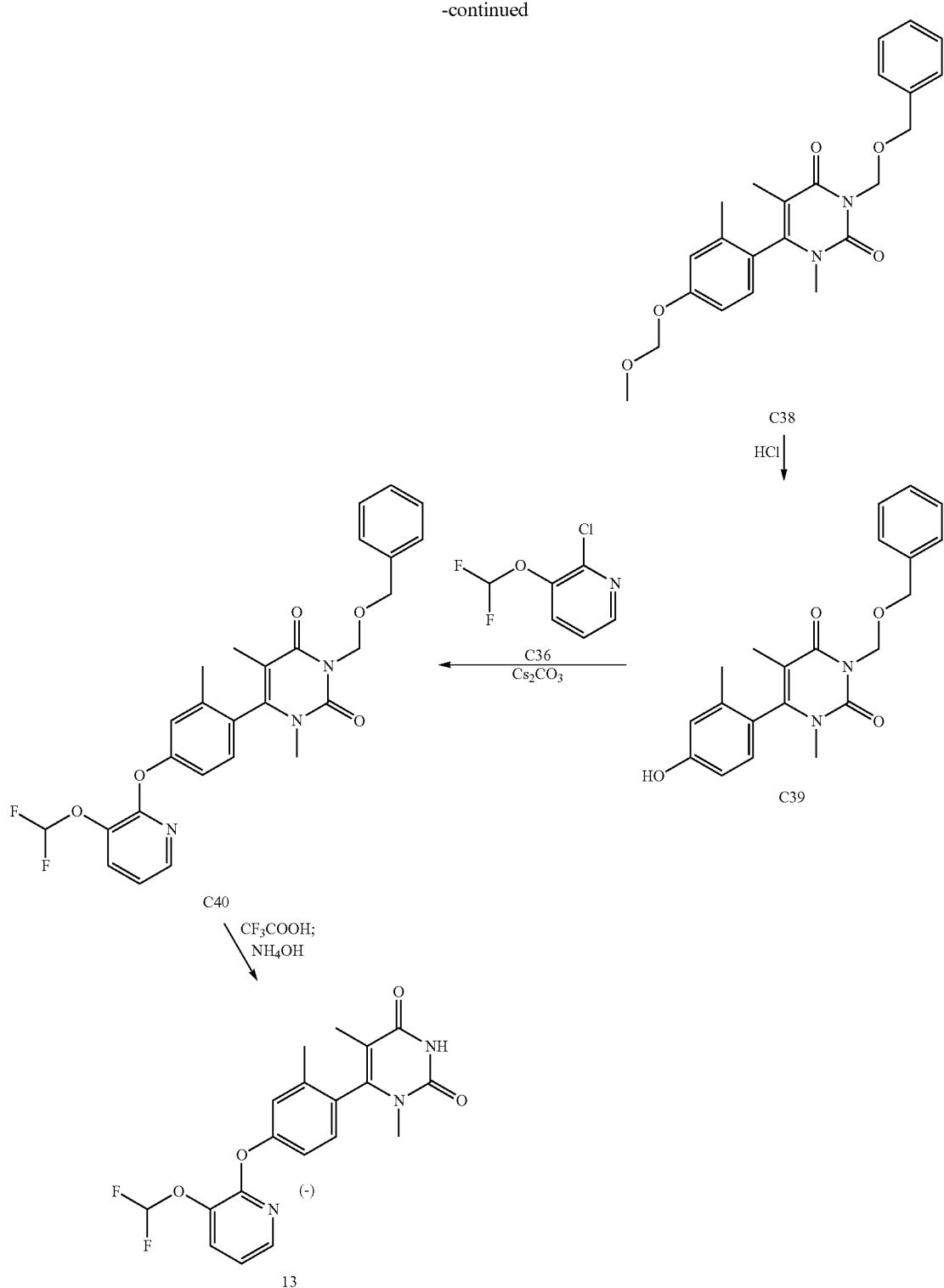

Step 1. Synthesis of 2-chloro-3-(difluoromethoxy)pyridine (C36)

This reaction was carried out 3 times. A mixture of potassium carbonate (282 g, 2.04 mol) and N,N-dimethylformamide (750 mL) was heated to 100° C. and slowly treated, in a drop-wise manner over 1 hour, with a solution of 2-chloropyridin-3-ol (66.7 g, 515 mmol) and sodium chloro(difluoro)acetate (200 g, 1.31 mol) in N,N-dimethylformamide (750 mL). After completion of the addition, the reaction mixture was stirred at 100° C. for 1 hour, then cooled to 25° C. and partitioned between water (10 L) and tert-butyl methyl ether (5 L). The aqueous layer was extracted with ethyl acetate (4×2.5 L), and the combined organic layers were washed with saturated aqueous sodium chloride solution (6×2.5 L), dried over sodium sulfate, filtered, and concentrated in vacuo. The combined crude products from the three reactions were purified via distillation at reduced pressure (30-40° C., 1-5 mm Hg) to provide the product as a colorless oil. Yield: 192 g, 1.07 mol, 69%. LCMS m/z 180.0 [M+H]$^+$. $^1$H NMR (400 MHz, CDCl$_3$) δ 8.26-8.30 (m, 1H), 7.60 (br d, J=8.2 Hz, 1H), 7.28 (br dd, J=8.0, 4.8 Hz, 1H), 6.60 (t, $J_{HF}$=72.5 Hz, 1H).

Step 2. Synthesis of 3-[(benzyloxy)methyl]-6-bromo-1,5-dimethylpyrimidine-2,4(1H, 3H)-dione (C37)

1,8-Diazabicyclo[5.4.0]undec-7-ene (6.00 mL, 40.2 mmol) was added to a suspension of C2 (8.00 g, 36.5 mmol) and benzyl chloromethyl ether (95%, 5.86 mL, 40.2 mmol) in acetonitrile (100 mL). After 90 hours at room temperature, the reaction mixture was concentrated in vacuo, diluted with water, and extracted several times with ethyl acetate. The combined organic layers were washed sequentially with water and with saturated aqueous sodium chloride solution, dried over magnesium sulfate, filtered, and concentrated under reduced pressure. Silica gel chromatography (Gradient: 10% to 25% ethyl acetate in heptane) afforded the product as a white solid. Yield: 10.1 g, 29.8 mmol, 82%. $^1$H NMR (400 MHz, CDCl$_3$) δ 7.24-7.39 (m, 5H), 5.52 (s, 2H), 4.71 (s, 2H), 3.63 (s, 3H), 2.11 (s, 3H).

Step 3. Synthesis of 3-[(benzyloxy)methyl]-6-[4-(methoxymethoxy)-2-methylphenyl]-1,5-dimethylpyrimidine-2,4(1H,3H)-dione (C38)

To a mixture of C37 (10.5 g, 31.0 mmol), [4-(methoxymethoxy)-2-methylphenyl]boronic acid (7.58 g, 38.7 mmol) and potassium carbonate (13 g, 94 mmol) in 1,4-dioxane (170 mL) was added [1,1'-bis(diphenylphosphino)ferrocene]dichloropalladium(II), dichloromethane complex (1.3 g, 1.6 mmol). The reaction mixture was stirred at 80° C. for 18 hours and filtered; the filtrate was concentrated in vacuo. Purification via silica gel chromatography (Gradient: 0% to 30% ethyl acetate in petroleum ether) provided the product as a yellow oil. Yield: 10.5 g, 25.6 mmol, 83%. $^1$H NMR (400 MHz, CDCl$_3$) δ 7.25-7.46 (m, 5H), 6.93-7.02 (m, 3H), 5.60 (AB quartet, $J_{AB}$=9.4 Hz, $\Delta v_{AB}$=9.7 Hz, 2H), 5.22 (s, 2H), 4.79 (s, 2H), 3.52 (s, 3H), 3.00 (s, 3H), 2.12 (br s, 3H), 1.63 (s, 3H).

Step 4. Synthesis of 3-[(benzyloxy)methyl]-6-(4-hydroxy-2-methylphenyl)-1,5-dimethylpyrimidine-2,4(1H,3H)-dione (C39)

To a solution of C38 (9.0 g, 22 mmol) in tetrahydrofuran (70 mL) was added aqueous hydrochloric acid (8 M, 70 mL), and the reaction mixture was stirred at room temperature for 1 hour. After extraction with ethyl acetate (5×100 mL), the combined organic layers were concentrated in vacuo; silica gel chromatography (Gradient: 0% to 50% ethyl acetate in petroleum ether) afforded the product as a white solid. Yield: 6.3 g, 17 mmol, 77%. LCMS m/z 389.0 [M+Na]$^+$. $^1$H NMR (400 MHz, CDCl$_3$) δ 7.43 (br d, J=7 Hz, 2H), 7.25-7.37 (m, 3H), 6.91 (d, J=7.9 Hz, 1H), 6.78-6.84 (m, 2H), 5.61 (AB quartet, $J_{AB}$=9.4 Hz, $\Delta v_{AB}$=9.2 Hz, 2H), 5.47 (s, 1H), 4.79 (s, 2H), 3.01 (s, 3H), 2.09 (s, 3H), 1.64 (s, 3H).

Step 5. Synthesis of 3-[(benzyloxy)methyl]-6-(4-{[3-(difluoromethoxy)pyridin-2-yl]oxy}-2-methylphenyl)-1,5-dimethylpyrimidine-2,4(1H,3H)-dione (C40)

A suspension of C39 (10 g, 27 mmol), C36 (5.88 g, 32.7 mmol), and cesium carbonate (99%, 13.5 g, 41.0 mmol) in dimethyl sulfoxide (200 mL) was heated to 80° C. for 18 hours. Compound C36 (2.9 g, 16 mmol) was added, and the reaction mixture was heated at 90° C. for 3 hours, then at 80° C. for 66 hours. After cooling to room temperature, the reaction mixture was diluted with water and extracted three times with ethyl acetate. The combined organic layers were washed with water (5×300 mL), washed with saturated aqueous sodium chloride solution (200 mL), dried over magnesium sulfate, filtered, and concentrated in vacuo. Purification via silica gel chromatography (Gradient: 25% to 50% ethyl acetate in heptane) provided the product as a viscous, light yellow oil. Yield: 10.8 g, 21.2 mmol, 78%. LCMS m/z 510.2 [M+H]$^+$. $^1$H NMR (400 MHz, CDCl$_3$) δ 8.05 (dd, J=4.9, 1.7 Hz, 1H), 7.61-7.65 (m, 1H), 7.40-7.44 (m, 2H), 7.30-7.36 (m, 2H), 7.24-7.29 (m, 1H), 7.11-7.16 (m, 2H), 7.10 (dd, J=7.9, 4.9 Hz, 1H), 7.08 (br d, J=8 Hz, 1H), 6.70 (t, $J_{HF}$=73.5 Hz, 1H), 5.61 (AB quartet, $J_{AB}$=9.5 Hz, $\Delta v_{AB}$=9.2 Hz, 2H), 4.79 (br s, 2H), 3.04 (s, 3H), 2.16 (br s, 3H), 1.66 (s, 3H).

Step 6. Synthesis of (−)-6-(4-{[3-(difluoromethoxy)pyridin-2-yl]oxy}-2-methylphenyl)-1,5-dimethylpyrimidine-2,4(1H,3H)-dione (13)

A mixture of C40 (10.8 g, 21.2 mmol) and trifluoroacetic acid (110 mL) was heated at 80° C. for 1 hour. The reaction mixture was concentrated in vacuo, treated with dichloromethane and concentrated again, then treated with tetrahydrofuran, concentrated under reduced pressure, and dried under high vacuum. The residue was diluted with tetrahydrofuran (50 mL), cooled in an ice bath, and treated with concentrated ammonium hydroxide (50 mL). The flask was removed from the ice bath and the reaction mixture was stirred at room temperature for 45 minutes; after removal of solvents in vacuo, purification via silica gel chromatography (Gradient: 25% to 100% ethyl acetate in heptane) provided a racemic mixture of 13 and its atropenantiomer. This was combined with material obtained from a similar reaction carried out on C40 (15.3 g, 30.0 mmol), and separated via supercritical fluid chromatography (Column: Phenomenex Lux Cellulose-2, 5 µm; Eluent: 3:2 carbon dioxide/methanol). The first-eluting atropenantiomer, which exhibited a negative (−) rotation, was assigned as atropenantiomer 13. Yield: 4.8 g, 12 mmol, 23%. This material was dissolved in hot ethyl acetate (200 mL) and slowly treated with heptane (100 mL) while maintaining the mixture at reflux. After slowly cooling to room temperature, the mixture was stirred at room temperature for 18 hours, then cooled to 0° C. and stirred for 30 minutes. Filtration afforded the product as a powdery white solid. Yield: 4.17 g, 10.7 mmol, 89% from the recrystallization. LCMS m/z 390.2 [M+H]$^+$. $^1$H NMR (400 MHz, DMSO-d$_6$) δ 11.45 (br s, 1H), 8.06 (dd, J=4.8, 1.5 Hz, 1H), 7.81 (br d, J=7.9 Hz, 1H), 7.32 (t, $J_{HF}$=73.4 Hz, 1H), 7.12-7.31 (m, 4H), 2.87 (s, 3H), 2.14 (s, 3H), 1.48 (s, 3H).

Examples 14 and 15

(−)-6-(4-{[3-(Difluoromethyl)pyridin-2-yl]oxy}-2-methylphenyl)-1,5-dimethylpyrimidine-2,4(1H,3H)-dione (14) and (+)-6-(4-{[3-(Difluoromethyl)pyridin-2-yl]oxy}-2-methylphenyl)-1,5-dimethylpyrimidine-2,4(1H,3H)-dione (15)

Step 2. Synthesis of (−)-6-(4-{[3-(difluoromethyl)pyridin-2-yl]oxy}-2-methylphenyl)-1,5-dimethylpyrimidine-2,4(1H,3H)-dione (14) and (+)-6-(4-{[3-(difluoromethyl)pyridin-2-yl]oxy}-2-methylphenyl)-1,5-dimethylpyrimidine-2,4(1H,3H)-dione (15)

Compound C41 was converted to a racemic mixture of the products using the method described for synthesis 13 in

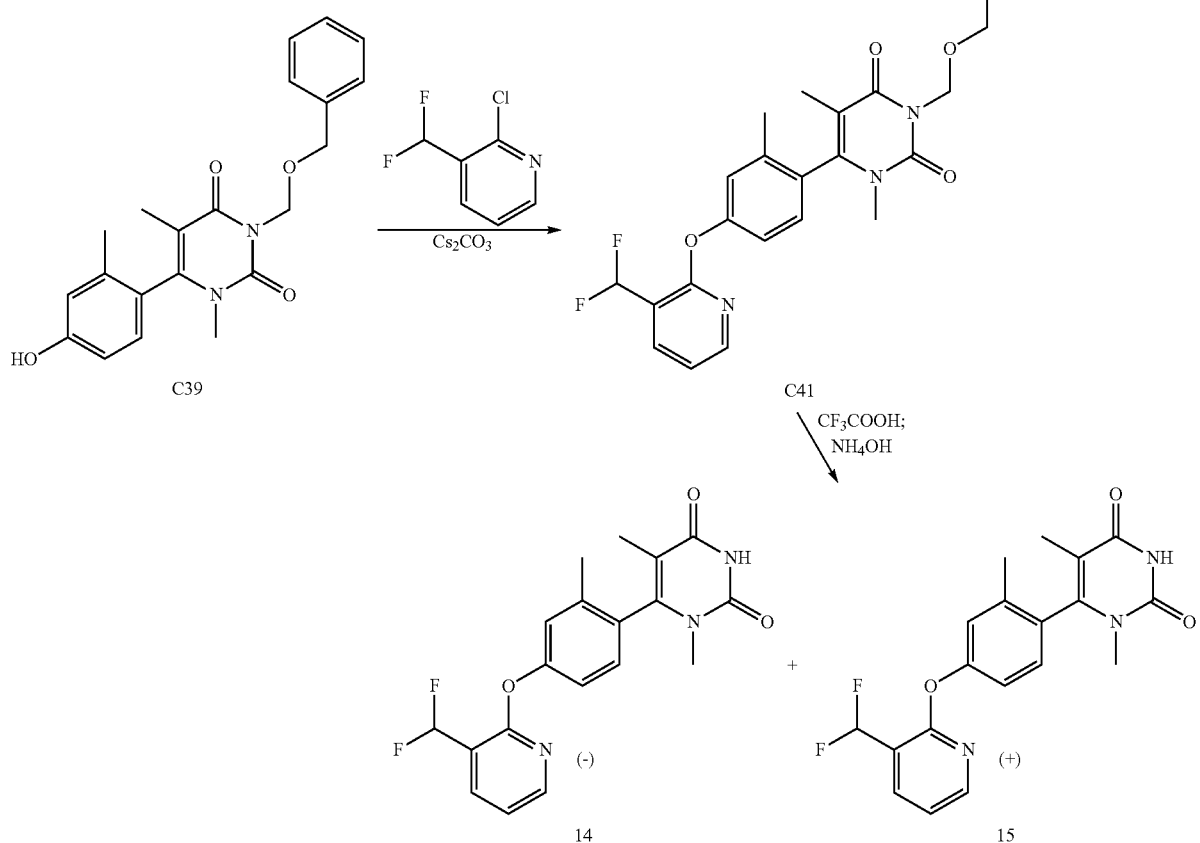

Step 1. Synthesis of 3-[(benzyloxy)methyl]-6-(4-{[3-(difluoromethyl)pyridin-2-yl]oxy}-2-methylphenyl)-1,5-dimethylpyrimidine-2,4(1H,3H)-dione (C41)

Compound C39 was reacted with 2-chloro-3-(difluoromethyl)pyridine using the method described for synthesis of C40 in Example 13. The product was obtained as a white solid. Yield: 17.3 g, 35.1 mmol, 86%. LCMS m/z 494.2 [M+H]$^+$. $^1$H NMR (400 MHz, CDCl$_3$) δ 8.27-8.31 (m, 1H), 8.02-8.07 (m, 1H), 7.41-7.46 (m, 2H), 7.32-7.37 (m, 2H), 7.26-7.31 (m, 1H), 7.08-7.21 (m, 4H), 7.03 (t, $J_{HF}$=55.1 Hz, 1H), 5.62 (AB quartet, $J_{AB}$=9.5 Hz, $\Delta\nu_{AB}$=9.5 Hz, 2H), 4.80 (br s, 2H), 3.05 (s, 3H), 2.17 (br s, 3H), 1.68 (s, 3H).

Example 13. This racemate was obtained as an off-white solid. Yield: 12.1 g, 32.4 mmol, 92%. It was separated into its component atropenantiomers via supercritical fluid chromatography (Column: Phenomenex Lux Cellulose-2, 5 μm; Eluent: 55:45 carbon dioxide/methanol). The first-eluting atropenantiomer exhibited a negative (−) rotation, and was designated as Example 14 (5.15 g). This material was dissolved in hot ethyl acetate, concentrated to a volume of 50 mL, and allowed to crystallize at room temperature; 14 was isolated as a white solid, 3.35 g. The filtrate was concentrated and similarly recrystallized to afford a white solid (450 mg). Combined yield of 14: 3.8 g, 10 mmol, 28%. The second-eluting atropenantiomer, obtained as an off-white solid exhibiting a positive (+) rotation, was designated as Example 15. Yield: 4.9 g, 13.1 mmol, 37%. 14: LCMS m/z 374.2 [M+H]$^+$. $^1$H NMR (400 MHz, CDCl$_3$) δ 8.47 (br s, 1H), 8.27-8.31 (m, 1H), 8.02-8.07 (m, 1H), 7.12-7.21 (m, 4H), 7.03 (t, $J_{HF}$=55.0 Hz, 1H), 3.06 (s, 3H), 2.21 (br s, 3H), 1.68 (s, 3H). 15: LCMS m/z 374.0 [M+H]$^+$. $^1$H NMR (600

MHz, CDCl$_3$) δ 8.98 (br s, 1H), 8.29 (br d, J=4.7 Hz, 1H), 8.04 (br d, J=7.5 Hz, 1H), 7.13-7.21 (m, 4H), 7.03 (t, J$_{HF}$=55.1 Hz, 1H), 3.06 (s, 3H), 2.21 (s, 3H), 1.68 (s, 3H).
Examples 16 and 17
(+)-5-(4-{[3-(Difluoromethyl)pyridin-2-yl]oxy}-2-methylphenyl)-4,6-dimethylpyridazin-3(2H)-one (16) and (−)-5-(4-{[3-(Difluoromethyl)pyridin-2-yl]oxy}-2-methylphenyl)-4,6-dimethylpyridazin-3(2H)-one (17)
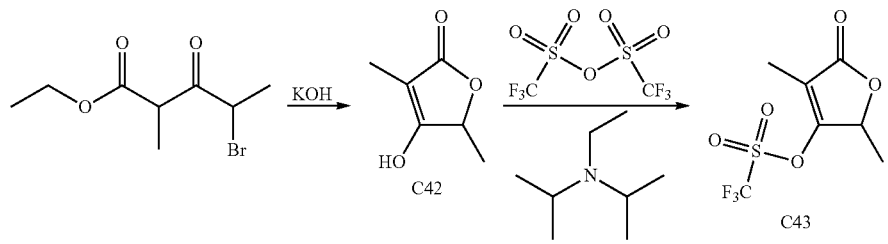
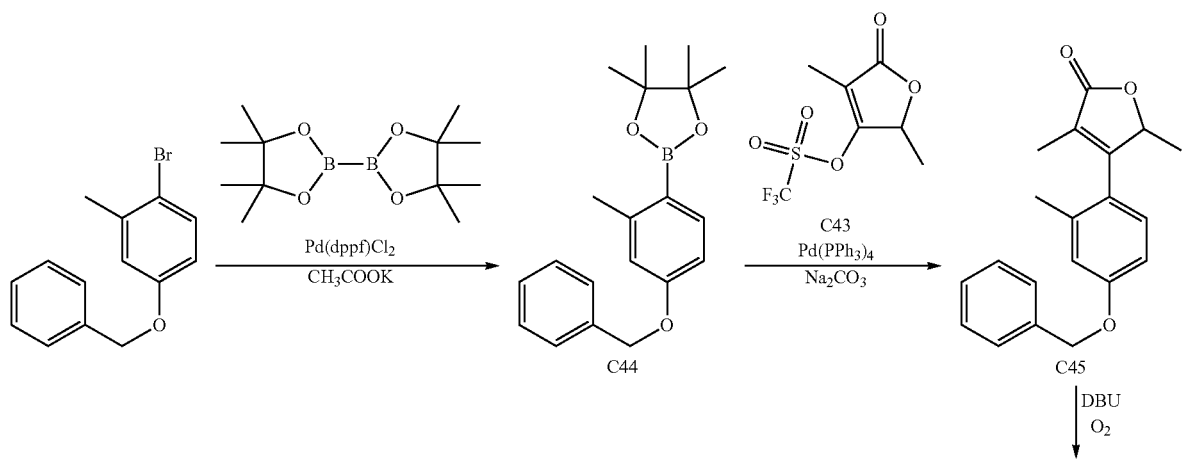
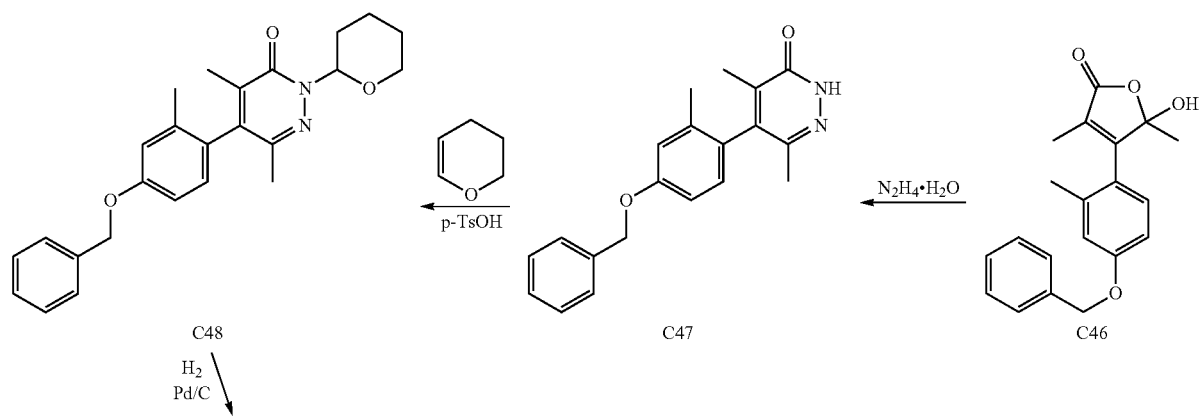

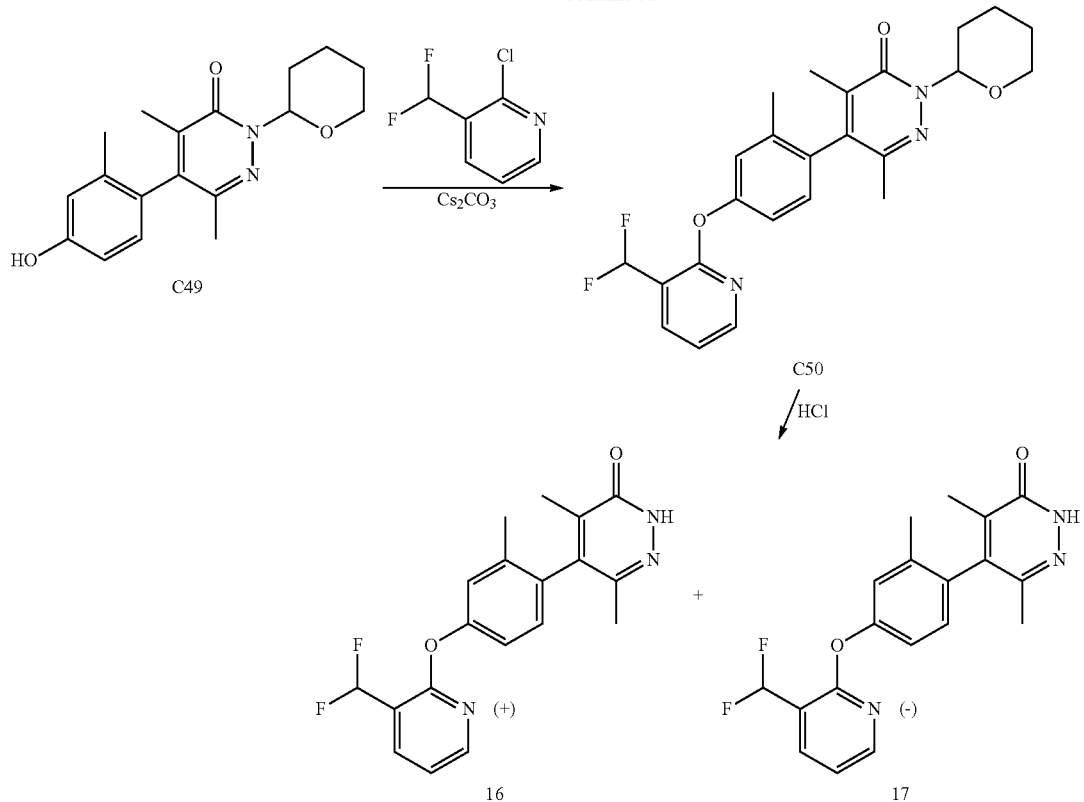

Step 1. Synthesis of 4-hydroxy-3,5-dimethylfuran-2(5H)-one (C42)

Methylation of ethyl 3-oxopentanoate according to the method of D. Kalaitzakis et al., *Tetrahedron: Asymmetry* 2007, 18, 2418-2426, afforded ethyl 2-methyl-3-oxopentanoate; subsequent treatment with 1 equivalent of bromine in chloroform provided ethyl 4-bromo-2-methyl-3-oxopentanoate. This crude material (139 g, 586 mmol) was slowly added to a 0° C. solution of potassium hydroxide (98.7 g, 1.76 mol) in water (700 mL). The internal reaction temperature rose to 30° C. during the addition. The reaction mixture was then subjected to vigorous stirring for 4 hours in an ice bath, at which point it was acidified via slow addition of concentrated hydrochloric acid. After extraction with ethyl acetate, the aqueous layer was saturated with solid sodium chloride and extracted three additional times with ethyl acetate. The combined organic layers were washed with saturated aqueous sodium chloride solution, dried over magnesium sulfate, filtered, and concentrated under reduced pressure to afford a mixture of oil and solid (81.3 g). This material was suspended in chloroform (200 mL); the solids were removed via filtration and washed with chloroform (2×50 mL). The combined filtrates were concentrated in vacuo and treated with a 3:1 mixture of heptane and diethyl ether (300 mL). The mixture was vigorously swirled until some of the oil began to solidify. It was then concentrated under reduced pressure to afford an oily solid (60.2 g). After addition of a 3:1 mixture of heptane and diethyl ether (300 mL) and vigorous stirring for 10 minutes, filtration afforded the product as an off-white solid. Yield: 28.0 g, 219 mmol, 37%. $^1$H NMR (400 MHz, CDCl$_3$) δ 4.84 (br q, J=6.8 Hz, 1H), 1.74 (br s, 3H), 1.50 (d, J=6.8 Hz, 3H).

Step 2. Synthesis of 2,4-dimethyl-5-oxo-2,5-dihydrofuran-3-yl trifluoromethanesulfonate (C43)

Trifluoromethanesulfonic anhydride (23.7 mL, 140 mmol) was added portion-wise to a solution of C42 (15.0 g, 117 mmol) and N,N-diisopropylethylamine (99%, 24.8 mL, 140 mmol) in dichloromethane (500 mL) at −20° C., at a rate sufficient to maintain the internal reaction temperature below −10° C. The reaction mixture was allowed to warm gradually from −20° C. to 0° C. over 5 hours. It was then passed through a plug of silica gel, dried over magnesium sulfate, and concentrated in vacuo. The residue was suspended in diethyl ether and filtered; the filtrate was concentrated under reduced pressure. Purification using silica gel chromatography (Gradient: 0% to 17% ethyl acetate in heptane) afforded the product as a pale yellow oil. Yield: 21.06 g, 80.94 mmol, 69%. $^1$H NMR (400 MHz, CDCl$_3$) δ 5.09-5.16 (m, 1H), 1.94-1.96 (m, 3H), 1.56 (d, J=6.6 Hz, 3H).

Step 3. Synthesis of 2-[4-(benzyloxy)-2-methylphenyl]-4,4,5,5-tetramethyl-1,3,2-dioxaborolane (C44)

Benzyl 4-bromo-3-methylphenyl ether was converted to the product using the method described for synthesis of C33 in Example 12. The product was isolated as a yellow gel. Yield: 15 g, 46 mmol, 67%. $^1$H NMR (400 MHz, CDCl$_3$) δ 7.73 (d, J=8.0 Hz, 1H), 7.30-7.46 (m, 5H), 6.76-6.82 (m, 2H), 5.08 (s, 2H), 2.53 (s, 3H), 1.34 (s, 12H).

Step 4. Synthesis of 4-[4-(benzyloxy)-2-methylphenyl]-3,5-dimethylfuran-2(5H)-one (C45)

Compound C43 (5.0 g, 19 mmol), C44 (7.48 g, 23.1 mmol), tetrakis(triphenylphosphine)palladium(0) (2.22 g, 1.92 mmol), and sodium carbonate (4.07 g, 38.4 mmol) were combined in 1,4-dioxane (100 mL) and water (5 mL), and heated at reflux for 2 hours. The reaction mixture was filtered and the filtrate was concentrated in vacuo. Purification using silica gel chromatography (Eluents: 10:1, then 5:1 petroleum ether/ethyl acetate) provided the product as a white solid. Yield: 5.8 g, 19 mmol, 100%. NMR (400 MHz, CDCl$_3$) δ 7.33-7.49 (m, 5H), 6.98 (d, J=8.5 Hz, 1H), 6.94 (br d, J=2.5 Hz, 1H), 6.88 (br dd, J=8.3, 2.5 Hz, 1H), 5.20 (qq, J=6.7, 1.8 Hz, 1H), 5.09 (s, 2H), 2.21 (s, 3H), 1.78 (d, J=1.8 Hz, 3H), 1.31 (d, J=6.8 Hz, 3H).

Step 5. Synthesis of 4-[4-(benzyloxy)-2-methylphenyl]-5-hydroxy-3,5-dimethylfuran-2(5H)-one (C46)

A solution of C45 (5.4 g, 18 mmol) and 1,8-diazabicyclo[5.4.0]undec-7-ene (13.3 g, 87.4 mmol) in acetonitrile (100 mL) was cooled to −60° C. Oxygen was bubbled into the reaction mixture for 20 minutes at −60° C.; the solution was then stirred at 50° C. for 18 hours. The reaction mixture was concentrated in vacuo and purified via silica gel chromatography (Eluent: 5:1 petroleum ether/ethyl acetate) to provide the product as a colorless oil. Yield: 3.5 g, 11 mmol, 61%. $^1$H NMR (400 MHz, CDCl$_3$), characteristic peaks: δ 7.33-7.49 (m, 5H), 6.92-6.96 (m, 1H), 6.88 (dd, J=8.5, 2.5 Hz, 1H), 5.09 (s, 2H), 2.20 (s, 3H), 1.73 (s, 3H).

Step 6. Synthesis of 5-[4-(benzyloxy)-2-methylphenyl]-4,6-dimethylpyridazin-3(2H)-one (C47)

A mixture of C46 (3.5 g, 11 mmol) and hydrazine hydrate (85% in water, 1.9 g, 32 mmol) in n-butanol (60 mL) was heated at reflux for 18 hours. After removal of volatiles under reduced pressure, the residue was stirred with ethyl acetate (20 mL) for 30 minutes, whereupon filtration provided the product as a white solid. Yield: 2.0 g, 6.2 mmol, 56%. $^1$H NMR (400 MHz, CDCl$_3$) δ 10.93 (br s, 1H), 7.33-7.51 (m, 5H), 6.96 (s, 1H), 6.88-6.94 (m, 2H), 5.10 (s, 2H), 2.04 (s, 3H), 1.95 (s, 3H), 1.91 (s, 3H).

Step 7. Synthesis of 5-[4-(benzyloxy)-2-methylphenyl]-4,6-dimethyl-2-(tetrahydro-2H-pyran-2-yl)pyridazin-3(2H)-one (C48)

A mixture of C47 (17.8 g, 55.6 mmol), 3,4-dihydro-2H-pyran (233 g, 2.77 mol) and p-toluenesulfonic acid monohydrate (2.1 g, 11 mmol) in tetrahydrofuran (800 mL) was heated at reflux for 18 hours. Triethylamine (10 mL, 72 mmol) was added, and the mixture was concentrated in vacuo. Silica gel chromatography (Gradient: 0% to 25% ethyl acetate in petroleum ether) afforded the product as a solid, presumed to be a mixture of diastereomeric atropisomers from its $^1$H NMR spectrum. Yield: 20 g, 49 mmol, 88%. $^1$H NMR (400 MHz, CDCl$_3$), characteristic peaks: δ 7.32-7.50 (m, 5H), 6.82-6.96 (m, 3H), 6.15 (br d, J=10.3 Hz, 1H), 5.08 (s, 2H), 4.14-4.23 (m, 1H), 3.76-3.85 (m, 1H), 2.28-2.41 (m, 1H), 2.01 and 2.04 (2 s, total 3H), 1.97 and 1.98 (2 s, total 3H), 1.89 and 1.89 (2 s, total 3H).

Step 8. Synthesis of 5-(4-hydroxy-2-methylphenyl)-4,6-dimethyl-2-(tetrahydro-2H-pyran-2-yl)pyridazin-3(2H)-one (C49)

Palladium (10% on carbon, 1.16 g, 1.09 mmol) was added to a solution of C48 (1.47 g, 3.63 mmol) in methanol (30 mL) and ethyl acetate (10 mL), and the mixture was hydrogenated (50 psi) on a Parr shaker for 18 hours at room temperature. The reaction mixture was filtered through diatomaceous earth, and the filter pad was rinsed with ethyl acetate; the combined filtrates were concentrated in vacuo and triturated with heptane, affording the product as a white solid, judged to be a mixture of diastereomeric atropisomers from its $^1$H NMR spectrum. Yield: 1.01 g, 3.21 mmol, 88%. $^1$H NMR (400 MHz, CDCl$_3$), characteristic peaks: δ 6.74-6.85 (m, 3H), 6.12-6.17 (m, 1H), 4.15-4.23 (m, 1H), 3.76-3.84 (m, 1H), 2.28-2.41 (m, 1H), 1.99 and 2.01 (2 s, total 3H), 1.97 and 1.98 (2 s, total 3H), 1.89 and 1.89 (2 s, total 3H).

Step 9. Synthesis of 5-(4-{[3-(difluoromethyl)pyridin-2-yl]oxy}-2-methylphenyl)-4,6-dimethyl-2-(tetrahydro-2H-pyran-2-yl)pyridazin-3(2H)-one (C50)

Compound C49 was reacted with 2-chloro-3-(difluoromethyl)pyridine using the method described for synthesis of C8 in Examples 3 and 4. The product was obtained as a white solid, presumed to be a mixture of diastereomeric atropisomers from its $^1$H NMR spectrum. Yield: 17.5 g, 39.6 mmol, 82%. LCMS m/z 358.2 [(M−tetrahydropyran)+1]. $^1$H NMR (400 MHz, DMSO-d$_6$) δ 8.31-8.35 (m, 1H), 8.11-8.15 (m, 1H), 7.29 (t, J$_{HF}$=54.5 Hz, 1H), 7.28-7.33 (m, 1H), 7.20-7.22 (m, 1H), 7.11-7.19 (m, 2H), 5.92-5.98 (m, 1H), 3.94-4.01 (m, 1H), 3.57-3.65 (m, 1H), 2.13-2.26 (m, 1H), 2.02 and 2.03 (2 br s, total 3H), 1.93-2.0 (m, 1H), 1.92 (s, 3H), 1.78 (s, 3H), 1.61-1.74 (m, 2H), 1.48-1.58 (m, 2H).

Step 10. Synthesis of (+)-5-(4-{[3-(difluoromethyl)pyridin-2-yl]oxy}-2-methylphenyl)-4,6-dimethylpyridazin-3(2H)-one (16) and (−)-5-(4-{[3-(difluoromethyl)pyridin-2-yl]oxy}-2-methylphenyl)-4,6-dimethylpyridazin-3(2H)-one (17)

Hydrogen chloride in 1,4-dioxane (4 M, 198 mL, 792 mmol) was added to a solution of C50 (17.5 g, 39.6 mmol) in dichloromethane (200 mL) and 1,4-dioxane (200 mL), and the reaction mixture was stirred at room temperature for 18 hours. After solvents had been removed in vacuo, the residue was suspended in diethyl ether (200 mL) and slowly treated with a half-saturated aqueous solution of sodium bicarbonate. The suspension was vigorously stirred for 15 minutes, then filtered; the collected solid was washed twice with water and twice with diethyl ether. The solid was then suspended in ethanol (200 mL), concentrated to dryness, resuspended in ethanol (200 mL) and concentrated once more. The residue was similarly treated with diethyl ether and with heptane to afford the racemic product as a white solid. Yield: 12.0 g, 33.6 mmol, 85%. LCMS m/z 358.2 [M+H]$^+$. $^1$H NMR (400 MHz, DMSO-d$_6$) δ 12.82 (br s, 1H), 8.32-8.36 (m, 1H), 8.10-8.15 (m, 1H), 7.29 (t, J$_{HF}$=54.2 Hz, 1H), 7.28-7.33 (m, 1H), 7.19-7.22 (m, 1H), 7.10-7.17 (m, 2H), 2.02 (s, 3H), 1.87 (s, 3H), 1.74 (s, 3H). Separation of the racemate into its component atropenantiomers was carried out via supercritical fluid chromatography (Column: Chiral Technologies, Chiralpak AS-H, 5 µm; Eluent: 85:15 carbon dioxide/methanol). The first-eluting atropenantiomer, obtained as a white solid that exhibited a positive (+) rotation, was designated as Example 16. Yield: 5.22 g, 14.6 mmol, 37%. The second-eluting atropenantiomer, also obtained as a white solid but with a negative (−) rotation, was designated as Example 17. Yield: 5.31 g, 14.8 mmol, 37%. 16: LCMS m/z 358.2 [M+H]$^+$. $^1$H NMR (400 MHz, CD$_3$OD) δ 8.23-8.27 (m, 1H), 8.08-8.12 (m, 1H), 7.26 (dd, J=7.5, 4.9 Hz, 1H), 7.18-7.20 (m, 1H), 7.12-7.14 (m, 2H), 7.12 (t, J$_{HF}$=55 Hz, 1H), 2.09 (br d, J=0.4 Hz, 3H), 2.00 (s, 3H), 1.90 (s, 3H). 17: LCMS m/z 358.2 [M+H]$^+$. $^1$H NMR (400 MHz, CD$_3$OD) δ 8.23-8.27 (m, 1H), 8.08-8.12 (m, 1H), 7.26 (dd, J=7.6, 5.0 Hz, 1H), 7.18-7.20 (m, 1H), 7.12-7.14 (m, 2H), 7.12 (t, J$_{HF}$=55 Hz, 1H), 2.09 (br d, J=0.5 Hz, 3H), 2.00 (s, 3H), 1.90 (s, 3H).
Example 18
6-{4-[(3-Chloropyridin-2-yl)sulfanyl]-2-methylphenyl}-1,5-dimethylpyrimidine-2,4(1H,3H)-dione (18)
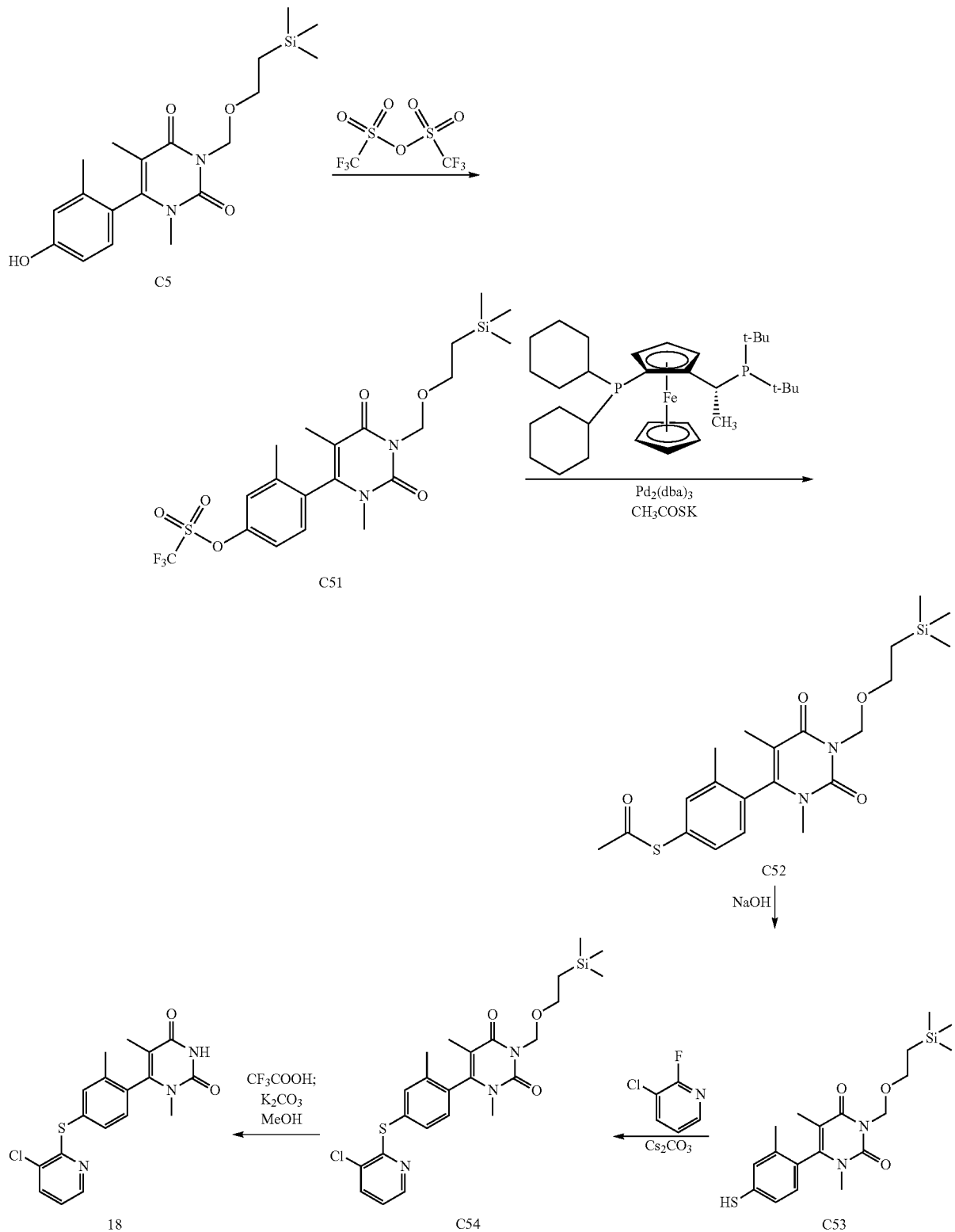

Step 1. Synthesis of 4-(3,5-dimethyl-2,6-dioxo-1-{[2-(trimethylsilyl)ethoxy]methyl}-1,2,3,6-tetrahydropyrimidin-4-yl)-3-methylphenyl trifluoromethanesulfonate (C51)

Trifluoromethanesulfonic anhydride (1.3 g, 4.6 mmol) was slowly added to a 0° C. solution of C5 (600 mg, 1.6 mmol) in pyridine (15 mL), and the reaction mixture was stirred at room temperature for 3 hours. After solvent had been removed under reduced pressure, the residue was purified by silica gel chromatography (Gradient: 5% to 17% ethyl acetate in petroleum ether) to afford the product as a yellow oil. Yield: 790 mg, 1.55 mmol, 97%. 1H NMR (400 MHz, CDCl$_3$) δ 7.27-7.33 (m, 2H), 7.21-7.25 (m, 1H), 5.50 (AB quartet, J$_{AB}$=9.2 Hz, Δv$_{AB}$=4.1 Hz, 2H), 3.73-3.79 (m, 2H), 3.02 (s, 3H), 2.26 (br s, 3H), 1.63 (s, 3H), 1.00-1.06 (m, 2H), 0.03 (s, 9H).

Step 2. Synthesis of S-[4-(3,5-dimethyl-2,6-dioxo-1-{[2-(trimethylsilyl) ethoxy]methyl}-1,2,3,6-tetrahydropyrimidin-4-yl)-3-methylphenyl] ethanethioate (C52)

Tris(dibenzylideneacetone)dipalladium(0) (27 mg, 29 µmol) and (R)-(−)-1-[(S$_P$)-2-(dicyclohexylphosphino)ferrocenyl]ethyldi-tert-butylphosphine (Josiphos ligand, 33 mg, 60 µmol) were added to a solution of C51 (305 mg, 0.600 mmol) in degassed toluene (7 mL), and the mixture was stirred for 5 minutes at room temperature. Potassium thioacetate (274 mg, 2.40 mmol) was added and the reaction mixture was heated at 120° C. for 24 hours. It was then filtered through a pad of diatomaceous earth, and the pad was washed with ethyl acetate; the combined filtrates were concentrated in vacuo. Silica gel chromatography (Gradient: 0% to 30% ethyl acetate in petroleum ether) provided the product as a brown gum. Yield: 172 mg, 0.396 mmol, 66%. $^1$H NMR (400 MHz, CDCl$_3$) δ 7.38-7.44 (m, 2H), 7.15 (d, J=7.8 Hz, 1H), 5.48-5.53 (m, 2H), 3.73-3.79 (m, 2H), 3.03 (s, 3H), 2.47 (s, 3H), 2.20 (s, 3H), 1.65 (s, 3H), 1.00-1.06 (m, 2H), 0.03 (s, 9H).

Step 3. Synthesis of 1,5-dimethyl-6-(2-methyl-4-sulfanylphenyl)-3-{[2-(trimethylsilyl)ethoxy]methyl}pyrimidine-2,4(1H,3H)-dione (C53)

A solution of C52 (300 mg, 0.69 mmol) and potassium hydroxide (168 mg, 2.99 mmol) in a mixture of methanol (10 mL) and water (3 drops) was stirred at room temperature for 3 hours. After neutralization with 1 M aqueous hydrochloric acid, the mixture was concentrated in vacuo. Preparative thin layer chromatography on silica gel (Eluent: 3:1 petroleum ether/ethyl acetate) afforded the product as a yellow syrup. Yield: 170 mg, 0.433 mmol, 63% yield.

Step 4. Synthesis of 6-{4-[(3-chloropyridin-2-yl)sulfanyl]-2-methylphenyl}-1,5-dimethyl-3-{[2-(trimethylsilyl)ethoxy]methyl}pyrimidine-2,4(1H,3H)-dione (C54)

Compound C53 was reacted with 3-chloro-2-fluoropyridine using the method described for synthesis of C8 in Examples 3 and 4. The product was obtained as a white solid. Yield: 20 mg, 40 µmol, 40%.

Step 5. Synthesis of 6-{4-[(3-chloropyridin-2-yl)sulfanyl]-2-methylphenyl}-1,5-dimethylpyrimidine-2,4(1H,3H)-dione (18)

A solution of C54 (20 mg, 40 µmol) in trifluoroacetic acid (5 mL) was stirred at room temperature for 18 hours. The reaction mixture was concentrated in vacuo and the residue was dissolved in methanol (5 mL). Potassium carbonate (69 mg, 0.50 mmol) was added, and the reaction mixture was stirred at room temperature for 3 hours and filtered; the filtrate was concentrated in vacuo and purified via preparative thin layer chromatography on silica gel (Eluent: 1:2 petroleum ether/ethyl acetate) to provide the product as a white solid. Yield: 7.5 mg, 20 µmol, 50%. LCMS m/z 374.0 [M+H]$^+$. $^1$H NMR (400 MHz, CDCl$_3$) δ 8.25 (dd, J=4.7, 1.6 Hz, 1H), 8.19 (br s, 1H), 7.64 (dd, J=7.9, 1.6 Hz, 1H), 7.55-7.57 (m, 1H), 7.51-7.55 (m, 1H), 7.15 (d, J=7.8 Hz, 1H), 7.06 (dd, J=7.9, 4.6 Hz, 1H), 3.05 (s, 3H), 2.21 (br s, 3H), 1.68 (s, 3H).

Example 19

1,5-Dimethyl-6-(7-{[3-(trifluoromethyl)pyridin-2-yl]oxy}-1H-indol-4-yl)pyrimidine-2,4(1H,3H)-dione (19)

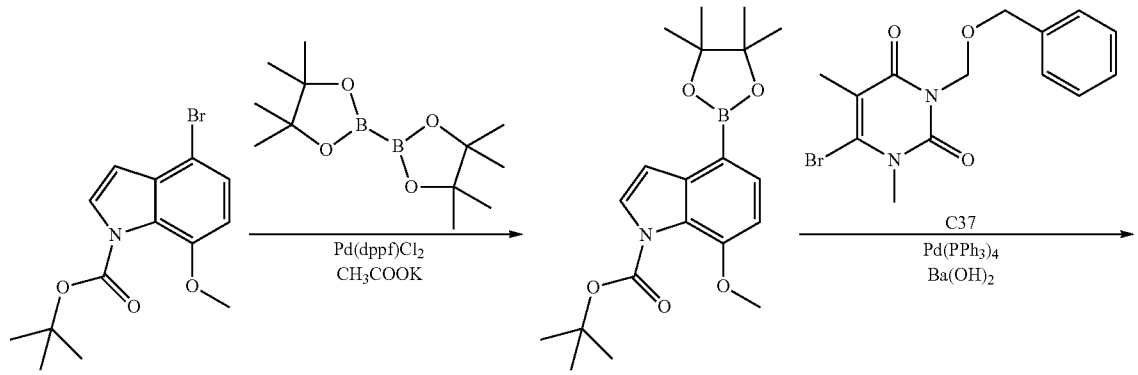

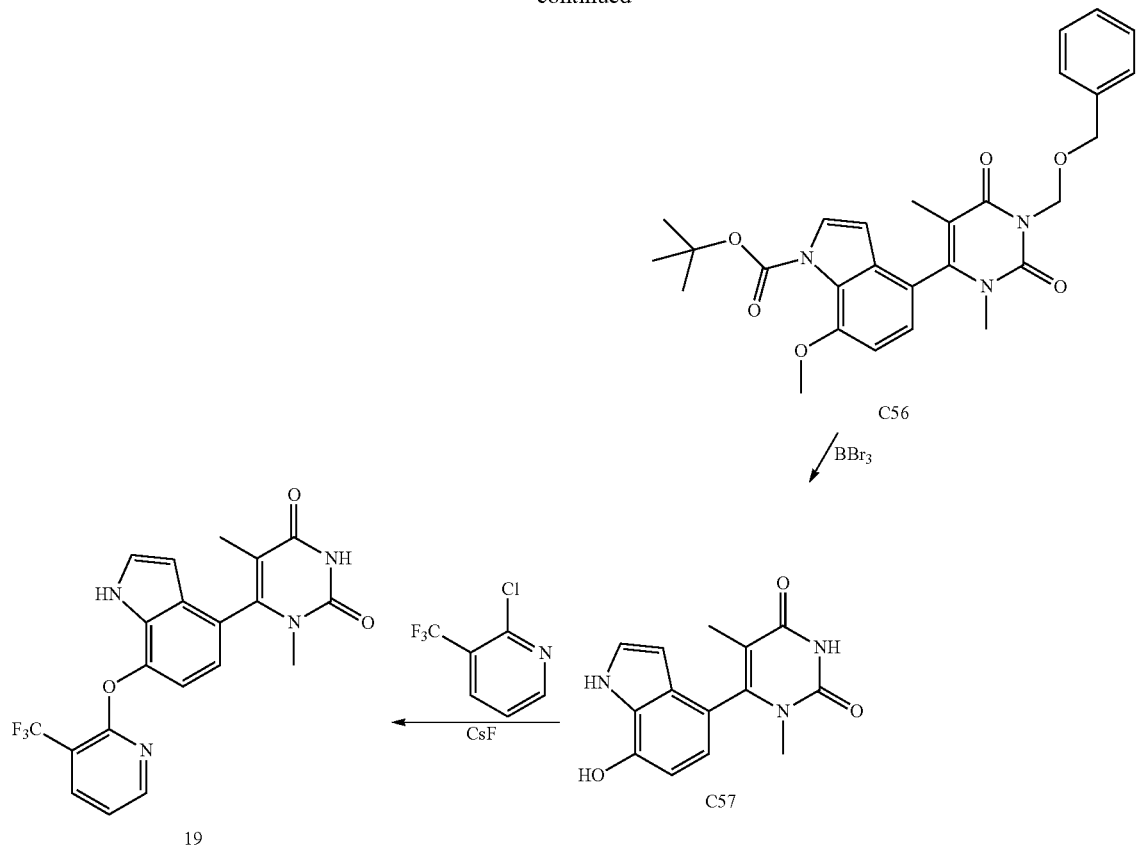

Step 1. Synthesis of tert-butyl 7-methoxy-4-(4,4,5,5-tetramethyl-1,3,2-dioxaborolan-2-yl)-1H-indole-1-carboxylate (C55)

To a solution of tert-butyl 4-bromo-7-methoxy-1H-indole-1-carboxylate (which may be prepared via tert-butoxycarbonyl protection of 4-bromo-7-methoxy-1H-indole) (1.0 g, 3.1 mmol) in 1,4-dioxane (20 mL) were added 4,4,4',4',5,5,5',5'-octamethyl-2,2'-bi-1,3,2-dioxaborolane (1.46 g, 5.75 mmol), potassium acetate (902 mg, 9.19 mmol) and [1,1'-bis(diphenylphosphino)ferrocene]dichloropalladium (II), dichloromethane complex (498 mg, 0.610 mmol). The reaction mixture was stirred for 5 hours at 120° C., then cooled and filtered; the filtrate was concentrated under reduced pressure and purified via silica gel chromatography (Gradient: 0% to 6% ethyl acetate in petroleum ether) to afford the product as a yellow solid. Yield: 520 mg, 1.4 mmol, 45%. $^1$H NMR (400 MHz, CDCl$_3$) δ 7.69 (d, J=8.0 Hz, 1H), 7.55 (d, J=3.5 Hz, 1H), 7.10 (d, J=3.6 Hz, 1H), 6.81 (d, J=8.0 Hz, 1H), 3.96 (s, 3H), 1.62 (s, 9H), 1.37 (s, 12H).

Step 2. Synthesis of tert-butyl 4-{1-[(benzyloxy)methyl]-3,5-dimethyl-2,6-dioxo-1,2,3,6-tetrahydropyrimidin-4-yl}-7-methoxy-1H-indole-1-carboxylate (C56)

To a solution of C55 (600 mg, 1.6 mmol) in 1,4-dioxane (20 mL) were added C37 (600 mg, 1.8 mmol), tetrakis(triphenylphosphine)palladium(0) (186 mg, 0.161 mmol) and barium hydroxide (830 mg, 4.8 mmol). The reaction mixture was stirred for 18 hours at 60° C., then cooled and filtered; the filtrate was concentrated in vacuo and subjected to silica gel chromatography (Gradient: 0% to 35% ethyl acetate in petroleum ether), providing the product as a yellow gum. Yield: 310 mg, 0.61 mmol, 38%. $^1$H NMR (400 MHz, CDCl$_3$) δ 7.60 (d, J=3.6 Hz, 1H), 7.45 (br d, J=7 Hz, 2H), 7.27-7.39 (m, 3H, assumed; partially obscured by solvent peak), 6.94 (AB quartet, J$_{AB}$=8.2 Hz, Δv$_{AB}$=35.2 Hz, 2H), 6.24 (d, J=3.6 Hz, 1H), 5.63 (AB quartet, J$_{AB}$=9.4 Hz, Δv$_{AB}$=6.7 Hz, 2H), 4.81 (s, 2H), 4.01 (s, 3H), 3.00 (s, 3H), 1.66 (s, 9H), 1.64 (s, 3H).

Step 3. Synthesis of 6-(7-hydroxy-1H-indol-4-yl)-1,5-dimethylpyrimidine-2,4(1H,3H)-dione (C57)

Boron tribromide (1.5 g, 6.0 mmol) was added drop-wise to a −78° C. solution of C56 (310 mg, 0.61 mmol) in dichloromethane (10 mL), and the reaction mixture was stirred for 18 hours at room temperature. After addition of methanol (10 mL) and sodium bicarbonate (1 g), the mixture was filtered and the filtrate was concentrated in vacuo. Silica gel chromatography (Gradient: 0% to 4% methanol in dichloromethane) afforded the product as a yellow gum. Yield: 40 mg, 0.15 mmol, 24%. $^1$H NMR (400 MHz, CD$_3$OD) δ 7.29 (d, J=3.0 Hz, 1H), 6.70 (AB quartet, J$_{AB}$=7.7 Hz, Δv$_{AB}$=41.9 Hz, 2H), 6.18 (d, J=3.1 Hz, 1H), 3.00 (s, 3H), 1.61 (s, 3H).

Step 4. Synthesis of 1,5-dimethyl-6-(7-{[3-(trifluoromethyl)pyridin-2-yl]oxy}-1H-indol-4-yl)pyrimidine-2,4(1H,3H)-dione (19)

2-Chloro-3-(trifluoromethyl)pyridine (133 mg, 0.733 mmol) and cesium fluoride (12 mg, 79 μmol) were added to a solution of C57 (20 mg, 74 μmol) in N,N-dimethylformamide (5 mL). The reaction mixture was stirred for 18 hours at 100° C., then cooled and filtered. The filtrate was concentrated under reduced pressure, and the residue was purified by preparative thin layer chromatography on silica gel (Eluent: 10:1 dichloromethane/methanol) to provide the product as a white solid. Yield: 9.2 mg, 22 μmol, 30%. LCMS m/z 417.0 [M+H]$^+$. $^1$H NMR (400 MHz, CD$_3$OD) δ 8.20-8.27 (m, 2H), 7.34 (d, J=3.1 Hz, 1H), 7.28 (br dd, J=7, 5 Hz, 1H), 7.01 (AB quartet, J$_{AB}$=7.9 Hz, Δv$_{AB}$=4.4 Hz, 2H), 6.35 (d, J=3.1 Hz, 1H), 3.05 (s, 3H), 1.65 (s, 3H).

Preparations

Preparations P1 and P2 describe preparations of some starting materials or intermediates used for preparation of certain exemplar compounds of the invention.

Preparation P1

6-(4-Hydroxy-2-methylphenyl)-1,5-dimethyl-pyrazin-2(1H)-one (P1)

maceous earth; the filter pad was thoroughly washed with ethyl acetate (2×1.5 L). The organic phase from the combined filtrates was dried over sodium sulfate, filtered, and concentrated in vacuo. Purification via silica gel chromatography (Gradient: 0% to 5% ethyl acetate in petroleum ether) provided the product as a yellow oil. Combined yield: 602 g, 3.38 mol, 68%. LCMS m/z 179.0 [M+H]$^+$. $^1$H NMR (400 MHz, CDCl$_3$) δ 7.05 (d, J=8.3 Hz, 1H), 6.70-6.77 (m, 2H), 3.79 (s, 3H), 3.65 (s, 2H), 2.22 (s, 3H), 2.14 (s, 3H).

Step 2. Synthesis of 1-(4-methoxy-2-methylphenyl)propane-1,2-dione (C59)

Compound C58 (6.00 g, 33.7 mmol) and selenium dioxide (7.47 g, 67.3 mmol) were suspended in 1,4-dioxane (50 mL) and heated at 100° C. for 18 hours. The reaction mixture was cooled to room temperature and filtered through diatomaceous earth; the filtrate was concentrated in vacuo. Silica gel chromatography (Eluent: 10% ethyl acetate in heptane) afforded the product as a bright yellow oil. Yield: 2.55 g, 13.3 mmol, 39%. LCMS m/z 193.1 [M+H]$^+$. $^1$H

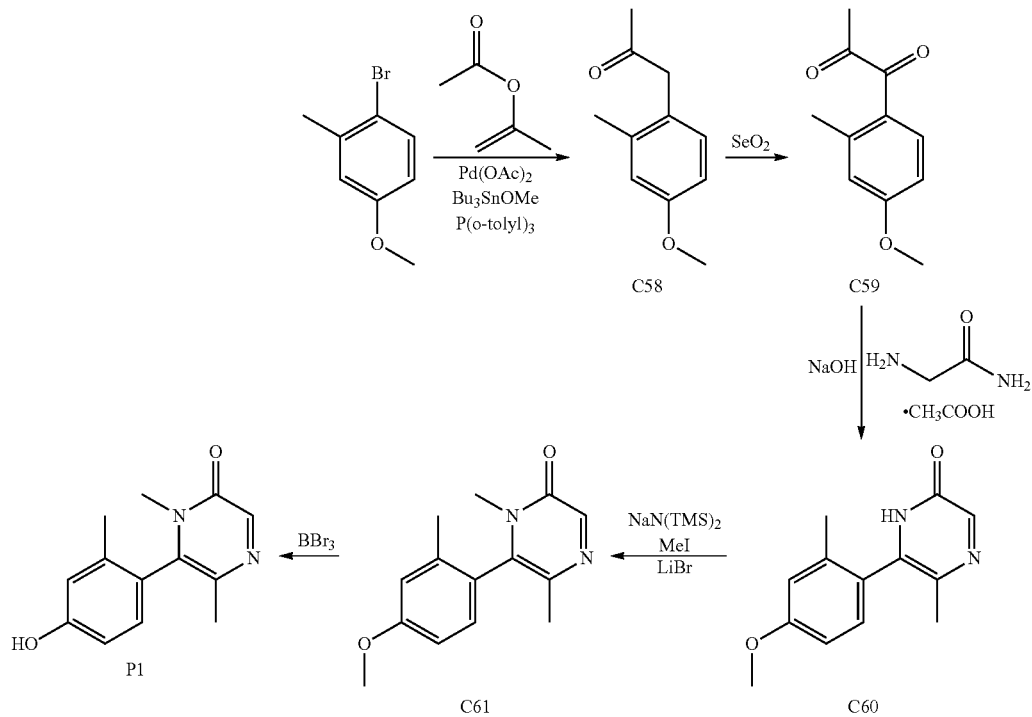

Step 1. Synthesis of 1-(4-methoxy-2-methylphenyl)propan-2-one (C58)

This experiment was carried out four times. Tributyl(methoxy)stannane (400 g, 1.24 mol), 1-bromo-4-methoxy-2-methylbenzene (250 g, 1.24 mol), prop-1-en-2-yl acetate (187 g, 1.87 mol), palladium(II) acetate (7.5 g, 33 mmol) and tri-o-tolylphosphine (10 g, 33 mmol) were stirred together in toluene (2 L) at 100° C. for 18 hours. After it had cooled to room temperature, the reaction mixture was treated with aqueous potassium fluoride solution (4 M, 400 mL) and stirred for 2 hours at 40° C. The resulting mixture was diluted with toluene (500 mL) and filtered through diato- NMR (400 MHz, CDCl$_3$) δ 7.66 (d, J=8.6 Hz, 1H), 6.81 (br d, half of AB quartet, J=2.5 Hz, 1H), 6.78 (br dd, half of ABX pattern, J=8.7, 2.6 Hz, 1H), 3.87 (s, 3H), 2.60 (br s, 3H), 2.51 (s, 3H).

Step 3. Synthesis of 6-(4-methoxy-2-methylphenyl)-5-methylpyrazin-2(1H)-one (C60)

Compound C59 (4.0 g, 21 mmol) and glycinamide acetate (2.79 g, 20.8 mmol) were dissolved in methanol (40 mL) and cooled to −10° C. Aqueous sodium hydroxide solution (12 N, 3.5 mL, 42 mmol) was added, and the resulting mixture was slowly warmed to room temperature. After stirring for 3 days, the reaction mixture was concentrated in vacuo. The residue was diluted with water, and 1 M aqueous hydrochloric acid was added until the pH was approximately 7. The aqueous phase was extracted with ethyl acetate, and the combined organic extracts were washed with saturated aqueous sodium chloride solution, dried over magnesium sulfate, filtered, and concentrated under reduced pressure. The resulting residue was slurried with 3:1 ethyl acetate/heptane, stirred for 5 minutes, filtered, and concentrated in vacuo. Silica gel chromatography (Eluent: ethyl acetate) provided the product as a tan solid that contained 15% of an undesired regioisomer; this material was used without further purification. Yield: 2.0 g. LCMS m/z 231.1 [M+H]$^+$. $^1$H NMR (400 MHz, CDCl$_3$) δ 8.09 (s, 1H), 7.14 (d, J=8.2 Hz, 1H), 6.82-6.87 (m, 2H), 3.86 (s, 3H), 2.20 (s, 3H), 2.11 (s, 3H).

Step 4. Synthesis of 6-(4-methoxy-2-methylphenyl)-1,5-dimethylpyrazin-2(1H)-one (C61)

Compound C60 (from the previous step, 1.9 g) was dissolved in N,N-dimethylformamide (40 mL). Lithium bromide (0.86 g, 9.9 mmol) and sodium bis(trimethylsilyl)amide (95%, 1.91 g, 9.89 mmol) were added, and the resulting solution was stirred for 30 minutes. Methyl iodide (0.635 mL, 10.2 mmol) was added and stirring was continued at room temperature for 18 hours. The reaction mixture was then diluted with water and brought to a pH of approximately 7 by slow portion-wise addition of 1 M aqueous hydrochloric acid. The aqueous layer was extracted with ethyl acetate and the combined organic layers were washed several times with water, dried over magnesium sulfate, filtered, and concentrated. Silica gel chromatography (Gradient: 75% to 100% ethyl acetate in heptane) afforded the product as a viscous orange oil. Yield: 1.67 g, 6.84 mmol, 33% over two steps. LCMS m/z 245.1 [M+H]$^+$. $^1$H NMR (400 MHz, CDCl$_3$) δ 8.17 (s, 1H), 7.03 (br d, J=8 Hz, 1H), 6.85-6.90 (m, 2H), 3.86 (s, 3H), 3.18 (s, 3H), 2.08 (br s, 3H), 2.00 (s, 3H).

Step 5. Synthesis of 6-(4-hydroxy-2-methylphenyl)-1,5-dimethylpyrazin-2(1H)-one (P1)

To a −78° C. solution of C61 (1.8 g, 7.4 mmol) in dichloromethane (40 mL) was added a solution of boron tribromide in dichloromethane (1 M, 22 mL, 22 mmol). The cooling bath was removed after 30 minutes, and the reaction mixture was allowed to warm to room temperature and stir for 18 hours. The reaction was cooled to −78° C., and methanol (10 mL) was slowly added; the resulting mixture was gradually warmed to room temperature. After the solvent had been removed in vacuo, methanol (20 mL) was added, and the mixture was again concentrated under reduced pressure. The residue was diluted with ethyl acetate (300 mL) and water (200 mL), the aqueous layer was brought to pH 7 via portion-wise addition of saturated aqueous sodium carbonate solution, and the mixture was extracted with ethyl acetate (3×200 mL). The combined organic layers were washed with water and with saturated aqueous sodium chloride solution, dried over magnesium sulfate, filtered, and concentrated in vacuo to afford the product as a light tan solid. Yield: 1.4 g, 6.0 mmol, 81%. LCMS m/z 231.1 [M+H]$^+$. $^1$H NMR (400 MHz, CDCl$_3$) δ 8.21 (s, 1H), 6.98 (d, J=8.2 Hz, 1H), 6.87-6.89 (m, 1H), 6.85 (br dd, J=8.2, 2.5 Hz, 1H), 3.22 (s, 3H), 2.06 (br s, 3H), 2.03 (s, 3H).

Preparation P2

6-(4-Hydroxy-2-methylphenyl)-1,5-dimethylpyrimidin-2(1H)-one (P2)

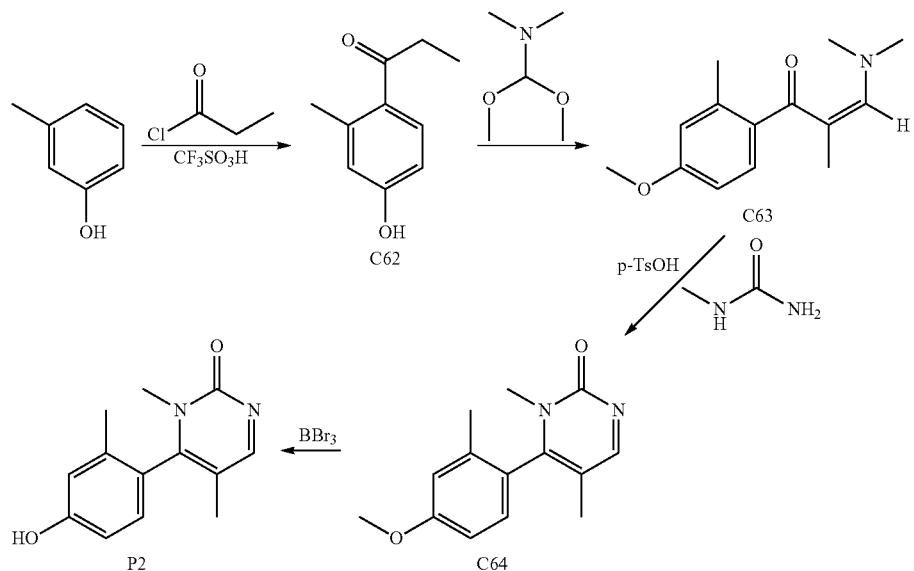

Step 1. Synthesis of 1-(4-hydroxy-2-methylphenyl)propan-1-one (C62)

3-Methylphenol (9.0 g, 83 mmol) was combined with trifluoromethanesulfonic acid (90 mL), cooled to −10° C., and treated in a drop-wise manner with propanoyl chloride (7.7 g, 83 mmol). The reaction mixture was stirred at −10° C. for 3 hours and then at room temperature for 18 hours, whereupon it was poured into ice water (600 mL). The resulting solid was collected via filtration and purified by silica gel chromatography (Gradient: 5% to 70% ethyl acetate in petroleum ether) to afford the product as an off-white solid. Yield: 6.7 g, 41 mmol, 49%. $^1$H NMR (400 MHz, CD$_3$OD) δ 7.75 (d, J=8.5 Hz, 1H), 6.64-6.69 (m, 2H), 2.92 (q, J=7.3 Hz, 2H), 2.45 (s, 3H), 1.13 (t, J=7.3 Hz, 3H).

Step 2. Synthesis of 3-(dimethylamino)-1-(4-methoxy-2-methylphenyl)-2-methylprop-2-en-1-one (C63)

This experiment was carried out in four batches. A mixture of C62 (1.0 g, 6.1 mmol) and N,N-dimethylformamide dimethyl acetal (15 mL) was stirred at 130° C. for 30 hours. The four reaction mixtures were combined and concentrated to dryness, providing the product as a dark oil. This was used for the next step without further purification. Yield: 5.0 g, 21 mmol, 86%.

Step 3. Synthesis of 6-(4-methoxy-2-methylphenyl)-1,5-dimethypyrimethylpyrimidin-2(1H)-one (C64)

This experiment was carried out in two batches. A mixture of C63 (from the previous step, 2.5 g, 11 mmol), 1-methylurea (1.35 g, 18.2 mmol) and p-toluenesulfonic acid (3.13 g, 18.2 mmol) in 1,4-dioxane (100 mL) was heated at reflux for 40 hours, then concentrated under reduced pressure. The residue was mixed with toluene (100 mL), treated with p-toluenesulfonic acid (3.13 g, 18.2 mmol) and heated at reflux for another 20 hours. The two crude products were combined and concentrated in vacuo. Purification via silica gel chromatography (Gradient: 0% to 5% methanol in dichloromethane) afforded the product as a brown solid. Yield: 2.5 g, 10 mmol, 45%. $^1$H NMR (400 MHz, CDCl$_3$) δ 8.52 (s, 1H), 6.98 (br d, half of AB quartet, J=9 Hz, 1H), 6.86-6.92 (m, 2H), 3.87 (s, 3H), 3.24 (s, 3H), 2.08 (s, 3H), 1.78 (s, 3H).

Step 4. Synthesis of 6-(4-hydroxy-2-methylphenyl)-1,5-dimethylpyrimidin-2(1H)-one (P2)

To a −70° C. solution of C64 (2.5 g, 10 mmol) in dichloromethane (100 mL) was added boron tribromide (17.9 g, 71.4 mmol) drop-wise. The reaction mixture was stirred at −60° C. to −70° C. for 1 hour and then at room temperature for 18 hours, whereupon it was cooled to −60° C. and quenched with methanol. Water (100 mL) was added, and the mixture was adjusted to a pH of 6 via slow addition of solid sodium bicarbonate. The mixture was extracted with dichloromethane (100 mL) and with ethyl acetate (5×100 mL); the combined organic layers were dried, filtered, and concentrated in vacuo. The residue was washed with a mixture of petroleum ether and ethyl acetate (4:1, 40 mL) and the solid was collected by filtration to afford the product as a yellow solid. Yield: 2.2 g, 9.5 mmol, 95%. LCMS m/z 231.0 [M+H]$^+$. $^1$H NMR (400 MHz, CD$_3$OD) δ 8.65 (s, 1H), 7.05 (d, J=8.3 Hz, 1H), 6.88-6.91 (br s, 1H), 6.87 (br dd, J=8.3, 2.2 Hz, 1H), 3.38 (s, 3H), 2.11 (s, 3H), 1.89 (s, 3H).

Method A

Method A describes a specific method for preparations of certain exemplar compounds of the invention.

Preparation of 1,5-dimethyl-6-[2-methyl-4-(substituted pyridin-2-yloxy)phenyl]pyrimidine-2,4(1H,3H)-diones

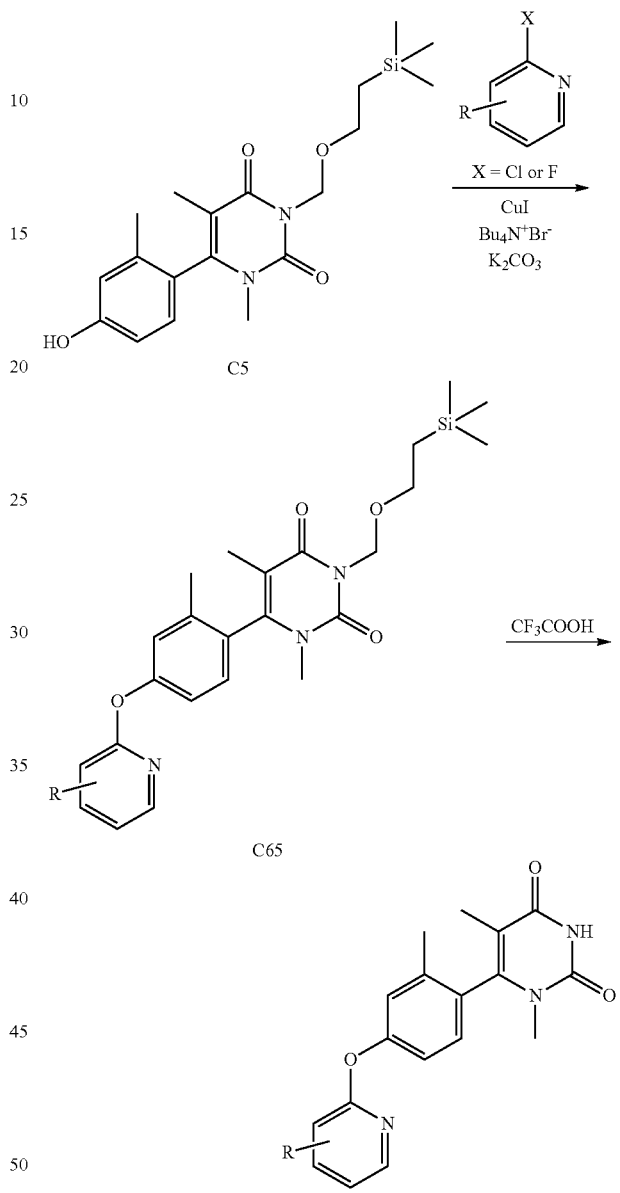

Step 1. Synthesis of 1,5-dimethyl-6-[2-methyl-4-(substituted pyridin-2-yloxy)phenyl]-3-{[2-(trimethylsilyl)ethoxy]methyl}pyrimidine-2,4(1H,3H)-diones (C65)

A solution of C5 in N,N-dimethylformamide (0.33 M, 300 μL, 100 μmol) was combined in a reaction vial with the appropriately substituted 2-chloropyridine or 2-fluoropyridine (100 μmol). Potassium carbonate (300 μmol), copper(I) iodide (10 μmol) and tetrabutylammonium bromide (20 μmol) were added under nitrogen, and the vial was capped and shaken at 130° C. for 16 hours. Solvent was removed using a SpeedVac® concentrator, and the residue was partitioned between ethyl acetate (1 mL) and water (1 mL); the aqueous layer was extracted with ethyl acetate (2×1 mL), and the combined organic layers were dried over magnesium sulfate, filtered, and concentrated to provide the crude product, which was used directly in the following step.

Step 2. Synthesis of 1,5-dimethyl-6-[2-methyl-4-(substituted pyridin-2-yloxy)phenyl]pyrimidine-2,4 (1H,3H)-diones The 1,5-dimethyl-6-[2-methyl-4-(substituted pyridin-2-yloxy)phenyl]-3-{[2-(trimethylsilyl)ethoxy]methyl}pyrimidine-2,4(1H,3H)-dione (C65) from the previous step was dissolved in a mixture of dichloromethane and trifluoroacetic acid (4:1, 1 mL), and the reaction vial was capped and shaken at 30° C. for 16 hours. After removal of solvents, the product was purified by high-performance liquid chromatography using one of the following systems: a) DIKMA Diamonsil(2) C18, 5 μm; Mobile phase A: water containing 0.225% formic acid; Mobile phase B: acetonitrile containing 0.225% formic acid; Gradient: 35% to 70% B; b) Phenomenex Gemini C18, 8 μm; Mobile phase A: aqueous ammonium hydroxide, pH 10; Mobile phase B: acetonitrile; Gradient: 35% to 75% B.

Table 1 below lists some additional exemplar compounds of invention (Examples 20-81) that were made using methods, intermediates, and preparations described herein.

TABLE 1

Examples 20-81 (including Method of Synthesis and Physicochemical Data).

| Example Number | Structure | Method of Synthesis: Example Number; Source of Non-commercial Starting Materials | $^1$H NMR (400 MHz, CDCl$_3$, δ (ppm); LCMS, observed ion m/z [M + H]$^+$ or HPLC retention time (minutes); LCMS m/z [M + H]$^+$ (unless otherwise indicated) |
|---|---|---|---|
| 20 | 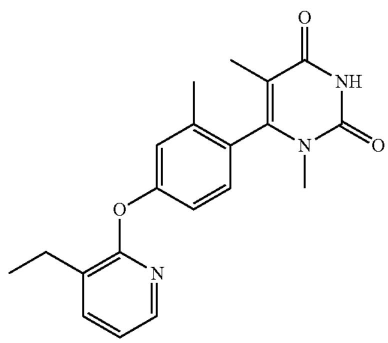 [SMILES: CCc1cccnc1Oc1ccc(-c2c(C)c(=O)[nH]c(=O)n2C)c(C)c1] | Ex 1 & 2; C5[1] | 8.25 (br s, 1H), 8.06 (br d, J = 4 Hz, 1H), 7.62 (br d, J = 7 Hz, 1H), 7.02-7.14 (m, 4H), 3.05 (s, 3H), 2.76 (q, J = 7.6 Hz, 2H), 2.18 (s, 3H), 1.68 (s, 3H), 1.30 (t, J = 7.5 Hz, 3H); 352.2 |
| 21 | 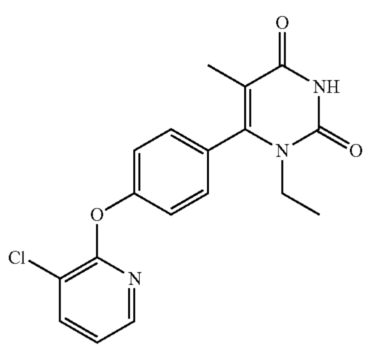 [SMILES: CCn1c(-c2ccc(Oc3ncccc3Cl)cc2)c(C)c(=O)[nH]c1=O] | Ex 5; C11[2] | $^1$H NMR (400 MHz, CD$_3$OD) δ 8.07 (br d, J = 4.9 Hz, 1H), 7.98 (br d, J = 7.8 Hz, 1H), 7.37 (AB quartet, J$_{AB}$ = 8.3 Hz, Δv$_{AB}$ = 35.9 Hz, 4H), 7.18 (dd, J = 7.7, 4.8 Hz, 1H), 3.63 (q, J = 7.0 Hz, 2H), 1.64 (s, 3H), 1.08 (t, J = 7.0 Hz, 3H); 358.0, 360.0 |
| 22 | 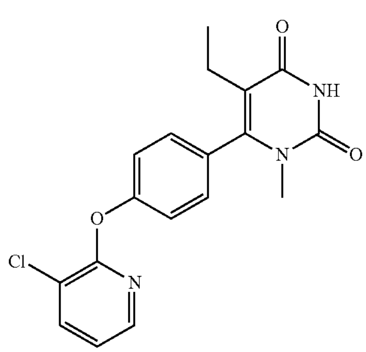 [SMILES: CCc1c(-c2ccc(Oc3ncccc3Cl)cc2)n(C)c(=O)[nH]c1=O] | Ex 6; C18[3] | $^1$H NMR (400 MHz, CD$_3$OD) δ 8.07 (dd, J = 4.8, 1.7 Hz, 1H), 7.98 (dd, J = 7.8, 1.6 Hz, 1H), 7.37 (br AB quartet, J$_{AB}$ = 8.7 Hz, Δv$_{AB}$ = 35.6 Hz, 4H), 7.17 (dd, J = 7.8, 4.9 Hz, 1H), 3.05 (s, 3H), 2.11 (q, J = 7.4 Hz, 2H), 0.95 (t, J = 7.4 Hz, 3H); 357.9 |

TABLE 1-continued

Examples 20-81 (including Method of Synthesis and Physicochemical Data).

| Example Number | Structure | Method of Synthesis: Example Number; Source of Non-commercial Starting Materials | $^1$H NMR (400 MHz, CDCl$_3$, δ (ppm); LCMS, observed ion m/z [M + H]$^+$ or HPLC retention time (minutes); LCMS m/z [M + H]$^+$ (unless otherwise indicated) |
|---|---|---|---|
| 23 | 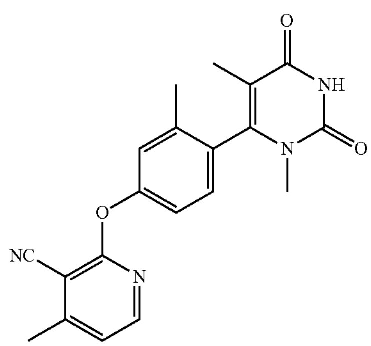 [SMILES: Cc1cc(Oc2nccc(C)c2C#N)ccc1-c1c(C)c(=O)[nH]c(=O)n1C] | Method A | 2.28 minutes[4]; 363 |
| 24 | 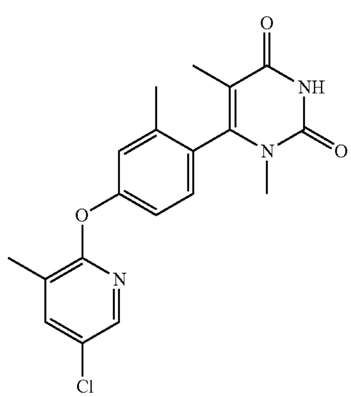 [SMILES: Cc1cc(Oc2ncc(Cl)cc2C)ccc1-c1c(C)c(=O)[nH]c(=O)n1C] | Method A | 2.67 minutes[4]; 372 |
| 25 | 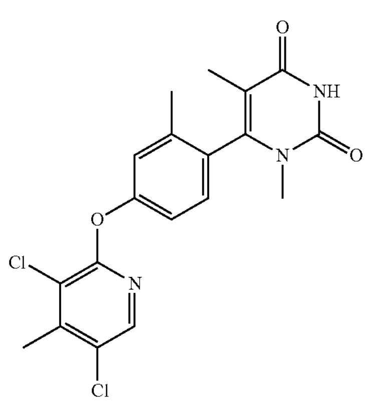 [SMILES: Cc1cc(Oc2ncc(Cl)c(C)c2Cl)ccc1-c1c(C)c(=O)[nH]c(=O)n1C] | Method A | 2.49 minutes[5]; 406 |

TABLE 1-continued

Examples 20-81 (including Method of Synthesis and Physicochemical Data).

| Example Number | Structure | Method of Synthesis: Example Number; Source of Non-commercial Starting Materials | $^1$H NMR (400 MHz, CDCl$_3$, δ (ppm); LCMS, observed ion m/z [M + H]$^+$ or HPLC retention time (minutes); LCMS m/z [M + H]$^+$ (unless otherwise indicated) |
|---|---|---|---|
| 26 | 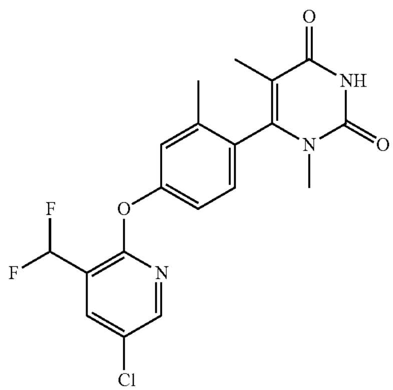 [SMILES: Cc1cc(Oc2ncc(Cl)cc2C(F)F)ccc1-c1c(C)c(=O)[nH]c(=O)n1C] | Method A | 3.00 minutes[6]; 408 |
| 27 | 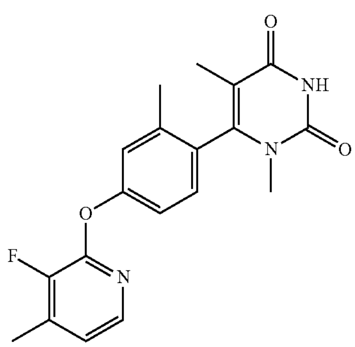 [SMILES: Cc1cc(Oc2nccc(C)c2F)ccc1-c1c(C)c(=O)[nH]c(=O)n1C] | Method A | 2.42 minutes[4]; 356 |
| 28 | 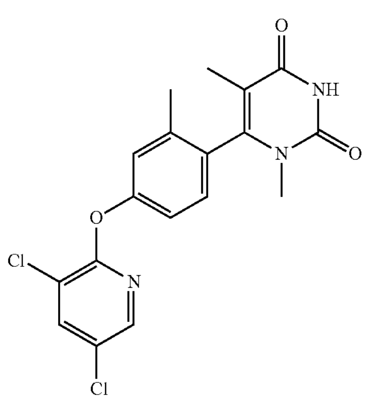 [SMILES: Cc1cc(Oc2ncc(Cl)cc2Cl)ccc1-c1c(C)c(=O)[nH]c(=O)n1C] | Method A | 3.06 minutes[6]; 392 |

TABLE 1-continued

Examples 20-81 (including Method of Synthesis and Physicochemical Data).

| Example Number | Structure | Method of Synthesis: Example Number; Source of Non-commercial Starting Materials | $^1$H NMR (400 MHz, CDCl$_3$, δ (ppm); LCMS, observed ion m/z [M + H]$^+$ or HPLC retention time (minutes); LCMS m/z [M + H]$^+$ (unless otherwise indicated) |
|---|---|---|---|
| 29 | 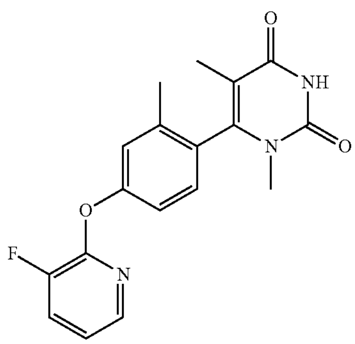 [SMILES: Cc1cc(Oc2ncccc2F)ccc1-c1c(C)c(=O)[nH]c(=O)n1C] | Ex 5; C5 | $^1$H NMR (400 MHz, CD$_3$OD) δ 7.95 (br d, J = 4.9 Hz, 1H), 7.72 (br dd, J = 9.3, 8.9 Hz, 1H), 7.25 (d, J = 8.3 Hz, 1H), 7.17-7.23 (m, 2H), 7.12-7.17 (m, 1H), 3.03 (s, 3H), 2.21 (s, 3H), 1.62 (s, 3H); 341.9 |
| 30 | 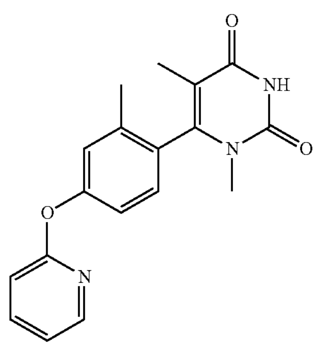 [SMILES: Cc1cc(Oc2ccccn2)ccc1-c1c(C)c(=O)[nH]c(=O)n1C] | Ex 5; C5 | $^1$H NMR (400 MHz, CD$_3$OD) δ 8.16-8.19 (m, 1H), 7.86-7.92 (m, 1H), 7.25 (d, J = 8.3 Hz, 1H), 7.16-7.20 (m, 2H), 7.09-7.14 (m, 1H), 7.06 (d, J = 8.2 Hz, 1H), 3.04 (s, 3H), 2.21 (s, 3H), 1.63 (s, 3H); 323.9 |
| 31 | 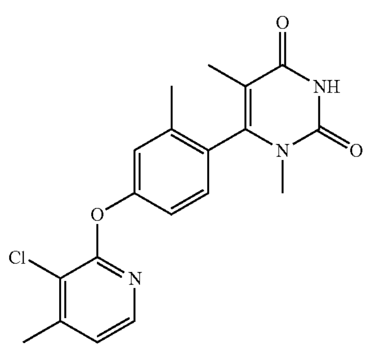 [SMILES: Cc1cc(Oc2nccc(C)c2Cl)ccc1-c1c(C)c(=O)[nH]c(=O)n1C] | Ex 5; C5 | $^1$H NMR (600 MHz, DMSO-d$_6$) δ 8.00 (d, J = 4.8 Hz, 1H), 7.27 (d, J = 8.3 Hz, 1H), 7.17-7.22 (m, 2H), 7.11 (br d, J = 8 Hz, 1H), 2.87 (s, 3H), 2.44 (s, 3H), 2.14 (s, 3H), 1.48 (s, 3H); 372.1, 374.1 |
| 32 | 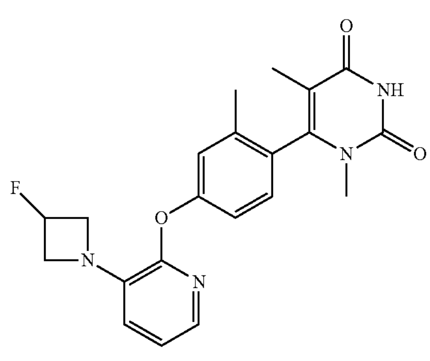 [SMILES: Cc1cc(Oc2ncccc2N2CC(F)C2)ccc1-c1c(C)c(=O)[nH]c(=O)n1C] | Ex 1 & 2; C5[7] | $^1$H NMR (400 MHz, CD$_3$OD) δ 7.58 (dd, J = 4.8, 1.6 Hz, 1H), 7.21 (d, J = 8.4 Hz, 1H), 7.08-7.13 (m, 2H), 7.01-7.05 (m, 2H), 5.28-5.49 (m, J$_{HF}$ = 57.6 Hz, 1H), 4.33 (br ddd, J = 19.4, 9.4, 5.8 Hz, 2H), 4.04 (br ddd, J = 23.8, 9.3, 3.5 Hz, 2H), 3.02 (s, 3H), 2.19 (br s, 3H), 1.62 (s, 3H); 397.0 |

TABLE 1-continued

Examples 20-81 (including Method of Synthesis and Physicochemical Data).

| Example Number | Structure | Method of Synthesis: Example Number; Source of Non-commercial Starting Materials | $^1$H NMR (400 MHz, CDCl$_3$, δ (ppm); LCMS, observed ion m/z [M + H]$^+$ or HPLC retention time (minutes); LCMS m/z [M + H]$^+$ (unless otherwise indicated) |
|---|---|---|---|
| 33 | 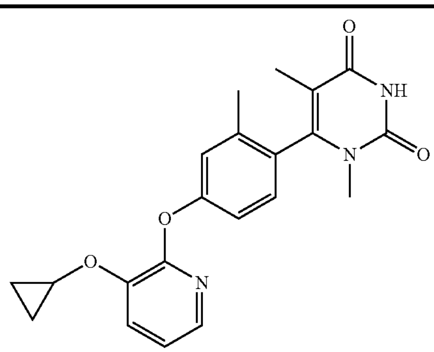 | Ex 1 & 2; C5[8] | 8.12 (br s, 1H), 7.81 (dd, J = 4.9, 1.6 Hz, 1H), 7.63 (dd, J = 7.8, 1.6 Hz, 1H), 7.06-7.14 (m, 4H), 3.82-3.88 (m, 1H), 3.03 (s, 3H), 2.17 (s, 3H), 1.66 (s, 3H), 0.85-0.90 (m, 4H); 380.0 |
| 34 | 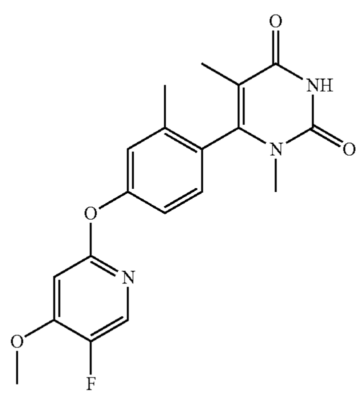 [SMILES: COc1cc(Oc2ccc(-c3c(C)c(=O)[nH]c(=O)n3C)c(C)c2)ncc1F] | C5[9,10,11] | 8.35 (br s, 1H), 7.93 (d, J = 2.8 Hz, 1H), 7.08-7.13 (m, 3H), 6.59 (d, J = 5.8 Hz, 1H), 3.99 (s, 3H), 3.04 (s, 3H), 2.18 (s, 3H), 1.67 (s, 3H); 372.0 |
| 35 | 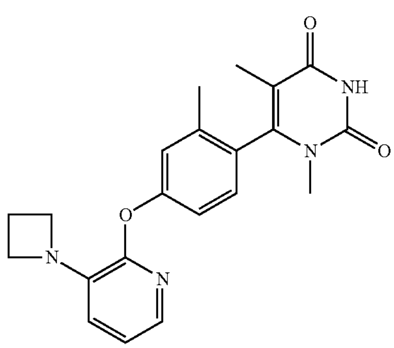 [SMILES: Cc1cc(Oc2ncccc2N2CCC2)ccc1-c1c(C)c(=O)[nH]c(=O)n1C] | Ex 1 & 2; C5[7] | $^1$H NMR (400 MHz, CD$_3$OD) δ 7.55 (dd, J = 4.8, 1.6 Hz, 1H), 7.19 (d, J = 8.4 Hz, 1H), 7.09 (dd, J = 7.8, 4.8 Hz, 1H), 7.04-7.06 (m, 1H), 6.97-7.02 (m, 2H), 4.01 (t, J = 7.3 Hz, 4H), 3.02 (br s, 3H), 2.34 (quintet, J = 7.3 Hz, 2H), 2.18 (s, 3H), 1.62 (s, 3H); 379.1 |
| 36 | 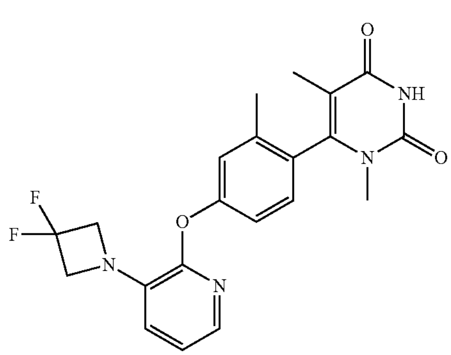 [SMILES: Cc1cc(Oc2ncccc2N2CC(F)(F)C2)ccc1-c1c(C)c(=O)[nH]c(=O)n1C] | Ex 1 & 2; C5[7] | $^1$H NMR (400 MHz, CD$_3$OD) δ 7.63 (dd, J = 4.4, 2.1 Hz, 1H), 7.22 (d, J = 8.3 Hz, 1H), 7.05-7.15 (m, 4H), 4.37 (t, J = 12.0 Hz, 4H), 3.03 (s, 3H), 2.20 (br s, 3H), 1.62 (s, 3H); 415.0 |

TABLE 1-continued

Examples 20-81 (including Method of Synthesis and Physicochemical Data).

| Example Number | Structure | Method of Synthesis: Example Number; Source of Non-commercial Starting Materials | $^1$H NMR (400 MHz, CDCl$_3$, δ (ppm); LCMS, observed ion m/z [M + H]$^+$ or HPLC retention time (minutes); LCMS m/z [M + H]$^+$ (unless otherwise indicated) |
|---|---|---|---|
| 37 | 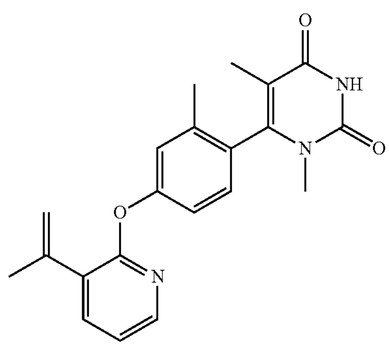 [SMILES: C=C(C)c1cccnc1Oc1ccc(-c2c(C)c(=O)[nH]c(=O)n2C)c(C)c1] | C5[12,10,11] | $^1$H NMR (400 MHz, CD$_3$OD) δ 8.06 (dd, J = 4.9, 1.8 Hz, 1H), 7.80 (dd, J = 7.5, 1.8 Hz, 1H), 7.22 (d, J = 8.3 Hz, 1H), 7.18 (dd, J = 7.3, 5.0 Hz, 1H), 7.10-7.13 (m, 1H), 7.03-7.08 (m, 1H), 5.25-5.30 (m, 2H), 3.03 (s, 3H), 2.19 (br s, 6H), 1.63 (s, 3H), 364.1 |
| 38 | 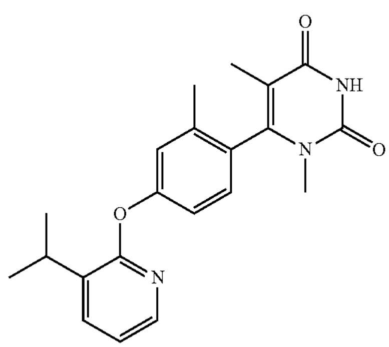 | Ex 37[13] | $^1$H NMR (400 MHz, CD$_3$OD), characteristic peaks: δ 7.97 (dd, J = 5.0, 1.9 Hz, 1H), 7.81-7.84 (m, 1H), 7.22 (d, J = 8.3 Hz, 1H), 7.17 (dd, J = 7.3, 5.1 Hz, 1H), 7.11-7.13 (m, 1H), 7.03-7.07 (m, 1H), 3.04 (s, 3H), 2.20 (br s, 3H), 1.63 (s, 3H), 1.33 (d, J = 6.9 Hz, 6H); 366.0 |
| 39 | 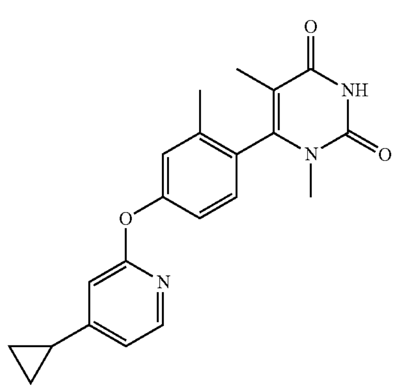 [SMILES: Cc1cc(Oc2cc(C3CC3)ccn2)ccc1-c1c(C)c(=O)[nH]c(=O)n1C] | Ex 1 & 2; C5[14] | $^1$H NMR (400 MHz, CD$_3$OD) δ 7.98 (d, J = 5.3 Hz, 1H), 7.23 (d, J = 8.3 Hz, 1H), 7.14 (br d, J = 2.3 Hz, 1H), 7.08 (br dd, J = 8.2, 2.2 Hz, 1H), 6.87 (dd, J = 5.4, 1.4 Hz, 1H), 6.78-6.80 (m, 1H), 3.03 (s, 3H), 2.20 (br s, 3H), 1.95-2.03 (m, 1H), 1.62 (s, 3H), 1.12-1.18 (m, 2H), 0.84-0.90 (m, 2H); 364.0 |

TABLE 1-continued

Examples 20-81 (including Method of Synthesis and Physicochemical Data).

| Example Number | Structure | Method of Synthesis: Example Number; Source of Non-commercial Starting Materials | $^1$H NMR (400 MHz, CDCl$_3$, δ (ppm); LCMS, observed ion m/z [M + H]$^+$ or HPLC retention time (minutes); LCMS m/z [M + H]$^+$ (unless otherwise indicated) |
|---|---|---|---|
| 40 | 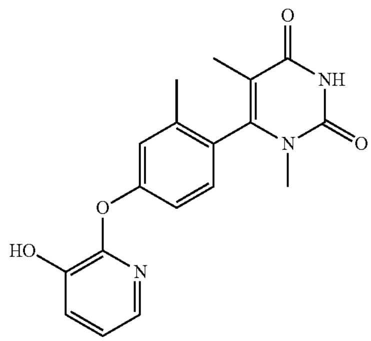 [SMILES: Cc1cc(Oc2ncccc2O)ccc1-c1c(C)c(=O)[nH]c(=O)n1C] | Ex 9 & 10; C27[15] | $^1$H NMR (600 MHz, DMSO-d$_6$) δ 9.91 (br s, 1H), 7.64-7.68 (m, 1H), 7.32 (br d, J = 7.9 Hz, 1H), 7.21 (d, J = 8.3 Hz, 1H), 7.04-7.09 (m, 2H), 7.00 (br d, J = 8.3 Hz, 1H), 2.86 (s, 3H), 2.12 (s, 3H), 1.47 (s, 3H); 340.1 |
| 41 | 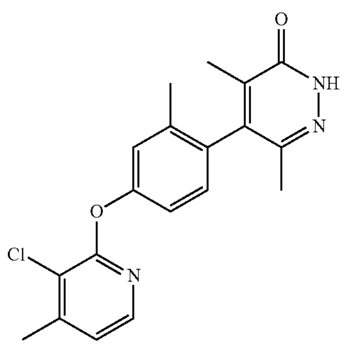 [SMILES: Cc1cc(Oc2nccc(C)c2Cl)ccc1-c1c(C)n[nH]c(=O)c1C] | Ex 16 & 17; C49[16] | 7.95 (d, J = 4.9 Hz, 1H), 7.14 (br d, J = 2.3 Hz, 1H), 7.10 (br dd, J = 8.3, 2.2 Hz, 1H), 7.02 (d, J = 8.3 Hz, 1H), 6.96 (dq, J = 4.9, 0.6 Hz, 1H), 2.48 (br s, 3H), 2.07 (br s, 3H), 2.00 (s, 3H), 1.96 (s, 3H); 356.2, 358.2 |
| 42 | 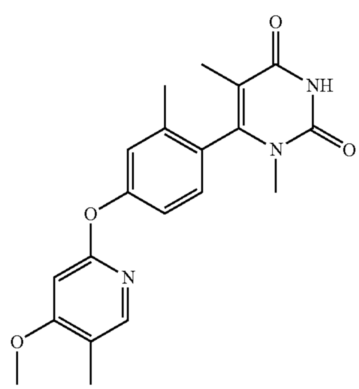 [SMILES: COc1cc(Oc2ccc(-c3c(C)c(=O)[nH]c(=O)n3C)c(C)c2)ncc1C] | Ex 5; C5 | $^1$H NMR (400 MHz, CD$_3$OD) δ 7.77-7.79 (m, 1H), 7.22 (d, J = 8.3 Hz, 1H), 7.12 (br d, J = 2 Hz, 1H), 7.07 (dd, J = 8, 2 Hz, 1H), 6.64 (s, 1H), 3.93 (s, 3H), 3.03 (s, 3H), 2.19 (br s, 3H), 2.13 (br s, 3H), 1.62 (s, 3H); 368.0 |
| 43 | 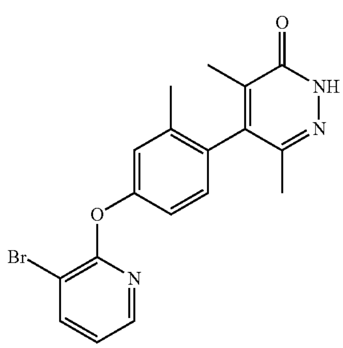 | Ex 16 & 17; C49 | 8.13 (dd, J = 4.8, 1.7 Hz, 1H), 7.97 (dd, J = 7.7, 1.7 Hz, 1H), 7.16 (br d, J = 2.2 Hz, 1H), 7.12 (br dd, J = 8.2, 2.3 Hz, 1H), 7.03 (br d, J = 8.2 Hz, 1H), 6.96 (dd, J = 7.7, 4.8 Hz, 1H), 2.09 (s, 3H), 2.00 (s, 3H), 1.96 (s, 3H); 386.1, 388.0 |

TABLE 1-continued

Examples 20-81 (including Method of Synthesis and Physicochemical Data).

| Example Number | Structure | Method of Synthesis: Example Number; Source of Non-commercial Starting Materials | $^1$H NMR (400 MHz, CDCl$_3$, δ (ppm); LCMS, observed ion m/z [M + H]$^+$ or HPLC retention time (minutes); LCMS m/z [M + H]$^+$ (unless otherwise indicated) |
|---|---|---|---|
| 44 | 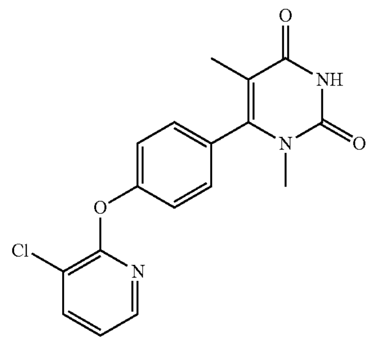 [SMILES: Cc1c(-c2ccc(Oc3ncccc3Cl)cc2)n(C)c(=O)[nH]c1=O] | Ex 5; C3[17] | 8.07 (dd, J = 4.9, 1.5 Hz, 1H), 7.97 (dd, J = 7.7, 1.4 Hz, 1H), 7.36 (br AB quartet, J$_{AB}$ = 8.6 Hz, Δν$_{AB}$ = 28.4 Hz, 4H), 7.17 (dd, J = 7.7, 4.8 Hz, 1H), 3.08 (s, 3H), 1.68 (s, 3H); 343.9 |
| 45 | (+) | Ex 5; C27, C36[18,19] | 8.29 (br s, 1H), 8.06 (dd, J = 4.8, 1.7 Hz, 1H), 7.63-7.66 (m, 1H), 7.16-7.18 (m, 1H), 7.11-7.15 (m, 2H), 7.11 (dd, J= 7.9, 4.8 Hz, 1H), 6.70 (t, J$_{HF}$ = 73.5 Hz, 1H), 3.05 (s, 3H), 2.20 (br s, 3H), 1.68 (s, 3H); 390.1 |
| 46 | 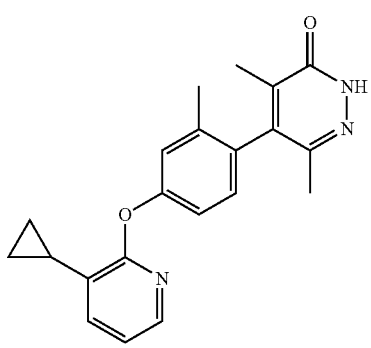 [SMILES: Cc1cc(Oc2ncccc2C2CC2)ccc1-c1c(C)n[nH]c(=O)c1C] | Ex 16 & 17; C49[20] | 10.15 (br s, 1H), 8.02 (dd, J = 5.0, 1.8 Hz, 1H), 7.28-7.32 (m, 1H), 7.11 (br d, J = 2 Hz, 1H), 7.07 (br dd, J = 8, 2 Hz, 1H), 6.98-7.02 (m, 2H), 2.18-2.26 (m, 1H), 2.07 (s, 3H), 1.99 (s, 3H), 1.95 (s, 3H), 1.01-1.07 (m, 2H), 0.74-0.79 (m, 2H); 348.0 |
| 47 | 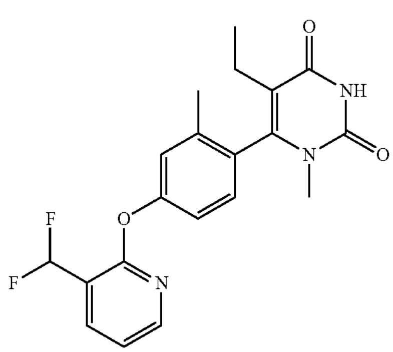 [SMILES: CCc1c(-c2ccc(Oc3ncccc3C(F)F)cc2C)n(C)c(=O)[nH]c1=O] | Ex 12; C17, C33 | $^1$H NMR (600 MHz, DMSO-d$_6$) δ 8.33-8.36 (m, 1H), 8.13 (br d, J = 7 Hz, 1H), 7.30-7.34 (m, 2H), 7.28 (t, J$_{HF}$ = 54 Hz, 1H), 7.23-7.25 (m, 1H), 7.17 (br d, J = 8.2 Hz, 1H), 2.83-2.86 (m, 3H), 2.16 (s, 3H), 2.01-2.09 (m, 1H), 1.70-1.78 (m, 1H), 0.82 (t, J = 7.3 Hz, 3H); 388.1 |

TABLE 1-continued

Examples 20-81 (including Method of Synthesis and Physicochemical Data).

| Example Number | Structure | Method of Synthesis: Example Number; Source of Non-commercial Starting Materials | $^1$H NMR (400 MHz, CDCl$_3$, δ (ppm); LCMS, observed ion m/z [M + H]$^+$ or HPLC retention time (minutes); LCMS m/z [M + H]$^+$ (unless otherwise indicated) |
|---|---|---|---|
| 48 | 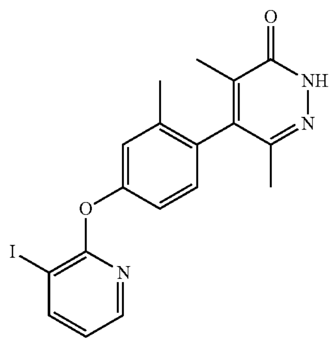 [SMILES: Cc1cc(Oc2ncccc2I)ccc1-c1c(C)n[nH]c(=O)c1C] | Ex 16 & 17; C49 | 10.43 (br s, 1H), 8.19 (dd, J = 7.6, 1.6 Hz, 1H), 8.14 (dd, J = 4.8, 1.6 Hz, 1H), 7.14-7.16 (m, 1H), 7.09-7.13 (m, 1H), 7.03 (d, half of AB quartet, J = 8.3 Hz, 1H), 6.82 (dd, J = 7.6, 4.9 Hz, 1H), 2.09 (br s, 3H), 1.99 (s, 3H), 1.95 (s, 3H); 433.9 |
| 49 | 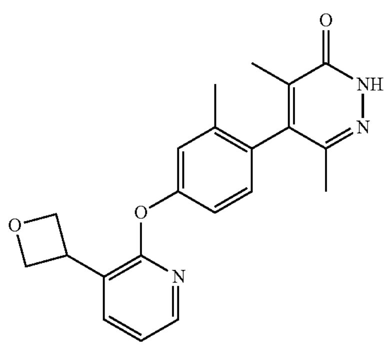 [SMILES: Cc1cc(Oc2ncccc2C2COC2)ccc1-c1c(C)n[nH]c(=O)c1C] | Ex 16 & 17; C49[21] | 10.64 (br s, 1H), 8.12 (br d, J = 5 Hz, 1H), 7.78 (br d, J = 7 Hz, 1H), 7.12 (dd, J = 7, 5 Hz, 1H), 7.06-7.09 (m, 1H), 7.02-7.06 (m, 1H), 7.00 (d, half of AB quartet, J = 8.2 Hz, 1H), 5.11 (dd, J = 8.4, 5.9 Hz, 2H), 4.93 (dd, J = 7.0, 6.3 Hz, 2H), 4.57-4.67 (m, 1H), 2.07 (s, 3H), 1.99 (s, 3H), 1.95 (s, 3H); 364.0 |
| 50 | 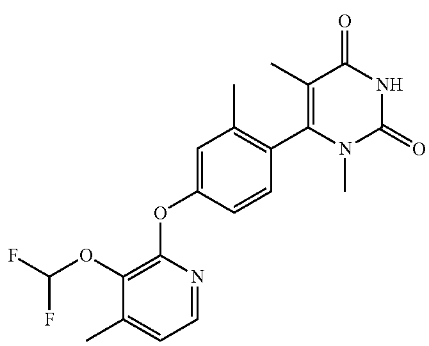 [SMILES: Cc1cc(Oc2nccc(C)c2OC(F)F)ccc1-c1c(C)c(=O)[nH]c(=O)n1C] | Ex 9 & 10; C27[22] | 8.21 (br s, 1H), 7.93 (d, J = 5.0 Hz, 1H), 7.15-7.17 (m, 1H), 7.12-7.14 (m, 2H), 6.99 (br d, J = 5.0 Hz, 1H), 6.75 (t, $J_{HF}$ = 75.3 Hz, 1H), 3.05 (s, 3H), 2.43 (br s, 3H), 2.20 (br s, 3H), 1.67 (s, 3H); 404.2 |
| 51 | 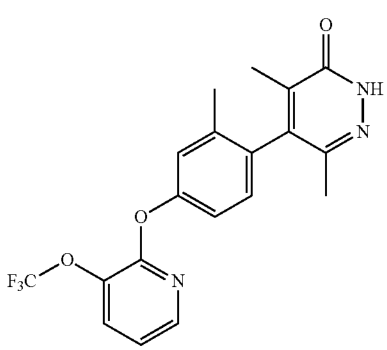 [SMILES: Cc1cc(Oc2ncccc2OC(F)(F)F)ccc1-c1c(C)n[nH]c(=O)c1C] | Ex 16 & 17; C49 | $^1$H NMR (400 MHz, CD$_3$OD) δ 8.11 (br dd, J = 4.8, 1.3 Hz, 1H), 7.88 (br d, J = 7.8 Hz, 1H), 7.24 (dd, J = 7.9, 4.9 Hz, 1H), 7.15-7.19 (m, 1H), 7.08-7.15 (m, 2H), 2.09 (s, 3H), 2.01 (s, 3H), 1.90 (s, 3H); 392.1 |

TABLE 1-continued

Examples 20-81 (including Method of Synthesis and Physicochemical Data).

| Example Number | Structure | Method of Synthesis: Example Number; Source of Non-commercial Starting Materials | $^1$H NMR (400 MHz, CDCl$_3$, δ (ppm); LCMS, observed ion m/z [M + H]$^+$ or HPLC retention time (minutes); LCMS m/z [M + H]$^+$ (unless otherwise indicated) |
|---|---|---|---|
| 52 | 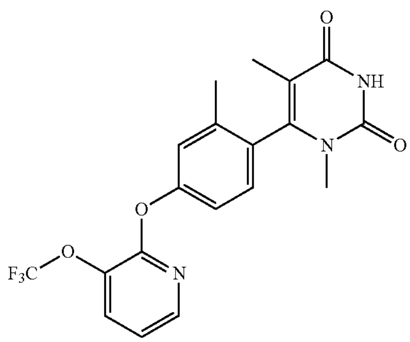 [SMILES: Cc1cc(Oc2ncccc2OC(F)(F)F)ccc1-c1c(C)c(=O)[nH]c(=O)n1C] | Ex 9 & 10; C27 | $^1$H NMR (400 MHz, CD$_3$OD) δ 8.12 (br d, J = 5 Hz, 1H), 7.90 (br d, J = 8 Hz, 1H), 7.23-7.29 (m, 2H), 7.19-7.22 (m, 1H), 7.15 (br d, J = 8 Hz, 1H), 3.03 (s, 3H), 2.22 (s, 3H), 1.63 (s, 3H); 408.1 |
| 53 | 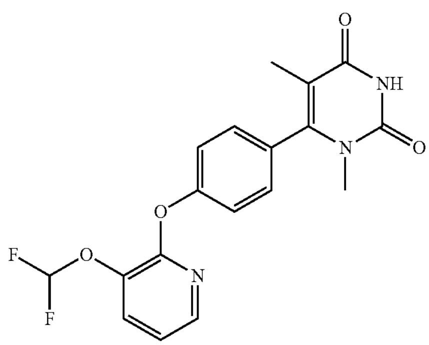 [SMILES: Cc1c(-c2ccc(Oc3ncccc3OC(F)F)cc2)n(C)c(=O)[nH]c1=O] | Ex 9 & 10; C36 | $^1$H NMR (400 MHz, CD$_3$OD) δ 8.01 (dd, J = 4.9, 1.6 Hz, 1H) 7.76 (br d, J = 8 Hz, 1H), 7.36 (br AB quartet, J$_{AB}$ = 8.8 Hz, Δν$_{AB}$ = 23.2 Hz, 4H), 7.22 (dd, J = 7.9, 4.9 Hz, 1H), 6.97 (t, J$_{HF}$ = 73.5 Hz, 1H), 3.08 (s, 3H), 1.68 (s, 3H); 376.0 |
| 54 | 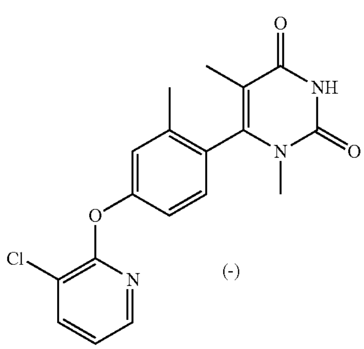 [SMILES: Cc1cc(Oc2ncccc2Cl)ccc1-c1c(C)c(=O)[nH]c(=O)n1C] | Ex 9 & 10; C27[23] | 11.45 (br s, 1H), 8.15 (dd, J = 4.8, 1.7 Hz, 1H), 8.09 (dd, J = 7.8, 1.7 Hz, 1H), 7.29 (d, J = 8.3 Hz, 1H), 7.21-7.25 (m, 2H), 7.15 (br dd, J = 8.3, 2.2 Hz, 1H), 2.87 (s, 3H), 2.15 (br s, 3H), 1.48 (s, 3H); 358.1, 360.2 |
| 55 | 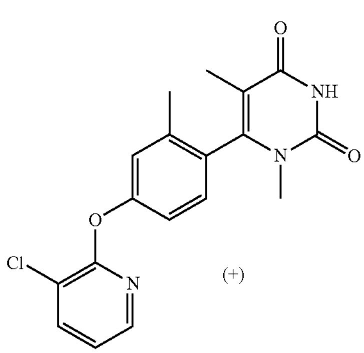 [SMILES: Cc1cc(Oc2ncccc2Cl)ccc1-c1c(C)c(=O)[nH]c(=O)n1C] | Ex 9 & 10; C27[23] | $^1$H NMR (400 MHz, DMSO-d$_6$) δ 11.45 (br s, 1H), 8.15 (dd, J = 4.8, 1.7 Hz, 1H), 8.09 (dd, J = 7.8, 1.7 Hz, 1H), 7.29 (d, J = 8.3 Hz, 1H), 7.21-7.25 (m, 2H), 7.15 (br dd, J = 8, 2.5 Hz, 1H), 2.87 (s, 3H), 2.15 (br s, 3H), 1.48 (s, 3H); 358.1, 360.2 |

TABLE 1-continued

Examples 20-81 (including Method of Synthesis and Physicochemical Data).

| Example Number | Structure | Method of Synthesis: Example Number; Source of Non-commercial Starting Materials | $^1$H NMR (400 MHz, CDCl$_3$, δ (ppm); LCMS, observed ion m/z [M + H]$^+$ or HPLC retention time (minutes); LCMS m/z [M + H]$^+$ (unless otherwise indicated) |
|---|---|---|---|
| 56 | 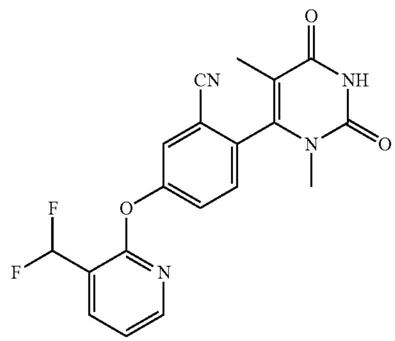 [SMILES: Cc1c(-c2ccc(Oc3ncccc3C(F)F)cc2C#N)n(C)c(=O)[nH]c1=O] | Ex 9 & 10; C26[24] | 2.56 minutes[25]; 385.1 |
| 57 | 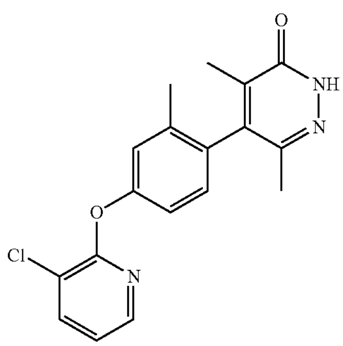 [SMILES: Cc1cc(Oc2ncccc2Cl)ccc1-c1c(C)n[nH]c(=O)c1C] | Ex 16 & 17; C49 | 10.88 (br s, 1H), 8.09 (dd, J = 4.8, 1.6 Hz, 1H), 7.81 (dd, J = 7.7, 1.6 Hz, 1H), 7.14-7.17 (m, 1H), 7.12 (br dd, J = 8, 2 Hz, 1H), 7.01-7.06 (m, 2H), 2.09 (S, 3H), 1.99 (s, 3H), 1.95 (S, 3H); 342.2 |
| 58 | 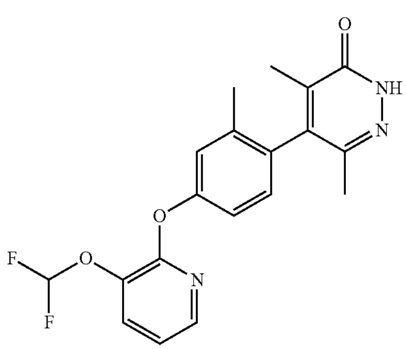 [SMILES: Cc1cc(Oc2ncccc2OC(F)F)ccc1-c1c(C)n[nH]c(=O)c1C] | Ex 16 & 17; C49, C36 | 10.32 (br s, 1H), 8.06 (dd, J = 4.8, 1.6 Hz, 1H), 7.63 (br d, J = 8 Hz, 1H), 7.13-7.16 (m, 1H), 7.07-7.13 (m, 2H), 7.03 (d, J = 8.4 Hz, 1H), 6.71 (t, J$_{HF}$ = 73.7 Hz, 1H), 2.08 (s, 3H), 1.99 (s, 3H), 1.94 (s, 3H); 374.2 |
| 59 | 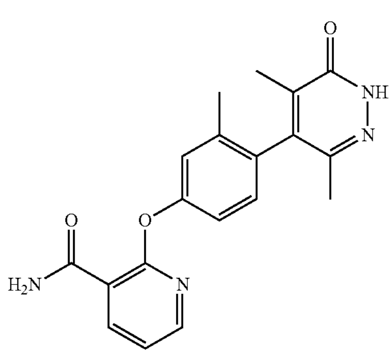 [SMILES: Cc1cc(Oc2ncccc2C(N)=O)ccc1-c1c(C)n[nH]c(=O)c1C] | Ex 16 & 17; C49[26] | $^1$H NMR (400 MHz, CD$_3$OD) δ 8.40 (dd, J = 7.5, 1.9 Hz, 1H), 8.24 (dd, J = 5.0, 1.9 Hz, 1H), 7.27 (dd, J = 7.5, 4.9 Hz, 1H), 7.24-7.26 (m, 1H), 7.14-7.21 (m, 2H), 2.10 (s, 3H), 2.07 (br s, 3H), 1.95 (br s, 3H); 351.1 |

TABLE 1-continued

Examples 20-81 (including Method of Synthesis and Physicochemical Data).

| Example Number | Structure | Method of Synthesis: Example Number; Source of Non-commercial Starting Materials | $^1$H NMR (400 MHz, CDCl$_3$, δ (ppm); LCMS, observed ion m/z [M + H]$^+$ or HPLC retention time (minutes); LCMS m/z [M + H]$^+$ (unless otherwise indicated) |
|---|---|---|---|
| 60 | 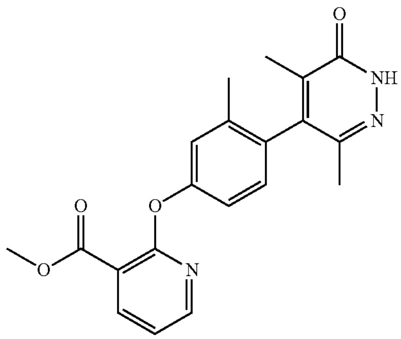 [SMILES: COC(=O)c1cccnc1Oc1ccc(-c2c(C)n[nH]c(=O)c2C)c(C)c1] | Ex 16 & 17[27] | $^1$H NMR (400 MHz, CD$_3$OD) δ 8.35 (dd, J = 7.6, 1.9 Hz, 1H), 8.29 (dd, J = 4.9, 2.0 Hz, 1H), 7.24 (dd, J = 7.6, 4.9 Hz, 1H), 7.13-7.16 (m, 1H), 7.11 (d, half of AB quartet, J = 8.0 Hz, 1H), 7.08 (br dd, half of ABX pattern, J = 8.3, 2.0 Hz, 1H), 3.93 (s, 3H), 2.08 (s, 3H), 2.00 (s, 3H), 1.90 (s, 3H); 366.1 |
| 61 | 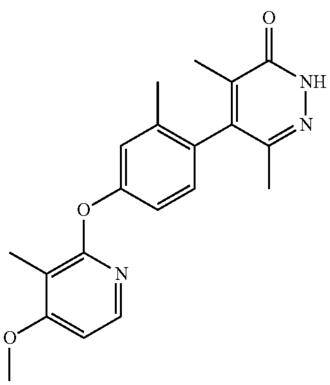 [SMILES: COc1ccnc(Oc2ccc(-c3c(C)n[nH]c(=O)c3C)c(C)c2)c1C] | Ex 1 & 2; C49[28,29] | 10.17 (br s, 1H), 8.02 (br d, J = 5 Hz, 1H), 6.94-7.06 (m, 3H), 6.65 (d, J = 6.0 Hz, 1H), 3.93 (s, 3H), 2.20 (s, 3H), 2.05 (s, 3H), 1.98 (s, 3H), 1.93 (s, 3H); 352.0 |
| 62 | 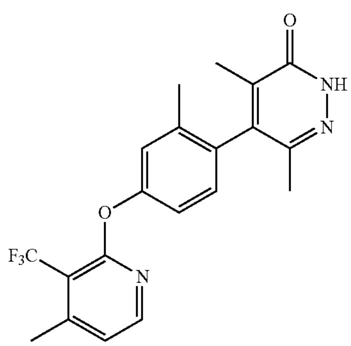 [SMILES: Cc1cc(Oc2nccc(C)c2C(F)(F)F)ccc1-c1c(C)n[nH]c(=O)c1C] | Ex 16 & 17; C49[30] | 10.46 (br s, 1H), 8.14 (d, J = 4.8 Hz, 1H), 7.10-7.14 (m, 1H), 7.05 (AB quartet, downfield doublet is broadened, J$_{AB}$ = 8.5 Hz, Δv$_{AB}$ = 23.3 Hz, 2H), 6.95 (br d, J = 5.0 Hz, 1H), 2.56-2.61 (m, 3H), 2.08 (s, 3H), 1.99 (s, 3H), 1.95 (br s, 3H); 390.3 |
| 63 | 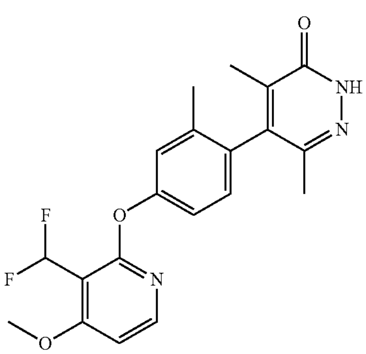 [SMILES: COc1ccnc(Oc2ccc(-c3c(C)n[nH]c(=O)c3C)c(C)c2)c1C(F)F] | Ex 16 & 17; C49[31] | 10.3 (v br s, 1H), 8.17 (br d, J = 6.0 Hz, 1H), 7.17 (t, J$_{HF}$ = 53.7 Hz, 1H), 7.12-7.14 (m, 1H), 7.09 (br dd, J = 8.2, 2.4 Hz, 1H), 7.01 (d, J = 8.3 Hz, 1H), 6.72 (br d, J = 6.0 Hz, 1H), 4.00 (s, 3H), 2.08 (br s, 3H), 1.99 (s, 3H), 1.95 (s, 3H); 388.2 |

TABLE 1-continued

Examples 20-81 (including Method of Synthesis and Physicochemical Data).

| Example Number | Structure | Method of Synthesis: Example Number; Source of Non-commercial Starting Materials | $^1$H NMR (400 MHz, CDCl$_3$, δ (ppm); LCMS, observed ion m/z [M + H]$^+$ or HPLC retention time (minutes); LCMS m/z [M + H]$^+$ (unless otherwise indicated) |
|---|---|---|---|
| 64 | 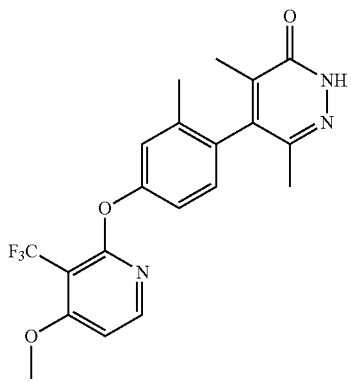 [SMILES: COc1ccnc(Oc2ccc(-c3c(C)n[nH]c(=O)c3C)c(C)c2)c1C(F)(F)F] | Ex 1 & 2; C49[32,33] | 8.19 (d, J = 5.8 Hz, 1H), 7.12 (br d, J = 2 Hz, 1H), 7.08 (br dd, half of ABX pattern J = 8, 2 Hz, 1H), 7.01 (d, half of AB quartet, J = 8.4 Hz, 1H), 6.75 (d, J = 5.8 Hz, 1H), 4.00 (s, 3H), 2.07 (s, 3H), 2.02 (s, 3H), 1.97 (s, 3H); 406.2 |
| 65 | (−) | Ex 1 & 2; C49[34,35] | $^1$H NMR (400 MHz, CD$_3$OD) δ 8.32-8.35 (m, 1H), 8.16-8.20 (m, 1H), 7.28 (ddq, J = 7.6, 5.0, 0.8 Hz, 1H), 7.17-7.19 (m, 1H), 7.10-7.16 (m, 2H), 2.09 (br s, 3H), 2.00 (s, 3H), 1.90 (s, 3H); 376.2[36] |
| 66 | (+) | Ex 1 & 2; C49[34,35] | $^1$H NMR (400 MHz, CD$_3$OD) δ 8.32-8.35 (m, 1H), 8.16-8.20 (m, 1H), 7.28 (ddq, J = 7.6, 5.0, 0.7 Hz, 1H), 7.17-7.20 (m, 1H), 7.10-7.16 (m, 2H), 2.09 (br s, 3H), 2.00 (s, 3H), 1.90 (s, 3H); 376.2[36] |

TABLE 1-continued

Examples 20-81 (including Method of Synthesis and Physicochemical Data).

| Example Number | Structure | Method of Synthesis: Example Number; Source of Non-commercial Starting Materials | $^1$H NMR (400 MHz, CDCl$_3$, δ (ppm); LCMS, observed ion m/z [M + H]$^+$ or HPLC retention time (minutes); LCMS m/z [M + H]$^+$ (unless otherwise indicated) |
|---|---|---|---|
| 67 | 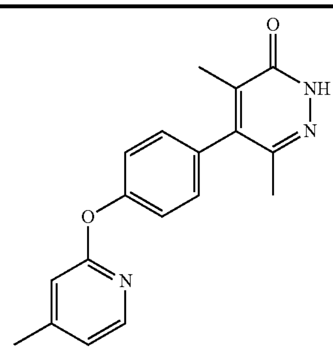 | Ex 16 & 17 | $^1$H NMR (400 MHz, CD$_3$OD) δ 8.03 (br d, J = 5.2 Hz, 1H), 7.21-7.29 (m, 4H), 7.01-7.04 (m, 1H), 6.89-6.90 (m, 1H), 2.40 (br s, 3H), 2.07 (s, 3H), 1.96 (s, 3H); 308.1 |
| 68 | 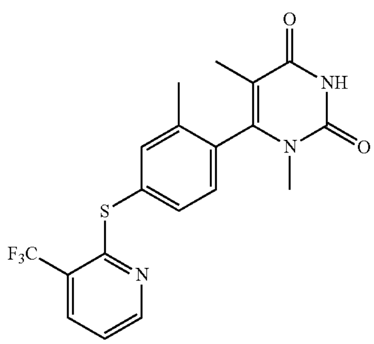 [SMILES: Cc1cc(Sc2ncccc2C(F)(F)F)ccc1-c1c(C)c(=O)[nH]c(=O)n1C] | Ex 18; C53 | 8.50 (br d, J = 5 Hz, 1H), 8.18 (br s, 1H), 7.94 (br d, J = 8 Hz, 1H), 7.54-7.56 (m, 1H), 7.51 (br d, J = 8 Hz, 1H), 7.21 (br dd, J = 8, 5 Hz, 1H), 7.14 (d, J = 7.9 Hz, 1H), 3.04 (s, 3H), 2.21 (br s, 3H), 1.67 (s, 3H); 408.1 |
| 69 | 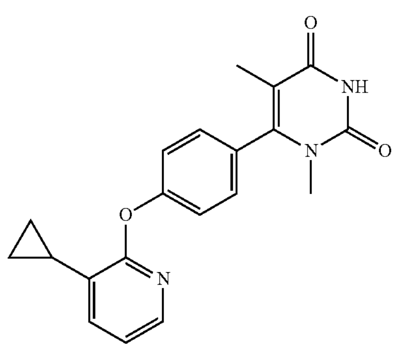 [SMILES: Cc1c(-c2ccc(Oc3ncccc3C3CC3)cc2)n(C)c(=O)[nH]c1=O] | Ex 13; C37, C6[37,38] | $^1$H NMR (400 MHz, CD$_3$OD) δ 7.95 (dd, J = 4.9, 1.9 Hz, 1H), 7.49 (ddd, J = 7.6, 1.9, 0.5 Hz, 1H), 7.30 (br AB quartet, J$_{AB}$ = 8.8 Hz, Δν$_{AB}$ = 44.0 Hz, 4H), 7.12 (ddd, J = 7.5, 4.9, 0.5 Hz, 1H), 3.08 (s, 3H), 2.16-2.24 (m, 1H), 1.68 (s, 3H), 1.00-1.05 (m, 2H), 0.77-0.82 (m, 2H); 350.2 |
| 70 | 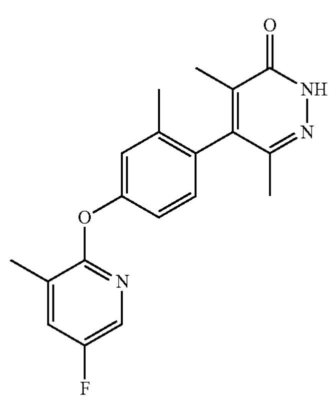 [SMILES: Cc1cc(Oc2ncc(F)cc2C)ccc1-c1c(C)n[nH]c(=O)c1C] | Ex 1 & 2; C49[39,40] | 2.80 minutes[25]; 340.3 |

TABLE 1-continued

Examples 20-81 (including Method of Synthesis and Physicochemical Data).

| Example Number | Structure | Method of Synthesis: Example Number; Source of Non-commercial Starting Materials | $^1$H NMR (400 MHz, CDCl$_3$, δ (ppm); LCMS, observed ion m/z [M + H]$^+$ or HPLC retention time (minutes); LCMS m/z [M + H]$^+$ (unless otherwise indicated) |
|---|---|---|---|
| 71 | 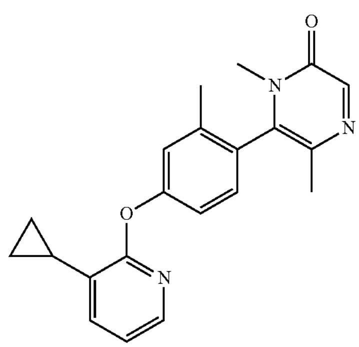 [SMILES: Cc1cc(Oc2ncccc2C2CC2)ccc1-c1c(C)ncc(=O)n1C] | Ex 1 & 2; P1, C6[41] | 3.13 minutes[6]; 348 |
| 72 | 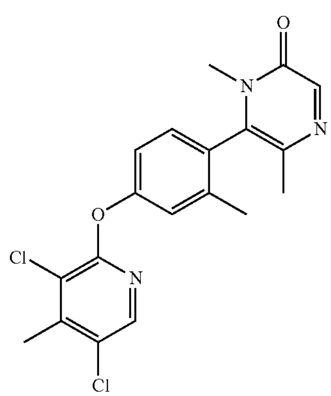 [SMILES: Cc1cc(Oc2ncc(Cl)c(C)c2Cl)ccc1-c1c(C)ncc(=O)n1C] | Ex 1 & 2; P1[41] | 3.34 minutes[42]; 390 |
| 73 | 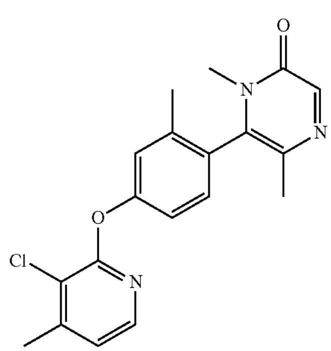 [SMILES: Cc1cc(Oc2nccc(C)c2Cl)ccc1-c1c(C)ncc(=O)n1C] | Ex 1 & 2; P1[41] | 3.17 minutes[6]; 356 |

TABLE 1-continued

Examples 20-81 (including Method of Synthesis and Physicochemical Data).

| Example Number | Structure | Method of Synthesis: Example Number; Source of Non-commercial Starting Materials | $^1$H NMR (400 MHz, CDCl$_3$, δ (ppm); LCMS, observed ion m/z [M + H]$^+$ or HPLC retention time (minutes); LCMS m/z [M + H]$^+$ (unless otherwise indicated) |
|---|---|---|---|
| 74 | 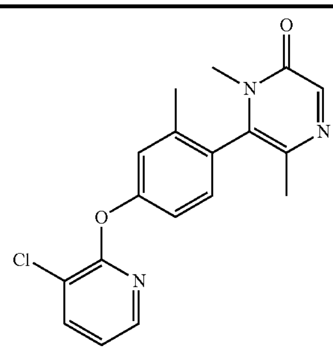 | Ex 1 & 2; P1[41] | 3.03 minutes[6]; 342 |
| 75 | 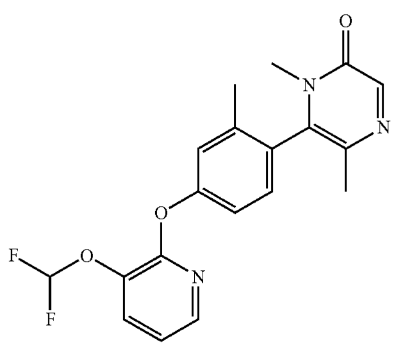 [SMILES: Cc1cc(Oc2ncccc2OC(F)F)ccc1-c1c(C)ncc(=O)n1C] | Ex 1 & 2; P1; C36[41] | 2.97 minutes[6]; 374 |
| 76 | 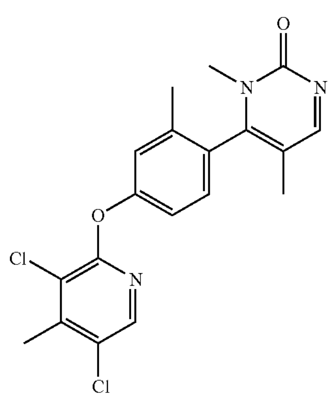 [SMILES: Cc1cc(Oc2ncc(Cl)c(C)c2Cl)ccc1-c1c(C)cnc(=O)n1C] | Ex 1 & 2; P2[41] | 3.06 minutes[42]; 390 |
| 77 | 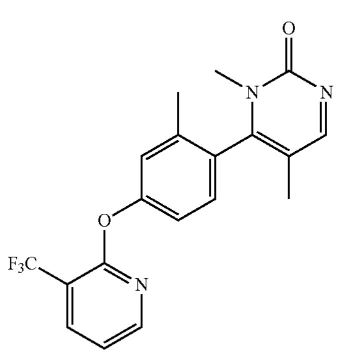 [SMILES: Cc1cc(Oc2ncccc2C(F)(F)F)ccc1-c1c(C)cnc(=O)n1C] | Ex 1 & 2; P2[41] | 2.95 minutes[6]; 376 |

TABLE 1-continued

Examples 20-81 (including Method of Synthesis and Physicochemical Data).

| Example Number | Structure | Method of Synthesis: Example Number; Source of Non-commercial Starting Materials | $^1$H NMR (400 MHz, CDCl$_3$, δ (ppm); LCMS, observed ion m/z [M + H]$^+$ or HPLC retention time (minutes); LCMS m/z [M + H]$^+$ (unless otherwise indicated) |
|---|---|---|---|
| 78 | 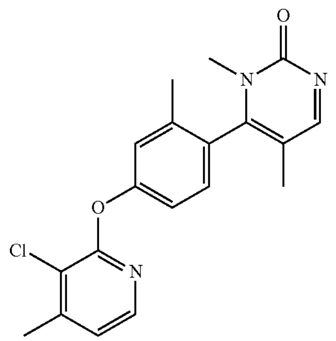 [SMILES: Cc1cc(Oc2nccc(C)c2Cl)ccc1-c1c(C)cnc(=O)n1C] | Ex 1 & 2; P2[41] | 2.96 minutes[6]; 356 |
| 79 | 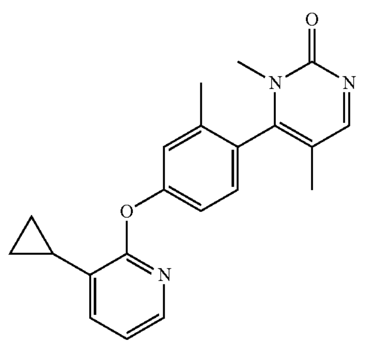 [SMILES: Cc1cc(Oc2ncccc2C2CC2)ccc1-c1c(C)cnc(=O)n1C] | Ex 1 & 2; P2; C6[41] | 2.91 minutes[6]; 348 |
| 80 | 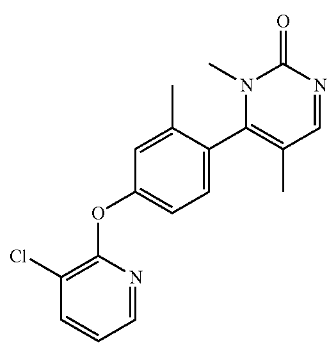 [SMILES: Cc1cc(Oc2ncccc2Cl)ccc1-c1c(C)cnc(=O)n1C] | Ex 1 & 2; P2[41] | 2.81 minutes[6]; 342 |
| 81 | 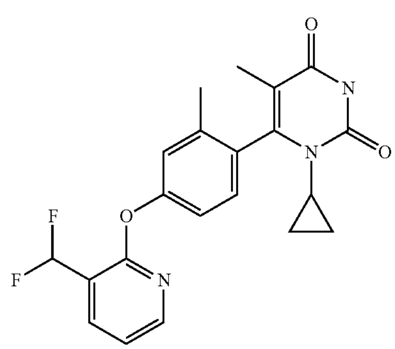 [SMILES: Cc1cc(Oc2ncccc2C(F)F)ccc1-c1c(C)c(=O)[nH]c(=O)n1C1CC1] | Ex 12; C33[43] | $^1$H NMR (600 MHz, DMSO-d$_6$) δ 8.31 (d, 1H), 8.11 (d, 1H), 7.35 (d, 1H), 7.35 (dd, 1H), 7.30 (t, 1H), 7.17 (d, 1H), 7.11 (br dd, 1H), 2.65 (m, 1H), 2.31 (m, 1H), 2.16 (s, 3H), 1.48 (s, 3H), 0.4-0.6 (m, 4H). |

1. In this case, reaction with the chloropyridine was carried out using tris(dibenzylideneacetone)dipalladium(0), 4,5-bis(diphenylphosphino)-9,9-dimethylxanthene (Xantphos) and potassium tert-butoxide in toluene at elevated temperature.

2. Compound C11 was reacted with (4-hydroxyphenyl) boronic acid, under the conditions described for the synthesis of C12 in Example 5, to provide 1-ethyl-6-(4-hydroxyphenyl)-5-methyl-3-{[2-(trimethylsilyl)ethoxy]methyl}pyrimidine-2,4(1H,3H)-dione.

3. Compound C18 was reacted with (4-hydroxyphenyl) boronic acid, under the conditions described for the synthesis of C19 in Example 6, to provide 5-ethyl-6-(4-hydroxyphenyl)-1-methyl-3-{[2-(trimethylsilyl)ethoxy]methyl}pyrimidine-2,4(1H,3H)-dione.

4. Conditions for analytical HPLC. Column: Waters XBridge C18, 2.1×50 mm, 5 μm. Mobile phase A: 0.05% ammonium hydroxide in water; Mobile phase B: acetonitrile. Gradient: 0 to 0.5 minutes, 5% B; 0.5 to 3.4 minutes, linear from 5% to 100% B. Flow rate: 0.8 mL/minute.

5. Conditions for analytical HPLC. Column: Waters XBridge C18, 2.1×50 mm, 5 μm. Mobile phase A: 0.0375% trifluoroacetic acid in water; Mobile phase B: 0.01875% trifluoroacetic acid in acetonitrile. Gradient: 0 to 0.5 minutes, 25% B; 0.5 to 3.5 minutes, linear from 25% to 100% B. Flow rate: 0.8 mL/minute.

6. Identical to footnote 5, except that the gradient used was: 0 to 0.6 minutes, linear from 1% to 5% B; 0.6 to 4.0 minutes, linear from 5% to 100% B.

7. The requisite 2-chloropyridine was prepared via reaction of 2-chloro-3-iodopyridine with a salt of the appropriate azetidine, using palladium(II) acetate, 1,1'-binaphthalene-2,2'-diylbis(diphenylphosphane) (BINAP) and cesium carbonate in toluene at elevated temperature.

8. Reaction of 2-chloropyridin-3-ol with bromocyclopropane, in the presence of cesium carbonate in N,N-dimethylacetamide at 150° C., afforded 2-chloro-3-(cyclopropyloxy)pyridine.

9. Reaction of 2-chloro-5-fluoropyridin-4-ol with iodomethane and silver carbonate provided 2-chloro-5-fluoro-4-methoxypyridine.

10. The reaction between phenol C5 and the chloropyridine was effected via reaction with copper(I) iodide and cesium carbonate in pyridine at 120° C.

11. Deprotection was carried out according to Example 5.

12. Reaction of ethyl 2-chloropyridine-3-carboxylate with methylmagnesium iodide yielded 2-(2-chloropyridin-3-yl)propan-2-ol.

13. Olefin reduction was effected via hydrogenation using palladium on carbon and N,N-diisopropylethylamine in methanol.

14. In this case, reaction with the chloropyridine was carried out using 4,5-bis(diphenylphosphino)-9,9-dimethylxanthene (Xantphos) in place of di-tert-butyl[3,4,5,6-tetramethyl-2',4',6'-tri(propan-2-yl)biphenyl-2-yl]phosphane.

15. 1-(2-Chloropyridin-3-yl)ethanone was converted to 2-chloro-3-(1,1-difluoroethoxy)pyridine using the method of D. B. Horne et al., *Tetrahedron Lett.* 2009, 50, 5452-5455. Upon deprotection, the difluoroethoxy group was also cleaved.

16. In this case, cesium fluoride was used in place of cesium carbonate in the reaction of the chloropyridine with phenol C49.

17. Compound C3 was reacted with (4-hydroxyphenyl) boronic acid, under the conditions described for preparation of C4 in Examples 1 and 2, to afford 6-(4-hydroxyphenyl)-1,5-dimethyl-3-{[2-(trimethylsilyl)ethoxy]methyl}pyrimidine-2,4(1H,3H)-dione.

18. In this case, the deprotection was carried out in trifluoroacetic acid at 100° C.

19. The racemic product was separated into its atropenantiomers via high-performance liquid chromatography (Column: Chiral Technologies, Chiralpak AD-H, 5 μm; Gradient: ethanol in heptane). This Example was the first-eluting atropenantiomer, and exhibited a positive (+) rotation.

20. Compound C49 was reacted with 2-chloro-3-iodopyridine to afford 5-{4-[(3-iodopyridin-2-yl)oxy]-2-methylphenyl}-4,6-di methyl-2-(tetrahydro-2H-pyran-2-yl)pyridazin-3(2H)-one; subsequent Suzuki reaction with cyclopropylboronic acid provided 5-{4-[(3-cyclopropylpyridin-2-yl)oxy]-2-methyl phenyl}-4,6-dimethyl-2-(tetrahydro-2H-pyran-2-yl)pyridazin-3(2H)-one. Deprotection in this case was carried out with trifluoroacetic acid rather than hydrochloric acid.

21. The requisite 2-chloro-3-(oxetan-3-yl)pyridine was prepared from (2-chloropyridin-3-yl)boronic acid using the method reported by M. A. J. Duncton et al., *Org. Lett.* 2008, 10, 3259-3262.

22. 2-Chloro-3-(difluoromethoxy)-4-methylpyridine was prepared from 2-chloro-4-methylpyridin-3-ol using conditions reported by L. F. Frey et al., *Tetrahedron* 2003, 59, 6363-6373.

23. The racemic product was separated into its component atropenantiomers using chiral separation. Conditions for analytical HPLC. Column: Chiralpak AD-H, 20×250 mm; Mobile phase A: Heptane; Mobile phase B: Ethanol; Gradient: 5.0% to 95% B, linear over 12 minutes; Flow rate: 28 mL/minute. The first-eluting atropenantiomer, which exhibited a positive (+) rotation, was designated as Example 55; the second-eluting one, which gave a negative (−) rotation, was designated as Example 54.

24. The requisite 2-[1-(3,4-dimethoxybenzyl)-3,5-dimethyl-2,6-dioxo-1,2,3,6-tetrahydropyrimidin-4-yl]-5-hydroxybenzonitrile was prepared via reaction of C26 with 5-hydroxy-2-(4,4,5,5-tetramethyl-1,3,2-dioxaborolan-2-yl)benzonitrile, mediated by chloro(2-dicyclohexylphosphino-2',6'-dimethoxy-1,1'-biphenyl)[2-(2'-amino-1,1'-biphenyl)]palladium(II) and potassium phosphate.

25. Conditions for analytical HPLC. Column: Waters Atlantis dC18, 4.6×50 mm, 5 μm; Mobile phase A: 0.05% trifluoroacetic acid in water (v/v); Mobile phase B: 0.05% trifluoroacetic acid in acetonitrile (v/v); Gradient: 5.0% to 95% B, linear over 4.0 minutes; Flow rate: 2 mL/minute.

26. Reaction of C49 with methyl 2-chloropyridine-3-carboxylate afforded methyl 2-{4-[3,5-dimethyl-6-oxo-1-(tetrahydro-2H-pyran-2-yl)-1,6-dihydropyridazin-4-yl]-3-methylphenoxy}pyridine-3-carboxylate; the ester group was converted to an amide via subjection to ammonium hydroxide in methanol at elevated temperature, to provide 2-{4-[3,5-dimethyl-6-oxo-1-(tetrahydro-2H-pyran-2-yl)-1,6-dihydropyridazin-4-yl]-3-methylphenoxy}pyridine-3-carboxamide.

27. Methyl 2-{4-[3,5-dimethyl-6-oxo-1-(tetrahydro-2H-pyran-2-yl)-1,6-dihydropyridazin-4-yl]-3-methylphenoxy}pyridine-3-carboxylate (see footnote 26) was deprotected to afford this Example.

28. 2,4-Dichloro-3-methylpyridine was converted to 2-chloro-4-methoxy-3-methylpyridine via reaction with sodium hydride/methanol.

29. In this case, the deprotection was carried out with trifluoroacetic acid in dichloromethane at room temperature.

30. The requisite 2-chloro-4-methyl-3-(trifluoromethyl) pyridine was prepared via reaction of 2-chloro-3-iodo-4- methylpyridine with methyl difluoro(fluorosulfonyl)acetate and copper(I) iodide in N,N-dimethylformamide at 90° C.

31. Reaction of 2-chloro-4-methoxypyridine-3-carbaldehyde with (diethylamino)sulfur trifluoride afforded 2-chloro-3-(difluoromethyl)-4-methoxypyridine.

32. Reaction of 2,4-dichloro-3-iodopyridine with sodium methoxide in methanol provided 2-chloro-3-iodo-4-methoxypyridine; this material was converted to 2-chloro-4-methoxy-3-(trifluoromethyl)pyridine as described in footnote 30.

33. The final deprotection was carried using hydrogen chloride in methanol, at room temperature.

34. Deprotection was carried out using the method described in Examples 16 and 17.

35. Separation of atropenantiomers was carried out via supercritical fluid chromatography (Column: Chiral Technologies, Chiralpak AS-H, 5 μm; Eluent: 85:15 carbon dioxide/methanol). The first-eluting atropenantiomer exhibited a positive (+) rotation, and was designated as Example 66. The second-eluting atropenantiomer displayed a negative (−) rotation, and was designated as Example 65.

36. In this case, mass spectrometry data was obtained on the racemate, prior to separation of the atropenantiomers.

37. Compound C37 was reacted with (4-hydroxyphenyl) boronic acid, using the method described for preparation of C4 in Examples 1 and 2, to afford 3-[(benzyloxy)methyl]-6-(4-hydroxyphenyl)-1,5-dimethylpyrimidine-2,4(1H,3H)-dione.

38. Conditions for reaction of the phenol with the chloropyridine were similar to those used for synthesis of C7 in Examples 1 and 2.

39. After the coupling reaction, the reaction mixture was partitioned between water and ethyl acetate. The organic layer was dried with sodium sulfate and concentrated in vacuo; this material was deprotected with hydrogen chloride in 1,4-dioxane.

40. Purification was effected via reversed phase high-performance liquid chromatography. Column: Waters Sunfire C18, 5 μm; Mobile phase A: 0.05% trifluoroacetic acid in water (v/v); Mobile phase B: 0.05% trifluoroacetic acid in acetonitrile (v/v); Gradient: 30% to 50% B.

41. Purification was carried out via reversed phase high-performance liquid chromatography using an appropriate gradient in one of the following systems: a) Column: Agela Durashell C18, 5 μm; Mobile phase A: ammonium hydroxide in water, pH 10; Mobile phase B: acetonitrile; b) Column: Phenomenex Gemini, 10 μm; Mobile phase A: ammonium hydroxide in water, pH 10; Mobile phase B: acetonitrile; c) Column: Phenomenex Gemini, 8 μm; Mobile phase A: 0.225% formic acid in water; Mobile phase B: acetonitrile; d) Column: YMS C18, 5 μm; Mobile phase A: ammonium hydroxide in water, pH 10; Mobile phase B: acetonitrile.

42. Conditions for analytical HPLC. Column: Waters XBridge C18, 2.1×50 mm, 5 μm. Mobile phase A: 0.0375% trifluoroacetic acid in water; Mobile phase B: 0.01875% trifluoroacetic acid in acetonitrile. Gradient: 0 to 0.5 minutes, 10% B; 0.5 to 4.0 minutes, linear from 10% to 100% B. Flow rate: 0.8 mL/minute.

43. Compound C33 was reacted with 6-bromo-3-(3,4-dimethoxybenzyl)-1-cyclopropyl-5-methylpyrimidine-2,4(1H, 3H)-dione, using the method described for Example 12, to yield Example 81. The intermediate, 6-bromo-3-(3,4-dimethoxybenzyl)-1-cyclopropyl-5-methylpyrimidine-2,4(1H, 3H)-dione, was prepared from commercially available 1-cyclopropyl urea following the methods described for the preparation of C10 and C34.

Example AA: Human D1 Receptor Binding Assay and Data

The affinity of the compounds described herein was determined by competition binding assays similar to those described in Ryman-Rasmussen et al., "Differential activation of adenylate cyclase and receptor internalization by novel dopamine D1 receptor agonists", *Molecular Pharmacology* 68(4):1039-1048 (2005). This radioligand binding assay used [$^3$H]-SCH23390, a radiolabeled D1 ligand, to evaluate the ability of a test compound to compete with the radioligand when binding to a D1 receptor.

D1 binding assays were performed using over-expressing LTK human cell lines. To determine basic assay parameters, ligand concentrations were determined from saturation binding studies where the $K_d$ for [$^3$H]-SCH23390 was found to be 1.3 nM. From tissue concentration curve studies, the optimal amount of tissue was determined to be 1.75 mg/mL per 96 well plate using 0.5 nM of [$^3$H]-SCH23390. These ligand and tissue concentrations were used in time course studies to determine linearity and equilibrium conditions for binding. Binding was at equilibrium with the specified amount of tissue in 30 minutes at 37° C. From these parameters, $K_i$ values were determined by homogenizing the specified amount of tissue for each species in 50 mM Tris (pH 7.4 at 4° C.) containing 2.0 mM $MgCl_2$ using a Polytron and spun in a centrifuge at 40,000×g for 10 minutes. The pellet was resuspended in assay buffer [50 mM Tris (pH 7.4@ RT) containing 4 mM $MgSO_4$ and 0.5 mM EDTA]. Incubations were initiated by the addition of 200 μL of tissue to 96-well plates containing test drugs (2.5 μL) and 0.5 nM [$^3$H]-SCH23390 (50 μL) in a final volume of 250 μL. Non-specific binding was determined by radioligand binding in the presence of a saturating concentration of (+)-Butaclamol (10 μM), a D1 antagonist. After a 30 minute incubation period at 37° C., assay samples were rapidly filtered through Unifilter-96 GF/B PEI-coated filter plates and rinsed with 50 mM Tris buffer (pH 7.4 at 4° C.). Membrane bound [$^3$H]-SCH23390 levels were determined by liquid scintillation counting of the filterplates in Ecolume. The $IC_{50}$ value (concentration at which 50% inhibition of specific binding occurs) was calculated by linear regression of the concentration-response data in Microsoft Excel. $K_i$ values were calculated according to the Cheng-Prusoff equation:

$$K_i = \frac{IC_{50}}{1+([L]/K_d)}$$

where [L]=concentration of free radioligand and $K_d$=dissociation constant of radioligand for D1 receptor (1.3 nM for [$^3$H]-SCH23390).

Example BB: D1 cAMP HTRF Assay and Data

The D1 cAMP (Cyclic Adenosine Monophosphate) HTRF (Homogeneous Time-Resolved Fluorescence) Assay used and described herein is a competitive immunoassay between native cAMP produced by cells and cAMP labeled with XL-665. This assay was used to determine the ability of a test compound to agonize (including partially agonize) D1. A Mab anti-cAMP labeled Cryptate visualizes the tracer. The maximum signal is achieved if the samples do not contain free cAMP due to the proximity of donor (Eu-cryptate) and acceptor (XL665) entities. The signal, therefore, is inversely proportional to the concentration of cAMP in the sample. A time-resolved and ratiometric measurement (em 665 nm/em 620 nm) minimizes the interference with medium. cAMP HTRF assays are commercially available, for example, from Cisbio Bioassays, IBA group.

Materials and Methods

Materials:

The cAMP Dynamic kit was obtained from Cisbio International (Cisbio 62AM4PEJ). Multidrop Combi (Thermo Scientific) was used for assay additions. An EnVision (PerkinElmer) reader was used to read HTRF.

Cell Cuture:

A HEK293T/hD1#1 stable cell line was constructed internally (Pfizer Ann Arbor). The cells were grown as adherent cells in NuncTs$_{00}$ flasks in high glucose DMEM (Invitrogen 11995-065), 10% fetal bovine serum dialyzed (Invitrogen 26400-044), 1×MEM NEAA (Invitrogen 1140, 25 mM HEPES (Invitrogen 15630), 1× Pen/Strep (Invitrogen 15070-063) and 500 µg/mL Genenticin (Invitrogen 10131-035) at 37° C. and 5% CO$_2$. At 72 or 96 hours post-growth, cells were rinsed with DPBS, and 0.25% Trypsin-EDTA was added to dislodge the cells. Media was then added and cells were centrifuged and media removed. The cell pellets were re-suspended in Cell Culture Freezing Medium (Invitrogen 12648-056) at a density of 4e7 cells/mL. One mL aliquots of the cells were made in Cryo-vials and frozen at −80° C. for future use in the D1 HTRF assay.

D1 cAMP HTRF Assay Procedure:

Frozen cells were quickly thawed, re-suspended in 50 mL warm media and allowed to sit for 5 min prior to centrifugation (1000 rpm) at room temperature. Media was removed and cell pellet was re-suspended in PBS/0.5 µM IBMX generating 2e5 cells/mL. Using a Multidrop Combi, 5 µL cells/well was added to the assay plate (Greiner 784085), which already contained 5 µL of a test compound. Compound controls [5 µM dopamine (final) and 0.5% DMSO (final)] were also included on every plate for data analysis. Cells and compounds were incubated at room temperature for 30 min. Working solutions of cAMP-D2 and anti-cAMP-cryptate were prepared according to Cisbio instructions. Using Multidrop, 5 µL cAMP-D2 working solution was added to the assay plate containing the test compound and cells. Using Multidrop, 5 µL anti-cAMP-cryptate working solutions was added to assay plate containing test compound, cells and cAMP-D2. The assay plate was incubated for 1 hour at room temperature. The assay plate was read on an EnVision plate reader using Cisbio recommended settings. A cAMP standard curve was generated using cAMP stock solution provided in the Cisbio kit.

Data Analysis:

Data analysis was done using computer software. Percent effects were calculated from the compound controls. Ratio $EC_{50}$ was determined using the raw ratio data from the EnVision reader. The cAMP standard curve was used in an analysis program to determine cAMP concentrations from raw ratio data. cAMP $EC_{50}$ was determined using the calculated cAMP data.

TABLE 2

Biological Data and Compound Name for Examples 1-81.

| Example Number | Human D1 Receptor Binding, $K_i$ (nM); Geometric mean of 2-5 determinations (unless otherwise indicated) | Compound Name |
| --- | --- | --- |
| 1 | 15.3 | (+)-6-{4-[(3-cyclopropylpyridin-2-yl)oxy]-2-methylphenyl}-1,5-dimethylpyrimidine-2,4(1H,3H)-dione |
| 2 | 3.11 | (−)-6-{4-[(3-cyclopropylpyridin-2-yl)oxy]-2-methylphenyl}-1,5-dimethylpyrimidine-2,4(1H,3H)-dione |
| 3 | 40.6[a] | (−)-6-{4-[(3-chloro-5-fluoropyridin-2-yl)oxy]-2-methylphenyl}-1,5-dimethylpyrimidine-2,4(1H,3H)-dione |
| 4 | 118[a] | (+)-6-{4-[(3-chloro-5-fluoropyridin-2-yl)oxy]-2-methylphenyl}-1,5-dimethylpyrimidine-2,4(1H,3H)-dione |
| 5 | 58.0[a] | 6-{4-[(3-chloropyridin-2-yl)oxy]-2-methylphenyl}-1-ethyl-5-methylpyrimidine-2,4(1H,3H)-dione |
| 6 | 33.1[a] | 6-{4-[(3-chloropyridin-2-yl)oxy]-2-methylphenyl}-5-ethyl-1-methylpyrimidine-2,4(1H,3H)-dione |
| 7 | 8.54 | (−)-1,5-dimethyl-6-(2-methyl-4-{[3-(trifluoromethyl)pyridin-2-yl]oxy}phenyl)pyrimidine-2,4(1H,3H)-dione |
| 8 | 21.0 | (+)-1,5-dimethyl-6-(2-methyl-4-{[3-(trifluoromethyl)pyridin-2-yl]oxy}phenyl)pyrimidine-2,4(1H,3H)-dione |
| 9 | 120[a] | (+)-6-{4-[(3-chloro-5-methylpyridin-2-yl)oxy]-2-methylphenyl}-1,5-dimethylpyrimidine-2,4(1H,3H)-dione |
| 10 | 82.3[a] | (−)-6-{4-[(3-chloro-5-methylpyridin-2-yl)oxy]-2-methylphenyl}-1,5-dimethylpyrimidine-2,4(1H,3H)-dione |
| 11 | 10.9[a] | 6-{4-[(3-chloro-4-methylpyridin-2-yl)oxy]phenyl}-1,5-dimethylpyrimidine-2,4(1H,3H)-dione |
| 12 | 55.1 | 6-(4-{[3-(difluoromethyl)pyridin-2-yl]oxy}-2-methylphenyl)-1-ethyl-5-methylpyrimidine-2,4(1H,3H)-dione |
| 13 | 6.91 | (−)-6-(4-{[3-(difluoromethoxy)pyridin-2-yl]oxy}-2-methylphenyl)-1,5-dimethylpyrimidine-2,4(1H,3H)-dione |
| 14 | 17.5 | (−)-6-(4-{[3-(difluoromethyl)pyridin-2-yl]oxy}-2-methylphenyl)-1,5-dimethylpyrimidine-2,4(1H,3H)-dione |
| 15 | 54.7 | (+)-6-(4-{[3-(difluoromethyl)pyridin-2-yl]oxy}-2-methylphenyl)-1,5-dimethylpyrimidine-2,4(1H,3H)-dione |

TABLE 2-continued

Biological Data and Compound Name for Examples 1-81.

| Example Number | Human D1 Receptor Binding, $K_i$ (nM); Geometric mean of 2-5 determinations (unless otherwise indicated) | Compound Name |
|---|---|---|
| 16 | 44.3 | (+)-5-(4-{[3-(difluoromethyl)pyridin-2-yl]oxy}-2-methylphenyl)-4,6-dimethylpyridazin-3(2H)-one |
| 17 | 59.1 | (−)-5-(4-{[3-(difluoromethyl)pyridin-2-yl]oxy}-2-methylphenyl)-4,6-dimethylpyridazin-3(2H)-one |
| 18 | 35.7 | 6-{4-[(3-chloropyridin-2-yl)sulfanyl]-2-methylphenyl}-1,5-dimethylpyrimidine-2,4(1H,3H)-dione |
| 19 | 12.9$^a$ | 1,5-dimethyl-6-(7-{[3-(trifluoromethyl)pyridin-2-yl]oxy}-1H-indol-4-yl)pyrimidine-2,4(1H,3H)-dione |
| 20 | 52.7 | 6-{4-[(3-ethylpyridin-2-yl)oxy]-2-methylphenyl}-1,5-dimethylpyrimidine-2,4(1H,3H)-dione |
| 21 | 314.2$^a$ | 6-{4-[(3-chloropyridin-2-yl)oxy]phenyl}-1-ethyl-5-methylpyrimidine-2,4(1H,3H)-dione |
| 22 | 82.7$^a$ | 6-{4-[(3-chloropyridin-2-yl)oxy]phenyl}-5-ethyl-1-methylpyrimidine-2,4(1H,3H)-dione |
| 23 | 45.9$^a$ | 2-[4-(3,5-dimethyl-2,6-dioxo-1,2,3,6-tetrahydropyrimidin-4-yl)-3-methylphenoxy]-4-methylpyridine-3-carbonitrile |
| 24 | 92.1$^a$ | 6-{4-[(5-chloro-3-methylpyridin-2-yl)oxy]-2-methylphenyl}-1,5-dimethylpyrimidine-2,4(1H,3H)-dione |
| 25 | 38.5$^a$ | 6-{4-[(3,5-dichloro-4-methylpyridin-2-yl)oxy]-2-methylphenyl}-1,5-dimethylpyrimidine-2,4(1H,3H)-dione |
| 26 | 117$^a$ | 6-(4-{[5-chloro-3-(difluoromethyl)pyridin-2-yl]oxy}-2-methylphenyl)-1,5-dimethylpyrimidine-2,4(1H,3H)-dione |
| 27 | 36.2$^a$ | 6-{4-[(3-fluoro-4-methylpyridin-2-yl)oxy]-2-methylphenyl}-1,5-dimethylpyrimidine-2,4(1H,3H)-dione |
| 28 | 88.9$^a$ | 6-{4-[(3,5-dichloropyridin-2-yl)oxy]-2-methylphenyl}-1,5-dimethylpyrimidine-2,4(1H,3H)-dione |
| 29 | 489 | 6-{4-[(3-fluoropyridin-2-yl)oxy]-2-methylphenyl}-1,5-dimethylpyrimidine-2,4(1H,3H)-dione |
| 30 | 156$^a$ | 1,5-dimethyl-6-[2-methyl-4-(pyridin-2-yloxy)phenyl]pyrimidine-2,4(1H,3H)-dione |
| 31 | 3.61 | 6-{4-[(3-chloro-4-methylpyridin-2-yl)oxy]-2-methylphenyl}-1,5-dimethylpyrimidine-2,4(1H,3H)-dione |
| 32 | 650$^a$ | 6-(4-{[3-(3-fluoroazetidin-1-yl)pyridin-2-yl]oxy}-2-methylphenyl)-1,5-dimethylpyrimidine-2,4(1H,3H)-dione |
| 33 | 224$^a$ | 6-(4-{[3-(cyclopropyloxy)pyridin-2-yl]oxy}-2-methylphenyl)-1,5-dimethylpyrimidine-2,4(1H,3H)-dione |
| 34 | 120$^a$ | 6-{4-[(5-fluoro-4-methoxypyridin-2-yl)oxy]-2-methylphenyl}-1,5-dimethylpyrimidine-2,4(1H,3H)-dione |
| 35 | 246$^a$ | 6-(4-{[3-(azetidin-1-yl)pyridin-2-yl]oxy}-2-methylphenyl)-1,5-dimethylpyrimidine-2,4(1H,3H)-dione |
| 36 | 826$^a$ | 6-(4-{[3-(3,3-difluoroazetidin-1-yl)pyridin-2-yl]oxy}-2-methylphenyl)-1,5-dimethylpyrimidine-2,4(1H,3H)-dione |
| 37 | 8.42$^a$ | 1,5-dimethyl-6-(2-methyl-4-{[3-(prop-1-en-2-yl)pyridin-2-yl]oxy}phenyl)pyrimidine-2,4(1H,3H)-dione |
| 38 | 31.1$^a$ | 1,5-dimethyl-6-(2-methyl-4-{[3-(propan-2-yl)pyridin-2-yl]oxy}phenyl)pyrimidine-2,4(1H,3H)-dione |
| 39 | 15.0$^a$ | 6-{4-[(4-cyclopropylpyridin-2-yl)oxy]-2-methylphenyl}-1,5-dimethylpyrimidine-2,4(1H,3H)-dione |
| 40 | 82.7$^a$ | 6-{4-[(3-hydroxypyridin-2-yl)oxy]-2-methylphenyl}-1,5-dimethylpyrimidine-2,4(1H,3H)-dione |
| 41 | 5.41$^a$ | 5-{4-[(3-chloro-4-methylpyridin-2-yl)oxy]-2-methylphenyl}-4,6-dimethylpyridazin-3(2H)-one |
| 42 | 187$^a$ | 6-{4-[(4-methoxy-5-methylpyridin-2-yl)oxy]-2-methylphenyl}-1,5-dimethylpyrimidine-2,4(1H,3H)-dione |
| 43 | 9.65 | 5-{4-[(3-bromopyridin-2-yl)oxy]-2-methylphenyl}-4,6-dimethylpyridazin-3(2H)-one |
| 44 | 87.3$^a$ | 6-{4-[(3-chloropyridin-2-yl)oxy]phenyl}-1,5-dimethylpyrimidine-2,4(1H,3H)-dione |
| 45 | 18.6 | (+)-6-(4-{[3-(difluoromethoxy)pyridin-2-yl]oxy}-2-methylphenyl)-1,5-dimethylpyrimidine-2,4(1H,3H)-dione |
| 46 | 7.66$^a$ | 5-{4-[(3-cyclopropylpyridin-2-yl)oxy]-2-methylphenyl}-4,6-dimethylpyridazin-3(2H)-one |
| 47 | 82.3 | 6-(4-{[3-(difluoromethyl)pyridin-2-yl]oxy}-2-methylphenyl)-5-ethyl-1-methylpyrimidine-2,4(1H,3H)-dione |
| 48 | 0.571 | 5-{4-[(3-iodopyridin-2-yl)oxy]-2-methylphenyl}-4,6-dimethylpyridazin-3(2H)-one |

TABLE 2-continued

Biological Data and Compound Name for Examples 1-81.

| Example Number | Human D1 Receptor Binding, $K_i$ (nM); Geometric mean of 2-5 determinations (unless otherwise indicated) | Compound Name |
|---|---|---|
| 49 | 288 | 4,6-dimethyl-5-(2-methyl-4-{[3-(oxetan-3-yl)pyridin-2-yl]oxy}phenyl)pyridazin-3(2H)-one |
| 50 | 10.1 | 6-(4-{[3-(difluoromethoxy)-4-methylpyridin-2-yl]oxy}-2-methylphenyl)-1,5-dimethylpyrimidine-2,4(1H,3H)-dione |
| 51 | 94.9 | 4,6-dimethyl-5-(2-methyl-4-{[3-(trifluoromethoxy)pyridin-2-yl]oxy}phenyl)pyridazin-3(2H)-one |
| 52 | 63.1[a] | 1,5-dimethyl-6-(2-methyl-4-{[3-(trifluoromethoxy)pyridin-2-yl]oxy}phenyl)pyrimidine-2,4(1H,3H)-dione |
| 53 | 109[a] | 6-(4-{[3-(difluoromethoxy)pyridin-2-yl]oxy}phenyl)-1,5-dimethylpyrimidine-2,4(1H,3H)-dione |
| 54 | 9.33 | (−)-6-{4-[(3-chloropyridin-2-yl)oxy]-2-methylphenyl}-1,5-dimethylpyrimidine-2,4(1H,3H)-dione |
| 55 | 24.2 | (+)-6-{4-[(3-chloropyridin-2-yl)oxy]-2-methylphenyl}-1,5-dimethylpyrimidine-2,4(1H,3H)-dione |
| 56 | 428[a] | 5-{[3-(difluoromethyl)pyridin-2-yl]oxy}-2-(3,5-dimethyl-2,6-dioxo-1,2,3,6-tetrahydropyrimidin-4-yl)benzonitrile |
| 57 | 30.5[a] | 5-{4-[(3-chloropyridin-2-yl)oxy]-2-methylphenyl}-4,6-dimethylpyridazin-3(2H)-one |
| 58 | 86.2 | 5-(4-{[3-(difluoromethoxy)pyridin-2-yl]oxy}-2-methylphenyl)-4,6-dimethylpyridazin-3(2H)-one |
| 59 | 1220[a] | 2-[4-(3,5-dimethyl-6-oxo-1,6-dihydropyridazin-4-yl)-3-methylphenoxy]pyridine-3-carboxamide, hydrochloride salt |
| 60 | 767[a] | methyl 2-[4-(3,5-dimethyl-6-oxo-1,6-dihydropyridazin-4-yl)-3-methylphenoxy]pyridine-3-carboxylate |
| 61 | 23.8 | 5-{4-[(4-methoxy-3-methylpyridin-2-yl)oxy]-2-methylphenyl}-4,6-dimethylpyridazin-3(2H)-one |
| 62 | 12.1 | 4,6-dimethyl-5-(2-methyl-4-{[4-methyl-3-(trifluoromethyl)pyridin-2-yl]oxy}phenyl)pyridazin-3(2H)-one |
| 63 | 13.4 | 5-(4-{[3-(difluoromethyl)-4-methoxypyridin-2-yl]oxy}-2-methylphenyl)-4,6-dimethylpyridazin-3(2H)-one |
| 64 | 4.17 | 5-(4-{[4-methoxy-3-(trifluoromethyl)pyridin-2-yl]oxy}-2-methylphenyl)-4,6-dimethylpyridazin-3(2H)-one |
| 65 | 34.4 | (−)-4,6-dimethyl-5-(2-methyl-4-{[3-(trifluoromethyl)pyridin-2-yl]oxy}phenyl)pyridazin-3(2H)-one |
| 66 | 26.9 | (+)-4,6-dimethyl-5-(2-methyl-4-{[3-(trifluoromethyl)pyridin-2-yl]oxy}phenyl)pyridazin-3(2H)-one |
| 67 | 345[a] | 4,6-dimethyl-5-{4-[(4-methylpyridin-2-yl)oxy]phenyl}pyridazin-3(2H)-one |
| 68 | 16.9 | 1,5-dimethyl-6-(2-methyl-4-{[3-(trifluoromethyl)pyridin-2-yl]sulfanyl}phenyl)pyrimidine-2,4(1H,3H)-dione |
| 69 | 38.3 | 6-{4-[(3-cyclopropylpyridin-2-yl)oxy]phenyl}-1,5-dimethylpyrimidine-2,4(1H,3H)-dione |
| 70 | 138[a] | 5-{4-[(5-fluoro-3-methylpyridin-2-yl)oxy]-2-methylphenyl}-4,6-dimethylpyridazin-3(2H)-one |
| 71 | 216[a] | 6-{4-[(3-cyclopropylpyridin-2-yl)oxy]-2-methylphenyl}-1,5-dimethylpyrazin-2(1H)-one |
| 72 | 227[a] | 6-{4-[(3,5-dichloro-4-methylpyridin-2-yl)oxy]-2-methylphenyl}-1,5-dimethylpyrazin-2(1H)-one |
| 73 | 43.4[a] | 6-{4-[(3-chloro-4-methylpyridin-2-yl)oxy]-2-methylphenyl}-1,5-dimethylpyrazin-2(1H)-one |
| 74 | 381[a] | 6-{4-[(3-chloropyridin-2-yl)oxy]-2-methylphenyl}-1,5-dimethylpyrazin-2(1H)-one |
| 75 | 87.0[a] | 6-(4-{[3-(difluoromethoxy)pyridin-2-yl]oxy}-2-methylphenyl)-1,5-dimethylpyrazin-2(1H)-one |
| 76 | 354[a] | 6-{4-[(3,5-dichloro-4-methylpyridin-2-yl)oxy]-2-methylphenyl}-1,5-dimethylpyrimidin-2(1H)-one |
| 77 | 337[a] | 1,5-dimethyl-6-(2-methyl-4-{[3-(trifluoromethyl)pyridin-2-yl]oxy}phenyl)pyrimidin-2(1H)-one |
| 78 | 32.3[a] | 6-{4-[(3-chloro-4-methylpyridin-2-yl)oxy]-2-methylphenyl}-1,5-dimethylpyrimidin-2(1H)-one |
| 79 | 109[a] | 6-{4-[(3-cyclopropylpyridin-2-yl)oxy]-2-methylphenyl}-1,5-dimethylpyrimidin-2(1H)-one |
| 80 | 349[a] | 6-{4-[(3-chloropyridin-2-yl)oxy]-2-methylphenyl}-1,5-dimethylpyrimidin-2(1H)-one |

TABLE 2-continued

Biological Data and Compound Name for Examples 1-81.

| Example Number | Human D1 Receptor Binding, $K_i$ (nM); Geometric mean of 2-5 determinations (unless otherwise indicated) | Compound Name |
|---|---|---|
| 81 | 58[a] | 1-cyclopropyl-6-(4-((3-(difluoromethyl)pyridin-2-yl)oxy)-2-methylphenyl)-5-methylpyrimidine-2,4(1H,3H)-dione |

[a]Value represents a single determination.

Various modifications of the invention, in addition to those described herein, will be apparent to those skilled in the art from the foregoing description. Such modifications are also intended to fall within the scope of the appendant claims. Each reference (including all patents, patent applications, journal articles, books, and any other publications) cited in the present application is hereby incorporated by reference in its entirety.

What is claimed is:

1. A method for treating a D1-mediated (or D1-associated) disease or disorder in a mammal, which method comprises administering to the mammal a therapeutically effective amount of a compound of Formula I:

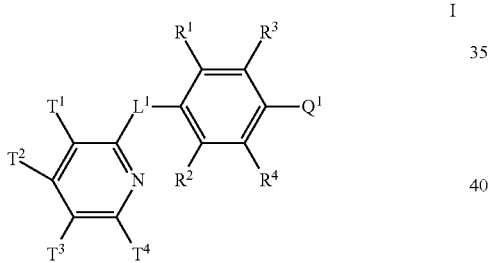

or a pharmaceutically acceptable salt thereof, wherein:
each of $T^1$, $T^2$, $T^3$, and $T^4$ is independently selected from the group consisting of H, halogen, —CN, —SF$_5$, —OH, —N(R$^a$)(R$^b$), —C(=O)—N(R$^a$)(R$^b$), —C(=O)—OR$^c$, —C(=O)—R$^d$, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, —S—($C_{1-6}$ alkyl), $C_{3-7}$ cycloalkyl, 4- to 7-membered heterocycloalkyl, $C_{3-7}$ cycloalkoxy, 5- or 6-membered heteroaryl, cyclopropylmethyl, and cyclobutylmethyl, wherein each of the $C_{1-6}$ alkyl, $C_{2-6}$ alkenyl, $C_{2-6}$ alkynyl, —S—($C_{1-6}$ alkyl), and $C_{1-6}$ alkoxy is optionally substituted with one or more substituents each independently selected from the group consisting of halogen, —OH, —CN, —N(R$^a$)(R$^b$), $C_{1-4}$ alkoxy, $C_{1-4}$ haloalkoxy, and —S—($C_{1-4}$ alkyl); and wherein each of the $C_{3-7}$ cycloalkyl, 4- to 7-membered heterocycloalkyl, $C_{3-7}$ cycloalkoxy, 5- or 6-membered heteroaryl, cyclopropylmethyl, and cyclobutylmethyl of $T^1$, $T^2$, and $T^3$ is optionally substituted with one or more substituents each independently selected from the group consisting of halogen, —OH, —CN, oxo, —N(R$^a$)(R$^b$), —C(=O)OH, —C(=O)—$C_{1-4}$ alkyl, —C(=O)—O—$C_{1-4}$ alkyl, —C(=O)—N(R$^a$)(R$^b$), $C_{1-4}$ alkyl, $C_{1-4}$ haloalkyl, $C_{1-4}$ hydroxylalkyl, $C_{1-4}$ cyanoalkyl, $C_{1-4}$ alkoxy, $C_{1-4}$ haloalkoxy, and —S—($C_{1-4}$ alkyl);

$L^1$ is selected from the group consisting of O, S, NH, N($C_{1-4}$ alkyl), N(—$C_{1-2}$ alkyl-$C_{3-4}$ cycloalkyl), and N($C_{3-6}$ cycloalkyl);

each of R$^a$ and R$^b$ is independently selected from the group consisting of H, $C_{1-4}$ alkyl, $C_{3-7}$ cycloalkyl, and cyclopropylmethyl;

or R$^a$ and R$^b$ together with the N atom to which they are attached form 4- to 7-membered heterocycloalkyl optionally substituted with one or more substituents each independently selected from the group consisting of halogen, —OH, —CN, oxo, —NH$_2$, —NH($C_{1-4}$ alkyl), —N($C_{1-4}$ alkyl)$_2$, —C(=O)OH, —C(=O)—$C_{1-4}$ alkyl, —C(=O)—O—$C_{1-4}$ alkyl, —C(=O)—NH$_2$, —C(=O)—NH($C_{1-4}$ alkyl), —C(=O)—N($C_{1-4}$ alkyl)$_2$, $C_{1-4}$ alkyl, $C_{1-4}$ haloalkyl, $C_{1-4}$ hydroxylalkyl, $C_{1-4}$ cyanoalkyl, $C_{1-4}$ alkoxy, —S—($C_{1-4}$ alkyl), and $C_{1-4}$ haloalkoxy;

each of R$^c$ and R$^d$ is independently $C_{1-4}$ alkyl, $C_{3-4}$ cycloalkyl-$C_{1-2}$ alkyl-, or $C_{3-4}$ cycloalkyl;

$Q^1$ is selected from the group consisting of $Q^{1b}$, $Q^{1c}$, $Q^{1d}$, and $Q^{1e}$:

-continued

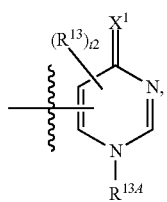

$Q^{1e}$ provided (a) that a ring carbon atom of the $Q^1$ ring is attached to the benzene ring of Formula I and (b) that when $L^1$ is NH, then the $Q^1$ ring is substituted with at least one non-H $R^9$, $R^{10}$, $R^{11}$, $R^{12}$, $R^{13}$, $R^{9A}$, $R^{10A}$, $R^{10B}$, $R^{11A}$, $R^{12A}$, or $R^{13A}$;

each of $X^1$ and $X^2$ is independently O or S;

each of $R^1$, $R^2$, $R^3$, and $R^4$ is independently selected from the group consisting of H, halogen, —OH, —NO$_2$, —CN, —SF$_5$, $C_{1-6}$ alkyl, $C_{1-6}$ haloalkyl, $C_{1-6}$ haloalkoxy, $C_{2-6}$ alkenyl, $C_{2-6}$ alkynyl, $C_{3-7}$ cycloalkyl, a 4- to 10-membered heterocycloalkyl, —N(R$^5$)(R$^6$), —N(R$^7$)(C(=O)R$^8$), —C(=O)—N(R$^5$)(R$^6$), —C(=O)—R$^8$, —C(=O)—OR$^8$, —N(R$^7$)(S(=O)$_2$R$^8$), —S(=O)$_2$—N(R$^5$)(R$^6$), —SR$^8$, and —OR$^8$, wherein each of the $C_{1-6}$ alkyl, $C_{3-7}$ cycloalkyl, and heterocycloalkyl is optionally substituted with 1, 2, or 3 substituents each independently selected from the group consisting of halogen, —CN, oxo, —OH, $C_{1-4}$ alkyl, $C_{1-4}$ alkoxy, $C_{1-4}$ haloalkyl, $C_{1-4}$ haloalkoxy, $C_{3-6}$ cycloalkyl, —N(R$^5$)(R$^6$), —N(R$^7$)(C(=O)R$^8$), —C(=O)—OR$^8$, —C(=O)H, —C(=O)R$^8$, —C(=O)N(R$^5$)(R$^6$), —N(R$^7$)(S(=O)$_2$R$^8$), —S(=O)$_2$—N(R$^5$)(R$^6$), —SR$^8$, and —OR$^8$;

or $R^2$ and $R^4$ together with the two carbon atoms to which they are attached form a fused 5- or 6-membered heteroaryl, a fused 5- or 6-membered heterocycloalkyl ring, a fused 5- or 6-membered cycloalkyl ring, or a fused benzene ring, wherein each of the fused rings is optionally substituted with 1, 2, or 3 substituents each independently selected from the group consisting of halo, —CN, —OH, $C_{1-4}$ alkyl, $C_{1-4}$ alkoxy, $C_{1-4}$ haloalkyl, and $C_{1-4}$ haloalkoxy, and wherein the fused heterocycloalkyl ring or fused cycloalkyl ring is further optionally substituted with 1, 2, or 3 oxo;

$R^5$ is H, $C_{1-4}$ alkyl, $C_{1-4}$ haloalkyl, or $C_{3-7}$ cycloalkyl;

$R^6$ is H or selected from the group consisting of $C_{1-4}$ alkyl, $C_{1-4}$ haloalkyl, $C_{3-7}$ cycloalkyl, a 4- to 10-membered heterocycloalkyl, $C_{6-10}$ aryl, a 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl-, wherein each of the selections from the group is optionally substituted with 1, 2, 3, or 4 substituents each independently selected from the group consisting of —OH, —CN, $C_{1-4}$ alkyl, $C_{3-7}$ cycloalkyl, $C_{1-4}$ hydroxylalkyl, —S—$C_{1-4}$ alkyl, —C(=O)H, —C(=O)—$C_{1-4}$ alkyl, —C(=O)—O—$C_{1-4}$ alkyl, —C(=O)—NH$_2$, —C(=O)—N($C_{1-4}$ alkyl)$_2$, $C_{1-4}$ haloalkyl, $C_{1-4}$ alkoxy, and $C_{1-4}$ haloalkoxy;

or $R^5$ and $R^6$ together with the N atom to which they are attached form a 4- to 10-membered heterocycloalkyl or a 5- to 10-membered heteroaryl, each optionally substituted with 1, 2, 3, 4, or 5 substituents each independently selected from the group consisting of halogen, —OH, oxo, —C(=O)H, —C(=O)—$C_{1-4}$ alkyl, —C(=O)OH, —C(=O)—O—$C_{1-4}$ alkyl, —C(=O)—NH$_2$, —C(=O)—N($C_{1-4}$ alkyl)$_2$, —CN, $C_{1-4}$ alkyl, $C_{1-4}$ alkoxy, $C_{1-4}$ hydroxylalkyl, $C_{1-4}$ haloalkyl, and $C_{1-4}$ haloalkoxy;

$R^7$ is selected from the group consisting of H, $C_{1-4}$ alkyl, and $C_{3-7}$ cycloalkyl;

$R^8$ is selected from the group consisting of $C_{1-6}$ alkyl, $C_{3-7}$ cycloalkyl, a 4- to 10-membered heterocycloalkyl, $C_{6-10}$ aryl, a 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl-, wherein each of the selections from the group is optionally substituted with 1, 2, or 3 substituents each independently selected from the group consisting of halogen, —CF$_3$, —CN, —OH, oxo, —S—$C_{1-4}$ alkyl, $C_{1-4}$ alkyl, $C_{1-4}$ haloalkyl, $C_{2-6}$ alkenyl, $C_{2-6}$ alkynyl, $C_{3-7}$ cycloalkyl, $C_{1-4}$ alkoxy, and $C_{1-4}$ haloalkoxy;

each $R^9$ and $R^{12}$ is independently selected from the group consisting of halogen, —OH, —CN, —SF$_5$, —NO$_2$, $C_{1-6}$ alkyl, $C_{1-6}$ haloalkyl, $C_{1-6}$ hydroxylalkyl, $C_{1-6}$ alkoxy, $C_{1-6}$ haloalkoxy, $C_{3-7}$ cycloalkyl, $C_{2-6}$ alkenyl, $C_{2-6}$ alkynyl, a 4- to 10-membered heterocycloalkyl, a 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, (5- to 10-membered heteroaryl)-$C_{1-4}$ alkyl-, —N(R$^5$)(R$^6$), —N(R$^7$)(C(=O)R$^8$), —S(=O)$_2$N(R$^5$)(R$^6$), —C(=O)—N(R$^5$)(R$^6$), —C(=O)—R$^8$, —C(=O)—OR$^8$, —SR$^8$, and —OR$^8$, wherein each of the $C_{1-6}$ alkyl, $C_{3-7}$ cycloalkyl, 4- to 10-membered heterocycloalkyl, 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl- is optionally substituted with 1, 2, 3, or 4 substituents each independently selected from the group consisting of halogen, —OH, —CN, —NO$_2$, $C_{1-4}$ alkyl, $C_{1-4}$ hydroxylalkyl, $C_{1-4}$ alkoxy, —N(R$^5$)(R$^6$), —S—($C_{1-4}$ alkyl), —S(=O)$_2$—($C_{1-4}$ alkyl), $C_{6-10}$ aryloxy, [($C_{6-10}$ aryl)-$C_{1-4}$ alkyloxy- optionally substituted with 1 or 2 $C_{1-4}$ alkyl], oxo, —C(=O)H, —C(=O)—$C_{1-4}$ alkyl, —C(=O)O—$C_{1-4}$ alkyl, —C(=O)NH$_2$, —NHC(=O)H, —NHC(=O)-($C_{1-4}$ alkyl), $C_{3-7}$ cycloalkyl, a 5- or 6-membered heteroaryl, $C_{1-4}$ haloalkyl, and $C_{1-4}$ haloalkoxy;

each of $R^{10}$, $R^{11}$ and $R^{13}$ is independently selected from the group consisting of halogen, —OH, —CN, —SF$_5$, —NO$_2$, $C_{1-6}$ alkyl, $C_{1-6}$ haloalkyl, $C_{1-6}$ hydroxylalkyl, $C_{1-6}$ alkoxy, $C_{1-6}$ haloalkoxy, $C_{3-7}$ cycloalkyl, $C_{2-6}$ alkenyl, $C_{2-6}$ alkynyl, $C_{6-10}$ aryl, a 4- to 10-membered heterocycloalkyl, a 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, (5- to 10-membered heteroaryl)-$C_{1-4}$ alkyl-, —N(R$^5$)(R$^6$), —N(R$^7$)(C(=O)R$^8$), —S(=O)$_2$N(R$^5$)(R$^6$), —C(=O)—N(R$^5$)(R$^6$), —C(=O)—R$^8$, —C(=O)—OR$^8$, —SR$^8$, and —OR$^8$, wherein each of the $C_{1-6}$ alkyl, $C_{3-7}$ cycloalkyl, $C_{6-10}$ aryl, 4- to 10-membered heterocycloalkyl, 5- to 10-membered heteroaryl, ($C_{3-7}$ cycloalkyl)-$C_{1-4}$ alkyl-, (4- to 10-membered heterocycloalkyl)-$C_{1-4}$ alkyl-, ($C_{6-10}$ aryl)-$C_{1-4}$ alkyl-, and (5- to 10-membered heteroaryl)-$C_{1-4}$ alkyl- is optionally substituted with 1, 2, 3, or 4 substituents each independently selected from the group consisting of halogen, —OH, —CN, —NO$_2$, C$_{1-4}$ alkyl, C$_{1-4}$ hydroxylalkyl, C$_{1-4}$ alkoxy, —N(R$^5$)(R$^6$), —S—(C$_{1-4}$ alkyl), —S(=O)$_2$—(C$_{1-4}$ alkyl), C$_{6-10}$ aryloxy, [(C$_{6-10}$ aryl)-C$_{1-4}$ alkyloxy- optionally substituted with 1 or 2 C$_{1-4}$ alkyl], oxo, —C(=O)H, —C(=O)—C$_{1-4}$ alkyl, —C(=O)O—C$_{1-4}$ alkyl, —C(=O)NH$_2$, —NHC(=O)H, —NHC(=O)—(C$_{1-4}$ alkyl), C$_{3-7}$ cycloalkyl, a 5- or 6-membered heteroaryl, C$_{1-4}$ haloalkyl, and C$_{1-4}$ haloalkoxy;

each of R$^{9A}$ and R$^{10A}$ is independently selected from the group consisting of H, C$_{1-6}$ alkyl, C$_{1-6}$ hydroxylalkyl, C$_{2-6}$ alkenyl, —S(=O)$_2$N(R$^5$)(R$^6$), —C(=O)—N(R$^5$)(R$^6$), —C(=O)—R$^8$, —C(=O)—OR$^8$, —SR$^{15}$, —C(R$^{14}$)$_2$—OH, —C(R$^{14}$)$_2$—OS(=O)$_2$H, —C(R$^{14}$)$_2$—OP(=O)(OH)$_2$, —C(R$^{14}$)$_2$—OR$^{15}$, —C(R$^{14}$)$_2$—OC(=O)—R$^{15}$, —C(R$^{14}$)$_2$—N(R$^5$)(R$^6$), each of R$^{10B}$, R$^{11A}$, R$^{12A}$, and R$^{13A}$ is independently selected from the group consisting of H, C$_{1-6}$ alkyl, C$_{1-6}$ haloalkyl, C$_{1-6}$ hydroxylalkyl, C$_{3-7}$ cycloalkyl, C$_{3-6}$ alkenyl, C$_{3-6}$ alkynyl, C$_{6-10}$ aryl, a 4- to 10-membered heterocycloalkyl, a 5- to 10-membered heteroaryl, (C$_{3-7}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, (5- to 10-membered heteroaryl)-C$_{1-4}$ alkyl-, —S(=O)$_2$N(R$^5$)(R$^6$), —C(=O)—N(R$^5$)(R$^6$), —C(=O)—R$^8$, and —C(=O)—OR$^8$, wherein each of the C$_{1-6}$ alkyl, C$_{3-7}$ cycloalkyl, C$_{6-10}$ aryl, 4- to 10-membered heterocycloalkyl, 5- to 10-membered heteroaryl, (C$_{3-7}$ cycloalkyl)-C$_{1-4}$ alkyl-, (4- to 10-membered heterocycloalkyl)-C$_{1-4}$ alkyl-, (C$_{6-10}$ aryl)-C$_{1-4}$ alkyl-, and (5- to 10-membered heteroaryl)-C$_{1-4}$ alkyl-, is optionally substituted with 1, 2, 3, or 4 substituents each independently selected from the group consisting of halogen, —OH, —CN, —NO$_2$, C$_{1-4}$ alkyl, C$_{1-4}$ hydroxylalkyl, C$_{1-4}$ alkoxy, —N(R$^5$)(R$^6$), —S—(C$_{1-4}$ alkyl), —S(=O)$_2$—(C$_{1-4}$ alkyl), C$_{6-10}$ aryloxy, [(C$_{6-10}$ aryl)-C$_{1-4}$ alkyloxy- optionally substituted with 1 or 2 C$_{1-4}$ alkyl], oxo, —C(=O)H, —C(=O)—C$_{1-4}$ alkyl, —C(=O)O—C$_{1-4}$ alkyl, —C(=O)NH$_2$, —NHC(=O)H, —NHC(=O)—(C$_{1-4}$ alkyl), —OC(=O)—C$_{1-4}$ alkyl, C$_{3-7}$ cycloalkyl, a 5- or 6-membered heteroaryl, C$_{1-4}$ haloalkyl, and C$_{1-4}$ haloalkoxy;

each R$^{14}$ is independently H or selected from the group consisting of C$_{1-10}$ alkyl, C$_{3-14}$ cycloalkyl, C$_{2-10}$ alkenyl, C$_{2-10}$ alkynyl, C$_{6-10}$ aryl, 4- to 10-membered heterocycloalkyl, 5- to 10-membered heteroaryl, (C$_{3-14}$ cycloalkyl)-C$_{1-10}$ alkyl-, (4- to 14-membered heterocycloalkyl)-C$_{1-10}$ alkyl-, (C$_{6-10}$ aryl)-C$_{1-10}$ alkyl-, (5- to 10-membered heteroaryl)-C$_{1-10}$ alkyl-, wherein each of the selections of the group is optionally substituted with 1, 2, 3, or 4 substituents each independently selected from the group consisting of halogen, —OH, —CN, —NO$_2$, C$_{1-4}$ alkyl, C$_{1-4}$ hydroxylalkyl, C$_{1-4}$ alkoxy, —N(R$^5$)(R$^6$), —N(R$^7$)C(=O)R$^8$, —N(R$^7$)C(=O)OR$^8$, —N(R$^7$)S(=O)$_2$R$^8$, —S(=O)$_2$N(R$^5$)(R$^6$), —C(=O)—N(R$^5$)(R$^6$), —C(=O)—R$^8$, —C(=O)—OR$^8$, —SR$^8$, —OR$^8$, —S(=O)$_2$—R$^8$, C$_{6-10}$ aryloxy, [(C$_{6-10}$ aryl)-C$_{1-4}$ alkyloxy- optionally substituted with 1 or 2 C$_{1-4}$ alkyl], oxo, —C(=O)H, —NHC(=O)H, C$_{3-7}$ cycloalkyl, a 5- or 6-membered heteroaryl, C$_{1-4}$ haloalkyl, and C$_{1-4}$ haloalkoxy;

R$^{15}$ is selected from the group consisting of C$_{1-20}$ alkyl, C$_{3-14}$ cycloalkyl, C$_{2-20}$ alkenyl, C$_{2-20}$ alkynyl, C$_{6-10}$ aryl, 4- to 14-membered heterocycloalkyl, 5- to 10-membered heteroaryl, (C$_{3-14}$ cycloalkyl)-C$_{1-20}$ alkyl-, (4- to 10-membered heterocycloalkyl)-C$_{1-20}$ alkyl-, (C$_{6-10}$ aryl)-C$_{1-20}$ alkyl-, (5- to 10-membered heteroaryl)-C$_{1-20}$ alkyl-, wherein each of the selections of the group is optionally substituted with 1, 2, 3, or 4 substituents each independently selected from the group consisting of halogen, —OH, —CN, —NO$_2$, C$_{1-4}$ alkyl, C$_{1-4}$ hydroxylalkyl, C$_{1-4}$ alkoxy, —N(R$^5$)(R$^6$), —N(R$^7$)C(=O)R$^8$, —N(R$^7$)C(=O)OR$^8$, —N(R$^7$)S(=O)$_2$R$^8$, —S(=O)$_2$N(R$^5$)(R$^6$), —C(=O)—N(R$^5$)(R$^6$), —C(=O)—R$^8$, —C(=O)—OR$^8$, —SR$^8$, —OR$^8$, —S(=O)$_2$—R$^8$, C$_{6-10}$ aryloxy, [(C$_{6-10}$ aryl)-C$_{1-4}$ alkyloxy- optionally substituted with 1 or 2 C$_{1-4}$ alkyl], oxo, —C(=O)H, —NHC(=O)H, C$_{3-7}$ cycloalkyl, a 5- or 6-membered heteroaryl, C$_{1-4}$ haloalkyl, and C$_{1-4}$ haloalkoxy;

t1 is 0, 1, or 2;

t2 is 0 or 1; and t3 is 0, 1, or 2, and wherein the D1-mediated (or D1-associated) disease or disorder is selected from the group consisting of schizophrenia, schizoaffective disorder, Parkinson's disease, and cognitive impairment.

2. The method of claim 1 wherein L$^1$ is O or S.

3. The method of claim 2 wherein the compound or a pharmaceutically acceptable salt thereof is a compound of Formula IB-1, IB-2, IB-3, IB-4, IB-5, IB-6, IB-7, IB-8, IB-9, or IB-10:

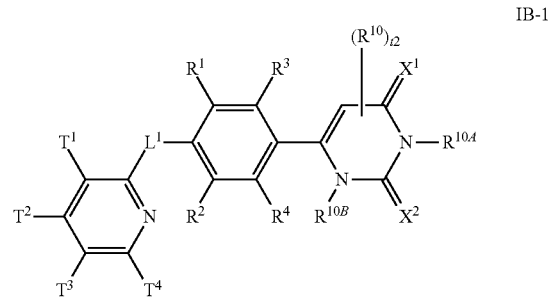

IB-1

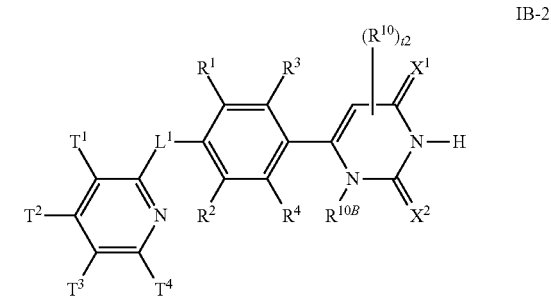

IB-2

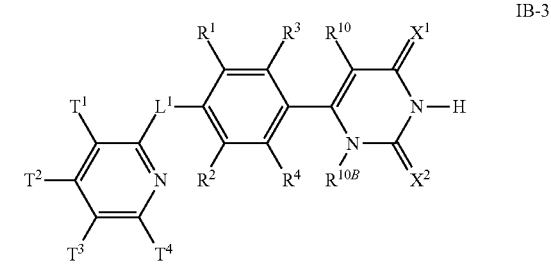

IB-3

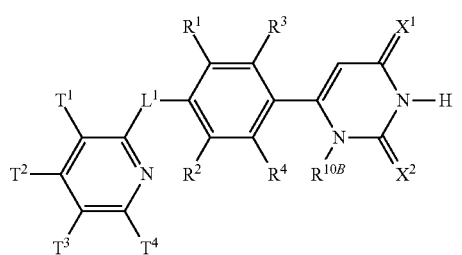

IB-4

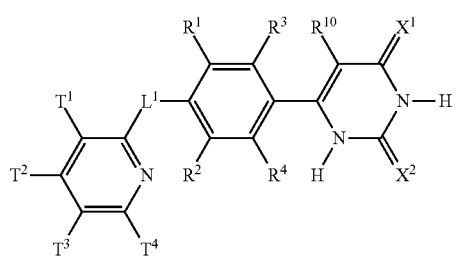

IB-5

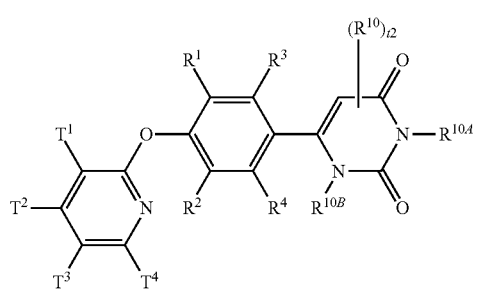

IB-6

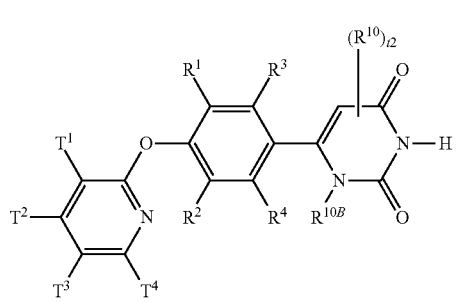

IB-7

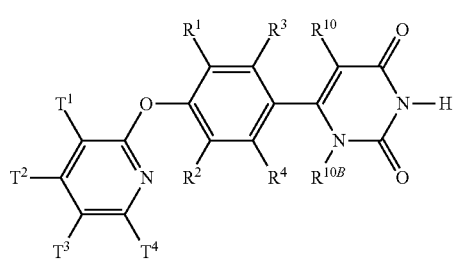

IB-8

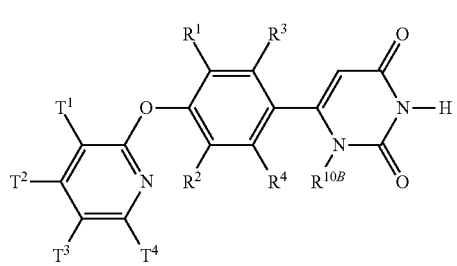

IB-9

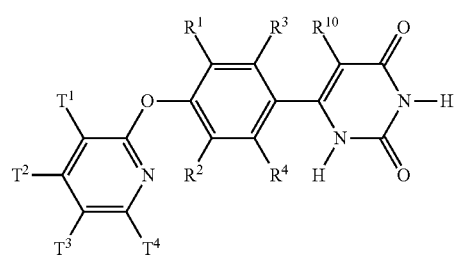

IB-10 or a pharmaceutically acceptable salt thereof.

4. The method of claim 3 wherein:

$R^{10}$ is selected from the group consisting of —CN, $C_{1-4}$ alkyl, $C_{3-4}$ cycloalkyl, cyclopropylmethyl, and cyclobutylmethyl, wherein the $C_{1-4}$ alkyl of $R^{10}$ is optionally substituted with 1, 2, 3, or 4 substituents each independently selected from the group consisting of halogen, —OH, —CN, $C_{1-4}$ alkoxy, and $C_{1-4}$ haloalkoxy; and wherein each of the $C_{3-4}$ cycloalkyl, cyclopropylmethyl, and cyclobutylmethyl of $R^{10}$ is optionally substituted with 1, 2, 3, or 4 substituents each independently selected from the group consisting of halogen, —OH, —CN, $C_{1-4}$ alkyl, $C_{1-4}$ haloalkyl, $C_{1-4}$ hydroxylalkyl, $C_{1-4}$ alkoxy, and $C_{1-4}$ haloalkoxy;

$R^{10A}$ is selected from the group consisting of H, $C_{1-3}$ alkyl, $C_{1-3}$ hydroxylalkyl, $C_{2-4}$ alkenyl, —S(=O)$_2$N$(R^5)(R^6)$, —C(=O)—N$(R^5)(R^6)$, —C(=O)—$R^8$, —C(=O)—OR$^8$, —C$(R^{14})_2$—OH, —C$(R^{14})_2$—OS(=O)$_2$H, —C$(R^{14})_2$—OP(=O)(OH)$_2$, —C$(R^{14})_2$—OR$^{15}$, and —C$(R^{14})_2$—OC(=O)—$R^{15}$; and $R^{10B}$ is selected from the group consisting of $C_{1-4}$ alkyl, $C_{3-4}$ cycloalkyl, cyclopropylmethyl, and cyclobutylmethyl, wherein the $C_{1-4}$ alkyl of $R^{10B}$ is optionally substituted with 1, 2, 3, or 4 substituents each independently selected from the group consisting of halogen, —OH, —CN, $C_{1-4}$ alkoxy, and $C_{1-4}$ haloalkoxy; and wherein each of the $C_{3-4}$ cycloalkyl, cyclopropylmethyl, and cyclobutylmethyl of $R^{10B}$ is optionally substituted with 1, 2, 3, or 4 substituents each independently selected from the group consisting of halogen, —OH, —CN, $C_{1-4}$ alkyl, $C_{1-4}$ haloalkyl, $C_{1-4}$ hydroxylalkyl, $C_{1-4}$ alkoxy, and $C_{1-4}$ haloalkoxy.

5. The method of claim 2 wherein the compound or a pharmaceutically acceptable salt thereof is a compound of Formula IC-1, IC-2, IC-3, IC-4, IC-5, or IC-6:

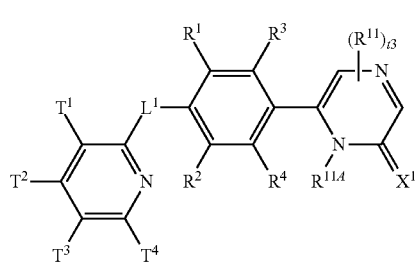

IC-1

-continued

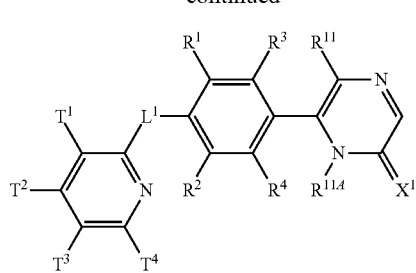

IC-2

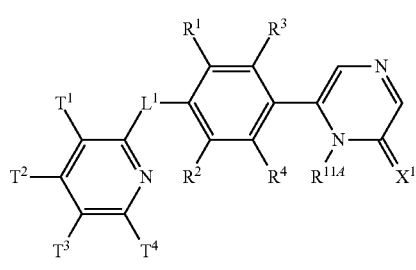

IC-3

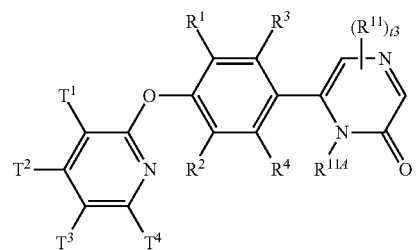

IC-4

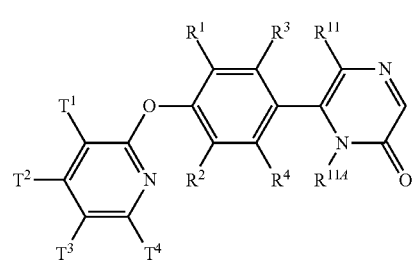

IC-5

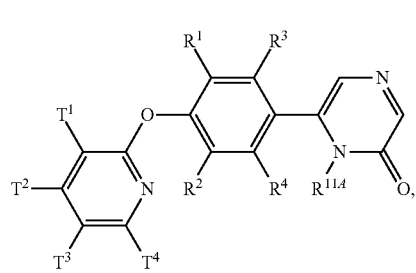

IC-6 or a pharmaceutically acceptable salt thereof.

6. The method of claim 5 wherein:

each $R^{11}$ is independently selected from the group consisting of —CN, $C_{1-4}$ alkyl, $C_{3-4}$ cycloalkyl, cyclopropylmethyl, and cyclobutylmethyl, wherein the $C_{1-4}$ alkyl of $R^{11}$ is optionally substituted with 1, 2, 3, or 4 substituents each independently selected from the group consisting of halogen, —OH, —CN, $C_{1-4}$ alkoxy, and $C_{1-4}$ haloalkoxy; and wherein each of the $C_{3-4}$ cycloalkyl, cyclopropylmethyl, and cyclobutylmethyl of $R^{11}$ is optionally substituted with 1, 2, 3, or 4 substituents each independently selected from the group consisting of halogen, —OH, —CN, $C_{1-4}$ alkyl, $C_{1-4}$ haloalkyl, $C_{1-4}$ hydroxylalkyl, $C_{1-4}$ alkoxy, and $C_{1-4}$ haloalkoxy; and $R^{11A}$ is selected from the group consisting of $C_{1-4}$ alkyl, $C_{3-4}$ cycloalkyl, cyclopropylmethyl, and cyclobutylmethyl, wherein the $C_{1-4}$ alkyl of $R^{11A}$ is optionally substituted with 1, 2, 3, or 4 substituents each independently selected from the group consisting of halogen, —OH, —CN, $C_{1-4}$ alkoxy, and $C_{1-4}$ haloalkoxy; and wherein each of the $C_{3-4}$ cycloalkyl, cyclopropylmethyl, and cyclobutylmethyl of $R^{11A}$ is optionally substituted with 1, 2, 3, or 4 substituents each independently selected from the group consisting of halogen, —OH, —CN, $C_{1-4}$ alkyl, $C_{1-4}$ haloalkyl, $C_{1-4}$ hydroxylalkyl, $C_{1-4}$ alkoxy, and $C_{1-4}$ haloalkoxy.

7. The method of claim 2 wherein the compound or a pharmaceutically acceptable salt thereof is a compound of Formula ID-1, ID-2, ID-3, ID-4, ID-5, ID-6, ID-7, ID-8, ID-9, or ID-10:

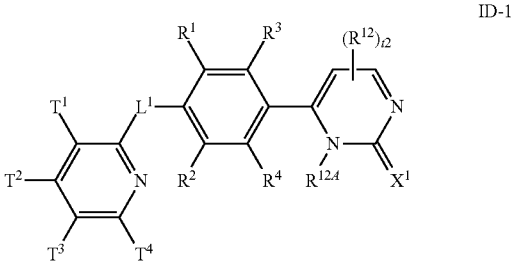

ID-1

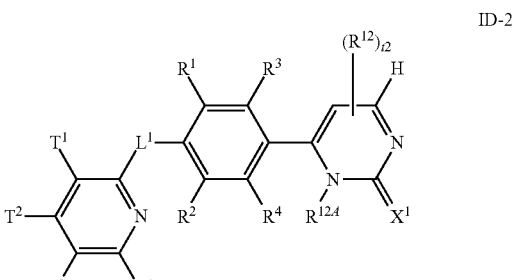

ID-2

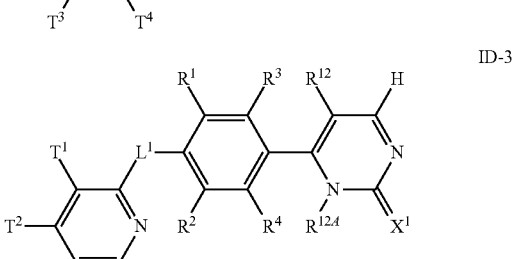

ID-3

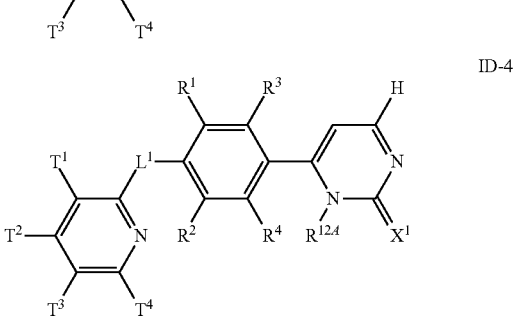

ID-4

-continued

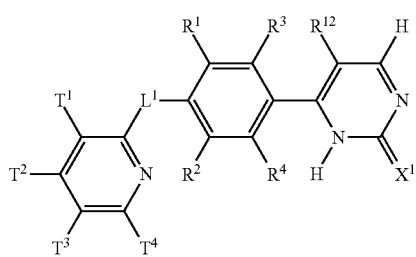

ID-5

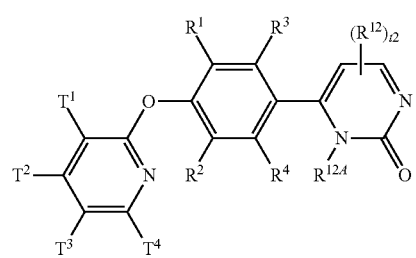

ID-6

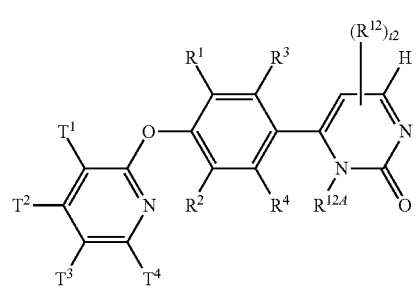

ID-7

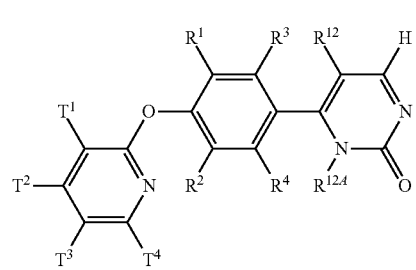

ID-8

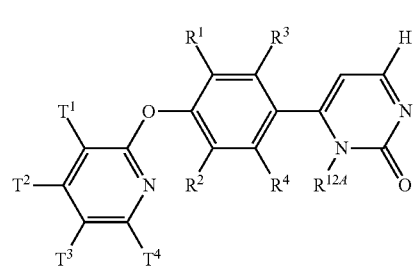

ID-9

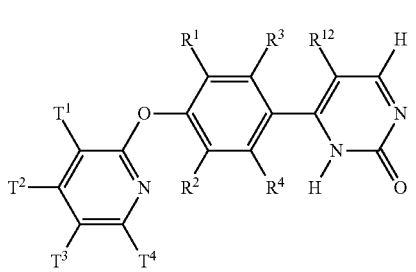

ID-10 or a pharmaceutically acceptable salt thereof.

8. The method of claim 7, wherein:

each $R^{12}$ is independently selected from the group consisting of —CN, $C_{1-4}$ alkyl, $C_{3-4}$ cycloalkyl, cyclopropylmethyl, and cyclobutylmethyl, wherein the $C_{1-4}$ alkyl of $R^{12}$ is optionally substituted with 1, 2, 3, or 4 substituents each independently selected from the group consisting of halogen, —OH, —CN, $C_{1-4}$ alkoxy, and $C_{1-4}$ haloalkoxy; and wherein each of the $C_{3-4}$ cycloalkyl, cyclopropylmethyl, and cyclobutylmethyl of $R^{12}$ is optionally substituted with 1, 2, 3, or 4 substituents each independently selected from the group consisting of halogen, —OH, —CN, $C_{1-4}$ alkyl, $C_{1-4}$ haloalkyl, $C_{1-4}$ hydroxylalkyl, $C_{1-4}$ alkoxy, and $C_{1-4}$ haloalkoxy; and $R^{12A}$ is selected from the group consisting of $C_{1-4}$ alkyl, $C_{3-4}$ cycloalkyl, cyclopropylmethyl, and cyclobutylmethyl, wherein the $C_{1-4}$ alkyl of $R^{12A}$ is optionally substituted with 1, 2, 3, or 4 substituents each independently selected from the group consisting of halogen, —OH, —CN, $C_{1-4}$ alkoxy, and $C_{1-4}$ haloalkoxy; and wherein each of the $C_{3-4}$ cycloalkyl, cyclopropylmethyl, and cyclobutylmethyl of $R^{12A}$ is optionally substituted with 1, 2, 3, or 4 substituents each independently selected from the group consisting of halogen, —OH, —CN, $C_{1-4}$ alkyl, $C_{1-4}$ haloalkyl, $C_{1-4}$ hydroxylalkyl, $C_{1-4}$ alkoxy, and $C_{1-4}$ haloalkoxy.

9. The method of claim 2 wherein the compound or a pharmaceutically acceptable salt thereof is a compound of Formula IE-1, IE-2, IE-3, IE-4, or IE-5, IE-6, IE-7, IE-8, IE-9, or IE-10:

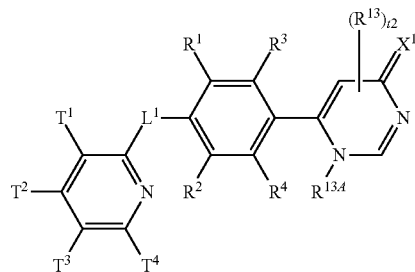

IE-1

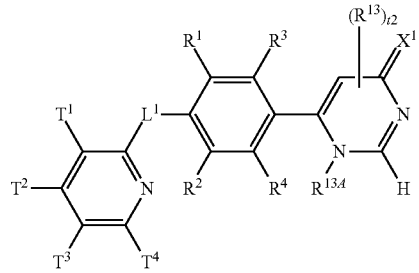

IE-2

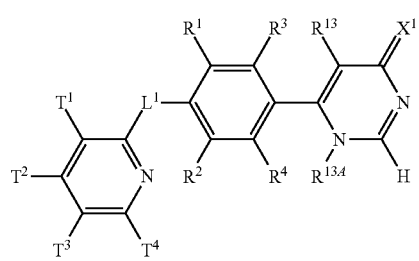

IE-3

IE-4 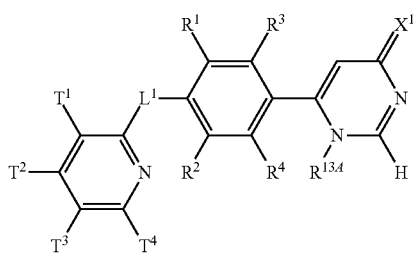

IE-5 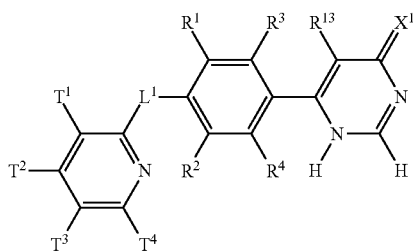

IE-6 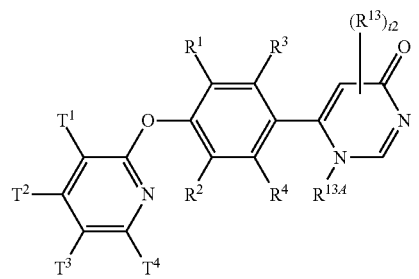

IE-7 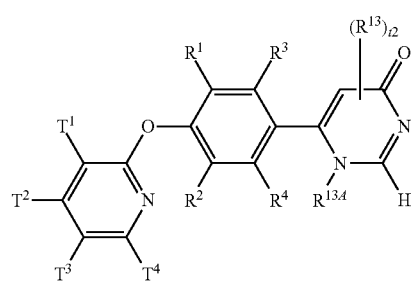

IE-8 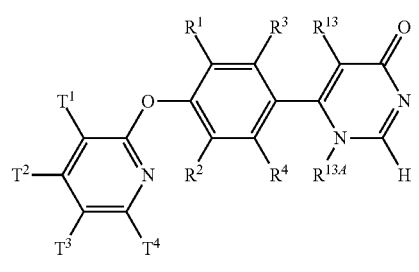

IE-9 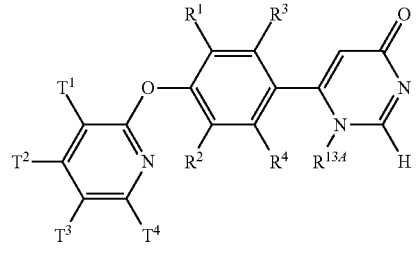

IE-10 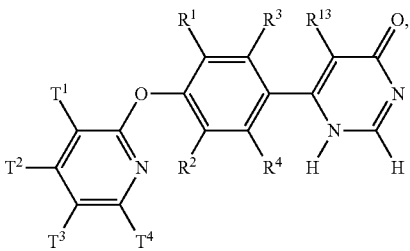

or a pharmaceutically acceptable salt thereof.

10. The method of claim 9 wherein:

each $R^{13}$ is independently selected from the group consisting of —CN, $C_{1-4}$ alkyl, $C_{3-4}$ cycloalkyl, cyclopropylmethyl, and cyclobutylmethyl, wherein the $C_{1-4}$ alkyl of $R^{13}$ is optionally substituted with 1, 2, 3, or 4 substituents each independently selected from the group consisting of halogen, —OH, —CN, $C_{1-4}$ alkoxy, and $C_{1-4}$ haloalkoxy; and wherein each of the $C_{3-4}$ cycloalkyl, cyclopropylmethyl, and cyclobutylmethyl of $R^{13}$ is optionally substituted with 1, 2, 3, or 4 substituents each independently selected from the group consisting of halogen, —OH, —CN, $C_{1-4}$ alkyl, $C_{1-4}$ haloalkyl, $C_{1-4}$ hydroxylalkyl, $C_{1-4}$ alkoxy, and $C_{1-4}$ haloalkoxy; and $R^{13A}$ is selected from the group consisting of $C_{1-4}$ alkyl, $C_{3-4}$ cycloalkyl, cyclopropylmethyl, and cyclobutylmethyl, wherein the $C_{1-4}$ alkyl of $R^{13A}$ is optionally substituted with 1, 2, 3, or 4 substituents each independently selected from the group consisting of halogen, —OH, —CN, $C_{1-4}$ alkoxy, and $C_{1-4}$ haloalkoxy; and wherein each of the $C_{3-4}$ cycloalkyl, cyclopropylmethyl, and cyclobutylmethyl of $R^{13A}$ is optionally substituted with 1, 2, 3, or 4 substituents each independently selected from the group consisting of halogen, —OH, —CN, $C_{1-4}$ alkyl, $C_{1-4}$ haloalkyl, $C_{1-4}$ hydroxylalkyl, $C_{1-4}$ alkoxy, and $C_{1-4}$ haloalkoxy.

11. The method of claim 2 wherein each of $R^1$ and $R^2$ is independently selected from the group consisting of H, halogen, —CN, $C_{1-6}$ alkyl, $C_{1-6}$ haloalkyl, —O—$C_{1-6}$ alkyl, $C_{1-6}$ haloalkoxy, $C_{3-6}$ cycloalkyl, —C(=O)—($C_{1-4}$ alkyl), -and C(=O)—O—($C_{1-4}$ alkyl), wherein each of the $C_{1-6}$ alkyl and $C_{3-6}$ cycloalkyl is optionally substituted with 1, 2, or 3, substituents each independently selected from the group consisting of halogen, —OH, —CN, $C_{1-4}$ alkyl, $C_{1-4}$ haloalkyl, $C_{1-4}$ alkoxy, and $C_{1-4}$ haloalkoxy.

12. The method of claim 2 wherein each of $R^1$ and $R^2$ is independently H, methyl, or halogen.

13. The method of claim 2 wherein each of $R^3$ and $R^4$ is independently selected from the group consisting of H, halogen, —CN, —$C_{1-4}$ alkyl, —O—$C_{1-4}$ alkyl, and $C_{3-4}$ cycloalkyl, wherein each of the $C_{1-4}$ alkyl and —O—$C_{1-4}$ alkyl of $R^3$ and $R^4$ is optionally substituted with 1, 2, or 3 substituents each independently selected from the group consisting of halogen, —OH, $C_{1-4}$ alkoxy, and $C_{1-4}$ haloalkoxy; and wherein the $C_{3-4}$ cycloalkyl of $R^3$ and $R^4$ is optionally substituted with 1, 2, or 3 substituents each independently selected from the group consisting of halogen, —OH, $C_{1-4}$ alkyl, $C_{1-4}$ haloalkyl, $C_{1-4}$ alkoxy, and $C_{1-4}$ haloalkoxy.

14. The method of claim 2 wherein $R^3$ is H; and $R^4$ is H, halogen, or methyl, wherein the methyl is optionally substituted with 1, 2, or 3 substituents each independently selected from the group consisting of halogen, —OH, and $C_{1-4}$ alkoxy.

15. The method of claim 2 wherein each of $T^1$, $T^2$, $T^3$, and $T^4$ is independently selected from the group consisting of H, halogen, —CN, $C_{1-4}$ alkyl, $C_{1-4}$ haloalkyl, $C_{2-4}$ alkenyl, $C_{1-4}$ alkoxy, $C_{1-4}$ haloalkoxy, and $C_{3-4}$ cycloalkyl, wherein each of the $C_{1-4}$ alkyl, $C_{2-4}$ alkenyl, and $C_{1-4}$ alkoxy of $T^1$, $T^2$, $T^3$, and $T^4$ is optionally substituted with one or more substituents each independently selected from the group consisting of halogen, —OH, —CN, $C_{1-4}$ alkoxy, and $C_{1-4}$ haloalkoxy; and wherein the $C_{3-4}$ cycloalkyl of $T^1$, $T^2$, $T^3$, and $T^4$ is optionally substituted with one or more substituents each independently selected from the group consisting of halogen, —OH, —CN, $C_{1-4}$ alkyl, $C_{1-4}$ haloalkyl, $C_{1-4}$ hydroxylalkyl, $C_{1-4}$ cyanoalkyl, $C_{1-4}$ alkoxy, and $C_{1-4}$ haloalkoxy.

16. The method of claim 2 wherein each of $T^1$, $T^2$, $T^3$, and $T^4$ is independently selected from the group consisting of H, halogen, $C_{1-4}$ alkyl, $C_{1-4}$ hydroxylalkyl, $C_{1-4}$ haloalkyl, $C_{1-4}$ alkoxy, $C_{1-4}$ haloalkoxy, $C_{3-4}$ cycloalkyl, and $C_{3-4}$ halocycloalkyl.

17. The method of claim 2 wherein each of $R^1$ and $R^2$ is H; $R^3$ is H and $R^4$ is methyl; $T^1$ is selected from the group consisting of halogen, cyclopropyl, halocyclopropyl, methyl, $C_1$ haloalkyl, methoxy, and $C_1$ haloalkoxy; and $T^4$ is H.

18. The method of claim 1 wherein:
the compound or pharmaceutically acceptable salt thereof is a compound of Formula IB-8 or a pharmaceutically acceptable salt thereof;
each of $R^{10}$ and $R^{10B}$ is independently selected from the group consisting of $C_{1-3}$ alkyl, haloalkyl, and cyclopropyl;
each of $R^1$ and $R^2$ is independently H, methyl, or halogen;
each of $R^3$ and $R^4$ is independently H, F, Cl, CN, or methyl wherein the methyl is optionally substituted with 1, 2, or 3 substituents each independently selected from the group consisting of halogen, —OH, and $C_{1-4}$ alkoxy;
$T^1$ is selected from the group consisting of halogen, $C_{1-2}$ alkyl, $C_{1-2}$ haloalkyl, $C_{1-2}$ hydroxylalkyl, $C_{1-2}$ alkoxy, $C_{1-2}$ haloalkoxy, cyclopropyl, and halocyclopropyl;
each of $T^2$ and $T^3$ is independently selected from the group consisting of H, halogen, $C_{1-2}$ alkyl, $C_{1-2}$ haloalkyl, $C_{1-2}$ hydroxylalkyl, $C_{1-2}$ alkoxy, $C_{1-2}$ haloalkoxy, cyclopropyl, and halocyclopropyl; and
$T^4$ is H.

19. The method of claim 18 wherein each of $R^{10}$ and $R^{10B}$ is independently selected from the group consisting of $C_{1-3}$ alkyl and cyclopropyl; each of $R^1$ and $R^2$ is H; $R^3$ is H; and $R^4$ is methyl.

20. The method of claim 1, wherein the compound or a pharmaceutically acceptable salt is a compound selected from the group consisting of:
6-{4-[(3-cyclopropylpyridin-2-yl)oxy]-2-methylphenyl}-1,5-dimethylpyrimidine-2,4(1H,3H)-dione;
6-{4-[(3-chloro-5-methylpyridin-2-yl)oxy]-2-methylphenyl}-1,5-dimethylpyrimidine-2,4(1H,3H)-dione;
6-(4-{[3-(difluoromethoxy)pyridin-2-yl]oxy}-2-methylphenyl)-1,5-dimethylpyrimidine-2,4(1H,3H)-dione,
6-{4-[(3-chloro-5-fluoropyridin-2-yl)oxy]-2-methylphenyl}-1,5-dimethylpyrimidine-2,4(1H,3H)-dione;
1,5-dimethyl-6-(2-methyl-4-{[3-(trifluoromethyl)pyridin-2-yl]oxy}phenyl)pyrimidine-2,4(1H,3H)-dione; and
6-{4-[(3-chloropyridin-2-yl)oxy]-2-methylphenyl}-1,5-dimethylpyrimidine-2,4(1H,3H)-dione,
(−)-6-{4-[(3-cyclopropylpyridin-2-yl)oxy]-2-methylphenyl}-1,5-dimethylpyrimidine-2,4(1H,3H)-dione;
(−)-6-{4-[(3-chloro-5-fluoropyridin-2-yl)oxy]-2-methylphenyl}-1,5-dimethylpyrimidine-2,4(1H,3H)-dione;
6-{4-[(3-chloropyridin-2-yl)oxy]-2-methylphenyl}-5-ethyl-1-methylpyrimidine-2,4(1H,3H)-dione;
(−)-1,5-dimethyl-6-(2-methyl-4-{[3-(trifluoromethyl)pyridin-2-yl]oxy}phenyl)pyrimidine-2,4(1H,3H)-dione;
(−)-6-{4-[(3-chloro-5-methylpyridin-2-yl)oxy]-2-methylphenyl}-1,5-dimethylpyrimidine-2,4(1H,3H)-dione;
6-{4-[(3-chloro-4-methylpyridin-2-yl)oxy]phenyl}-1,5-dimethylpyrimidine-2,4(1H,3H)-dione;
(−)-6-(4-{[3-(difluoromethoxy)pyridin-2-yl]oxy}-2-methylphenyl)-1,5-dimethylpyrimidine-2,4(1H,3H)-dione;
6-{4-[(3-chloropyridin-2-yl)sulfanyl]-2-methylphenyl}-1,5-dimethylpyrimidine-2,4(1H,3H)-dione;
(−)-6-{4-[(3-chloropyridin-2-yl)oxy]-2-methylphenyl}-1,5-dimethylpyrimidine-2,4(1H,3H)-dione;
6-{4-[(3-cyclopropylpyridin-2-yl)oxy]phenyl}-1,5-dimethylpyrimidine-2,4(1H,3H)-dione;
6-{4-[(3-chloro-4-methylpyridin-2-yl)oxy]-2-methylphenyl}-1,5-dimethylpyrazin-2(1H)-one;
6-{4-[(3-chloro-4-methylpyridin-2-yl)oxy]-2-methylphenyl}-1,5-dimethylpyrimidin-2(1H)-one; and
1-cyclopropyl-6-(4-((3-(difluoromethyl)pyridin-2-yl)oxy)-2-methylphenyl)-5-methylpyrimidine-2,4(1H,3H)-dione,
or a pharmaceutically acceptable salt thereof.

* * * * *